US007125557B1

(12) United States Patent
Markl et al.

(10) Patent No.: US 7,125,557 B1
(45) Date of Patent: Oct. 24, 2006

(54) NUCLEIC ACID MOLECULE COMPRISING A NUCLEIC ACID SEQUENCE WHICH CODES FOR A HAEMOCYANIN, AND COMPRISING AT LEAST ONE INTRON SEQUENCE

(76) Inventors: Jürgen Markl, An der Mahlsteig 12, 55296 Gau-Bischofsheim (DE); Benjamin Altenhein, Elsaesser Platz 7, 65195 Wiesbaden (DE); Bernhard Lieb, Konrad-Adenauer-Strasse 27, 55129 Mainz (DE); Thomas Stiefel, Steinkopfstrasse 22, 70184 Stuttgart (DE)

( * ) Notice: Subject to any disclaimer, the term of this patent is extended or adjusted under 35 U.S.C. 154(b) by 292 days.

(21) Appl. No.: 10/049,988

(22) PCT Filed: Aug. 21, 2000

(86) PCT No.: PCT/EP00/08129

§ 371 (c)(1),
(2), (4) Date: Jul. 15, 2002

(87) PCT Pub. No.: WO01/14536

PCT Pub. Date: Mar. 1, 2001

(30) Foreign Application Priority Data

Aug. 20, 1999 (DE) ................................ 199 39 578

(51) Int. Cl.
*A61K 47/00* (2006.01)
*C07K 14/00* (2006.01)

(52) U.S. Cl. .................... 424/278.1; 530/530; 530/855

(58) Field of Classification Search ................ 530/350, 530/857; 424/278.1
See application file for complete search history.

(56) References Cited

U.S. PATENT DOCUMENTS

| | | | |
|---|---|---|---|
| 5,021,560 | A | 6/1991 | Montreuil et al. |
| 5,831,033 | A | 11/1998 | Zetter et al. |
| 5,888,775 | A | 3/1999 | Tal et al. |

FOREIGN PATENT DOCUMENTS

| | | | |
|---|---|---|---|
| EP | 0 244 295 | A1 | 11/1987 |
| EP | 0 621 039 | A1 | 10/1994 |
| WO | WO 94/11019 | | 5/1994 |
| WO | WO 00/55192 | | 9/2000 |

OTHER PUBLICATIONS

Keller et al., European Journal of Biochemistry, 1999, 264, 27-38.*

The 1995 Sigma Product Catalog. p. 520, product #: H 7017.*

Lieb et al., "Structures of two molluscan hemocyanin genes: Significance for gene evolution", *PNAS* 98(8):4546-4551 (Apr. 2001).

Hamilton, et al., "Periodate-Sensitive Immunological Cross-Reactivity Between Keyhole Limpet Haemocyanin (KLH) and Serodiagnaostic *Schistosoma mansoni* Egg Antigens," *Parasitology*, 118:83-89 (Jan. 1999).

Miller et al., "Sequence of the *Octopus dofleini* Hemocyanin Subunit: Structural and Evolutionary Implications," *J. Mol. Biol.* 278:827-842 (Jan. 1998).

Stoeva, et al., "Primary Structure and Unusual Carbohydrate Moiety of Functional Unit 2-c of Keyhole Limpet Hemocyanin (KLH)," *Biochimica et Biophysica Acta*,, 1435:94-109 (Sep. 1999).

Gebauer, et al., Keyhole Limpet Hemocyanin Type 2 (KLH2): Detection and Immunolocalization of a Labile Functional Unit h, *Journal of Structural Biology* 128:280-286 (Oct. 1999).

Harris, et al., "Immunoelectron Microscopy of Hemocyanin from the Keyhole Limpet (*Megathura crenulata*): A Parallel Subunit Model," *Journal of Structural Biology*, 111:96-104 (Nov. 1993).

Carrera, et al., "Cocaine Vaccines: Antibody Protection Against Relapse in a Rat Model," *Proc. Natl. Acad. Sci, USA*, 97(11):6202-6206 (May 23, 2000).

Söhngen, et al., "Mass Determination, Subunit Organization and Control of Oligomerization States of Keyhole Limpet Hemocyanin (KLH)," *Eur. J. Biochem.*, 248:602-624 (May 1997).

Carrera, et al., "Suppression of Psychoactive Effects of Cocaine by Active Immunization," *Nature*, 378:727-730 (Dec. 14, 1995).

Lieb, et al., The Sequence of a Gastropod Hemocyanin (HtH1 from *Haliotis tuberculata), Journal of Biological Chemistry*, 275(8):5675-5681 (Feb. 25, 2000)

Lieb, et al., "Subunit Organization of the Abalone *Haliotis tuberculata* Hemocyanin Type 2(HtH2), and the cDNA Sequence Encoding its Functional Units d, e, f, g and h," *Eur. J. Biochem.* 265:134-144 (Jul. 1999).

Swerdlow, et al., "Keyhole Limpet Hemocyanin: Structural and Functional Characterization of Two Different Subunits and Multimers," *Comp. Biochem. Physiol.* 113B (3):537-548 (1996).

(Continued)

*Primary Examiner*—Robert A. Wax
*Assistant Examiner*—Suzanne M. Noakes
(74) *Attorney, Agent, or Firm*—Welsh & Katz, Ltd.

(57) ABSTRACT

A nucleic acid molecule or construct alone or with a promoter suitable for expression control is contemplated that codes for a haemocyanin, a haemocyanin domain or a fragment thereof with the immunological properties of at least one domain of haemocyanin, and comprises at least one intron sequence, as well as haemocyanin fusion proteins. The construct furthermore can comprise a nucleic acid sequence that codes for an antigen. Host cells are also contemplated that contain the nucleic acid molecule or construct and a recombinant expression product thereof. The invention furthermore relates to a pharmaceutical composition that comprises the expression product and antibodies obtainable by immunization of an animal therewith, as well as the use the antibodies in screening methods for the identification of tumors.

6 Claims, 44 Drawing Sheets

OTHER PUBLICATIONS

Keller, et al., "Abalone (*Haliotis tuberculata*) Hemocyanin Type 1 (HtH1): Organization of the 400 kDa Subunit, and Amino Acid Sequence of its Functional Units f, g and h," *Eur. J. Biochem.* 264:27-39 (May 1999).

Harris, et al., "Keyhole Limpet Haemocyanin (KLH): Purification of Intact KLH1 Through Selective Dissociation of KLH2," *Micron*, 26(3):201-212 (Feb. 1995).

Gebauer, et al., "Quaternary Structure, Subunits and Domain Patterns of Two Discrete Forms of Keyhole Limpet Hemocyanin: KLH1 and KLH2," *Zoology* 98:51-68 (Feb. 1994).

Drexel, et al., "Complete Amino-Acid Sequence of a Functional Unit from a Molluscan Hemocyanin (*Helix pomatia*)," *Bio. Chem. Hoppe-Seyler* 368:617-635 (Jun. 1987).

Geyer et al., "Identification and Characterization of Keyhole Limpet Hemocyanin N-Glycans Mediating Cross-reactivity with Schistosoma mansoni", *J. of Biol. Chem.*, 280(49):40731-40748 (2005).

Kurokawa et al., "Hemocyanin from the keyhole dlimpet *Megathura crenulata* (KLH) carries a novel type of N-glycans with Gal(β1-6)Man-motifs", *Eur. J. Biochem*, 269:5459-5473 (2002).

* cited by examiner 50 nm

M KLH HtH
205
116
97
66
45

HtH1
HtH2

HtH1
HtH2

50 nm

A340 nm
0,09
0,06
0,03
0
HtH1
HtH2
0
20
40
60
80
fraction (no.)

elastase
a
e
h
f
g
c
d
ab
b

E M
205
116
97
66
45 d e

V8-protease
c
defg(h)
h
ab

M V
defgh
defg
ab
h
c
205
116
97
66
45 ab a c h
papain
gh g
trypsin
a
h
de
e
f
g
ab
c
d
b f
e
g
d
de
chymotrypsin
a
e
fg
c
ab
h
d f
g
fg

Fig. 4a

Genomic sequence of the HtH1 gene

SIGNAL PEPTIDE SEQUENCE 1S-1 (1st part)

GGCTTGTTCAGTTTCTACTCGTCGCCCTTGTG

INTRON 1S-1/1S-2 (SEQ ID NO:109)

GTAAGTCAACGTCTTTGTTTTAAGTTTGATGCATATCTATCATTGCGTTTTAAAATACCA
TTACAACCAACGTGTCTCTATTGGTCTTCACCTGTTTAACGTATATATTGTTTTTAATGT
GAAAATCTGAGATTATTTTCATTTCCGTCAATATTCGTAAAATACTATACAAATAAAATT
GCTTCAGCCTATTGCATTGGCAGTTTTCGCAGAATAACGAGGGAAGGCGTACATAAAATA
TAAACCAGTGTATATTCAAGCATGTTTATAATTTCTTTATAGATTATAACATCATATCAA
AACACCAATCTGGATTTAAACCCGTGAATCCAAAGTATACCAATTAACGGAACTTTATCA
TGTTTTATCAAAGGTTTAGATGAGGGTAAAGAAGTCCGAGCTATATTTTGCGATATCAG
CAAAGCCTTCTATCACGTCTTGCACACAGGGCTGGTATCTAAACTCGAATCCACAGGAAT
AAATATTTCAGCCGATAGAGAACAGTCGGTGGCTATCATTGGTCACAAAACAAGTCCAAA
ATCTGCATTAGCCGGTGTTCCCCAAGGCTCTGTCTTGGGGCCACTATTATTTCTCACCTA
TATAAACGATTCAACTAATGGAATATAAAGCAACGTAAACCTCACCGCAGATGAAACACT
AAGTTATAGACAATCCGTTTAAAACCCAGCCACTGCTTAATAATGACTTAGGCCGTCTTT
CAGACTGGGCTAGTAAGCGGCAGGTTAAATTTCACCTTGAAAAGACAGAAACCATGGTAT
ATTTCAAAAACACGAATGCAAGTCCTAAACTTCAACTACTACTTGATGATACTGGGATTT
CTAAAGTGTGTGAACAAAAACACATTGGCCTGATCCTACAAGATAACCAGACAGAAACCA
TGTTTTTTTTCAATAACACGAATGCAAGTCCTAAACTTCAACTACTACTTGATGATACTG
GGATTTCTAAAGTGTGTGGTGAACACAAACACCTTGGCCTGATTCTGCAAGATAATGGAA
AATGTCAGAAACATAAGCAAGTTGATGTGGGGTTTTCTGGGGGTTGTGACAACACCGAAA
GACCCTGCAACTAATGTTAGCTCAAAGGGTTTTACACCCGGTCACAAGTGGGGATCGACC
CAGGCACCTTTTGCCTTTGACAGCTCGCCTTTCAAAAAATCTCAATTCGAAAACGAAATC
TAATAATTTCATGAGCGATACAACCGTTTTTCATAATGCTGTGGTACCGCATACTGTGGA
AACATCTGTCTACCCATTTGGTAGTCCCCCATAAAATGTATTTATGTTTATAAACACAAT
GTTTATAGGGTTACAGTTAGAAGAAGCATTTCTATTGGCTAATGTACATTGCTTGTTTTT
ACTATTGTGCAAAGGCATATTACAGGTCTTTTAGGAAATTAAATACTGTTTAAATCACAT
ACACTACCGGTAATCCTATTATGCTTATCCTGCCAACATTCTGCCCAAGCAAACGCATGA
AAGTTAAAGCTGAGTGTAAAATACTGATTGCTGTGTTACTTCACAACCAGTGGACTGAAT
ACAACCATGTTTTTTCTTGAAAGTCACAAACATCCAGTCGGTTTCTAATGTGTTAAGTTT
CTAGTTTCATAAAGAGCATGACGTAATGGTGAATAGGAGTTATCAATGTTTCTATCTAAT
GACTCCTAGTTCGTTACTTTTTTAATAAAACATCCATGTGTTTAATGTTTGGCCACAGAT
ATAACAAGAAAGAAATCGGATAAAATCTACATTTTGACCAATCGGAAGGCTGCCCCCTCC
CTAATCCTAATCATTTTTGTGCCTCAAAACATACTCAACCAGACATTTGAACTATGTATA
TATCAGAATGAAATGGTAACAATAAACTTGTATGTTGACCAGACAGAATTAGGGTGAATC
TGAATACCAACTATTGTCACATATGAATATGGATAAGCTCTGCGCGTGCGTGCGGGCGGT
GTAGTGCGTGTGTGTCTGTGTGTGTGTGTGTGTGCGTTTGTGTGTGTGTCTGCGTGCGTG
TGTGTGCGCGTGTGTGCGTGTGTGTGTGTGTGCAGTGTGCCGAGTGTGTGTGTGTGTGTG
TGCACAGACATGTGGTTGAGACACACTTGATTCAGTGCAGGATTATGTCCTTCAACCGAG
TGTAGTCTTTAAGTGTGCCTGGAAACAAAAAACTGCGTTGGGTTGCATCGCCTCTGTAGC
AAGCTTGGACGCGTCACGCAGCTCTGATACCACGTATTGGCACCATGTTTCATCGGTCTC
ACGCGAATATTATGCTATGTGTGGCGTATCATACCATAGGTTGGGAACGTTTCAATACTG
TACCGAGCTTGGGCGTGTCACAAAGCTATGATAAGATGACAACACGTCTTGGCATCTTGT
TTCCTCGGTATCACGCGCTGTTATGCTATGTGTGGCTATCACACCTTAGGTTGGGAAAGT

Fig. 4b

TTCCACATTTTCCAGCCTCGTACATGTTTCCTTTTGTTTTTCCTTAGTTATCAGCATAC
CGTATATTCTATATTTAATGAGCATTTGTATTTTTCTACAG

SIGNAL PEPTIDE SEQUENCE 1S-2(2nd part)

GTGGGGGCTGGAGCAG

INTRON 1S-2/1A-1 (SEQ ID NO:110)

GTGAGTTTCTTAACATTGTCATGGTACATGGATATACGCTCAGTGGGAAAGCAGGATATC
CCCTTGGTTCAAGTATTCACTTGTCACGCCAAGTGTTCGATTCCCAACATGGAATACTGT
CATATAGTAAATTGATACACTACTTACATTTAATTCTCCACTAAACGTCAACGTCCTTTA
CTTCATGGCCCACATGGTCCGTATTAGTGAGTGAGTGAGTCAGGGCATAAGTATTTAACG
TCAAATCAGCAATATTTCAGCCATATTGTGACAAGAATTGAATATAAATAATTATACTTA
TAATGCTTATAAATATAAATTATATAAATACCTATAACTATAAATTAGTTATACTAGTAT
TTATCAAAACATATTTGCCACGACACTGCACGCCGATACTTCAAGTGTCTTCACCTCAAG
CGTGTAACTCCTCATACTCTGTAATAAGTATGTACACTAAGTGAGTGCTATCATCTCCAT
GCTTCATTAGTTTCGTCAGATGCGTGTATCCATACGAGTACATTCAGATTATGGGATCCA
GAGCTTTCTTATCTCAAGTATTTCCGATTGTAAAGCCATACTACTTCCCCAATGACTGAC
GAGACAGATGGCAACCGTTCTTTCCTCCTGACTAGGTGAGTGCCACTGATAAATCATTAT
GCCTTTAACATTAGGAATGTTAGCAGTGCACATGTTTCAGAATTGCGACCTTATGGTTGT
AAAGATTACAAACTTTACAACTTACTTGAGACAGGTTCCATATGTCGTATCTGAAATAGT
GTGAAGGTATCTGATTCGATGCAATACACAGACATATAAACATATTGTCGCCCTGCTATT
CCGGAAAGGTCATTTTGTATGTAACGTTCCTTAATGGACACAAACGGAATTATTAGTTAA
ACATACTCAACAAAACTATGTTATTTTGCAATGGGTAGCACCGAAATCTACCGACAGTGG
TTCGTAAAAGTAGAACATTCTGACATAAAGAAAAATCATTGGCTTTAAATATATGCAAGT
TACTTGTCTCTAACAACCAGTTTTATACACATTTCAGAGAACGGGGAATCCGCGATGACA
ATATCAACGAGTATATACAGAATATATAATTAAAAACGATGAGTGCCTGGCAAGGGAAAG
AGCGAGATTTGCCAAACAGGGGGGTGGTGTTGAGCTTGAATCGTGGAGAAACGTAGATTG
AAAGACAAGATGACATCTAATGATCCGAAAATCAAACACAGGATTAACTGGGATGCAGAA
GAATGAATATCTCAAGCATACATGCAACACTTCATGAATGCATCTCAAACATTTTCGTCA
GATCGGATGCATGAAGATTTGTAAAGCAATGGTTTAAATTGTCCCTAAACGTTTAGTTGG
AGATGTATGAGGCTAGGCTGTATGTTGAACGAAACCATTTAACATTGTTGTTCATGATTA
TTTAATATTTTTTCATTTTATAGATGTACAATAAAATTGGAAACTAAACATTTCCCTTTA
TTGTTTTGTATTTACCTGTTCATGGGTATGTTTTGAAAGATCGTGATATTTAGTTGGCAT
TCACAAGTTGGAAAAAGGTCACTCAGTTTGATTTCAAGTTTATGTAACCTCTTTATCTGA
CGCTCCAAAATATGTATAGCCTTGTTCATCTGTCGGTATGTGGATATTCCTACTTCAGGG
TAGGGTAGCATTAATACTTACAAAACATAACGTGTACCAGATTTCAGTCACCTCAGAGAT
GATAATGCATGTCGATATGATAGGTCAAAACTTTCGATATCAATCACAATGAACCTATGG
ACCCTGAATCGGAATGATACGTTACACTTTAGAAACAATTCACAAATATGACTGTCACCC
TTTCAGGTAATAATGTTTGACGGACTACGATAGTGCTGAACAGCAGGAGAGGCAACATGG
TTCGATTGTGAGACAGGTTTAGTGTATTTGTTTGCGAATTTAAGGTTCTGAATCACAATA
GACACGGTTCAGTTAATGGATAAACCAATCATTAGATAGATAGAGATTAGTCGCGATATT
GCTGGGATAAAGCTTAGTGGGACGTTAAGTCCCATCTCAATCTCTCTCATTTTTTCCAAA
ACAGTTTTAATTCAGGCTCATGACAAGGTCGTACTGTTGCAAAGGATTCTACTTCAAGCA
GAGATGTCTCATGAATACAGTACAGGGTTTTTGAAGTTTATCCAGTGCAGCGCTGGCACC
ATCTCTGCATGCGAATTATACCATCCATGCCGCTCTAGGCTATTTGTATTAAGTCTGTAG
AATTAAATTCGCGAGTTGCAAATACTGCTCACCATTATCTGCCTCAACCCAGTTTGGGTA
CATGCGATTTACACAATATTATGTATAATGTTCGCTTTTCGAAAACAAAACACCTAAATT
CATCCAAAGTTTTGGGAGATTTTATTCGAGAAATCAACCTGAGATGTTGAATCGGGAGCT
GCGCTTATTCAATGGTGGACTCGGAAGGGAAGTAACCGCTGATGAGGCAAAACAATAACG

Fig. 4c

CAAACATATGGAAGTGGAACTCTTTGAACCAGTATTATGTTTGTGTGGACATGTATGTGT
TAATTTGACCATTCGAACAACTTTACTATTCTATTCATAATGTGTTTAGATTTACATTTG
AATTAAAAGAGATGAGTTTAAGATATTAATATTTTCCTTTTATAGTCTGTCGTGATTGTA
GGGCAATATTTATGTATGTTCGTTCATTTTTCATTTATCATTTGGAAAGGTATATCATAA
GATTATTATTATCATTCTTGAAGTAATGTATACATATATATATGTCTTGAGTAGCTTATT
TTCAATTTATTATCATCCGTCATCCAATTTTATTTCACGAAAGTATAAGAAATAACGAGA
GAGAGAGAGAGAGAGAGAGAGAAAAGACAGAAATGAAGTTAGGAGATATNAGTTATCAAGAA
AACAACAGTTTGAATTTTTTGTTTAGACAAGATATCATATCAATAACCTCGCACTATTAC
GGGAATAGGCGGGCGTTCCATATGCACAATGAATCGTCAGTTAAAATCAACATTAAACTT
AAAATACTCCTCATATTTAAAGTTGATCTACCTCTTGTATTATTGTAGACTATTAGACAG
AAGTCGACAGTGACACCAGCAACCAGATATCATACCCAGACTTAAAAAGCTGTTTCCTTG
ATGTTTCAATTTATTTCCATTTCCATTATTTCCCTTTATTGGTTTCCATTTATCAAACTT
ACCATCTGCACCAGTGGGAGATTGATATGTTGTATTTATTTATATTTCTTGTACTACAAT
ATCAAGAATGTATAGGAGCTATTCCTTGTTCCTAAAACCGGATAGATCCATAATTTCCAT
TTTGGGATAAATGGAAACTAAACACAACTTTTACAGTAAACACGAGTGAGCAAGTTGAGT
TTTACGCCGTTTTTAGTAGTATTCCAGCAATATCGCGGCGGGGGACACCAGAAATGGGCT
TCACACAGTGAATGCATGTGGGGATTCGAACCCGGGTCTTCGGCGTGACGAGTGAACGCT
TTAGCCACTAGGCTACCCCACCGCCTATTTATAGTTAAGACGAATACTTTTCTCAAGCCT
CAAATATGTCCATTCTAGAGAGACTGAATCTGATCCTGAATCTGCGGACCGGTCTTGAAT
ATCATCCCACTAACTCATTGTACAAAGTACCTGTAGATTGTCAGTTCAAAGACAGATTTC
ACAACCCTATTATATTTTGTCCTGCTCATTAAGATATTCAGACTCACTCAAACTGCTAAA
TGATTTTAATCCTACTTTGAGATGTTTTAACTTTTATTCGATGCATTTTTGCGTTCTGCG
TCCTGTATAAAGGTAAAGCAGGTAAACTAACCTAACCTGTTGATTTATTTCATAGTTTTG
CGATCAGATTGAAACCGGAATGCACAGTGAAGTGTGGCATACATCTTTCCACAGAGATAC
TGGATACTAGGTGGTACAACCGCATTGGCTTTGTGAAAGGATATTAGTGTTTTATGAGAC
TGACTCATGTTTCAATGCTTAGAGCGGAATGATCTCGGTCTTCATGAAAAATATTGTGTT
GAAGTAACCCCCCAGTCCCTAACAGAACGTGGGGAAAGCAGATGGATATGCCAAGACATC
TTCGCATGGTGTGAAGATGATCGTTACAACATCTGCAGAAAAAGTTATTTCTGTGAAGAA
TATGCCAAAGCATCACTGTGAGTGTTTTGAAGATGTGATATGGCAACACGCAGCGTGTAA
TTATGCTTTGTGTGTATTTCTGAAGATCCGTATGAGCATGGCGCCAAACTATCAGTTAAA
TGGCTATGCGAAGATCTTCCCGAGATGGTAAACACATATTTTGGCCATTTTCTTTGTAAG
TGGGCGACACAGAAGATCCCCCTGATTGTGTGGATGAGGACACAAAAACGGGTCCCCCTT
CCTTTGCTGATGCTAATGACGCCCTGGAAACATTGAAAGACTTCTTCTCCAGCAAGCAAG
CCACCAACCACAAGTTGTATAAATCGCTTGCGGACTTGAATACGGCAGTTGGACAGATAC
ATACAGCCAGAGAGGGCCGAACTAAAACATCTAAACATGGAAAAACTGTAAAGACAGGCT
TTGTTGTACGACGTACGTAAATTCATTGAATGTTTGAAAAGGTAGAAAATTATTAAATCT
TTGAAACCTCGCTCTGTTTGTTTGTTATTGTCCCCCACATTTGCAAATGGTATCCAAAAA
GGGCAGACACATTTGTTTTAATCTTAGCCAGGTTCAATTTAGCCTTGCGCCCAGACTCAT
TGTATCTGGTGAAGGCTATAGGTGGCCACGTCTTCTAAGATGCTATGCTATTCTTACCAG
AATCCAATGTAAAGAGTTCAAACGCATGGTTCGCTTTGATTGTGATTCTTTCTTAGCACC
TCTCTCCTACCCAGAGTTCACCTGCACTGCTCCTGACTCACAATAAGCTGACGTGCTGTC
ATATATGTGCAACATTGTATACGTTGGCGTTAAGCCCAACTCACTTCCGCTGTCTTTTGG
CAG

DOMAIN 1A-1 (1st part of domain a)

ACAACGTCGTCAGAAAGGACGTGAGTCACCTCACAGTTGACGAGGTGCAAGCTCTTCACG
GCGCCCTCCATGACGTCACTGCATCTACAGGGCCTCTGAGTTTCGAAGACATAACATCTT
ACCATGCCGCACCAGCGTCGTGTGACTACAAGGGACGGAAGATCGCCTGCTGTGTCCACG
GTATGCCCAGTTTCCCCTTCTGGCACAGGGCATATGTCGTCCAAGCCGAGCGGGCACTGT

Fig. 4d

TGTCCAAACGGAAGACTGTCGGAATGCCTTACTGGGACTGGACGCAAACGCTGACTCACT
TACCATCTCTTGTGACTGAACCCATCTACATTGACAGTAAAGGTGGAAAG

INTRON 1A-1/1A-2 (SEQ ID NO:111)

GTAACTACAAACGTCGTCCCATTCATACAGGAGAAATATACAATTGTGTTGTAAGAGCGG
TATACTGTTTGCCAACTGTGTAATTGAAACGTTGATGATGGTGTCTTTGTATTTCAATTT
GTATGCACTTAGACATGATCAATGTTTCTGATGTGTCAAGGATGTTCGGTGTGTCACTTT
CAAAAGATCAAATTCATATGACGTACACAGAGCAAGAACCAACAGTAAGAAGTCTGTATG
ACTTCGCTCTTAAAAGCAATGGAAAAATATTTTCACTTAACACCTAGCCCATAATCACGC
ATATTAGATTATTCAAGCGATGTCAACATGTTTTTAATATCAATCTCATGGTTCTGATAT
TACCGGAGACATGCAACAGGCTGCCATTATAGCCAGGAAATCTTATGAATATGTGCATAT
TTTTTCTTTGATTCTGTATGACGAGAAATATTCGGAGGCAAAGATTGTGTTTTCAGAACA
GAATCAGGGTATCAGTGACATCGTCACTGCATGGCTACAATATTGCTGATGTGACTGTTT
CTCCAAGGATTTTCATCTCACTGTCTGTACTTTGAATCTACAAATTCGTATTAAAGTTAT
GACAATTTTACCCCTGCCTATTTGTAAACGAAATATAACATGAGTGTTTATGCTGACAG

DOMAIN 1A-2 (2nd part of domain a)

GCTCAAACCAACTACTGGTACCGCGGCGAGATAGCGTTCATCAATAAGAAGACTGCGCGA
GCTGTAGATGATCGCCTATTCGAGAAGGTGGAGCCTGGTCACTACACACATCTTATGGAG
ACTGTCCTCGACGCTCTCGAACAGGACGAATTCTGTAAATTTGAAATCCAGTTCGAGTTG
GCTCATAATGCTATCCATTACTTGGTTGGCGGTAAATTTGA

INTRON 1A-2/1A-3 (SEQ ID NO:112)

GTAAGTTTGGTTTACAGTTTCATTATAAAAACATAGCAGTTTTAAGTTTAGGGGCAGATT
CTAATCTCTAATATTCCTTTCAACTCACTTTATTGGTGCCTTCTTGGAGTGACATTTAGA
AACTAAGACAAGAGGAAGATGAACAATGTTTGTAGGGATAGACAGCTTGGATGCAATTTC
GGACCAGATTCTAACAGCGTCATGAAGCAAGTGATACACAACGTTATCAATAACGAGAAT
ATACACATAGATGGTTTGAGTTTATAAATGAACTATTAACGGCATTGTGGTTATAGACAG
TGAGGAAGACGCCAGATAGACAAAGGGTAGGGGCCTTGGTTAGATAATGAGAAGTTGAAG
AGGTGTAATAACTTAAATCTCTCTTGACTATTGATTGTGTCTAAGAGTTTTCTTATCTTA
CAGTCGGCCAGTTGGGTCAAAGATGGTGTGATTCGGATGTGCTTTGTGTGTTCTGCGATG
GCTGATTTAGAGTCAGTTTACTTCAGATGAATGAAGTTCCCCGATTCTTATGTTTAAGTT
TGTTTCACCTACGCATGAAGACATCACCAGCAGGGTCGTCTTTATTTCTAGTAGCTTATT
TACAGCAAGCTTGTAACGTATGCTGAATTGCTGTGCCTCTGTAGAACACAGCATCTATGT
TTGCTTGCTTCTTTAGTAGACTGCGGATGTGATGGTTGGTTACCTGGTATGCTGACGAAA
GAATTGTTGACGTGGTGGTTTGCCTTGATGGGTTCGTTGACTTGGTTTGTTGGATACTGA
TTAAGGTGACTCTGCTGGGAGGCTTGGATTCTGGGGCCGGTGTTCTTTGCTCTCCTGTCT
AGGGTGGCGATTATTTCCCAACCCACTTGTTCCATTACACTCAAAACCTGCTATCAATTT
ACAG

DOMAIN 1A-3 (3rd part of domain a)

ATATTCAATGTCAAACTTGGAATACACCTCCTACGACCCCATCTTCTTCCTCCACCACTC
CAACGTTGACCGCCTCTTCGCCATCTGGCAGCGTCTTCAGGAACTGCGAGGAAAGAATCC
CAATGCAATGGACTGTGCACATGAACTCGCTCACCAGCAACTCCAACCCTTCAACAGGGA
CAGCAATCCAGTCCAGCTCACAAAGGACCACTCGACACCTGCTGACCTCTTTGATTACAA
ACAACTTGGATACAG

Fig. 4e

INTRON 1A-3/1A-4 (SEQ ID NO:113)

GTGAGACATTATTACACTTCTATTTAGTAGTGGGGGCGGGATAGCTCAGGTGGTAGAGCG
TCGGCCTTCAGCTTCTAGTCTCGCCCACAAGAGCGCGCTGGCTAAAGGGCCGGAGTTAGA
TTCCCGCGGGCGGCAGGCAATATCTCCGAAGGGGAGAACAGTTCTCCAGTCGGTGAAATT
GGGGTGCAATGTTGTACCACTGAAATGCGTGCAGCACCAACCATCCAAATACCAGCCTTG
CCGCGCTGGTCTGACTACATAGTACCACCCGGATTCAACCGGGCTATATAGGTTCTCCTC
CAGCAGTAAATCTGACAGTCGCCATATAGCTGGGATATTGCTGAGTGCGACGTTAAGCCC
CAACTCACTCACTTTATATTTAGTATTCTATTTAGTATCGACGCATGACCATGTGTGGTG
GTCTACTCATCTCAACACGACCGATTAACGTTAAGAGCTGCCAACATGATTCTCTTTCTC
TCTTTAGCCTCTTTATGCCAAAAGCTATATATTAATGTAGGACCCTACATATATTATTTC
CAG

DOMAIN 1A-4 (4th part of domain a)

CTACGACAGCTTAAACCTGAATGGAATGACGCCAGAACAGCTGAAAACAGAACTAGACGA
ACGCCACTCCAAAGAACGTGCGTTTGCAAGCTTCCGACTCAGTGGCTTTGGGGGTTCTGC
CAACGTTGTTGTCTATGCATGTGTCCCTGATGATGATCCACGCAGTGATGACTACTGCGA
GAAAGCAGGCGACTTCTTCATTCTTGGGGGTCAAAGCGAAATGCCGTGGAGATTCTACAG
ACCCTTCTTCTATGATGTAACTGAAGCGGTACATCACCTTGGAGTCCCGCTAAGTGGCCA
CTACTATGTGAAAACAGAACTCTTCAGCGTGAATGGCACAGCACTTTCACCTGATCTTCT
TCCTCAACCAACTGTTGCCTACCGACCTGGGAAAGGTCACCTTGACC

INTRON 1A-4/1B (SEQ ID NO:114)

GTAAGTTGATTGTCTTAATATTGTTTTAATTTTTGCAGAAATTTGATTTTAAATTGTGTA
ATAACAGTACACATTTTTACGCAACAGCAGTCATTATTGTGTGTGAAGATGTCAAACCAG
AAAGGTTTCAATCGTGAAAACAAAAACAATTCTCTATCTGTATACCCCTCAATACCAGTA
TGATCACAAATCTAGGAAATATTACAATACTGCTTCATAGAGTAACTGCTGTTTGTGGCA
GAGCTGGATACGAAGTTTCTGATAGTTCACAGCTACATGATAGTAAATGAACCTGTACAC
ATCAACGGTTGATCATGAAAATTTTGTATGTGTGAAAGTGCTACCTGTATTAGTGAACGT
GCTACCTGTATAACTGAAAGTGCTACCTGTATGACTGAAAGTGCTACCTGTATGCTGAAA
GTGCTACCTGTATTAGTGAACGTGCTACCTGTATAACTGAAAGTGCTACCTGTATGACTG
AAAGTGCTACCTGTATTAGTGAAAGTGCTACCTGTATGAGTGAACGTGCTACCTGTATAA
CTGAAAGTGCTACCTGTATGACTGAAAGTGCTACCTGTATTAGTGAAAGTGCTGCCTGTA
TTAGTGAAAGTGCTACCTGTATGACTGAGCGTGTTACCTGTATGACTGAACGTGCTACCT
GTATTAGTGAAAGTGTAATCTGTATGAGTGAAAGTGCTACCTGTATTAGTGAAAGTGCTA
CTTGTATTAGTGAAAGTGCTACATGTATGACTGAAAGTGCTACATGTATGAATGAGAGTG
CTACCTGTGTGACTGAAAGTGCTACCTGTATTAGTGAAAGTGCTACCTGTATGACTGAAC
GTGCTACCTGTATTAGTGATAGTGTCACTGGTACCAACTGGATGTTCTCACTTCTTTGGC
GAATATCTGGGCTCAAAACAGTTTTTCAGTATCATAGTCGTATCAGTTTGATTTGTATGT
GCAGTGGAATCATTTTCGTCAAATAATCAAAACTGGTGTTGAACTGGCGTTCACGTTTTA
TGGTTGTAAAACAAATTCTGTAAGTAAAGATATTTTAGGGATATCTGTATGACATGAACT
GAATTGCTTAAGGTTAGCATGCCATGACAAATTGCTGAATGTCTGAGGATTGGTGGAGCA
ATAAATCATTATTAAGACAAAAATCAGAAACGTCCATTTTCACTTTTAACAGTGTATCTG
TCTGAATGCCCCCTACTTTTTGGAAGAGTATATATGAATTATCGGCAATATAAAACGTTA
AATGGCAAATGTCGGGCATATGTCAGGACATTATTACCGCAGTTTATAGTCATATTTACC
GGGTCTAGGACAATTGTCACCCCGACAATTGCCACCCGGACAATTGCCACCCAAAAATAA
AATATACGTAAACAGAAAACAAATATTGCTTTCAGCCTTTATTGAGTTAGATAATGACAT
TTATGTTGATAAATATGTCGTTTGATAATAATAATAACAATAATATAATATTACAATACT
GCAATAGTACTATCAGTACTTATCATTTTATCACAGATTATATATAGATTCTAGAGTCCG

Fig. 4f

ATGTTGTAGGCAACACTTCGTCGGTAGGCCGTTAGGTAGTTATCATTAGGGCTGAGTATT
GCGCCAAATTTCGTATTGCTATATACTGCGATACACGGTTACCTGTTTTGCAATACGTAA
ACTTAGGCAAATATGACAGTTTTTCCATGATTATTTTCACGTTTCAATGCTTAAAATGGT
CTTATCTGTTATCTCCTTGAAGGTTTAATAAAATAACAATAAACATAAATCATTATTGAA
AATTAATGAACAAAAGTAAAGCGCTTCTCAGTTACCTTAACCTAACTTATTTATGAATGG
GATTACTATCCAAGAATGTGAAATTCACAAACACCTTGGGATAACACTGCAAAACGACTG
TTCATGGGACGGACATGAAAAAGGTGAGTCCCATGTTAAACTGTTGAGAAAGTTTCCTAT
ACTGTTTGTCCCGAAAAAGGCTAAAGACCATGTACTAATCAATTATTCTATCTATTTTCG
ATTACTGTTCTCATATTTGGGACAACTGTGCAGATCGGTAGCATCCAAGCTCGTCTAAAT
CGGTTTGATAAACCTTGTCAAATAACATGTTGTCTCAACATCCAAGCTCACCTAAACCTT
GTCAATACCTGCATCTGAACAAATGTATATTTAAGACGATAGCATCCAAGCTCATCTTTA
AAATGAATATTTTCTCTTTTTCTACCAAAACATTATTTGGTTGACAGTTGTCCTCCCTAT
TATAGTAAAAAGAACTGGGTGGCAATTGTCCTAGGTGGCAATTGTCCGGATGGCAATTGT
CCGGGTGGCAATTGTCCGGGTGGCAGTTGTCCAGGTGGCTATTGTCCTGTTCCCATATTT
ACGTATCCCATTTTCTGCTCTGTAATTTTAAATAAACTCACCTGCCTAAGGTAAGACGAC
ATGTGTCACGTGAACATCGTTTGGGGGCAAGGGCGGAATCCCTTCGTTGAAAGTAAATGA
ATACTGTACATAGAGATGCGTATCTTGAACTCTTTATTAGCTTTGATATTGTGCTTAATA
TTACATGAATGTATTTCAATATGTAATTATGTGTTCAAATGAATGGTTGACTTGAATGGT
TTTATTGCTTTATATGCTACATCAACATGTGTGTTTCTTTTCATTTCAG

DOMAIN 1B

CACCTGTGCATCATCGCCACGATGACGATCTTATTGTTCGAAAAAATATAGATCATTTGA
CTCGTGAAGAGGAATACGAGCTAAGGATGGCTCTGGAGAGATTCCAGGCCGACACATCCG
TTGATGGGTACCAGGCTACAGTAGAGTACCATGGCCTTCCTGCTCGTTGTCCACGACCAG
ATGCAAAAGTCAGGTTCGCCTGTTGTATGCATGGCATGGCATCCTTCCCTCACTGGCACC
GGCTGTTCGTTACCCAGGTGGAAGATGCTCTTGTACGGCGTGGATCGCCTATCGGTGTTC
CTTATTGGGACTGGACAAAACCTATGACTCACCTTCCAGACTTGGCATCAAATGAGACGT
ACGTAGACCCGTATGGACATACACATCATAATCCATTCTTCAATGCAAATATATCTTTTG
AGGAGGGACACCATCACACGAGCAGGATGATAGATTCGAAACTGTTTGCCCCAGTCGCTT
TTGGGGAGCATTCCCATCTGTTTGATGGAATCCTGTACGCATTTGAGCAGGAAGATTTCT
GCGACTTTGAGATTCAGTTTGAGTTAGTCCATAATTCTATTCATGCGTGGATAGGCGGTT
CCGAAGATTACTCCATGGCCACCCTGCATTACACAGCCTTTGACCCCATTTTCTACCTTC
ATCATTCCAATGTCGATCGTCTATGGGCAATCTGGCAAGCTCTTCAAATCAGGAGACACA
AGCCATATCAAGCCCACTGTGCACAGTCTGTGGAACAGTTGCCAATGAAGCCATTTGCTT
TCCCATCACCTCTTAACAACAACGAGAAGACACATAGTCATTCAGTCCCGACTGACATTT
ATGACTACGAGGAAGTGCTGCACTACAGCTACGATGATCTAACGTTTGGTGGGATGAACC
TTGAAGAAATAGAAGAAGCTATACATCTCAGACAACAGCATGAACGAGTCTTCGCGGGAT
TTCTCCTTGCTGGAATAGGAACATCTGCACTTGTTGACATTTTCATAAATAAACCGGGGA
ACCAACCACTCAAAGCTGGAGATATTGCCATTCTTGGTGGTGCCAAGGAAATGCCTTGGG
CGTTTGACCGCTTGTATAAGGTCGAAATAACTGACTCATTGAAGACACTTTCTCTCGATG
TCGATGGAGATTATGAAGTCACTTTTAAAATTCATGATATGCACGGAAACGCTCTTGATA
CGGACCTGATTCCACACGCAGCAGTTGTTTCTGAGCCAGCTCACC

INTRON 1B/1C (SEQ ID NO:115)

GTAAGTAAATTTACAAAATTTGGTGTTCTCTAACTATCCTAAGTATTCAATCGTTAGCGT
GTACCTATCTGCATAATGCAATACCCTGACTCCATATAAGTATAGTATATTTACTCTGGT
CGAAAACAAACAAATTGAAAACAAGAGTGGACGTGCTGTTATGATTTCTTTTTCATTCTT
GGTTCGTTGTGTAATGCCACAGCCAGCAATTCCAGATATATAGCGACGGTCTATGAATAC
TCCAGTCTGGACCAGACAATCGTGTGGAATGGTTTAGGCACATTATATCAAATTCATTGT

Fig. 4g

TGAAGATATGAGTTATGAGGTCACAATGTTGTCTTGTTACCCCGTGTCAGTAGTGACGTC
ATTTCATGACTGAAATCTCTTCAACGCCGTTTAGCAATAATAGGCTCAGTAGTATTCAAC
CAATTACAATCAGTAGAAAATTCTCTATACTATTCTTATGTTGCATCCTGATATCCCTAT
GCAAAAATTAGTCATCTAATATAATCATTTTCGATAAATACTTTGGGCAAACAAATCAAT
GTAACATCTATTTTCTTTCAG

DOMAIN 1C

CTACCTTTGAGGATGAAAAGCACAGCTTACGAATCAGAAAAAATGTCGACAGCTTGACTC
CTGAAGAAACAAATGAACTGCGTAAAGCCCTGGAGCTTCTTGAAAATGATCATACTGCAG
GTGGATTCAATCAGCTTGGCGCCTTCCATGGAGAGCCTAAATGGTGCCCTAATCCTGAAG
CGGAGCACAAGGTTGCATGCTGTGTTCATGGCATGGCTGTTTTCCCTCATTGGCACAGGC
TTCTTGCTCTCCAGGCGGAGAATGCTCTTAGAAAGCATGGGTACAGTGGTGCTCTACCAT
ACTGGGATTGGACTCGCCCCCTTTCCCAACTTCCTGATCTGGTTAGTCATGAGCAGTATA
CAGATCCTTCCGACCATCACGTGAAGCATAACCCGTGGTTCAATGGCCACATCGATACAG
TAAATCAGGATACCACCAGAAGCGTACGGGAGGATCTTTATCAACAACCTGAATTTGGAC
ATTTCACGGATATTGCTCAACAAGTCCTCTTAGCATTAGAACAAGATGACTTCTGTTCGT
TTGAAGTGCAGTATGAGATTTCCCATAATTTTATCCATGCACTTGTAGGAGGAACCGACG
CTTATGGCATGGCATCGCTGAGATATACAGCATACGATCCAATCTTTTTCTTGCATCATT
CAAACACCGACAGGATCTGGGCTATTTGGCAATCCCTGCAAAAATACAGAGGCAAACCGT
ACAACACTGCCAACTGCGCCATAGAATCTATGAGAAGGCCCCTGCAACCATTTGGACTAA
GCAGTGCCATTAACCCTGACAGAATCACCAGAGAGCATGCTATCCCGTTTGATGTCTTCA
ACTATAGAGATAACCTTCATTACGTATATGATACCCTGGAATTTAATGGTTTGTCGATTT
CACAACTTGATAGAGAGCTGGAAAAAATCAAGAGTCACGAAAGAGTATTTGCTGGATTCT
TGCTGTCGGGGATTAAAAAATCTGCTCTTGTGAAATTCGAAGTTTGTACTCCACCTGATA
ATTGTCATAAAGCAGGGGAGTTTTATCTACTCGGGGACGAAAACGAGATGGCTTGGGCCT
ATGACCGACTTTTCAAGTATGATATTACTCAGGTTCTGGAAGCAAACCATCTACACTTCT
ATGATCATCTCTTCATTCGCTACGAAGTCTTTGATCTTAAAGGAGTGAGTTTGGGAACTG
ACCTGTTCCACACTGCAAATGTGGTACATGATTCCGGCACAG

INTRON 1C/1D (SEQ ID NO:116)

GTACGTGGATTTGATTACATAGCAATGCTATATGATTTCAGTAATTACAACCTCAAGTCA
TGTAGCCGTTTTAGATTGCATTACATCAAACAGCATTGGATTAAATTGGGGGATTGTCCA
GGCCGCATTATGTTGCATTCCGAAAATAGTTTGTGTCCAGTGTCCACGTTTAAAATTAAA
CCATTTTAATCATATTAGGGATAATTTTAATAGATGTTATAGTGCTTTATTTCATATTGT
TACAGTGGACAGTCACCAAGGACATATTTTACTCTATAGATACACAAACACCAATTAAAA
CCCTGCTTTGGAAAGTCTAACTTTTTCCCCACAG

DOMAIN 1D

GCACCCGTGATCGTGATAACTACGTTGAAGAAGTTACTGGGGCCAGTCATATCAGGAAGA
ATTTGAACGACCTCAATACCGGAGAAATGGAAAGCCTTAGAGCTGCTTTCCTGCATATTC
AGGACGACGGAACATATGAATCTATTGCCCAGTACCATGGCAAACCAGGCAAATGTCAAT
TGAATGATCATAATATTGCGTGTTGTGTCCATGGTATGCCTACCTTCCCCCAGTGGCACA
GACTGTATGTGGTTCAGGTGGAGAATGCTCTCCTAAACAGGGGATCTGGTGTGGCTGTTC
CTTACTGGGAGTGGACTGCTCCCATAGACCATCTACCTCATTTCATTGATGATGCAACAT
ACTTCAATTCCCGACAACAGCGGTACGACCCTAACCCTTTCTTCAGGGGAAAGGTTACTT
TTGAAAACGCAGTCACAACAAGGGACCCACAAGCCGGGCTCTTCAACTCAGATTATATGT
ATGAGAATGTTTTACTTGCACTGGAGCAGGAAAATTATTGTGACTTTGAAATTCAGTTTG
AGCTTGTTCATAACGCACTTCATTCCATGCTGGGAGGTAAAGGGCAGTACTCCATGTCCT

Fig. 4h

CCCTGGACTATTCTGCGTTTGATCCCGTCTTCTTCCTACATCATGCCAACACGGACAGAC
TGTGGGCAATCTGGCAGGAACTACAAAGATTCCGAGAACTGCCTTATGAAGAAGCGAACT
GTGCAATCAACCTCATGCATCAACCACTGAAGCCGTTCAGTGATCCACATGAGAATCACG
ACAATGTCACTTTGAAATACTCAAAACCACAGGACGGATTCGACTACCAGAACCACTTCG
GATACAAGTATGACAACCTTGAGTTCCATCACTTATCTATCCCAAGTCTTGATGCTACCC
TGAAGCAAAGGAGAAATCACGACAGAGTGTTTGCGGGCTTCCTTCTTCATAACATAGGAA
CTTCTGCTGACATAACTATCTACATATGTCTGCCTGACGGACGGCGTGGCAATGACTGCA
GTCATGAGGCGGGAACATTCTATATCCTCGGAGGCGAAACAGAGATGCCTTTTATCTTTG
ACCGTTTGTATAAATTTGAAATCACCAAACCACTGCAACAGTTAGGAGTCAAGCTGCATG
GTGGAGTTTTCGAACTGGAGCTTGAGATCAAGGCATACAACGGTTCCTATCTGGATCCCC
ATACCTTTGATCCAACTATCATCTTTGAACCTGGAACAG

INTRON 1D/1E (SEQ ID NO:117)

GTAATGCCATCTTAATACAGTTCGTTCGTTAAATTATATATGTTCGTTTACAACACCATA
CCTTGAATTGAGGTAATACATCACTTGATATTGATAATGTAATGGTAATTGTTCTTGTTT
GTAAAACCGTTTCTGGGGTGTTTATTCACTATCCACCTGGTGGATAGTGAGTAAACACAT
TCGGTTTAATATGGGTATCTAATGGACAGTGAAGTGTGCTGGCTAGGCAGATACCTTGGT
TTCTGTGAATGGAGGTAGTAGAAAGGGGTTTTGATGATTGCAG

DOMAIN 1E

ATACCCATATCTTGGACCACGACCATGAGGAAGAGATACTTGTCAGGAAGAATATAATTG
ATTTGAGCCCAAGGGAGAGGGTTTCTCTAGTCAAAGCTTTGCAAAGAATGAAGAATGATC
GCTCCGCTGATGGGTACCAAGCCATTGCCTCTTTCCATGCCCTGCCACCACTCTGTCCCA
ATCCATCTGCAGCTCACCGTTATGCTTGCTGTGTCCATGGCATGGCTACATTTCCCCAGT
GGCACAGACTGTACACTGTTCAGGTTCAGGATGCCCTGAGGAGACATGGTTCACTTGTTG
GTATTCCTTACTGGGACTGGACAAAACCAGTCAACGAGTTACCCGAGCTTCTTTCTTCAG
CAACATTTTATCATCCAATCCGGAATATTAATATTTCAAATCCATTCCTCGGGGCTGACA
TAGAATTTGAAGGACCGGGCGTTCATACAGAGAGGCACATAAATACTGAGCGCCTGTTTC
ACAGTGGGGATCATGACGGATACCACAACTGGTTCTTCGAAACTGTTCTCTTTGCTTTGG
AACAGGAAGATTACTGCGATTTTGAAATACAATTTGAGATAGCCCATAATGGCATCCACA
CATGGATTGGTGGAAGCGCAGTATATGGCATGGGACACCTTCACTATGCATCATATGATC
CAATTTTCTACATCCACCATTCACAGACGGACAGAATATGGGCTATTTGGCAAGAGCTGC
AGAAGTACAGGGGTCTATCTGGTTCGGAAGCAAACTGTGCCATTGAACATATGAGAACAC
CCTTGAAGCCTTTCAGCTTTGGGCCACCCTACAATTTGAATAGTCATACGCAAGAATATT
CAAAGCCTGAGGACACGTTTGACTATAAGAAGTTTGGATACAGATATGATAGTCTGGAAT
TGGAGGGGCGATCAATTTCTCGCATTGATGAACTTATCCAGCAGAGACAGGAGAAAGACA
GAACTTTTGCAGGGTTCCTCCTTAAAGGTTTTGGTACATCCGCATCTGTGTCATTGCAAG
TTTGCAGAGTTGATCACACCTGTAAAGATGCGGGCTATTTCACTATTCTGGGAGGATCAG
CCGAAATGCCATGGGCATTCGACAGGCTTTATAAGTATGACATTACTAAAACTCTTCACG
ACATGAACCTGAGGCACGAGGACACTTTCTCTATAGACGTAACTATCACGTCTTACAATG
GAACAGTACTCTCGGGAGACCTCATTCAGACGCCCTCCATTATATTTGTACCTGGACGCC

INTRON 1E/1F-1 (SEQ ID NO:118)

GTGAGTACCTGTTTGCACTAAGACTTCTGTAGGCTAAAAGTGTAAGAAATATCAATTAAT
TTCAATTCACCCAAACTTGAAAACGGTACCTATATAGGTTAACTTTTTGTCTACAGTAAA
CTGAACATACCTACACATTTCATGAAATGATCTCTCAATATTTTCCACCAACAG

Fig. 4i

DOMAIN 1F-1 (1st part of domain f)

ATAAACTCAACTCACGGAAACATACACCTAACAGAGTCCGCCATGAGCTAAGTAGCCTTA
GTTCCCGTGACATAGCAAGCTTGAAGGCAGCTTTGACAAGCCTTCAACATGATAATGGGA
CTGATGGTTATCAAGCTATTGCTGCCTTCCATGGCGTTCCTGCGCAGTGCCACGAGCCAT
CTGGACGTGAG

INTRON 1F-1/1F-2 (SEQ ID NO:119)

GTAAATTTACAGAGCTTTATGAAGTGTGTTCAGAGTGAAGAGACCAAGATATACTTATAC
CCAAAACTAGCTAGCAACAGACGATTTCACTTGTTTCGGACACTTTGTATTATACGTTGG
ATCCCAAGGTAAACGGAAACGTAACCGAGAATCAGTCCGTAAAGTGAGTGAGTGAGTTTG
GGGCTTAACGTCGCACTCAGCAATACCCCAGCTATGTGGCGACTCTCAGATTTACTGCTG
GAGGAGAACCTACATAGCCCGGTTTAACCCGTGTGGTATGTAGTAAGACCAGCGCGGCAT
GGCTGGTATCTGACGGACGAAGGGTGGCGCTGCACGTATTCCAGTGGTACAACACTGCAC
CCCAATTTCACCGACCGGAGAACTGATCTCCCCTTCGGAGATATCGCCTGCCTTCCACGG
GATTCGAACTCGGTGACCTTCAAGCCAGCGCGCTTCTAGCGGGGGCGATTAGAGGTTNAA
GGCCGACGGCTCTACCACCTTAACTATCCCCCGGCCCCACTCCTGACGGAAATGTTTATA
ATTCAGCCTTTGTTTTCTTATTAAACACTCTTGGCAGATTTTCTATAGATAATGGATTCA
CATGTAGACAGTCTCCCATTGTTGTAACTGGTAGTCAAGAGTTAGAATCTGAATACATTC
TCCAAGATGGATCAAGGAAAACAATAATTACTTGATGTTGCAG

DOMAIN 1F-2 (2nd part of domain f)

ATCGCCTGTTGCATCCACGGCATGGCGACGTTTCCTCACTGGCACCGGTTGTACACTCTG
CAGTTGGAGCAAGCGCTGCGCAGACACGGGTCCAGTGTTGCTGTTCCATACTGGGACTGG
ACCAAGCCAATCACCGAACTGCCACACATTCTGACAGACGGAGAATATTATGACGTTTGG
CAAAATGCCGTCTTGGCCAATCCGTTTGCAAGAGGTTATGTGAAAATTAAAGATGCATTT
ACGGTGAGAAATGTCCAGGAAAGTCTGTTCAAAATGTCAAGTTTTGGAAAGCACTCGCTT
CTGTTTGACCAGGCTTTGTTGGCTCTTGAACAAACTGACTACTGTGACTTCGAAGTTCAG
TTTGAAGTGATGCATAACACGATCCATTATCTCGTAGGAGGGCGTCAAACGTACGCCTTC
TCCTCTCTCGAGTATTCCTCATACGATCCAATCTTCTTTATTCACCACTCGTTTGTTGAC
AAAATATGGGCTGTATGGCAAGAACTGCAAAGCAGGAGACATCTACAGTTTAGAACAGCT
GATTGTGCTGTGGGCCTCATGGGTCAGGCAATGAGGCCTTTCAACAAGGATTTCAACCAC
AACTCGTTCACCAAGAAGCACGCAGTCCCTAATACAGTATTTGATTATGAAGATCTTGGC
TATAACTATGACAACCTTGAAATCAGTGGTTTAAACTTAAATGAGATCGAGGCGTTAATA
GCAAAACGCAAGTCACATGCTAGAGTCTTTGCTGGGTTCCTGTTGTTTGGATTAGGAACT
TCGGCTGATATACATCTGGAAATTTGCAAGACATCGGAAAACTGCCATGATGCTGGTGTG
ATTTTCATCCTTGGAGGTTCTGCAGAGATGCATTGGGCATACAACCGCCTCTACAAGTAT
GACATTACAGAAGCATTGCAGGAATTTGACATCAACCCTGAAGATGTTTTCCATGCTGAT
GAACCATTTTTCCTGAGGCTGTCGGTTGTTGCTGTGAATGGAACTGTCATTCCATCGTCT
CATCTTCACCAGCCAACGATAATCTATGAACCAGGCGAAG

INTRON 1F-2/1G-1 (SEQ ID NO:120)

GTGAGATATATGCAAATTGAATGTTGTCCAGATGCGTTGTTTACATTTATATGCTTGGAA
TTGTCCTGAACGAATACAGTGGAATAACCAAAAGCTGAAAAATAAAAAGATATATACTTC
ATTCTGAATTTGTCAGTATTGCTGACCCAAAAACACGTTATCCATGTCGACACTATATTT
GCCTTTCTGAATCTGAGACTGCGTTATGTTTCTAATAATCACGAAATATGGTATACAGGT
TGTGTATCTGTAGAATACCCAAGGCAGAATTTAAAGGGTCACACCCTGTTTAATACAG

Fig. 4j

DOMAIN 1G-1 (1st part of domain g)

ATCACCATGACGACCATCAGTCGGGAAGCATAGCAGGATCCGGGGTCCGCAAGGACGTGA
ACACCTTGACTAAGGCTGAGACCGACAACCTGAGGGAGGCGCTGTGGGGTGTCATGGCAG
ACCACGGTCCCAATGGCTTTCAAGCTATTGCTGCTTTCCATGGAAAACCAGCTTTGTGTC
CCATGCCTGATGGCCACAACTACTCATGTTGTACTCACG

INTRON 1G-1/1G-2 (SEQ ID NO:121)

GTAAGTTTGTGTTGGTTAGTGTTGGTTGCATGTTTTGCCATATCGATAGTATCAGTGTGG
TAACATCTGGTTTCTAGTTCATTCAGTTCACCTTATCAGAAGCTGTTTGCTCTCGTCTAC
AATAGTGACGTCTTTCAGTTTTAGAACCGTGTACATCCGGGTTATATTGGTCTCCAGCAA
CCCGTGCTTGTCGTGGGAGGCCACTGATGGGAACGGGTGGTCAGACTCGCTCACTTAGTT
GACACATGTCAATTGCGAAGATCGATGCTGAGGTTGTTAAACATTGGATTGTCTGGTCCA
GACTCGATTATTTACAGACAGCCGCCATGTACCTGGAATATTGCTGAGTGCGGCGTTAAA
CAACAAACTAGTCAGACTAATCTTTCACTGTTTATAATGATGGCTCGAACCTAGCACTCA
TGTCCCAAGTTGGCGAACATCTGGAAGGGAATTTCAAATGAAAAGAACAATCTTTCACGT
CTATTGGTATCACGCTCCTGGAGAAGAACATGATGTTCACGGCGTTACTTCCTCTTACCT
GTTTTACTTGTTCCCACGTTTCTTCATATTTAAAGAGTATTTGGGTATTAGAGCTTTGGT
GCTGTTACAATGCTACTCAACTGTTCAGTGCGGGCGACCGCGCTTGTTTACACATTAAGT
TTTGTTTGTTGGTTGGTTTGTGTGTGTGTGTGTATGTGTGTGTGTGTGTGTGTGTGTGTA
TGTGTGTGTGTGTGTATCTATGTCTATGTGTCTGTGTCTGTGTGTCTGTCTATGTGTGTG
TGTGTCTGTGTCTATGTGTGTGTCTGCGTGTGTGTCTGTGTCCGTATGTGGCTGTGTCTA
TGTGTGTGTGTGTCTGTGTTTATGTGTGTATATGCGTGTGTGTCTGTGTCCGTATGTGGC
TGTGTCTATGTGTGTGACATGCAATACATGCTGTGATACTCACTAGCTGCGTCTATCGAC
CAG

DOMAIN 1G-2 (2nd part of domain g)

GCATGGCTACCTTCCCACACTGGCATCGCCTCTACACCAAGCAGATGGAGGATGCAATGA
GGGCGCATGGGTCTCATGTCGGCCTGCCCTACTGGGACTGGACTGCTGCCTTCACCCACC
TGCCAACACTGGTCACCGACACGGACAACAACCCCTTCCAACAT

INTRON 1G-2/1G-3 (SEQ ID NO:122)

GTAAGAGCGGGGTAGGGATGGGGTGGTAGGGGGTGGGTTGTTCTATTACTTCCCGCTTCA
CTTGTATGAAATGGATAACCTTGGCTGCATCCCAATTGCGTGATCGATTCTCTTTCGATT
CACTCGTGCGATTAGACTGCCTTATTTACTATAGTAGTTAGAATGTTGCTCAGTGCGCCG
TTAAACAACTAATACACAAAACCGCATTTGTTTTATATGGTCACTCTACTGTTTATCACG
TATATGTATGTTCCGACTCACTGGTTGGTGCGTACCATTCTACTGTCACACTGAGAGCCA
ATGTTCTCAGATGTGTGAAATGTTTGAAAGCCGTTTCTACATAATATTGCAGGAATACCA
TTGTAGAATGTAGTCAAACAGGTAACAATCTGTTAGTGAGCCCAGTTCGAGGTTGCGTTG
TAGGGTGTAGTCCAACAGGTAGGCAGTCCATAAGCATAGTTTTTAAGCATTTTAGATCAT
CTATAATTAACCACATGGTTAGCCGCTATGTTTAGTTTAATCCAGTATAAGTTAGAACTG
TTATATTTCGAAGGGAAGTGAGTAAATCCTTATTCCTTGACTACCATTTAATAGATTTCC
CAATGACTCCATTCAACTCCTAACTTTCACATCACTGCTCTCTTCAACAG

DOMAIN 1G-3 (3rd part of domain g)

GGACACATTGATTATCTCAATGTCAGCACAACTCGATCTCCCCGAGACATGCTGTTCAAC
GACCCCGAGCATGGATCAGAGTCGTTCTTCTACAGACAAGTCCTCTTAGCTCTGGAACAA

Fig. 4k

ACTGATTTCTGCAAATTCGAAGTTCAGTTTGAGATAACCCACAATGCCATCCATTCCTGG
ACAGGTGGCCACAGCCCCTACGGAATGTCCACTCTCGACTTCACTGCCTACGATCCTCTC
TTCTGGCTTCACCACTCCAACACCGACAGAATCTGGGCTGTCTGGCAAGCTTTGCAAGAA
TACAGAGGACTTCCATACAACCATGCCAATTGTGAGATCCAGGCAATGAAAACGCCCCTG
AGGCCTTTCAGTGACGATATCAACCACAACCCAGTCACAAAGGCTAACGCGAAGCCATTA
GATGTGTTCGAGTATAATCGGTTGAGCTTCCAGTACGACAACCTCATCTTCCATGGATAC
AGTATTCCGGAACTTGATCGCGTGCTTGAAGAAAGAAAGGAGGAGGACAGAATATTTGCT
GCCTTCCTTCTCAGTGGAATCAAGCGTAGTGCTGATGTAGTGTTCGACATATGCCAGCCA
GAACACGAATGTGTGTTCGCAGGGACTTTTGCGATTTTGGGAGGGGAGCTAGAAATGCCC
TGGTCCTTCGACAGACTGTTCCGCTATGATATCACCAAGGTGATGAAGCAGCTACACCTG
AGGCATGACTCTGACTTTACCTTCAGGGTGAAGATTGTCGGCACCGACGACCACGAGCTT
CCTTCAGACAGTGTCAAAGCACCAACTATTGAATTTGAACCGGGCG

INTRON 1G-3/1H (SEQ ID NO:123)

GTGAGTACGACAGGCATTTCTAGTAAAAACCTACTTTTGGTAAAAGGTTCGAGAAATCAC
TTGAAGCAACAACATGATTTTGTAACGCCTATTACACGTGAACATGTCACACCCGGTGAT
GCCGTTTAATGGACATGCCTCTGTTAATGAAAGGGGTAAGTACATGTGTATGGGGATGGG
ATGGGAGCCACCTGTCCCAATTTCATAGGTCCCTAGGATCCCAGTTGCGTAGGAATCCCC
TGATTAATGCCTTGTGAATTCCTCCTGGAATTGTCCTGGCCCAAATTTTTACAAACCCGC
CCCGATATACCTTGGAAATAATTGGGCCTAAGGGTGGGGCTTTTAAGGACCAAGAACCCA
ACCTAAACCCCAACCCATTTTTTCCCACCCATTCCAGGTTTTGTTTTACCAAATAAAAAG
GTTTCCACTTTGAGGAAACCCCTTTAAGGGTTCTTTTCAGGGCTTTTTTTCTTTTCTGGGA
ATTCCAATTCCGGGGGAACAAAATACATATATTTCACAGACCTTTGGTCAAATTTATATA
ATTTCCGACTTCATGTCATAGGTTTGTCTTTCTTCCTACACAG

DOMAIN 1H

TGCACAGAGGCGGAAACCACGAAGATGAACACCATGATGACAGACTCGCAGATGTCCTGA
TCAGGAAAGAAGTTGACTTCCTCTCCCTGCAAGAGGCCAACGCAATTAAGGATGCACTGT
ACAAGCTCCAGAATGACGACAGTAAAGGGGGCTTTGAGGCCATAGCTGGCTATCACGGGT
ATCCTAATATGTGTCCAGAAAGAGGTACCGACAAGTATCCCTGCTGTGTCCACGGAATGC
CCGTGTTCCCCCACTGGCACCGCCTGCATACCATTCAGATGGAGAGAGCTCTGAAAAACC
ATGGCTCTCCAATGGGCATTCCTTACTGGGATTGGACAAAGAAGATGTCGAGTCTTCCAT
CTTTCTTTGGAGATTCCAGCAACAACAACCCTTTCTACAAATATTACATCCGGGGCGTGC
AGCACGAAACAACCAGGGACATTAATCAGAGACTCTTTAATCAAACCAAGTTTGGTGAAT
TTGATTACCTATATTACCTAACTCTGCAAGTCCTGGAGGAAAACTCGTACTGTGACTTTG
AAGTTCAGTATGAGATCCTCCATAACGCCGTCCACTCCTGGCTTGGAGGAACTGGAAAGT
ATTCCATGTCTACCCTGGAGCATTCGGCCTTTGACCCTGTCTTCATGATTCACCACTCGA
GTTTGGATAGAATCTGGATCCTTTGGCAGAAGTTGCAAAAGATAAGAATGAAGCCTTACT
ACGCATTGGATTGTGCTGGCGACAGACTTATGAAAGACCCCCTGCATCCCTTCAACTACG
AAACCGTTAATGAAGATGAATTCACCCGCATCAACTCTTTCCCAAGCATACTGTTTGACC
ACTACAGGTTCAACTATGAATACGATAACATGAGAATCAGGGGTCAGGACATACATGAAC
TTGAAGAGGTAATTCAGGAATTAAGAAACAAAGATCGCATATTTGCTGGTTTTGTTTTGT
CGGGCTTACGGATATCAGCTACAGTGAAAGTATTCATTCATTCGAAAAACGATACAAGTC
ACGAAGAATATGCAGGAGAATTTGCAGTTTTGGGAGGTGAGAAGGAGATGCCGTGGGCAT
ATGAAAGAATGCTGAAATTGGACATCTCCGATGCTGTACACAAGCTTCACGTGAAAGATG
AAGACATCCGTTTTAGAGTGGTTGTTACTGCCTACAACGGTGACGTTGTTACCACCAGGC
TGTCTCAGCCATTCATCGTCCACCGTCCAGCCCATGTGGCTCACGACATCTTGGTAATCC
CAGTAGGTGCGGGCCATGACCTTCCGCCTAAAGTCGTAGTAAAGAGCGGCACCAAAGTCG

Fig. 4I

AGTTTACACCAATAGATTCGTCGGTGAACAAAGCAATGGTGGAGCTGGGCAGCTATACTG
CTATGGCTAAATGCATCGTTCCCCCTTTCTCTTACCACGGCTTTGAACTGGACAAAGTCT
ACAGCGTCGATCACGGAGACTACTACATTGCTGCAGGTACCCACGCGTTGTGTGAGCAGA
ACCTCAGGCTCCACATCCACGTGGAACACGAGTAG

3´UTR

TTCACAG

INTRON 3´UTR (SEQ ID NO:124)

GTGAGGAGAAGGCCCCAGGCTAGCAGGGCAATGGATGAAGGAAATAGGGGCAAAGGGAAT
AGCAGTTACACCATCGACATTTCCAACCTCCTCAGAAACTAATATATAGCCTTAATACAA
CCAGCCAAGACTCAACGGGCAGCCGGGGTGGGGGGATTTGGTGGTCGCTGTTTCAGACCA
GGGTGCAAAATATCAGTGCGCAAATCAACATGTTGCGTGTCAGACACTGACACAGCAGTC
ATTGAACCTGCAGACCCATAACAGGAAAATGGGGCAGATACGATCAAAGACAGTGTAAAA
TAGGGATAAGTAGGCATATGCAACCACCTGATGGAAATGAAAAGGGGTAAGTTTAAACCC
CGGCTACCAAAGGTCCAATGGTTCCTTAACCCAGCTTACGCTATCCCTCTAATTTCAGTA
TTGAGCTGATTTCTGTCGAGTTCATGTAAACTGTATACTTTCTGTATTATTACAG

3´UTR

GTTGCTATGCCGACTGCGCTATATTGGTGAACGAGACGATGAGGACATCTCTGAAAGAGT
TCGCCAAGTGATGTGTAGGTCACGGAAGTATTGTTGAGCTAACAATATGATGATTTCAAA
ATGACTTGGCGCTCTAGGACAAAGACATAATTCATCAGCACCCTGTGCACCAACTCTTTG
TTTGCTGCAAACGTCTGACAAGCGACACGTCAATCAACAAGCTGTTCAAACTCAAGTGGA
TGTAACTAGAATCGTTGGGCCATCGTTCACAAAGTATTGACAGATGTCACACATGATGGC
GAGAAACACTTTAGAACTTTTAATGACCTAGAGTGACTTGTAAATATGTAAATATATTCT
TCAAAGACTCAGCTGAACTATTGTTGGATAACACATCAATTCCCTCAACAAAATGCTTTA
TCTTCACATGGATGTATGTAATGTGGCCGGCAATAAAGTATATATATGTAT

Fig. 5a

Primary structure of the HtH1 protein

SIGNAL PEPTIDE

LVQFLLVALVVGAGA

DOMAIN A

DNVVRKDVSHLTVDEVQALHGALHDVTASTGPLSFEDITSYHAAPASCDYKGRKIACCVHGMPSFP
FWHRAYVVQAERALLSKRKTVGMPYWDWTQTLTHLPSLVTEPIYIDSKGGKAQTNYWYRGEIAFIN
KKTARAVDDRLFEKVEPGHYTHLMETVLDALEQDEFCKFEIQFELAHNAIHYLVGGKFEYSMSNLE
YTSYDPIFFLHHSNVDRLFAIWQRLQELRGKNPNAMDCAHELAHQQLQPFNRDSNPVQLTKDHSTP
ADLFDYKQLGYSYDSLNLNGMTPEQLKTELDERHSKERAFASFRLSGFGGSANVVVYACVPDDDPR
SDDYCEKAGDFFILGGQSEMPWRFYRPFFYDVTEAVHHLGVPLSGHYYVKTELFSVNGTALSPDLL
PQPTVAYRPGK

DOMAIN B

GHLDPPVHHRHDDDLIVRKNIDHLTREEEYELRMALERFQADTSVDGYQATVEYHGLPARCPRPDA
KVRFACCMHGMASFPHWHRLFVTQVEDALVRRGSPIGVPYWDWTKPMTHLPDLASNETYVDPYGHT
HHNPFFNANISFEEGHHHTSRMIDSKLFAPVAFGEHSHLFDGILYAFEQEDFCDFEIQFELVHNSI
HAWIGGSEDYSMATLHYTAFDPIFYLHHSNVDRLWAIWQALQIRRHKPYQAHCAQSVEQLPMKPFA
FPSPLNNNEKTHSHSVPTDIYDYEEVLHYSYDDLTFGGMNLEEIEEAIHLRQQHERVFAGFLLAGI
GTSALVDIFINKPGNQPLKAGDIAILGGAKEMPWAFDRLYKVEITDSLKTLSLDVDGDYEVTFKIH
DMHGNALDTDLIPHAAVVSEPAH

DOMAIN C

PTFEDEKHSLRIRKNVDSLTPEETNELRKALELLENDHTAGGFNQLGAFHGEPKWCPNPEAEHKVA
CCVHGMAVFPHWHRLLALQAENALRKHGYSGALPYWDWTRPLSQLPDLVSHEQYTDPSDHHVKHNP
WFNGHIDTVNQDTTRSVREDLYQQPEFGHFTDIAQQVLLALEQDDFCSFEVQYEISHNFIHALVGG
TDAYGMASLRYTAYDPIFFLHHSNTDRIWAIWQSLQKYRGKPYNTANCAIESMRRPLQPFGLSSAI
NPDRITREHAIPFDVFNYRDNLHYVYDTLEFNGLSISQLDRELEKIKSHERVFAGFLLSGIKKSAL
VKFEVCTPPDNCHKAGEFYLLGDENEMAWAYDRLFKYDITQVLEANHLHFYDHLFIRYEVFDLKGV
SLGTDLFHTANVVHDSGT

DOMAIN D

GTRDRDNYVEEVTGASHIRKNLNDLNTGEMESLRAAFLHIQDDGTYESIAQYHGKPGKCQLNDHNI
ACCVHGMPTFPQWHRLYVVQVENALLNRGSGVAVPYWEWTAPIDHLPHFIDDATYFNSRQQRYDPN
PFFRGKVTFENAVTTRDPQAGLFNSDYMYENVLLALEQENYCDFEIQFELVHNALHSMLGGKGQYS
MSSLDYSAFDPVFFLHHANTDRLWAIWQELQRFRELPYEEANCAINLMHQPLKPFSDPHENHDNVT
LKYSKPQDGFDYQNHFGYKYDNLEFHHLSIPSLDATLKQRRNHDRVFAGFLLHNIGTSADITIYIC
LPDGRRGNDCSHEAGTFYILGGETEMPFIFDRLYKFEITKPLQQLGVKLHGGVFELELEIKAYNGS
YLDPHTFDPTIIFEPGT

DOMAIN E

DTHILDHDHEEEILVRKNIIDLSPRERVSLVKALQRMKNDRSADGYQAIASFHALPPLCPNPSAAH
RYACCVHGMATFPQWHRLYTVQVQDALRRHGSLVGIPYWDWTKPVNELPELLSSATFYHPIRNINI
SNPFLGADIEFEGPGVHTERHINTERLFHSGDHDGYHNWFFETVLFALEQEDYCDFEIQFEIAHNG

Fig. 5b

IHTWIGGSAVYGMGHLHYASYDPIFYIHHSQTDRIWAIWQELQKYRGLSGSEANCAIEHMRTPLKP
FSFGPPYNLNSHTQEYSKPEDTFDYKKFGYRYDSLELEGRSISRIDELIQQRQEKDRTFAGFLLKG
FGTSASVSLQVCRVDHTCKDAGYFTILGGSAEMPWAFDRLYKYDITKTLHDMNLRHEDTFSIDVTI
TSYNGTVLSGDLIQTPSIIFVPGR

DOMAIN F

HKLNSRKHTPNRVRHELSSLSSRDIASLKAALTSLQHDNGTDGYQAIAAFHGVPAQCHEPSGREIA
CCIHGMATFPHWHRLYTLQLEQALRRHGSSVAVPYWDWTKPITELPHILTDGEYYDVWQNAVLANP
FARGYVKIKDAFTVRNVQESLFKMSSFGKHSLLFDQALLALEQTDYCDFEVQFEVMHNTIHYLVGG
RQTYAFSSLEYSSYDPIFFIHHSFVDKIWAVWQELQSRRHLQFRTADCAVGLMGQAMRPFNKDFNH
NSFTKKHAVPNTVFDYEDLGYNYDNLEISGLNLNEIEALIAKRKSHARVFAGFLLFGLGTSADIHL
EICKTSENCHDAGVIFILGGSAEMHWAYNRLYKYDITEALQEFDINPEDVFHADEPFFLRLSVVAV
NGTVIPSSHLHQPTIIYEPGE

DOMAIN G

DHHDDHQSGSIAGSGVRKDVNTLTKAETDNLREALWGVMADHGPNGFQAIAAFHGKPALCPMPDGH
NYSCCTHGMATFPHWHRLYTKQMEDAMRAHGSHVGLPYWDWTAAFTHLPTLVTDTDNNPFQHGHID
YLNVSTTRSPRDMLFNDPEHGSESFFYRQVLLALEQTDFCKFEVQFEITHNAIHSWTGGHSPYGMS
TLDFTAYDPLFWLHHSNTDRIWAVWQALQEYRGLPYNHANCEIQAMKTPLRPFSDDINHNPVTKAN
AKPLDVFEYNRLSFQYDNLIFHGYSIPELDRVLEERKEEDRIFAAFLLSGIKRSADVVFDICQPEH
ECVFAGTFAILGGELEMPWSFDRLFRYDITKVMKQLHLRHDSDFTFRVKIVGTDDHELPSDSVKAP
TIEFEPG

DOMAIN H

VHRGGNHEDEHHDDRLADVLIRKEVDFLSLQEANAIKDALYKLQNDDSKGGFEAIAGYHGYPNMCP
ERGTDKYPCCVHGMPVFPHWHRLHTIQMERALKNHGSPMGIPYWDWTKKMSSLPSFFGDSSNNNPF
YKYYIRGVQHETTRDINQRLFNQTKFGEFDYLYYLTLQVLEENSYCDFEVQYEILHNAVHSWLGGT
GKYSMSTLEHSAFDPVFMIHHSSLDRIWILWQKLQKIRMKPYYALDCAGDRLMKDPLHPFNYETVN
EDEFTRINSFPSILFDHYRFNYEYDNMRIRGQDIHELEEVIQELRNKDRIFAGFVLSGLRISATVK
VFIHSKNDTSHEEYAGEFAVLGGEKEMPWAYERMLKLDISDAVHKLHVKDEDIRFRVVVTAYNGDV
VTTRLSQPFIVHRPAHVAHDILVIPVGAGHDLPPKVVVKSGTKVEFTPIDSSVNKAMVELGSYTAM
AKCIVPPFSYHGFELDKVYSVDHGDYYIAAGTHALCEQNLRLHIHVEHE

Fig. 6a

Genomic sequence of the HtH2 gene

DOMAIN 2A-1 (1st part of domain a)
[domain a, parts 1-4: SEQ ID NO:156]

GGTCTTCCGTACTGGGACTGGACGCAGCATCTGACTCAACTCCCAGATCTGGTGTCAGACCCCTTG
TTTGTCGACCCGGAAGGAGGAAAG

INTRON 2A-1/2A-2 (SEQ ID NO:125)

GTAAGGGATCTCAGATCCGTCAGAGTGAGTGAGTGAGTGAGTGAGTGCCCAGCAACTGAAGCTAGG
CCGCCCTACTGGGGATCACAGGGAATGTATGTCAATGGTTGAAGAAAGGAGCAGTGGGTTACAACG
CCGCGTTCAAAGTCATGGCAGTTTCATAGCGCATTGTGCGCGCGTGTGTATCTGTGTGCGCGCGTG
TGTGCTTGCGTGCGTGTGAGTGAGTCCGCTTGTGCATTTGTACTAGCACAGACTAATGCTGGTTCT
AGAGAGCCTACTGATAAATGTTTACATTAAGATCTTTACAGTATACTGAGATTCGAGCCCAGACCA
GCGGAACACCAGGCAGGGTAACAACAAATAACGCCTTTCCACACAACCGACGCAGCCTAAAGTGGC
TCTGATAGGCTGATACCGGTGTATTCTTAGAACTTGTAATTTGTGCTTTGCCATAATACATGTACT
TCAGTTAACTGTAATACAGCATAAGACTGGACCGGTGTTTACGACGCAATGAGCAATAATTACTCT
ACGAAAAGATTTGGTTAGACATATTCAATAATTGTAACATTCATTAACAATGAACACCACGTGCAC
TCTCGTTTGTGTCAACGTATTCATAATCATTCTCATGCATCTGTTAGCTCAGATATTTTGATGTTT
CAAGAGATTTGTACGAACGTATGGGCTGGTGCCCCATGAAATTACATACAATGAATTCAGGTGAAA
TACCTGGCGAGACAATAAGATCTTACTAGTGCTGCCACTTCAGTATGGTGTCCCCGATGGTGTCTG
GTGTATGGGTGTGTTTGGCGTCAGTTGTTACTGGAAAAGTCAGCTCTAATTATGTCTTTATGTGGT
TAAAGACCCCATAACCTAGATGTCTGGGTTTAACTTAACATGATAGTAACAGTCGGCTGTATAGCC
TGACGCTTAAACGTTAGATGAATAAGGACTATATTGTGTTGTATAACATTTCTATAACCTCCTTTC
TATATCATTTAG

DOMAIN 2A-2 (2nd part of domain a)

GCCCATGACAACGCATGGTATCGTGGAAACATCAAGTTTGAGAATAAGAAGACTGCAAGAGCTGTT
GACGATCGCCTTTTCGAGAAGGTTGGACCAGGAGAGAATACCCGACTCTTTGAAGGAATTCTCGAT
GCTCTTGAACAGGATGAATTCTGCAACTTCGAGATCCAGTTTGAGTTGGCTCACAACGCTATCCAC
TACCTGGTTGGCGGCCGTCACAC

INTRON 2A-2/2A-3 (SEQ ID NO:126)

GTGAGTCACGTTCTCTGATGGTCACGAGTCACGTTCTCTGATGGTCACGAGTCACGTTCTCTGATG
GTCACGAGTCACGTTCTCTGATGGTCACGAGTCACATTCTCTGATGGTCACGAGTCACATTCTCTG
TTGAGTGAAGTCTCAGTACCATTTATTTCTCTTACCTTCTTCTAACCAGGGGTTTCAGCGTGGATC
GTCTGAGAAGTTAGCGCAAATCTATATTGAAGTCATTTTTCTATCATATAACCATCGTTATATCCA
CGTGCGAAAGTGTTCATTAATTATTTTTATTTTCATTTATGAAGGTCTAAAAGAAAATATGTATTG
TTGGAAACTATATTCGAAGGTGAAGGCAACACGAGTGTATTAATATTCTCAATATCAATGTACGCT
CTGTCAGCACCTGTTTCACCAGGAACTACACCTTTAGCGTACCAAAATATCAGCTGATGATTTCGA
AGCGGACTATACCCTCACCACTTGTTTTGTGTGTGTATTTATGTGTGCATGTGTGTGCGTGCGTGC
GTGTGTGTGTGTGTCCTACGTATGTTGATATTTTGTTCTGACTGTATATGTTCGTGCTTACCATTG
AAG

Fig. 6b

DOMAIN 2A-3 (3rd part of domain a)

GTACTCCATGTCTCATCTCGAGTACACCTCCTACGACCCCCTCTTCTTCCTCCATCACTCCAACAC
CGACCGCATCTTCGCCATCTGGCAACGTCTTCAGGTACTCAGAGGAAAGGACCCCAACACCGCCGA
CTGCGCACACAACCTCATCCATGAGCCCATGGAACCGTTCCGTCGGGACTCGAACCCTCTTGACCT
CACCAGGGAAAACTCCAAACCAATTGACAGCTTTGATTATGCCCACCTTGGCTACCA

INTRON 2A-3/2A-4 (SEQ ID NO:127)

GTATGTATGATTCTAATAATGAATGTTTTTACCTCCGGTTTAAACAATATTTTAGTATTACGAAAG
GAGAAGTACCTCGAGAGGTCTAGGTCTCAGATGTTTAGAAACCCATGAAGACAGGTATGCTTCTGA
AAAACAAAGTAACATCATGAGGCTAAAGTTCAGATTCAAACCATCGTAGTTCGAATCCAGCATGCA
AAGGGCCCTAACCCTGTAGATGGCGCTGCTTGAAACAGAGTAGTCTGTTCAGGGTCAGTACTGTCC
CCACAAACATCATAGTCAGGGTCAGTACTGTCCCCACAAACATCATAGTCAGGGTCAGTACTGTCC
CCACAAACATCACAGTCAGGGTTAATTTTGGATTCGGTTTCGAATGCGAAGAAGACAGTCACGCCC
TGACACTGGACCGAGGTTGCCGAGAAAGCTCGTGATATTGCTGGAATACTGCCCAGTAAAACCATC
ATTTATTTTAGGCTATTTATTACGAAAAATAATAATATGTATAGAAATGCATATGATCGCTGTTTG
AATGTAAAATTTAGAATGGGTTTGGGAGTGTTCACTATTTTTTCATCAAAATTTCATGTATTTTAA
CCGATCGACGCTGAAGACAAACTACCGTTAATCAGGCAGTTCATTCATATCTGATAGGGAATATTG
GTTGTTAACCAACGCTACATTGTGTCCAG

DOMAIN 2A-4 (4th part of domain a)

GTATGATGACTTGACCCTGAACGGTATGACCCCAGAGGAATTGAACTCATATCTGCATGAACGGTC
AGGCAAGGAGGGGGTGTTCGCAAGCTTCCGACTCTCAGGTTTTGGCGGCTCTGCTAACGTTGTTGT
CTACGCATGCCGTCCTGCCCACGATGAAATGGCTGTCGATCAGTGCGACAAAGCCGGCGACTTCTT
TGTGTTGGGCGGACCCACCGAGATGCCCTGGAGGTTTTACAGAGCATTCCACTTCGACGTCACCGA
CAGCATCGACAACATCGACAAGGACCGCCACGGCCACTATTATGTAAAGGCGGAATTATTCAGTGT
AAATGGAAGTGCGCTACCGAATGATCTCCTGCCTCAACCCACCATCTCACACAGGCCAGCCCGCGG
ACACGTTGATG

INTRON 2A-4/2B (SEQ ID NO:128)

GTAAATGGCCATTGTATACATGCATTCATTTGGACTTTGAGTGAGTGAGTGGATGCGTATTCAGTA
AGTGAGAGTGTGAGTGGGTATTAGGTCTGTGAGTGGGTTGGTGAGTGGATGGGTGAGTAAGAGTGG
GTTGGTGAGAAAGTGAGTGAGTCACTTGGTGGGTGCGTTAGTGGAAGCGTGATTGAGTGGATGGGA
GGTAGGTGAGTGAGTGAATTGGTGGGGGGGTGAGTGAGGTTAACGCTGTTCTGCTGTTCAATCACA
CCACATGTTGCCAGCTTACTGTGCAGGACGAATCCAGGGTTGTGTTAAATTTTATATGTTTATATA
TAACGATGGACGTGTCTGGATGTGGCGAATGTGTCAAGAGAATTATGCGGCTTTGTGCTGCTCCGC
GTATTTATTGCACGCGCGTTGGTACGCGGTTGATAAAGTAGTTCAAAACATTTCCCAGCCATCTTT
GTCTGTTGTGAAAACCTACTCCAGGACCATCCATTTCAATATGTGTCTGCGTTCATGGAGTTATAC
ATGTTAAACTGTAGAGCGCAGATGAGCACACTTGAGCATTTCTTCAGTAAATCAGAATGTGTATAT
TTCAAAATTTACCAAATGCAATATCATCAAGCAAATTATGCAGCTCTATAGTAACATCGGAGTCAA
TGGTCCAGTGTGCCCTCGGCTGCCATTCCGACCTCCCTGGCCAGAATACACCCCGGTCAGGATCAG
TTATCCGTCAGAAGGCACGGTGCGGAATGAAAACATAAACACATAGTCGCTTAGTAGTATGCTGAT
TTAGGCACGCAAAATCCGAATGTGAATTACTGTGAATTGCATTACCTGTTACAG

Fig. 6c

DOMAIN 2B

AGGCCCCAGCTCCCTCCTCGGATGCTCACCTCGCCGTCAGGAAGGATATCAACCATCTGACACGCG
AGGAGGTGTACGAGCTGCGCAGAGCTATGGAGAGATTCCAGGCCGACACATCCGTTGATGGGTACC
AGGCTACGGTTGAGTATCACGGCTTACCTGCTCGATGTCCATTCCCCGAGGCCACAAATAGGTTCG
CCTGTTGCATCCACGGCATGGCGACATTCCCTCATTGGCACAGACTGTTCGTTACCCAGGTGGAAG
ATGCACTGATCAGGCGAGGATCCCCTATAGGGGTCCCCTACTGGGACTGGACTCAGCCTATGGCAC
ATCTCCCAGGACTTGCAGACAACGCCACCTATAGAGATCCCATCAGCGGAGACAGCAGACACAACC
CGTTCCACGATGTTGAAGTTGCCTTTGAAAATGGGCGTACAGAACGTCACCCAGATAGTAGATTGT
TTGAACAACCTCTATTTGGCAAACATACGCGTCTCTTCGACAGTATAGTCTATGCTTTTGAGCAGG
AGGACTTCTGCGATTTTGAAGTTCAATTTGAGATGACCCATAATAATATTCACGCCTGGATTGGTG
GCGGCGGGAAGTATTCCATGTCTTCTCTACACTACACAGCCTTCGACCCTATCTCCTACCTTCATC
ACTCCAACACTGACCGTCTCTGGGCAATTTGGCAAGCGTTGCAGATACGAAGAAACAAACCGTATA
AGGCTCATTGTGCTTGGTCTGAGGAACGCCAGCCTCTCAAACCTTTCGCCTTCAGTTCCCCACTGA
ACAACAACGAAAAAACCTACGAAAACTCGGTGCCCACCAACGTTTACGACTACGAAGGAGTCCTTG
GCTATACTTATGATGACCTCAACTTCGGGGGCATGGACCTGGGTCAGCTTGAGGAATACATCCAGA
GGCAGAGACAGAGAGACAGGACCTTTGCTGGCTTCTTTCTGTCACATATTGGTACATCAGCGAATG
TTGAAATCATTATAGACCATGGGACTCTTCATACCTCCGTGGGCACGTTTGCTGTTCTTGGCGGAG
AGAAGGAGATGAAATGGGGATTTGACCGTTTGTACAAATATGAGATTACAGATGAACTGAGGCAAC
TTAATCTCCGTGCTGATGATGGTTTCAGCATCTCTGTTAAAGTAACTGATGTTGATGGCAGTGAGC
TGTCCTCTGAACTCATCCCATCTGCTGCTATCATCTTCGAACGAAGCCATA

INTRON 2B/2C (SEQ ID NO:129)

GTAAGTAGCTACCTGTTTATTCAATTTTTTCGCTTTGCCAATCAATTCATTCAGCTTGAAATTCAA
TAATTGTGTTTTGCATGGCTGAAAACCAATTTGAACTCTTTTCTTTTCTCAGGTCGAACTCAAATA
AATAATCACTAATTGTTATGCACGCGGGTAGGGCATACATACTATATCCACATCGGTCATCTCAAA
ATGCAAACAAATTGTCTTATTTCCGTTGGGACAAGCAAACCCCCTTTCCTGTAATCTTGCCTTTGG
CATCCACTGGAATTAATGTTGACTGGTAATTGATACTGGCTCTCTTCTTGCATAGAGTTAATATCT
ATAGTTTGTAAATCTTTATGATTTTGCTATTTATATTTCGACAGCATGCTATAGACACCCTAGACT
ATTGTATAGCCACTTGTATTGTTTTTCCATTTATTATTTATAACAGAACATGGCTTGTAATTTTTA
TTTACCTTCCAG

DOMAIN 2C

TTGACCATCAGGACCCTCATCAGGACACAATCATCAGGAAAAATGTTGATAATCTTACACCCGAGG
AAATTAATTCTCTGAGGAGGGCAATGGCAGACCTTCAATCAGACAAAACCGCCGGTGGATTCCAGC
AAATTGCTGCTTTTCACGGGGAACCCAAATGGTGCCCAAGTCCCGATGCTGAGAAGAAGTTCTCCT
GCTGTGTCCATGGAATGGCTGTCTTCCCTCACTGGCACAGACTCCTGACCGTGCAAGGCGAGAATG
CCCTGAGAAAGCATGGATGTCTCGGAGCTCTCCCCTACTGGGACTGGACTCGGCCCCTGTCTCACC
TACCTGATTTGGTAAGTCAGCAGAACTACACCGATGCCATATCCACCGTGGAAGCCCGAAACCCCT
GGTACAGCGGCCATATTGATACAGTTGGTGTTGACACAACAAGAAGCGTCCGTCAAGAACTGTATG
AAGCTCCCGGATTTGGTCATTATACTGGGGTCGCTAAGCAAGTGCTTCTGGCTTTGGAGCAGGATG
ACTTCTGTGATTTTGAAGTCCAGTTTGAGATAGCTCACAATTTCATCCACGCTCTTGTCGGCGGAA
GCGAGCCATATGGTATGGCGTCACTCCGTTACACTACTTATGATCCAATTTTCTACCTCCATCATT
CTAACACTGACAGACTCTGGGCTATATGGCAGGCTCTACAAAAGTACAGGGGCAAACCTTACAATT
CCGCCAACTGTGCCATTGCTTCTATGAGAAAACCCCTACAGCCCTTTGGTCTGACTGATGAGATCA
ACCCGGATGATGAGACAAGACAGCATGCTGTTCCTTTCAGTGTCTTTGATTACAAGAACAACTTCA
ATTATGAATATGACACCCTTGACTTCAACGGACTATCAATCTCCCAGCTGGACCGTGAACTGTCAC
GGAGAAAGTCTCATGACAGAGTATTTGCCGGATTTTTGCTGCATGGTATTCAGCAGTCTGCACTAG

Fig. 6d

TTAAATTCTTTGTCTGCAAATCAGATGATGACTGTGACCACTATGCTGGTGAATTCTACATCCTTG
GTGATGAAGCTGAAATGCCATGGGGCTATGATCGTCTTTACAAATATGAGATCACTGAGCAGCTCA
ATGCCCTGGATCTACACATCGGAGATAGATTCTTCATCAGATACGAAGCGTTTGATCTTCATGGTA
CAAGTCTTGGAAGCAACATCTTCCCCAAACCTTCTGTCATACATGACGAAGGGGCAG

INTRON 2C/2D (SEQ ID NO:130)

GTGAGAACATTGATAATAGTTCAAATGAAGTATATCCGATTCAAGCTGTCGATACAAGATGAGATA
CATAATCACAATGTTTGTATTAGATATCTCTCTTAATTTAATGCCGCTTTTATCAATATTCGAGCA
ATCCTTCAGCAACATACACCAGCAAATGTTTCATCAACAGACTATATTATTTAATATTTTAAAAAT
CCTTCTCTGTTGTTATAAATACTTAAAGTATCGAATTCCTTGAATGCGTCTTCTCTGCAGCATATA
GTTAAGTTGTTGTGTTTCTCTGTCAG

DOMAIN 2D

GTCACCATCAGGCTGACGAGTACGACGAAGTTGTAACTGCTGCAAGCCACATCAGAAAGAATTTAA
AAGATCTGTCAAAGGGAGAAGTAGAGAGCCTAAGGTCTGCCTTCCTGCAACTTCAGAACGACGGAG
TCTATGAGAATATTGCCAAATTCCACGGCAAGCCTGGGTTGTGTGATGATAACGGTCGCAAGGTTG
CCTGTTGTGTCCATGGAATGCCCACCTTCCCCCAGTGGCACAGACTCTATGTCCTCCAGGTGGAGA
ATGCTTTGCTGGAGAGAGGATCTGCCGTCTCTGTGCCATACTGGGACTGGACTGAAACATTTACAG
AGCTGCCATCTTTGATTGCTGAGGCTACCTATTTCAATTCCCGTCAACAAACGTTTGACCCTAATC
CTTTCTTCAGAGGTAAAATCAGTTTTGAGAATGCTGTTACAACACGTGATCCCCAGCCTGAGCTGT
ACGTTAACAGGTACTACTACCAAAACGTCATGTTGGCTTTTGAACAGGACAACTACTGCGACTTCG
AGATACAGTTTGAGATGGTTCACAATGTTCTCCATGCTTGGCTTGGTGGAAGAGCTACTTATTCTA
TTTCTTCTCTTGATTATTCTGCATTCGACCCTGTGTTTTTCCTTCACCATGCGAACACAGATAGAT
TGTGGGCCATCTGGCAGGAGCTGCAGAGGTACAGGAAGAAGCCATACAATGAAGCGGATTGTGCCA
TTAACCTAATGCGCAAACCTCTACATCCCTTCGACAACAGTGATCTCAATCATGATCCTGTAACCT
TTAAATACTCAAAACCCACTGATGGCTTTGACTACCAGAACAACTTTGGATACAAGTATGACAACC
TTGAGTTCAATCATTTCAGTATTCCCAGGCTTGAAGAAATCATTCGTATTAGACAACGTCAAGATC
GTGTGTTTGCAGGATTCCTCCTTCACAACATTGGGACATCCGCAACTGTTGAGATATTCGTCTGTG
TCCCTACCACCAGCGGTGAGCAAAACTGTGAAAACAAAGCCGGAACATTTGCCGTACTCGGAGGAG
AAACAGAGATGGCGTTTCATTTTGACAGACTCTACAGGTTTGACATCAGTGAAACACTGAGGGACC
TCGGCATACAGCTGGACAGCCATGACTTTGACCTCAGCATCAAGATTCAAGGAGTAAATGGATCCT
ACCTTGATCCACACATCCTGCCAGAGCCATCCTTGATTTTTGTGCCTGGTTCAA

INTRON 2D/2E (SEQ ID NO:131)

GTAAGAAAGTTTCACTGTCTAAATCTTTTTTTATGATAGAGGGTAGAGAAGTGGAGACAATGTGAC
AATATATTGAATAAAGTTGTTTAAAATTTATAACTCTCATAAGTTCATATTATGCTGAAGCTGTAG
CCATCTATAACTGTGTAACATGAAATGTTAAGACATTAACCTAAATACTTCAGCTGATAACAAAAC
AATGTTAATACATACGTCAATGTAACATTTTCTTATCTTTAGGTTATAGCATAAACACTTCAGAGA
TACAGTGACGAAAACCTCTATTTAAATATTTCAG

DOMAIN 2E

GTTCTTTCCTGCGTCCTGATGGGCATTCAGATGACATCCTTGTGAGAAAAGAAGTGAACAGCCTGA
CAACCAGGGAGACTGCATCTCTGATCCATGCTCTGAAAAGTATGCAGGAAGACCATTCACCTGATG
GGTTCCAAGCCATTGCCTCTTTCCATGCCCTGCCACCACTCTGCCCTTCACCATCTGCAACTCACC
GTTATGCTTGCTGTGTCCACGGCATGGCTACATTTCCCCAGTGGCACAGACTGTACACTGTACAGT

Fig. 6e

TCCAGGATGCACTGAGGAGACATGGAGCTGCAGTAGGTGTACCGTATTGGGATTGGCTGCGACCGC
AGTCTCACCTACCAGAGCTTGTCACCATGGAGACATACCATGATATTTGGAGTAACAGAGATTTCC
CCAATCCTTTCTACCAAGCCAATATTGAGTTTGAAGGAGAAAACATTACAACAGAGAGAGAAGTCA
TTGCAGACAAACTTTTTGTCAAAGGTGGACACGTTTTTGATAACTGGTTCTTCAAACAAGCCATCC
TAGCGCTTGAGCAGGAAAACTACTGTGACTTTGAGATTCAGTTTGAAATTCTTCACAACGGCGTTC
ACACGTGGGTCGGAGGCAGTCGTACCCACTCTATCGGACATCTCCATTACGCATCCTACGACCCTC
TTTTCTACCTCCACCATTCCCAGACAGACCGTATTTGGGCAATCTGGCAAGAACTCCAGGAACAGA
GAGGGCTCTCAGGTGATGAGGCTCACTGTGCTCTCGAGCAAATGAGAGAACCATTGAAGCCTTTCA
GCTTCGGCGCTCCTTATAACTTGAATCAGCTAACACAGGATTTCTCCCGACCCGAGGACACCTTCG
ACTACAGGAAGTTTGGTTATGAATATGACAATTTAGAATTCCTAGGAATGTCAGTTGCTGAACTGG
ATCAATACATTATTGAACATCAAGAAAATGATAGAGTATTCGCTGGGTTCCTGTTGAGTGGATTCG
GAGGTTCCGCATCAGTTAATTTCCAGGTTTGTAGAGCTGATTCCACATGTCAGGATGCTGGGTACT
TCACCGTTCTTGGTGGCAGTGCTGAGATGGCGTGGGCATTTGACAGGCTATACAAATATGACATTA
CTGAAACTCTGGAGAAAATGCACCTTCGATATGATGATGACTTCACAATCTCTGTCAGTCTGACCG
CCAACAACGGAACTGTCCTGAGCAGCAGTCTAATCCCAACACCGAGTGTCATATTCCAGCGGGGAC
ATC

INTRON 2E/2F-1 (SEQ ID NO:132)

GTAAGTAGTAAACTGCTCAGATTGTTTTCATAATTACTCCACTATTAAGTAAAAAGTACTAGTAAT
TCAATAGTACTGTTCACAGAGAAATGTAACACAATAGACCACAGAGTCCATTTGTTAAACGCCTTT
GGCTTGGTAAGTCTGAGATTTTGGTGACTGATGGAAAGCTAAAATATATTTTGACAG

DOMAIN 2F-1 (1st part of domain f)

GTGACATAAATACCAAGAGCATGTCAGCGAACCGTGTTCGCCGTGAGCTGAGCGATCTGTCTGCGA
GGGACCCGTCTAGTCTCAAGTCTGCTCTGCGAGACCTACAGGAGGATGATGGCCCCAACGGATACC
AGGCTCTTGCAGCCTTCCATGGGCTACCAGCAGGCTGCCATGATAGCCAGGGAAATGAG

INTRON 2F-1/2F-2 (SEQ ID NO:133)

GTATATTTAAGTATTTTATCTTACGCATGACCCTGACCCTATTTATTTTTTTTTAATCCTCGGATT
TGTTTAATCCTGTTACCAGCGAAGGTCCGGGTTAGAATTGATCTTCAGTCAACTATTCTTGTCGTA
GGACTAACGAGTTGTCTGGCTTGCTTACTCGGTTGACACGTGTCAACGGATCCCAATTGCAATTAG
ATCGATGCTCATGCTGTTGATCCCTGGATTGCCTGGTCCGGACTCCACATACCGCCGCCATATTGC
TGGTATATTGTCGAATGCGACGCTAAACAGCAAGCCAACCAACAATACTGAGACCTGGTGGTACAT
GTCAGTTCTCTATTGCTGGGGTTCCAAACATAGCCATCAGTTGAAATATTTCATACATAGAAGAAT
ACCTCTGAATATGATGATGAAACATTTACTTAGACTTGCCTGTGAGCCCCAGGCAAAATGCACTGT
AAAAATACACTGACAGAGGATTAGGCATTCTTGGGAGTACTGTATAGTTAGTTGCATACATATTAG
CGTTCCCTCACTAAAACGAATCTCTGAATGCTATCAATTAAAGATCATGATGCTTTGATTGTGTCT
ACTGTATTTAAAATGGTGTTAAGATTTGCAATTACAATATACACAAACACGTTTCCTGCATCTCGG
AGAATGCAATCTTTCGTTGTACGCGTCTGTTTTCATATTTTTATGCATGTAGTTTGCACTACTTAG
CGTCCAATAAATCCATTCACAAAATCACACAAACAAACGATTTTAGGAATGTGACTGTAGCTGCAA
CGAATATACCTGATCCTTTCTTGTTCCAG

DOMAIN 2F-2 (2nd part of domain f)

ATCGCATGTTGCATTCACGGTATGCCGACCTTCCCCCAGTGGCACAGACTGTACACCCTGCAGTTG
GAGATGGCTCTGAGGAGACATGGATCATCTGTCGCCATCCCCTACTGGGACTGGACAAAGCCTATC

Fig. 6f

TCCGAACTCCCCTCGCTCTTCACCAGCCCTGAGTATTATGACCCATGGCATGATGCTGTGGTAAAC
AACCCATTCTCCAAAGGTTTTGTCAAATTTGCAAATACCTACACAGTAAGAGACCCACAGGAGATG
CTGTTCCAGCTTTGTGAACATGGAGAGTCAATCCTCTATGAGCAAACTCTTCTTGCTCTAGAGCAA
ACCGACTACTGTGATTTTGAGGTACAGTTTGAGGTCCTCCATAACGTGATCCACTACCTTGTTGGC
GGACGTCAGACCTACGCATTGTCTTCTCTGCATTATGCATCCTACGACCCATTCTTCTTTATACAC
CATTCCTTTGTGGATAAGATGTGGGTAGTATGGCAAGCTCTTCAAAAGAGGAGGAAACTTCCATAC
AAGCGAGCTGACTGTGCTGTCAACCTAATGACTAAACCAATGAGGCCATTTGACTCCGATATGAAT
CAGAACCCATTCACAAAGATGCACGCAGTTCCCAACACACTCTATGACTACGAGACACTGTACTAC
AGCTACGATAATCTCGAAATAGGTGGCAGGAATCTCGACCAGCTTCAGGCTGAAATTGACAGAAGC
AGAAGCCACGATCGCGTTTTTGCTGGATTCTTGCTTCGTGGAATCGGAACTTCTGCTGATGTCAGG
TTTTGGATTTGTAGAAATGAAAATGACTGCCACAGGGGTGGAATAATTTTCATCTTAGGTGGAGCC
AAGGAAATGCCATGGTCATTTGACAGAAACTTCAAGTTTGATATCACCCATGTACTCGAGAAAGCT
GGCATTAGCCCAGAGGACGTGTTTGATGCTGAGGAGCCATTTTATATCAAGGTTGAGATCCATGCT
GTTAACAAGACCATGATACCATCGTCTGTGATCCCAGCCCCAACTATCATCTATTCTCCTGGGGAA
G

INTRON 2F-2/2G-1 (SEQ ID NO:134)

GTGAGAGAACCAGTAATAGCTACTGTCTACAAAGAATGTGTTCATTTAAAGACCTGACTGTAGGCC
GATGGCTGCTGTCATCTCCTCCGCCTCCTCCTCCTGTTCCTCCTCCGAAGGGGTCAGCTTCAGGTT
CTCTTGCCAATATGCCAAGCAGACCTCCTGAGCAGGCAGTATATATACGTAAGGGAAGCAAGTATG
GACCATCGCGCGGCATGTAGAGATACAATGATCAGCTGTCTGCTGTTCCACTCCTGTCAGACAATG
AGATAAACATGAATACAGTATTACTCAGCAGCGTTCCAATTTTCAACCCTCGTATTTATTAAAAAA
AGGAATTTTTAATATATTTTTCTCCTTGTTGAAATATTTTAGTAACTGTTAATCGATATAGAGTGG
AGTAGTGACGCTTTATTTCGGTTCATTCTCGAAACAAAAATATAATAGTCCACTGAACTCTCTTAA
ATTGTTTTTACAACCTTCAACTGCCACAGACGTAATCCCTCACGTTATTTTGAGCTGACAACGTGT
TGAATTGAGTGTGTTCCGAATTCTAAATAAGCATGTATATATTTACGTCTCATGCAAGTAATATAT
GTTTAACTGATGACGTCACTTGGTGACCACTGATTTAGTTCCTTTGTCATAATTGCAGTTTCTGTT
GTCACGGGGACGGTGGGGAAGCCAGGTTCCTCCTGTCACGCTGAATATCCCGTTCGAATCCCCCAC
ATGGGTACAAAGTGTGATGCCTATTTCTGGTGTCCCCCACCGTGATATTGCTGGAATAAGTGGCTT
AATACCATATACACTCACTCTATTGTCACACTACTGCCACCGGCTCACACCTCTGATGCTTCTGTT
CTATCCAG

DOMAIN 2G-1 (1st part of domain g)

GTCGCGCTGCTGACAGTGCACACTCAGCCAACATTGCTGGCTCTGGGGTGAGGAAGGACGTCACGA
CCCTCACTGTGTCTGAGACCGAGAACCTAAGACAGGCTCTTCAAGGTGTCATCGATGATACTGGTC
CCAATGGTTACCAAGCAATAGCATCCTTCCACGGAAGTCCTCCAATGTGCGAGATGAACGGCCGCA
AGGTTGCCTGTTGTGCTCACG

INTRON 2G-1/2G-2 (SEQ ID NO:135)

GTAATTAATGGATGTGAAGTCAATGTCCGAGGGTATAATAAGGATTTAAATACTTCAGTCGTGTAA
TACTGTATGACATGTGTATTGGATGGTGTAGGTATTACAGGTTATAAGGCCAGTGTGTGTTGGGAC
GGTTACTTTCCTGCACTAGTAATAAGCATTGTATTTAGCTAGCTTTTATCATATAACTTTAGTTTC
ATGGTTTGTGGCAATTGAAATCGAAATTTTCTTTCATTTCAAGGTTATCGCACTCGTGTGTTAGAA
TAGTTACTATGCTGCATTGAGAATAACACTATAGTAATAAAGCATATCATACAGTAAGAATAACAC
TATAGTAATAAAGTATATCATACAGTAAGAATGTCATTGTATGATAAATAGGTTATCACACTCGTG
TGTTTTAGAATGGTTACTATCCCAGGAATAACCACTATGTATTACATGTATATTGGGCAGTGTAAG
TAGTAGCATTGTATATTAAATCAGTATATCGTGCTTCAAAACACCAGGATATATGGGGTATACAGT

Fig. 6g

GGGCAGTGTAAGTAGCAACATTGTATATTAAATCAGTATATCGTACTTCAAAACACCAGGATTATG
GGGTATACAGTGGGCAGTGTAAGTAGTAGCATTGTATATTAAATCAGTATATCGTACTTCAAAACA
CCAGGATATAATTCAGTATATCGTGCTTCAAAACACCAGGATATAATTCAGTATATCGTGCTTCAA
AACACCAGGATATATGGGATATACAGTGCGGGTTTGCATACAACCTCCACCCTTTACAG

DOMAIN 2G-2 (2nd part of domain g)

GTATGGCCTCCTTCCCACACTGGCACAGACTGTATGTGAAGCAGATGGAAGACGCCCTGGCTGACC
ACGGATCACATATCGGCATCCCTTACTGGGACTGGACAACTGCCTTCACAGAGTTACCCGCCCTTG
TCACAGACTCCGAGAACAATCCCTTCCATGAG

INTRON 2G-2/2G-3 (SEQ ID NO:136)

GTCAGTTTAGTCTCCTGTCTGAGCTAACGATACCAATTTCCTATTTTCGAGAACCACGATGACGAG
AAAACAAGCAATATAGATATAGATGCAGTATAGATCAAGTTAATGAATTCATTGCTATATGTTTGC
TTGTAATAAACTTTAAGAAAACGAGAGCATGCACACAAATGAAACAAACAATTATGTGTTTGATAG
GAATATGATATATGTATTTGGGGGCTGACGTGAGCAGGGTTGAAGGGACAGTTTACATTGTCAGTA
ACACTGGGAGTATTCTTTGATCCACAATATATAGTTTCATTGTGTTCAGCAGTTACAACTAACATT
ATATCATACATTACGTCGTAACATGCTTCTTTTGTCCTCTTCTGCCAG

DOMAIN G-3 (3rd part of domain g)

GGTCGCATTGATCATCTCGGTGTAACCACGTCACGTTCCCCCAGAGACATGCTGTTTAACGACCCA
GAGCAAGGATCAGAGTCGTTCTTCTATAGACAAGTCCTCCTGGCTTTGGAGCAGACTGACTACTGC
CAGTTCGAAGTCCAGTTTGAGCTGACCCACAACGCCATTCACTCCTGGACAGGTGGACGTAGCCCT
TACGGAATGTCGACCCTCGAGTTCACAGCCTACGATCCTCTCTTCTGGCTTCACCACTCCAACACC
GACAGAATCTGGGCTGTCTGGCAAGCACTGCAGAAATACCGAGGACTCCCATACAACGAAGCACAC
TGTGAAATCCAGGTTCTGAAACAGCCCTTGAGGCCATTCAACGATGACATCAACCACAATCCAATC
ACCAAGACTAATGCCAGGCCTATCGATTCATTTGATTATGAGAGGTTTAACTATCAGTATGACACC
CTTAGCTTCCATGGTAAGAGCATCCCTGAACTGAATGACCTGCTCGAGGAAAGAAAAAGAGAAGAG
AGAACATTTGCTGCCTTCCTTCTTCGTGGAATCGGTTGCAGTGCTGATGTCGTCTTTGACATCTGC
CGCCCCAATGGTGACTGTGTCTTTGCAGGAACCTTTGCTGTGCTGGGAGGGGAGCTAGAAATGCCT
TGGTCCTTCGACAGACTGTTCCGCTATGACATCACCAGAGTCATGAATCAGCTCCATCTCCAGTAT
GATTCAGATTTCAGTTTCAGGGTGAAGCTTGTTGCAACCAATGGCACTGAGCTTTCATCAGACCTC
CTCAAGTCACCAACAATTGAACATGAACTTGGAG

INTRON 2G-3/2H (SEQ ID NO:137)

GTATGTTATCTTATTATCAAATGTGTAATCAGATACTGGAGACGTTTTCATATTAACTTGGTCAGC
ATTAGTTGATGATTTTGGTGCGATATTGACGACAAGGAGTTAAGCATTAACACGTTCAACACATCT
TTAATCTGATATGAGAAGGGAATAAATTGATCCAGTATTGATGATTGAAGTTAGATTAACAGTGAA
AGATATACCAGTTTTGATAATCGTATAAAACAGTAGCAGAATTGTATCGTGAAAACTAAATGTGGG
AAGGCGAACGCCAAGCAGATTTTAGATTACGATCGTGTGCTAGAATAATTCACAATAACCCAGACG
TCGGAAATGTGGTTGTCTATGGCAATAGTTACGATTAATTGCTAACATGCACGATTTACCTATTTC
AG

DOMAIN 2H

CCCACAGAGGACCAGTTGAAGAAACAGAAGTCACTCACCAAAATACTGACGGCAATGCACACTTCC
ATCGTAAGGAAGTTGATTCGCTGTCCCTGGATGAAGCAAACAACTTGAAGAATGCCCTTTACAAGC

Fig. 6h

TACAGAACGACCACAGTCTAACAGGATACGAAGCAATCTCTGGTTACCATGGATACCCGAATCTGT
GTCCGGAAGAAGGCGATGACAAATACCCCTGCTGCGTCCACGGAATGGCCATCTTCCCCCACTGGC
ACAGACTCTTGACCATCCAACTGGAAAGAGCTCTCGAGCACAATGGTGCACTGCTTGGTGTTCCTT
ACTGGGACTGGACCAAGGACCTGTCGTCACTGCCGGCGTTCTTCTCCGACTCCAGCAACAACAATC
CCTACTTCAAGTACCACATCGCAGGTGTTGGTCACGACACCGTCAGAGAGCCAACTAGTCTTATAT
ATAACCAGCCCCAAATCCATGGTTATGATTATCTCTATTACCTAGCATTGACCACGCTTGAAGAAA
ACAATTACTGTGACTTTGAGGTTCAGTATGAGATCCTCCACAACGCCGTCCACTCCTGGCTTGGAG
GATCCCAGAAGTATTCCATGTCTACCCTGGAGTATTCGGCCTTTGACCCTGTCTTTATGATCCTTC
ACTCGGGTCTAGACAGACTTTGGATCATCTGGCAAGAACTTCAGAAGATCAGGAGAAAGCCCTACA
ACTTCGCTAAATGTGCTTATCATATGATGGAAGAGCCACTGGCGCCCTTCAGCTATCCATCTATCA
ACCAGGACGAGTTCACCCGTGCCAACTCCAAGCCTTCTACAGTTTTTGACAGCCATAAGTTCGGCT
ACCATTACGATAACCTGAATGTTAGAGGTCACAGCATCCAAGAACTCAACACAATCATCAATGACT
TGAGAAACACAGACAGAATCTACGCAGGATTTGTTTTGTCAGGCATCGGTACGTCTGCTAGTGTCA
AGATCTATCTCCGAACAGATGACAATGACGAAGAAGTTGGAACTTTCACTGTCCTGGGAGGAGAGA
GGGAAATGCCATGGGCCTACGAGCGAGTTTTCAAGTATGACATCACAGAGGTTGCAGATAGACTTA
AACTAAGTTATGGGGACACCTTTAACTTCCGACTAGAGATCACATCCTACGATGGATCGGTGGTAA
ACAAGAGCCTACCCAATCCTTTCATCATCTACAGACCTGCCAATCATGACTACGATGTTCTTGTTA
TCCCAGTAGGAAGAAACCTTCACATCCCTCCCAAAGTTGTCGTCAAGAGAGGCACCCGCATCGAGT
TCCACCCAGTCGATGATTCAGTTACGAGACCAGTTGTTGATCTTGGAAGCTACACTGCACTCTTCA
ACTGTGTGGTACCACCGTTCACATACCGCGGATTCGAACTGAACCACGTCTATTCTGTCAAGCCTG
GTGACTACTATGTTACCGGACCAACGAGAGACCTTTGCCAGAATGCAGATGTCAGGATTCATATCC
ATGTTGAGGATGAGTAA

3´UTR

CGCAACAG

INTRON 3´UTR (SEQ ID NO:138)

GTGAGATAAGAAACCCTTCTAACAGTAATACGACACCACATTACAGCTTAAACATGATTGCCATCG
ATGTTTTCATGTGTAGTATACGCTTTTCAGTTCTACATAATTTTGTTTTTCAAATCAAGTTTAGCA
AATGAATCTATCACTGGAAAATAGGGTAGGGTAGCCAAGTGGTTAAAGCGGTCACTGATCACGCCA
AAGACGAGTGTCCTAACCTGCATGGGTACAAAAGTGAAGACCATTGCTGGTGTCTACCGCCGTAAT
ATTGTTTTTAGTATTGCTAAAACTTATACTCACCCATGCGCTGTAAAAGTGGAATAATAATCATAT
TTCAACAAAAGCACAAAACCATTTCATTTTCATGAAAGCCTCTTGTTCACCTGAAAGACGCAAGAG
AACAATAGTTCCTAACATTATTTTCAGACATTGGAAATGTCCTGCACGTGTAAACCATATATCCTT
TGAAATTTTTACGACTGCATCGTATACAATTTATGATATAAATTTAAAACTTTATTTCAG

3´UTR

GTTTCTTGGTCTCCACATATTCACACATCAGCACCAAACGGTTTCGAAGGACATTGGCGTTCTTCT
CTGGCAATGCATTTCAATACAACATTGAAAATGACTTCAGCATATCAGTGTGCTTCGAACGTGTTC
CGGAAGTACTCAAATGTGCTATGACTGAATTATTGTACATACATAACTTATTGATGTTCAATAAAT
AAATGTTGAAACG

Fig. 7a

Primary structure of the HtH2 protein

DOMAIN A (SEQ ID NO:156)

GLPYWDWTQHLTQLPDLVSDPLFVDPEGGKAHDNAWYRGNIKFENKKTARAVDDRLFEKVGPGENT
RLFEGILDALEQDEFCNFEIQFELAHNAIHYLVGGRHTYSMSHLEYTSYDPLFFLHHSNTDRIFAI
WQRLQVLRGKDPNTADCAHNLIHEPMEPFRRDSNPLDLTRENSKPIDSFDYAHLGYQYDDLTLNGM
TPEELNSYLHERSGKEGVFASFRLSGFGGSANVVVYACRPAHDEMAVDQCDKAGDFFVLGGPTEMP
WRFYRAFHFDVTDSIDNIDKDRHGHYYVKAELFSVNGSALPNDLLPQPTISHRPARGHVDEAPAPS
SDAHLAVRKDINHLTREEVYELRRAMERFQADTSVDGYQATVEYHGLPARCPFPEATNRFACCIHG
MATFPHW

DOMAIN B

HRLFVTQVEDALIRRGSPIGVPYWDWTQPMAHLPGLADNATYRDPISGDSRHNPFHDVEVAFENGR
TERHPDSRLFEQPLFGKHTRLFDSIVYAFEQEDFCDFEVQFEMTHNNIHAWIGGGGKYSMSSLHYT
AFDPISYLHHSNTDRLWAIWQALQIRRNKPYKAHCAWSEERQPLKPFAFSSPLNNNEKTYENSVPT
NVYDYEGVLGYTYDDLNFGGMDLGQLEEYIQRQRQRDRTFAGFFLSHIGTSANVEIIIDHGTLHTS
VGTFAVLGGEKEMKWGFDRLYKYEITDELRQLNLRADDGFSISVKVTDVDGSELSSELIPSAAIIF
ERSH

DOMAIN C

IDHQDPHQDTIIRKNVDNLTPEEINSLRRAMADLQSDKTAGGFQQIAAFHGEPKWCPSPDAEKKFS
CCVHGMAVFPHWHRLLTVQGENALRKHGCLGALPYWDWTRPLSHLPDLVSQQNYTDAISTVEARNP
WYSGHIDTVGVDTTRSVRQELYEAPGFGHYTGVAKQVLLALEQDDFCDFEVQFEIAHNFIHALVGG
SEPYGMASLRYTTYDPIFYLHHSNTDRLWAIWQALQKYRGKPYNSANCAIASMRKPLQPFGLTDEI
NPDDETRQHAVPFSVFDYKNNFNYEYDTLDFNGLSISQLDRELSRRKSHDRVFAGFLLHGIQQSAL
VKFFVCKSDDDCDHYAGEFYILGDEAEMPWGYDRLYKYEITEQLNALDLHIGDRFFIRYEAFDLHG
TSLGSNIFPKPSVIHDEGA

DOMAIN D

GHHQADEYDEVVTAASHIRKNLKDLSKGEVESLRSAFLQLQNDGVYENIAKFHGKPGLCDDNGRKV
ACCVHGMPTFPQWHRLYVLQVENALLERGSAVSVPYWDWTETFTELPSLIAEATYFNSRQQTFDPN
PFFRGKISFENAVTTRDPQPELYVNRYYYQNVMLAFEQDNYCDFEIQFEMVHNVLHAWLGGRATYS
ISSLDYSAFDPVFFLHHANTDRLWAIWQELQRYRKKPYNEADCAINLMRKPLHPFDNSDLNHDPVT
FKYSKPTDGFDYQNNFGYKYDNLEFNHFSIPRLEEIIRIRQRQDRVFAGFLLHNIGTSATVEIFVC
VPTTSGEQNCENKAGTFAVLGGETEMAFHFDRLYRFDISETLRDLGIQLDSHDFDLSIKIQGVNGS
YLDPHILPEPSLIFVPGSS

DOMAIN E

SFLRPDGHSDDILVRKEVNSLTTRETASLIHALKSMQEDHSPDGFQAIASFHALPPLCPSPSATHR
YACCVHGMATFPQWHRLYTVQFQDALRRHGAAVGVPYWDWLRPQSHLPELVTMETYHDIWSNRDFP
NPFYQANIEFEGENITTEREVIADKLFVKGGHVFDNWFFKQAILALEQENYCDFEIQFEILHNGVH
TWVGGSRTHSIGHLHYASYDPLFYLHHSQTDRIWAIWQELQEQRGLSGDEAHCALEQMREPLKPFS
FGAPYNLNQLTQDFSRPEDTFDYRKFGYEYDNLEFLGMSVAELDQYIIEHQENDRVFAGFLLSGFG
GSASVNFQVCRADSTCQDAGYFTVLGGSAEMAWAFDRLYKYDITETLEKMHLRYDDDFTISVSLTA
NNGTVLSSSLIPTPSVIFQRGH

Fig. 7b

DOMAIN F

RDINTKSMSANRVRRELSDLSARDPSSLKSALRDLQEDDGPNGYQALAAFHGLPAGCHDSQGNEIA
CCIHGMPTFPQWHRLYTLQLEMALRRHGSSVAIPYWDWTKPISELPSLFTSPEYYDPWHDAVVNNP
FSKGFVKFANTYTVRDPQEMLFQLCEHGESILYEQTLLALEQTDYCDFEVQFEVLHNVIHYLVGGR
QTYALSSLHYASYDPFFFIHHSFVDKMWVVWQALQKRRKLPYKRADCAVNLMTKPMRPFDSDMNQN
PFTKMHAVPNTLYDYETLYYSYDNLEIGGRNLDQLQAEIDRSRSHDRVFAGFLLRGIGTSADVRFW
ICRNENDCHRGGIIFILGGAKEMPWSFDRNFKFDITHVLEKAGISPEDVFDAEEPFYIKVEIHAVN
KTMIPSSVIPAPTIIYSPGE

DOMAIN G

GRAADSAHSANIAGSGVRKDVTTLTVSETENLRQALQGVIDDTGPNGYQAIASFHGSPPMCEMNGR
KVACCAHGMASFPHWHRLYVKQMEDALADHGSHIGIPYWDWTTAFTELPALVTDSENNPFHEGRID
HLGVTTSRSPRDMLFNDPEQGSESFFYRQVLLALEQTDYCQFEVQFELTHNAIHSWTGGRSPYGMS
TLEFTAYDPLFWLHHSNTDRIWAVWQALQKYRGLPYNEAHCEIQVLKQPLRPFNDDINHNPITKTN
ARPIDSFDYERFNYQYDTLSFHGKSIPELNDLLEERKREERTFAAFLLRGIGCSADVVFDICRPNG
DCVFAGTFAVLGGELEMPWSFDRLFRYDITRVMNQLHLQYDSDFSFRVKLVATNGTELSSDLLKSP
TIEHEL

DOMAIN H

GAHRGPVEETEVTHQNTDGNAHFHRKEVDSLSLDEANNLKNALYKLQNDHSLTGYEAISGYHGYPN
LCPEEGDDKYPCCVHGMAIFPHWHRLLTIQLERALEHNGALLGVPYWDWTKDLSSLPAFFSDSSNN
NPYFKYHIAGVGHDTVREPTSLIYNQPQIHGYDYLYYLALTTLEENNYCDFEVQYEILHNAVHSWL
GGSQKYSMSTLEYSAFDPVFMILHSGLDRLWIIWQELQKIRRKPYNFAKCAYHMMEEPLAPFSYPS
INQDEFTRANSKPSTVFDSHKFGYHYDNLNVRGHSIQELNTIINDLRNTDRIYAGFVLSGIGTSAS
VKIYLRTDDNDEEVGTFTVLGGEREMPWAYERVFKYDITEVADRLKLSYGDTFNFRLEITSYDGSV
VNKSLPNPFIIYRPANHDYDVLVIPVGRNLHIPPKVVVKRGTRIEFHPVDDSVTRPVVDLGSYTAL
FNCVVPPFTYRGFELNHVYSVKPGDYYVTGPTRDLCQNADVRIHIHVEDE

Fig 8a

Genomic sequence of the KLH1 gene

DOMAIN 1B

GGCCTACCGTACTGGGACTGGACTGAACCCATGACACACATTCCGGGTCTGGCAGGAAACAAAACT
TATGTGGATTCTCATGGTGCATCCCACACAAATCCTTTTCATAGTTCAGTGATTGCATTTGAAGAA
AATGCTCCCCACACCAAAAGACAAATAGATCAAAGACTCTTTAAACCCGCTACCTTTGGACACCAC
ACAGACCTGTTCAACCAGATTTTGTATGCCTTTGAACAAGAAGATTACTGTGACTTTGAAGTCCAA
TTTGAGATTACCCATAACACGATTCACGCTTGGACAGGAGGAAGCGAACATTTCTCAATGTCGTCC
CTACATTACACAGCTTTCGATCCTTTGTTTTACTTTCACCATTCTAACGTTGATCGTCTTTGGGCC
GTTTGGCAAGCCTTACAGATGAGACGGCATAAACCCTACAGGGCCCACTGCGCCATATCTCTGGAA
CATATGCATCTGAAACCATTCGCCTTTTCATCTCCCCTTAACAATAACGAAAAGACTCATGCCAAT
GCCATGCCAAACAAGATCTACGACTATGAAAATGTCCTCCATTACACATACGAAGATTTAACATTT
GGAGGCATCTCTCTGGAAAACATAGAAAAGATGATCCACGAAAACCAGCAAGAAGACAGAATATAT
GCCGGTTTTCTCCTGGCTGGCATACGTACTTCAGCAAATGTTGATATCTTCATTAAAACTACCGAT
TCCGTGCAACATAAGGCTGGAACATTTGCAGTGCTCGGTGGAAGCAAGGAAATGAAGTGGGGATTT
GATCGCGTTTTCAAGTTTGACATCACGCACGTTTTGAAAGATCTCGATCTCACTGCTGATGGCGAT
TTCGAAGTTACTGTTGACATCACTGAAGTCGATGGAACTAAACTTGCATCCAGTCTTATTCCACAT
GCTTCTGTCATTCGTGAGCATGCACGTGGTAAGCTGAATAGAG

INTRON 1B/1C(SEQ ID NO:139)

GTTTTGTAATAATTATGTAGAATTCTTTACCTCAGAATAAGATGAGGTCACATGGGTTTTGCAAAA
CTATTACGTTCGAATTAATATTAATAATACCGGACCCTCCACTGGTACATATTTATCTTTATAACG
ATAATAGCGATGATGATGATGATGATGATGATGATGATGATGATGATAATGATGATGCCGGTATTG
CACGTAATCCAGCCGACTTAGATGACACCCTAAGGGTGCAGAAAGTATAACAATTAGATTGCGTTT
GCATCTGTGTATGCGTGTGCTTTAACCAAAAGTCAAAATAAAAGTGCAAACCCCTTAGTTTATTCAT
TTGATAGAGCCTTTTACGATAAGAACAATGTAATAAATTAGAACATAACTGAAACCTCCGAAAGAA
GGCCTGTTTGTCAAGAGAGGTATCGACATGATTGACTTATAAACCTGTGCTTCTATATTTTGGAAC
TGTCCACTTTCTTGTTGTGTGTACTGTAATCACATCGCACTATGGCTGCAAGACGTGTACGAGTAC
ACTATATACTTACCTAATGACCAACCACAAGGCTGGCTTTGTTAATATTGTTATTTCACAGAAATA
AACACAGAATTCCAGCATTTGGCTGGTGTATTTAGCAAAACACCGATATGACACTCATGTTTTATT
ACATTTTTTTCAG

DOMAIN 1C

TTAAATTTGACAAAGTGCCAAGGAGTCGTCTTATTCGAAAAAATGTAGACCGTTTGAGCCCCGAGG
AGATGAATGAACTTCGTAAAGCCCTAGCCTTACTGAAAGAGGACAAAAGTGCCGGTGGATTTCAGC
AGCTTGGTGCATTCCATGGGGAGCCAAAATGGTGTCCTAGTCCCGAAGCATCTAAAAAAATTTGCCT
GCTGTGTTCACGGCATGTCTGTGTTCCCTCACTGGCATCGACTGTTGACGGTTCAGAGTGAAAATG
CTTTGAGACGACATGGCTACGATGGAGCTTTGCCGTACTGGGATTGGACCTCTCCTCTTAATCACC
TTCCCGAACTGGCAGATCATGAGAAGTACGTCGACCCTGAAGATGGGGTAGAGAAGCATAACCCTT
GGTTCGATGGTCATATAGATACAGTCGACAAAACAACAACAAGAAGTGTTCAGAATAAACTCTTCG
AACAGCCTGAGTTTGGTCATTATACAAGCATTGCCAAACAAGTACTGCTAGCGTTGGAACAGGACA
ATTTCTGTGACTTTGAAATCCAATATGAGATTGCCCATAACTACATCCATGCACTTGTAGGAGGCG
CTCAGCCTTATGGTATGGCATCGCTTCGCTACACTGCTTTTGATCCACTATTCTACTTGCATCACT
CTAATACAGATCGTATATGGGCAATATGGCAGGCTTTACAGAAGTACAGAGGAAAACCGTACAACG
TTGCTAACTGTGCTGTTACATCGATGAGAGAACCTTTGCAACCATTTGGCCTCTCTGCCAATATCA
ACACAGACCATGTAACCAAGGAGCATTCAGTGCCATTCAACGTTTTTGATTACAAGACCAATTTCA
ATTATGAATATGACACTTTGGAATTTAACGGTCTCTCAATCTCTCAGTTGAATAAAAAGCTCGAAG

Fig. 8b

CGATAAAGAGCCAAGACAGGTTCTTTGCAGGCTTCCTGTTATCTGGTTTCAAGAAATCATCTCTTG
TTAAATTCAATATTTGCACCGATAGCAGCAACTGTCACCCCGCTGGAGAGTTTTACCTTCTGGGTG
ATGAAAACGAGATGCCATGGGCATACGATAGAGTCTTCAAATATGACATAACCGAAAAACTCCACG
ATCTAAAGCTGCATGCAGAAGACCACTTCTACATTGACTATGAAGTATTTGACCTTAAACCAGCAA
GCCTGGGAAAAGATTTGTTCAAGCAGCCTTCAGTCATTCATGAACCAAGAATAG

INTRON 1C/1D (SEQ ID NO:140)

GTACTTGTTATATGTTTCGAATATTGCCGATACCTTCAATATATATACTTTATCAAAGTAATTGAT
TAATCTGAAGTAATTTTCCTTTCCAGTAGAGATTCAGTTGATACAACAAGAATTCGCCCTGTTGTA
TGTCACTTTATTTTCATCAAACGATTCGAAGTGAGCTGTCCATGCCACAATGGGGTCTCTGTAACT
TTCTCGTATGGGGTATAGATTATATAGACGTGGCAGACCTTACGTATAACTAATATTTGTGTAATG
TCGTTTCAG

DOMAIN 1D

GTCACCATGAAGGCGAAGTATATCAAGCTGAAGTAACTTCTGCCAACCGTATTCGAAAAAACATTG
AAAATCTGAGCCTTGGTGAACTCGAAAGTCTGAGAGCTGCCTTCCTGGAAATTGAAAACGATGGAA
CTTACGAATCAATAGCTAAATTCCATGGTAGCCCTGGTTTGTGCCAGTTAAATGGTAACCCCATCT
CTTGTTGTGTCCATGGCATGCCAACTTTCCCTCACTGGCACAGACTGTACGTGGTTGTCGTTGAGA
ATGCCCTCCTGAAAAAAGGATCATCTGTAGCTGTTCCCTATTGGGACTGGACAAAACGAATCGAAC
ATTTACCTCACCTGATTTCAGACGCCACTTACTACAATTCCAGGCAACATCACTATGAGACAAACC
CATTCCATCATGGCAAAATCACACACGAGAATGAAATCACTACTAGGGATCCCAAGGACAGCCTCT
TCCATTCAGACTACTTTTACGAGCAGGTCCTTTACGCCTTGGAGCAGGATAACTTCTGTGATTTCG
AGATTCAGTTGGAGATATTACACAATGCATTGCATTCTTTACTTGGTGGCAAAGGTAAATATTCCA
TGTCAAACCTTGATTACGCTGCTTTTGATCCTGTGTTCTTCCTTCATCACGCAACGACTGACAGAA
TCTGGGCAATCTGGCAAGACCTTCAGAGGTTCCGAAAACGGCCATACCGAGAAGCGAATTGCGCTA
TCCAATTGATGCACACGCCACTCCAGCCGTTTGATAAGAGCGACAACAATGACGAGGCAACGAAAA
CGCATGCCACTCCACATGATGGTTTTGAATATCAAAACAGCTTTGGTTATGCTTACGATAATCTGG
AACTGAATCACTACTCGATTCCTCAGCTTGATCACATGCTGCAAGAAAGAAAAAGGCATGACAGAG
TATTCGCTGGCTTCCTCCTTCACAATATTGGAACATCTGCCGATGGCCATGTATTTGTATGTCTCC
CAACTGGGGAACACACGAAGGACTGCAGTCATGAGGCTGGTATGTTCTCCATCTTAGGCGGTCAAA
CGGAGATGTCCTTTGTATTTGACAGACTTTACAAACTTGACATAACTAAAGCCTTGAAAAAGAACG
GTGTGCACCTGCAAGGGGATTTCGATCTGGAAATTGAGATTACGGCTGTGAATGGATCTCATCTAG
ACAGTCATGTCATCCACTCTCCCACTATACTGTTTGAGGCCGGAACAG

INTRON 1D/1E (SEQ ID NO:141)

GTAACTATTTTGTCACTGTAACCAACAACTGCAGTCTATTTTGCAATTACGATAATAACAATTTTT
GAAATATATCTTTATTAAAGCAAAGGTTTCTAGAGACAAACAGCCGGCTCTAATTATTTTTTCGAA
CTTACGCTTGAGTAAAGATCTGCAAATGGCAACCCTACCTATACTATTAAAAATATAATGTTACAT
TCGTATCTGAATGTTTAATAAATCACTTCATATTCTGTTGCAG

DOMAIN 1E

ATTCTGCCCACACAGATGATGGACACACTGAACCAGTGATGATTCGCAAAGATATCACACAATTGG
ACAAGCGTCAACAACTGTCACTGGTGAAAGCCCTCGAGTCCATGAAAGCCGACCATTCATCTGATG
GGTTCCAGGCAATCGCTTCCTTCCATGCTCTTCCTCCTCTTTGTCCATCACCAGCTGCTTCAAAGA
GGTTTGCGTGCTGCGTCCATGGCATGGCAACGTTCCCACAATGGCACCGTCTGTACACAGTCCAAT
TCCAAGATTCTCTCAGAAAACATGGTGCAGTCGTTGGACTTCCGTACTGGGACTGGACCCTACCTC

Fig. 8c

GTTCTGAATTACCAGAGCTCCTGACCGTCTCAACTATTCATGACCCGGAGACAGGCAGAGATATAC
CAAATCCATTTATTGGTTCTAAAATAGAGTTTGAAGGAGAAAACGTACATACTAAAAGAGATATCA
ATAGGGATCGTCTCTTCCAGGGATCAACAAAAACACATCATAACTGGTTTATTGAGCAAGCACTGC
TTGCTCTTGAACAAACCAACTACTGCGACTTCGAGGTTCAGTTTGAAATTATGCATAATGGTGTTC
ATACCTGGGTTGGAGGCAAGGAGCCCTATGGAATTGGCCATCTGCATTATGCTTCCTATGATCCAC
TTTTCTACATCCATCACTCCCAAACTGATCGTATTTGGGCTATATGGCAATCGTTGCAGCGTTTCA
GAGGACTTTCTGGATCTGAGGCTAACTGTGCTGTAAATCTCATGAAAACTCCTCTGAAGCCTTTCA
GCTTTGGAGCACCATATAATCTTAATGATCACACGCATGATTTCTCAAAGCCTGAAGATACATTCG
ACTACCAAAAGTTTGGATACATATATGACACTCTGGAATTTGCAGGGTGGTCAATTCGTGGCATTG
ACCATATTGTCCGTAACAGGCAGGAACATTCAAGGGTCTTTGCCGGATTCTTGCTTGAAGGATTTG
GCACCTCTGCCACTGTCGATTTCCAGGTCTGTCGCACAGCGGGAGACTGTGAAGATGCAGGGTACT
TCACCGTGTTGGGAGGTGAAAAAGAAATGCCTTGGGCCTTTGATCGGCTTTACAAGTACGACATAA
CAGAAACCTTAGACAAGATGAACCTTCGACATGACGAAATCTTCCAGATTGAAGTAACCATTACAT
CCTACGATGGAACTGTACTCGATAGTGGCCTTATTCCCACACCGTCAATCATCTATGATCCTGCTC
ATC

INTRON 1E/1F (SEQ ID NO:142)

GTAAGTATACACACATTATTTCTCTTCTGCTATATCAGATGAAGAGAACGTTGTATCACTAACCTA
GTCTTGTTTGATTTGTGGTTTCGTTTGCTTCCTGAACAGTAGGGTTGATTTAACTTCTCTGTTTCG
TCTGTACCAATGAAAGACTATGATGCTTGTGTGAAGATGCTTTGTTCATGAGTCAGTCTGTTCTTG
TAATGCTTTGATCTTTGCCATCAACATTCTTGAAATTAATTATGGTTTCCCTTAAATACTTACATA
TTACATTTAAACGTCGCTGCTTGTCTGATTGCATATTCTTTCAAAAATAACTATATATTCCAG

DOMAIN 1F-1 (1st part of domain f)

ATGATATTAGTTCGCACCACCTGTCGCTCAACAAGGTTCGTCATGATCTGAGTACACTGAGTGAGC
GAGATATTGGAAGCCTTAAATATGCTTTGAGCAGCTTGCAGGCAGATACCTCAGCAGATGGTTTTG
CTGCCATTGCATCCTTCCATGGTCTGCCTGCCAAATGTAATGACAGCCACAATAACGAG

INTRON 1F-1/1F-2 (SEQ ID NO:143)

GTAAATATACAGTGAAATCCGGATAAGTAAAATCCAGATAAGAAAAAAAACATTTTCTGTGGTCCC
GGCATGTTTCTTCTTCATCTATCATTATTTTGATACGGATAAGTAAAAATCGGCTGAGTAAAACAT
CCGGGTAAGTAAAATGATTTTCGAGGTCTCTTCATCGGATAAGTAAGATACACAAGTGATCATTCC
AATAAACACTAACTGATGCAACACAATACCAGCGCACAGTGTTTTCACTACGTTTGTTTGTATTGT
AATTAACAATTAACACTTAAGTGTTTCCCAATGTGTCCGTGTGCAAACTGATTGGGACAAAGCTTG
CAACAAGCCCGGCAATTCCATGTCGTTTATGTCTACGTTTGTTATTCTGACTGCTTGGAGGGGTTC
GGAAAAAAATAAAAAACGGGTAAATATTATAAAAAATTCACGGTGCCTTGAAATTTTAGGTGTCCG
GATTTCACTGTAGATGATTAATTTCTCACTTGTAAACAAAAGGACCCCAGTACCCTCATTCGTGAC
GTACGTTATAAAATGTAATTATAAAAAGCCCATTATCATGTTATACGTGATCTTGNCTTGCAATTA
TNCTACCGCTTTCTTGATTTTTTAAAGCAATTTCTCCCTCTATGAACTTATTAACATAGCACTCCT
GCAAAAGAAAACAGTCACTGCATGGATCCATATTGAATGTTGCTGCTTATTTCTCATTTTATTACT
CACAGATATTTCAAGAACATCGTACTCTCTAACCAGGCTAAAGCAAAGAGGGTTACATTTTAGCCG
ACAAGTTCACTAGCTGAGTGGAACACGTATATATTAATGGAGATGACTCTGGTCATGATGATTAGG
ACAATTATCATGACGTTATCATTGATCATGACCATGTCAGTATAATAGATAGCTAACAAATAATGT
AATTACTAATTATGAAGCAATGGTGCATTTGCAG

DOMAIN 1F-2 (2nd part of domain f)

Fig. 8d

GTGGCATGCTGTATCCATGGAATGCCTACATTCCCCCACTGGCACAGACTCTACACCCTCCAATTT
GAGCAAGCTCTAAGAAGACATGGCTCTAGTGTAGCAGTACCCTACTGGGACTGGACAAAGCCAATA
CATAATATTCCACATCTGTTCACAGACAAAGAATACTACGATGTCTGGAGAAATAAAGTAATGCCA
AATCCATTTGCCCGAGGGTATGTCCCCTCACACGATACATACACGGTAAGAGACGTCCAAGAAGGC
CTGTTCCACCTGACATCAACGGGTGAACACTCAGCGCTTCTGAATCAAGCTCTTTTGGCGCTGGAA
CAGCACGACTACTGCGATTTTGCAGTCCAGTTTGAAGTCATGCACAACACAATCCATTACCTAGTG
GGAGGACCTCAAGTCTATTCTTTGTCATCCCTTCATTATGCTTCATATGATCCGATCTTCTTCATA
CACCACTCCTTTGTAGACAAGGTTTGGGCTGTCTGGCAGGCTCTTCAAGAAAAGAGAGGCCTTCCA
TCAGACCGTGCTGACTGCGCTGTTAGTCTGATGACTCAGAACATGAGGCCTTTCCATTACGAAATT
AACCATAACCAGTTCACCAAGAAACATGCAGTTCCAAATGATGTTTTCAAGTACGAACTCCTGGGT
TACAGATACGACAATCTGGAAATCGGTGGCATGAATTTGCATGAAATTGAAAAGGAAATCAAAGAC
AAACAGCACCATGTGAGAGTGTTTGCAGGGTTCCTCCTTCACGGAATTAGAACCTCAGCTGATGTC
CAATTCCAGATTTGTAAAACATCAGAAGATTGTCACCATGGAGGCCAAATCTTCGTTCTTGGGGGG
ACTAAAGAGATGGCCTGGGCTTATAACCGTTTATTCAAGTACGATATTACCCATGCTCTTCATGAC
GCACACATCACTCCAGAAGACGTATTCCATCCCTCTGAACCATTCTTCATCAAGGTGTCAGTGACA
GCCGTCAACGGAACAGTTCTTCCGGCTTCAATCCTGCATGCACCAACCATTATCTATGAACCTGGT
CTCGGTG

INTRON 1F-2/1G-1 (SEQ ID NO:144)

GTCTCGGTGAGTTATTAAAAGAAACAAAATATTTACCATTACCATTGTTAACTACAAAAATGAGTG
AGATATCTTATATCACTGGTACACTACTGATATTTTATGCAATGAAATTACTATTTTTCCAGGTAC
GCTTCAACCCCTCCCCCCCCCCCCCCCCCCCCCCCCCCCCCCCCCCCCCCCATCATGCTTTTCTGT
AAAACATAAAACACCAATTAACAATGTTCTTAGTGTGTTTGTTGACTCCCTTCCACTGCAACGCCT
ACATAATCAAAGTGTTCGTTTTTTTCCAAACTTTCCAGTTAGTGTTGAAGACTAAAAAGTTAAATA
AGCATTCACATAACTTCTAAGAGCAACTGGGACCATGCAGTTACGTATTGATATTTCTGTGAGAGT
GAAGCAAAACACTGTTTTTCAAGCTTAGGTTTATCAATCAAAATGTCCAATAGTTCATGTTATCGA
AAAGGCAGCGAAGGATAAGAGGCTCCGAGACATCTTGTCTATTCTCGTGTTCATATGATATCAACT
GAGGAGCTTCCATTACATTTTTGACCTTATCATTTAAAGACATACATGGAACATTTTCATTTTACA
GTTAAAGTGAACCACTTCAGGTTCAACTTCAACTTCGAATTCAACTTCTGTTGTGTGTTTTATGAG
CCGACTGAAATAGAGTGCCTTACTTTCACTTCTAGTTTCGTTCTGTCTCGTCATCGTTGTTTCTTT
CAGTGTGCATAGTACACGCCTAGTATAGAACACACGAACTTGTCCTTACTTAATAGATTCTGAAAC
TATTATGTGGAAAGTTGGCAGGCTATAGTAACATCCTGGCAAAATTATCATGTATCCTCTTGTTTG
TCATAATTAG

DOMAIN 1G-1 (1st part of domain g)

ACCATCACGAAGATCATCATTCTTCTTCTATGGCTGGACATGGTGTCAGAAAGGAAATCAACACAC
TTACCACTGCAGAGGTGGACAATCTCAAAGATGCCATGAGAGCCGTCATGGCAGACCACGGTCCAA
ATGGATACCAGGCTATAGCAGCGTTCCATGGAAACCCACCAATGTGCCCTATGCCAGATGGAAAGA
ATTACTCGTGTTGTACACATG

INTRON G1-1/1G-2 (SEQ ID NO:145)

GTATGTATTTCCCACTGGTGGTCGCTGACTGCCAACACATACTTGTAATTTATTCATGAAAGTATA
ATAGTTTGTTTGAAAGTATATTTATAACCATCTTGCACAAGCGTCACGAATTTTCACCACAAAGCT
TCAAAACGCCCAAAACATTCTAATAGCGATATATTTGTTAAAAGACCAAAATATAGCCTTACAACA
ATAGATTATTTTAATAAGACCAGTCAGTGCATGCAAATCGATTGGAAACTTTGAAATAAAATATTC
TATGTACTAACTGCCAATCTCATAATACTTGCCTTGGATGTGCTTCTTTTTCACATTCGCGTCGAG
CTTCAACTCCAATGCATAAGCTTAAAAATAATCATAAACACAAACAAATAGCCACAGAGGCGACGA
TCCCTCCAGGCCAGGCTTTATTTGTCTCTTATAGAATATATCGCTATTAGAATGTTTTTGACGTTT

Fig. 8e

TGAAGCTTTGTGGGTGAAAATTCGTGATGTTTATGCGTGGTATTTATGTAAGATGAAAATAAATAT
ATCTTTTCAAACAAGATTTTAGTATTTTGAAGACTTCTATGAATAAATTACACTTATGTGTTAGGT
TATTGGTCACTGAGCGCTTGTGGTATTTTCCCTTCTTCAATTTGTTTGTTCTTTGTTCAATTTCGA
ATAGTTATCCTACTGTGGATAGTCTATATGAGAATCGTTGAAAGAATAATACAATTCTAATGGATT
GCAACTTCTTTAACTTTTATTTGCAACTGCCACGTTTCGGTATACGTTCTTATGCCGTCATCAAGC
ATACGAGTGTACATGTATGCCAAAACGCTGCAAATAAAAATTAAAGAAGTTGCAATCCATAAGAAT
TTCAATGTTCTTTCATCATCACATCAACTTCTAAAAATGCCTATAAAACAATCAACAAACGTACAA
TAGTACATTACCGGATCTCGCAGCATGACCACGTCGATATCTAAACAATATCACTATCCATTAATA
GGATCAAGAGTAGGTACAGACATGTTCAGTTATAAATACTCTTCAAAAAAGTAGGGGAACTTGGAA
TTTCAAGGTCAATAACAAACTAATGATAATAACAATTGGTCCCAAATAATAACAATTGGTCCCAAA
CTAATTGTATCTTTACAAAGAAGAAATTGAGTGAACAATTCACCCGGTATTTTATTACCTAAACCG
TTTCTCTTGCTGTTATGGTGCGTGAAAGAAGAAATGGGTAAGAAACGGAAATTGACATTTTTGCGT
CAGTGGTGCGTAATGCCCCCATTGTTGGCCAAACACTGATTGATTCGCTGAGGCATCGTGCATACG
CGTCTACCTATGGTAATTTGATGCAGTCTGTCCCATTCTTCCACCAACGCCTGGACAAGTTCATCT
AGCGTGGCTGGTGGCCTTTCACGTTGACGCACACGTCGGCCCAAGATGTCCCAGACATTTTCAATG
GCCAGGGCTCATTGCTGGTCAGGGCATCCTATGGATATTGTGCCGTTGAAGGTGGTTATGTTGTTC
ACATTGAAATTCCAAGTTCTCCTACTCTTTTTAAGAGGAGGTTCACAAAGTACGTTCTTTCATGTT
GGTGAAGAGAATATCAAGGTCTTCTAAGGGATTGTGTCTTATAATATTTGATTTTAAGAAGTTTGA
TATTATCTGCATCCTTCCCAAGAAATTGCAAATGTTCACACACTATTGCGTTTGATAATGTTTTTG
GGGAAATAAACTGTCCAGGACTGCTAAATAGTAATTATTGCTACTTTTAG

DOMAIN 1G-2 (2nd part of domain g)

GCATGGCTACTTTCCCCCACTGGCACAGACTGTACACAAAACAGATGGAAGATGCCTTGACCGCCC
ATGGTGCCAGAGTCGGCCTTCCTTACTGGGACGGGACAACTGCCTTTACAGCTTTGCCAACTTTTG
TCACAGATGAAGAGGACAATCCTTTCCATCAT

INTRON 1G-2/1G-3 (SEQ ID NO:146)

*GTGAGTTCACGTAAGCCTACGAGATCAACATTACTCCTTAACAGCCACGGCATCATGTACCGATAT
ATCACAAACAAAAGTATTCAAAGCTTTAAACACGATATGTATGGTTCAAGAATGACATCATTAAAC
AAGGACATGAGTCTGAAATAAACATGACTTGACACCGTTGTGGTCACAGTTTTGTTTCTCATTGGT
GAACCTGTGAAACAACCTTTCAAACCAAAAGATGCCTATTAATATTGTTAATTCCCATGAATTAGG
AGATACACACATTCTACTGTCATTT............................AATAACCGCTTC
CAGCATGAAAACACAATATGATTATCTCAATTCTACCATTACTAATTATAATTTTGACTGGCATTA
TTTGACGACGCGTAAAACATCGCTGCTTTACAGACTGCACTGCGGTAACTGTGACGTTTTCATGAC
GTCACTACATTCTATTCAAAACATTTCCACAGAAGAGCGAGACCACGGCCGTGATGGGTTCTGGGC
AGATGATTACCCAAGTATATATTTATAATAACTTGACTGCTTGCCTGAATAATGTTGACACATGAC
AACGAATTTGTGATAGCGTAAGAAGCGTGAATACTGTGAATAGTGTGAGGGGTGTTTGCTGAGAGT
TAACCACCGTTAATTGCAAAATTCCCGAATACTTGCATTTGCAGTCGAAGAAGAATTGCATTCTTA
CTCCTGTGAATGGACTCATTGTTATTTAGCAGCGGTTATTGAGGTTTTGATCACCTCTAAATAGAC
AATCAGGATGCGGCAAACCGGAAAATTATAGCAGAATCTGTAATTCAAGATGGGCTTGCCTGTGAA
AATATGCTGCGAGTTCAGTAACACTTTTCCCTTTCGATCATGGCCTGTTTTGCTCTGAATCTGGTC
TTTCAGAGGATCCCTGCTTTTTTAAAACTAAAGTCCTCCCAACTCACTTATATTTATGTTTTTTAA
TTATTTATAGTTTTAATATGAACAACAAATCATATTTATTTACACATTATATTTTTCAG*

DOMAIN 1G-3 (3rd part of domain g)

GGTCACATAGACTATTTGGGAGTGGATACAACTCGGTCGCCCCGAGACAAGTTGTTCAATGATCCA
GAGCGAGGATCAGAATCGTTCTTCTACAGGCAGGTTCTCTTGGCTTTGGAGCAGACAGAT

Fig. 9a

Primary structure of the KLH1 protein

DOMAIN B

GLPYWDWTEPMTHIPGLAGNKTYVDSHGASHTNPFHSSVIAFEENAPHTKRQIDQRLFKPATFGHH
TDLFNQILYAFEQEDYCDFEVQFEITHNTIHAWTGGSEHFSMSSLHYTAFDPLFYFHHSNVDRLWA
VWQALQMRRHKPYRAHCAISLEHMHLKPFAFSSPLNNNEKTHANAMPNKIYDYENVLHYTYEDLTF
GGISLENIEKMIHENQQEDRIYAGFLLAGIRTSANVDIFIKTTDSVQHKAGTFAVLGGSKEMKWGF
DRVFKFDITHVLKDLDLTADGDFEVTVDITEVDGTKLASSLIPHASVIREHARGKLNR

DOMAIN C

VKFDKVPRSRLIRKNVDRLSPEEMNELRKALALLKEDKSAGGFQQLGAFHGEPKWCPSPEASKKFA
CCVHGMSVFPHWHRLLTVQSENALRRHGYDGALPYWDWTSPLNHLPELADHEKYVDPEDGVEKHNP
WFDGHIDTVDKTTTRSVQNKLFEQPEFGHYTSIAKQVLLALEQDNFCDFEIQYEIAHNYIHALVGG
AQPYGMASLRYTAFDPLFYLHHSNTDRIWAIWQALQKYRGKPYNVANCAVTSMREPLQPFGLSANI
NTDHVTKEHSVPFNVFDYKTNFNYEYDTLEFNGLSISQLNKKLEAIKSQDRFFAGFLLSGFKKSSL
VKFNICTDSSNCHPAGEFYLLGDENEMPWAYDRVFKYDITEKLHDLKLHAEDHFYIDYEVFDLKPA
SLGKDLFKQPSVIHEPRI

DOMAIN D

GHHEGEVYQAEVTSANRIRKNIENLSLGELESLRAAFLEIENDGTYESIAKFHGSPGLCQLNGNPI
SCCVHGMPTFPHWHRLYVVVVENALLKKGSSVAVPYWDWTKRIEHLPHLISDATYYNSRQHHYETN
PFHHGKITHENEITTRDPKDSLFHSDYFYEQVLYALEQDNFCDFEIQLEILHNALHSLLGGKGKYS
MSNLDYAAFDPVFFLHHATTDRIWAIWQDLQRFRKRPYREANCAIQLMHTPLQPFDKSDNNDEATK
THATPHDGFEYQNSFGYAYDNLELNHYSIPQLDHMLQERKRHDRVFAGFLLHNIGTSADGHVFVCL
PTGEHTKDCSHEAGMFSILGGQTEMSFVFDRLYKLDITKALKKNGVHLQGDFDLEIEITAVNGSHL
DSHVIHSPTILFEAG

DOMAIN E

TDSAHTDDGHTEPVMIRKDITQLDKRQQLSLVKALESMKADHSSDGFQAIASFHALPPLCPSPAAS
KRFACCVHGMATFPQWHRLYTVQFQDSLRKHGAVVGLPYWDWTLPRSELPELLTVSTIHDPETGRD
IPNPFIGSKIEFEGENVHTKRDINRDRLFQGSTKTHHNWFIEQALLALEQTNYCDFEVQFEIMHNG
VHTWVGGKEPYGIGHLHYASYDPLFYIHHSQTDRIWAIWQSLQRFRGLSGSEANCAVNLMKTPLKP
FSFGAPYNLNDHTHDFSKPEDTFDYQKFGYIYDTLEFAGWSIRGIDHIVRNRQEHSRVFAGFLLEG
FGTSATVDFQVCRTAGDCEDAGYFTVLGGEKEMPWAFDRLYKYDITETLDKMNLRHDEIFQIEVTI
TSYDGTVLDSGLIPTPSIIYDPAH

DOMAIN F

HDISSHHLSLNKVRHDLSTLSERDIGSLKYALSSLQADTSADGFAAIASFHGLPAKCNDSHNNEVA
CCIHGMPTFPHWHRLYTLQFEQALRRHGSSVAVPYWDWTKPIHNIPHLFTDKEYYDVWRNKVMPNP
FARGYVPSHDTYTVRDVQEGLFHLTSTGEHSALLNQALLALEQHDYCDFAVQFEVMHNTIHYLVGG
PQVYSLSSLHYASYDPIFFIHHSFVDKVWAVWQALQEKRGLPSDRADCAVSLMTQNMRPFHYEINH
NQFTKKHAVPNDVFKYELLGYRYDNLEIGGMNLHEIEKEIKDKQHHVRVFAGFLLHGIRTSADVQF
QICKTSEDCHHGGQIFVLGGTKEMAWAYNRLFKYDITHALHDAHITPEDVFHPSEPFFIKVSVTAV
NGTVLPASILHAPTIIYEPGLG

Fig. 9b

DOMAIN G

DHHEDHHSSSMAGHGVRKEINTLTTAEVDNLKDAMRAVMADHGPNGYQAIAAFHGNPPMCPMPDGK
NYSCCTHGMATFPHWHRLYTKQMEDALTAHGARVGLPYWDGTTAFTALPTFVTDEEDNPFHHGHID
YLGVDTTRSPRDKLFNDPERGSESFFYRQVLLALEQTD

Fig. 10a

Genomic sequence of the KLH2 gene

DOMAIN 2B

GGCCTGCCCTACTGGGATTGGACCATGCCAATGAGTCATTTGCCAGAACTGGCTACAAGTGAGACC
TACCTCGATCCAGTTACTGGGGAAACTAAAAACAACCCTTTCCATCACGCCCAAGTGGCGTTTGAA
AATGGTGTAACAAGCAGGAATCCTGATGCCAAACTTTTTATGAAACCAACTTACGGAGACCACACT
TACCTCTTCGACAGCATGATCTACGCATTTGAGCAGGAAGACTTCTGCGACTTTGAAGTCCAATAT
GAGCTCACGCATAATGCAATACATGCATGGGTTGGAGGCAGTGAAAAGTATTCAATGTCTTCTCTT
CACTACACTGCTTTTGATCCTATATTTTACCTCCATCACTCAAATGTTGATCGTCTCTGGGCCATT
TGGCAAGCTCTTCAAATCAGGAGAGGCAAGTCTTACAAGGCCCACTGCGCCTCGTCTCAAGAAAGA
GAACCATTAAAGCCTTTTGCATTCAGTTCCCCACTGAACAACAACGAGAAAACGTACCACAACTCT
GTCCCCACTAACGTTTATGACTATGTGGGAGTTTTGCACTATCGATATGATGACCTTCAGTTTGGC
GGTATGACCATGTCAGAACTTGAGGAATATATTCACAAGCAGACACAACATGATAGAACCTTTGCA
GGATTCTTCCTTTCATATATTGGAACATCAGCAAGCGTAGATATCTTCATCAATCGAGAAGGTCAT
GATAAATACAAAGTGGGAAGTTTTGTAGTACTTGGTGGATCCAAAGAAATGAAATGGGGCTTTGAT
AGAATGTACAAGTATGAGATCACTGAGGCTCTGAAGACGCTGAATGTTGCAGTGGATGATGGGTTC
AGCATTACTGTTGAGATCACCGATGTTGATGGATCTCCCCCATCTGCAGATCTCATTCCACCTCCT
GCTATAATCTTTGACGTGGTCAGAG

INTRON 2B/2C (SEQ ID NO:147)

GTATTTAAAAAAGTAATAAAACCATATTTTCGAATGCGCTTTATGAAATATCGTGTGACTGGTTCT
TTAGTTTACATGGAGTGTAACAACATGCTCCATCAGTTGACATATACTGCTCACACAAAGTAAGGG
ATATTTGATAATGATAACAAATATAATCAAAGCGGTTATACTATCAAGACTTATTCACATAATTAC
AGGTGAAGGGAGGTGTGATCGTGTTCACTGATCAGGTTGAGGCCAGAGAAGTCCCAGTTTGAGTCT
TGCAGAAGATGATGTTTAGGCATGGGGTCGAATCACCAAAATCACATGACTTCAATAACGGGTTGG
ACCACCTCGAGCGACGATGCAAGCAGTAGAGCGTCTACGCATGCTCCTGATAAGGCGACCAATCTG
TTCCTGGGGAATCAGTCGCCACTCCTCTTGTAGTGCCACGCTCATTTCTGCTACGGTCCTGGGTAC
CTGCTATCGGGTCTTGATCCGTATCCCAAGGATGTCCCACACATGTTCAAGGTGAGAGGTCGGGGA
ACATCGCTGGCCACGGTAAGGTCTGAATTTGATGCCGTTGAAAGTGAGCTCTGACAACCTGAGCAT
GGTGAGCTCTGACGTTGTCGTCCTGAAAGATGAATCCAGCTCCATGACAGCGAGCAAAGGGCAGGA
CGTGTTGGTCAATGCAGTTGTCTCTGCAGTACACACCTGTCACTCGCCACTCACAAGCGTGTAGAT
CTGTACGACCAGTCATGGAGATCCCAGCCCACATCATAACGGACCCCTATCCATACCGATCATGAG
CCACCATAGCAGCGTCTTGATGACGTTCTCCCTGTCGCCTCGACATCCTCACACGGCCAAAAGGAA
CGTGGACTCGTCACTGAACATGACATTAGCCAACCTGGCACTTGTCCACCGCTGATGTTGGCGAGA
CCATTCCAGTCGAGCTCTTCGGTGTCTGGCTTTCATCGATAACACGACGTAAGGTCTGCGGGCGTG
CAAGACGGCTCTATGCAGGCGATTTCGGATTGTCTGGGTGCTAACTCTGATCCCAGGTGCCTGCTG
AAGTTGATGCTGGATCTGTGTGGCATTGAGATGGCGATTCCTTAGGACTGTGGAGATGATGAATCG
ATCTTGACTTATGGTGGTGACATTAGGACGTCGGGTTCGTGTCCTATCCTGCACTCTTCCAGTTGT
TCGGTGACGCTCTGGTACCCGGCTGATTACTGACTGAGAATATCCATCTGCCGTGCGACATGAGCC
TGTGTTGGCCCAGCCTGAAGCATTGCAATCGCCAGAGACGCTCTTCAAAAGTCATTCGACGCATGG
TTTTCTGTTCACAAATGACAGCGTAAAACAGTTTTTGGTGCTTTTATGCTTCCCAAGAGCATGAAA
AACACGTTCTATGGGTCGTGCACACCTTACATGACAAGTGTGAAAAGTGACTTGCACCCCCTTGTG
TGTTCGGATGCACACTCTGTTTACGTACTGATGCGATTTGGCGTCTAAACATGTTTTGGCGTCTAA
ACATGTTTTCCTGCATGATTCATATACTATTTTGTCATATTCCTGGCATCAAACCAAACTACAGTG
AAATATATTTCAATATCCCCTACTTTGTGTGAGTAGTATAGATCACTGCAGACAACATATAGACAA
TGCAGTTACACCGTCAACAATCCCAGTCATTAATTATGATGACACTTCCACACATAGTGTCAGTGA
TTGTAATTCAACTGTACACACTTTTCCCGTGAACATTCAGGATCTATATGACTAAATATATAACAT
TAGTATACGTGCAGTTTTGTATCGCTACGACATTGTTGTAACTCTTTGTTTAATCATTTAACAG

Fig. 10b

DOMAIN 2C

CTGATGCCAAAGACTTTGGCCATAGCAGAAAAATCAGGAAAGCCGTTGATTCTCTGACAGTCGAAG
AACAAACTTCGTTGAGGCGAGCTATGGCAGATCTACAGGACGACAAAACATCAGGGGGTTTCCAGC
AGATTGCAGCATTCCACGGAGAACCAAAATGGTGTCCAAGCCCCGAAGCGGAGAAAAAATTTGCAT
GCTGTGTTCATGGAATGGCTGTTTTCCCTCACTGGCACAGATTGCTGACAGTTCAAGGAGAAAATG
CTCTGAGGAAACATGGATTTACTGGTGGATTGCCCTATTGGGACTGGACTCGGCCAATGAGCGCCC
TTCCACATTTTGTTGCTGATCCTACTTACAATGATTCTGTTTCCAGCCTCGAAGAAGATAACCCAT
GGTATCATGGTCACATAGATTCTGTTGGGCATGATACTACAAGAGCTGTGCGTGATGATCTTTATC
AATCTCCTGGTTTCGGTCACTACACAGATATTGCAAAACAAGTCCTTCTGGCCTTTGAGCAGGACG
ATTTCTGTGATTTTGAGGTACAATTTGAAATTGCCCATAATTTCATACATGCTCTGGTTGGTGGTA
ACGAACCATACAGTATGTCATCTTTGAGGTATACTACATACGATCCAATCTTCTTCTTGCACCGCT
CCAATACAGACCGACTTTGGGCCATTTGGCAAGCTTTGCAAAAATACCGGGGGAAACCATACAACA
CTGCAAACTGTGCCATTGCATCCATGAGAAAACCACTTCAGCCATTTGGTCTTGATAGTGTCATAA
ATCCAGATGACGAAACTCGTGAACATTCGGTTCCTTTCCGAGTCTTCGACTACAAGAACAACTTCG
ACTATGAGTATGAGAGCCTGGCATTTAATGGTCTGTCTATTGCCCAACTGGACCGAGAGTTGCAGA
GAAGAAAGTCACATGACAGAGTCTTTGCAGGATTCCTTCTTCATGAAATTGGACAGTCTGCACTCG
TGAAATTCTACGTTTGCAAACACAATGTATCTGACTGTGACCATTATGCTGGAGAATTCTACATTT
TGGGAGATGAAGCTGAGATGCCTTGGAGGTATGACCGTGTGTACAAGTACGAGATAACACAGCAGC
TGCACGATTTAGATCTACATGTTGGAGATAATTTCTTCCTTAAATATGAAGCCTTTGATCTGAATG
GCGGAAGTCTTGGTGGAAGTATCTTTTCTCAGCCTTCGGTGATTTTCGAGCCAGCTGCAG

INTRON 2C/2D (SEQ ID NO:148)

GTATGTTTTAAATGTCACTTATCCGTGATCTGTAATGAAGTTAGCAATTCACTTTATCAACTGTTT
GGCTGTACTGTTTCAGTGCGAGTTTTACTTAGGTTGGATTAATTAAAATATTCAAGCTCATAAATG
TTTTGATTCAACTTTTGTTATTTATTTCAAACAG

DOMAIN 2D

GTTCACACCAGGCTGATGAATATCGTGAGGCAGTAACAAGCGCTAGCCACATAAGAAAAAATATCC
GGGACCTCTCAGAGGGAGAAATTGAGAGCATCAGATCTGCTTTCCTCCAAATTCAAAAAGAGGGTA
TATATGAAAACATTGCAAAGTTCCATGGAAAACCAGGACTTTGTGAACATGATGGACATCCTGTTG
CTTGTTGTGTCCATGGCATGCCCACCTTTCCCCACTGGCACAGACTGTACGTTCTTCAGGTGGAGA
ATGCGCTCTTAGAACGAGGGTCTGCAGTTGCTGTTCCTTACTGGGACTGGACCGAGAAAGCTGACT
CTCTGCCATCATTAATCAATGATGCAACTTATTTCAATTCACGATCCCAGACCTTTGATCCTAATC
CTTTCTTCAGGGGACATATTGCCTTCGAGAATGCTGTGACGTCCAGAGATCCTCAGCCAGAACTAT
GGGACAATAAGGACTTCTACGAGAATGTCATGCTGGCTCTTGAGCAAGACAACTTCTGTGACTTTG
AGATTCAGCTTGAGCTGATACACAACGCCCTTCATTCTAGACTTGGAGGAAGGGCTAAATACTCCC
TTTCGTCTCTTGATTATACCGCATTTGATCCTGTATTTTTCCTTCACCATGCAAACGTTGACAGAA
TCTGGGCCATCTGGCAGGACTTGCAGAGATATAGAAAGAAACCATACAATGAGGCTGACTGCGCAG
TCAACGAGATGCGTAAACCTCTTCAACCATTTAATAACCCAGAACTTAACAGTGATTCCATGACGC
TTAAACACAACCTCCCACAAGACAGTTTTGATTATCAAAACCGCTTCAGGTACCAATATGATAACC
TTCAATTTAACCACTTCAGCATACAAAAGCTAGACCAAACTATTCAGGCTAGAAAACAACACGACA
GAGTTTTTGCTGGCTTTATTCTTCACAACATTGGGACATCTGCTGTTGTAGATATTTATATTTGCG
TTGAACAAGGAGGAGAACAAAACTGCAAGACAAAGGCGGGTTCCTTCACGATTCTGGGGGGAGAAA
CAGAAATGCCATTCCACTTTGACCGCTTGTACAAATTTGACATAACGTCTGCTCTGCATAAACTTG
GTGTTCCCTTGGACGGACATGGATTCGACATCAAAGTTGACGTCAGAGCTGTCAATGGATCGCATC
TTGATCAACACATCCTCAACGAACCGAGTCTGCTTTTTGTTCCTGGTGAACGTAAGAATATATATT
ATG

Fig. 10c

INTRON 2D/2E (SEQ ID NO:149)

GTTATAAAGCAGTATATTCTCTTCAAAAAAGTAGGGGAACTTGGAATTTCAAGGTAAATAACATAA
CTACCTTCAACGGCACAATATCCATATGATGCCCTGGCCAGCAATGAGGCCTGATCTTTTCCCCAT
TAAAAATGTCTGGAACATCTTGGGCAAACGTGTGCGTCAACGTAAAACGCCACCAGTCACGCTAGA
TGAACTTGTCCAGGCGTTGGTGGAAGAATGGGACAGACTGCATCAATTACCATAAGTAGACTCATT
TGCAGCGAATCAGTCAGTGTTTGACCAATAACGGGGGCATTACGCACTACTGACGCAAAACAATGT
CAATTTCCGTTTCTTACCCATTCCTTCTTTCACGGACCATAACAGCAAGAGAAACTGNTTAGGTAA
TGAAATACCGGTGAATTATTGTTAACTGGATTCCTTCTTTGTAAAGATACAATTAGTTTGGGACCA
ATTATTATTATCATTAGTTTGTTATTGACCTTGAAATTCGAAGTTCCTCTACATTTTTTAAGGAGT
TTATTTGATTGACAATGAAATGTAAGAAAAGAGCAAATCGTAAAATACGTTAAAAATTATTCCTTA
AACATCAGTCTCTAACTTCAGTTTAAATTGCCAGTAACACGTGTTATATGATGTTTCCGTTTCTCT
TTGTTTTTTAGCATTCAACTTATTTGATATAACGTTTTACTGTTTTAGATTCACATCAAACTGCAG

DOMAIN 2E

ATGGGCTTTCACAACATAATCTTGTGCGAAAAGAAGTAAGCTCTCTTACAACACTGGAGAAACATT
TTTTGAGGAAAGCTCTCAAGAACATGCAAGCAGATGATTCTCCAGACGGATATCAAGCTATTGCTT
CTTTCCACGCTTTGCCTCCTCTTTGTCCAAGTCCATCTGCTGCACATAGACACGCTTGTTGCCTCC
ATGGTATGGCTACCTTCCCTCAGTGGCACAGACTCTACACAGTTCAGTTCGAAGATTCTTTGAAAC
GACATGGTTCTATTGTCGGACTTCCATATTGGGATTGGCTGAAACCGCAGTCTGCACTCCCTGATT
TGGTGACACAGGAGACATACGAGCACCTGTTTTCACACAAAACCTTCCCAAATCCGTTCCTCAAGG
CAAATATAGAATTTGAGGGAGAGGGAGTAACAACAGAGAGGGATGTTGATGCTGAACACCTCTTTG
CAAAAGGAAATCTGGTTTACAACAACTGGTTTTGCAATCAGGCACTATATGCACTAGAACAAGAAA
ATTACTGTGACTTTGAAATACAGTTCGAAATTTTGCATAATGGAATTCATTCATGGGTTGGAGGAT
CAAAGACCCATTCAATAGGTCATCTTCATTACGCATCATACGATCCACTGTTCTATATCCACCATT
CGCAGACAGATCGCATTTGGGCTATCTGGCAAGCTCTCCAGGAGCACAGAGGTCTTTCAGGGAAGG
AAGCACACTGCGCCCTGGAGCAAATGAAAGACCCTCTCAAACCTTTCAGCTTTGGAAGTCCCTATA
ATTTGAACAAACGCACTCAAGAGTTCTCCAAGCCTGAAGACACATTTGATTATCACCGATTCGGGT
ATGAGTATGATTCCCTCGAATTTGTTGGCATGTCTGTTTCAAGTTTACATAACTATATAAAACAAC
AACAGGAAGCTGATAGAGTCTTCGCAGGATTCCTTCTTAAAGGATTTGGACAATCAGCATCCGTAT
CGTTTGATATCTGCAGACCAGACCAGAGTTGCCAAGAAGCTGGATACTTCTCAGTTCTCGGTGGAA
GTTCAGAAATGCCGTGGCAGTTTGACAGGCTTTACAAGTACGACATTACAAAAACGTTGAAAGACA
TGAAACTGCGATACGATGACACATTTACCATCAAGGTTCACATAAAGGATATAGCTGGAGCTGAGT
TGGACAGCGATCTGATTCCAACTCCTTCTGTTCTCCTTGAAGAAGGAAAGC

INTRON 2E/2F (SEQ ID NO:150)

GTATGTATCTCATGTTTCTCAAATAATTTGATTTTCAATGCCCTTACTATAAAGCACAGTTATTGT
TCAGTGCCAGTAACCGTTTATTTACGTAAATGTTACAGGCTATTATAATCAAAAATACATTACCGA
TATTGTTTACCACACAATTATATCATTGTCAAAATCTACCCCCATTACCTGCGTTTTGAATTTGTA
ACCTTCTGACAAAAATGAATTAGCAAGAGCTCTGATGAAGAACATAATGAACAACACCTATCTTTC
TTCTTTCAATGACGGTTTAACAATACAATGCACAATGTAAAAAAATATATATATATATATAATTTT
ATATCTACAGTTAATGCAAATGACTCCACTAATTCAGGGAAACACATTTTCAG

DOMAIN 2F-1 (1st part of domain f)

ATGGGATCAATGTACGTCACGTTGGTCGTAATCGGATTCGTATGGAACTATCTGAACTCACCGAGA
GAGATCTCGCCAGCCTGAAATCTGCAATGAGGTCTCTACAAGCTGACGATGGGGTGAACGGTTATC
AAGCCATTGCATCATTCCACGGTCTCCCGGCTTCTTGTCATGATGATGAGGGACATGAG

Fig. 10d

INTRON 2F (SEQ ID NO:151)

GTAAAATAAAACGTCCAGTCATCGGAAACCCGCCCAGATATATGGGTTTTTTCTATTTAAACAAA
AAAGCAGAGACAAAAAGATTATTAAAAGTCACATTTAACTTGATATCAGATCAATAGTTTGGCTAG
TTAGTGCTCTATATCCCTCAAATCCTTCGAATCTTTAAGCCTCGTGATATTTTGACAAACAGAGAA
GACTTAGTAGCCCAGACTTTCCCTTATTTTTCCTGAAAATCTTAATACGGATATTAAATGGATTC
ATTCTGCAACCTACAACCATAGCCCATATGTTATTATTTCAG

DOMAIN 2F-2 (2nd part of domain f)

ATTGCCTGTTGTATCCACGGAATGCCAGTATTCCCACACTGGCACAGGCTTTACACCCTGCAAATG
GACATGGCTCTGTTATCTCACGGATCTGCTGTTGCTATTCCATACTGGGACTGGACCAAACCTATC
AGCAAACTGCCTGATCTCTTCACCAGCCCTGAATATTACGATCCTTGGAGGGATGCAGTTGTCAAT
AATCCATTTGCTAAAGGCTACATTAAATCCGAGGACGCTTACACGGTTAGGGATCCTCAGGACATT
TTGTACCACTTGCAGGACGAAACGGGAACATCTGTTTTGTTAGATCAAACTCTTTTAGCCTTAGAG
CAGACAGATTTCTGTGATTTTGAGGTTCAATTTGAGGTCGTCCATAATGCTATTCACTACTTGGTG
GGTGGTCGACAAGTTTATGCTCTTTCTTCTCAACACTATGCTTCATATGACCCAGCCTTCTTTATT
CATCACTCCTTTGTTGACAAAATATGGGCAGTCTGGCAAGCTCTGCAAAAGAAGAGAAAGCGTCCC
TATCATAAAGCGGATTGTGCTCTTAACATGATGACCAAACCAATGCGACCATTTGCACACGATTTC
AATCACAATGGATTCACAAAAATGCACGCAGTCCCCAACACTCTATTTGACTTTCAGGACCTTTTC
TACACGTATGACAACTTAGAAATTGCTGGCATGAATGTTAATCAGTTGGAAGCGGAAATCAACCGG
CGAAAAAGCCAAACAAGAGTCTTTGCCGGGTTCCTTCTACATGGCATTGGAAGATCAGCTGATGTA
CGATTTTGGATTTGCAAGACAGCTGACGACTGCCACGCATCTGGCATGATCTTTATCTTAGGAGGT
TCTAAAGAGATGCACTGGGCCTATGACAGGAACTTTAAATACGACATCACCCAAGCTTTGAAGGCT
CAGTCCATACACCCTGAAGATGTGTTTGACACTGATGCTCCTTTCTTCATTAAAGTGGAGGTCCAT
GGTGTAAACAAGACTGCTCTCCCATCTTCAGCTATCCCAGCACCTACTATAATCTACTCAGCTGGT
GAAG

INTRON 2F-2/2G (SEQ ID NO:152)

GTGAGAGAAACTATAATAGTGTATGTCGGCAAAAAATGTGCTCATATCATGACTCTGTTGGCCGGT
GGTTGCTCTCCTCTCCTCCTCCACCACCACCGGTACCTCCACCTGTCAGGGCATCAATGTACCATG
AAAATGTCTACAATACTAGGCCTCCTGTAGAAGCACGTAAGATTTACATGGCCGGTTTGTAACTAG
TTTAAAGTGCTTCACAGTAACCAAAACCAGTCTCTAAAGATTAATGTCTGTTTAAAATTTAATGCC
ACATTTTCAACTGACATATTCTTGCAATTAAGTACAAATGAAGTAGTATAAATTATCCACAAATAG
CGTGATGCACCACAAATATAAACCGAGTGCTTTTTTGGCATTCCCCACTTGTTCTGGCATGATCAC
ATCATAGATCTCGTTCATGAAGATACTGTTGGATGCTTTTTCCCAATATGCCCCAATCTGTTAAAT
TATTTACACGACCGCAGTGTGTACTTTCATCACTCAGATCTTTACAATGTGTTTGTAACGTTTACA
ATTAGCGTTATGATTGAAATATTACCCCCTGCTACGTTAAATCACATTCACTCACTCATCTGATGT
ACTTTACAGGTCATACCGATGATCACGGCTCAG

DOMAIN 2G-1 (1st part of domain g)

ATCATATTGCTGGCAGTGGAGTCAGGAAAGACGTGACGTCTCTTACCGCATCTGAGATAGAGAACC
TGAGGCATGCTCTGCAAAGCGTGATGGATGATGATGGACCCAATGGATTCCAGGCAATTGCTGCTT
ATCACGGAAGTCCTCCCATGTGTCACATGCCTGATGGTAGAGACGTTGCATGTTGTACTCATG

INTRON 2G-1/2G-2 (SEQ ID NO:153)

GTCAGTATTCTCCAATATGTTTGACTAGTGTCTTGCTCATGTATCAACTATTTTAGGCAACGTTTT
TGATTGTTATGGTATTTTCATGATATGATTTTATTGCTACCTCTATACCCAAACAAAAATGTTTTA

Fig. 10e

TCAACAATTGTTTGAGTTTTAATGCAAGAAAATTATCAGGAGTAGCGTGCAAAAATGACTGGAAGG
CATGGTGTACTTCTGTGTGTACATACAAGTGGGTAATGCCTTATTGAACTCGTAATCACTCGTTTC
AG

DOMAIN 2G-2 (2nd part of domain g)

GAATGGCATCTTTCCCTCACTGGCACAGACTGTTTGTGAAACAGATGGAGGATGCACTGGCTGCGC
ATGGAGCTCACATTGGCATACCATACTGGGATTGGACAAGTGCGTTTAGTCATCTGCCTGCCCTAG
TGACTGACCACGAGCACAATCCCTTCCACCAC

INTRON 2G-2/2G-3 (SEQ ID NO:154)

GTCAGTATTCTCCAATATGTTTGACTAGTGTCTTGCTCATGTATCAACTATTTTAGGCAACGTTTT
TGATTGTTATGGTATTTTCATGATATGATTTTATTGCTACCTCTATACCCAAACAAAAATGTTTTA
TCAACAATTGTTTGAGTTTTAATGCAAGAAAATTATCAGGAGTAGCGTGCAAAAATGACTGGAAGG
CATGGTGTACTTCTGTGTGTACATACAAGTGGGTAATGCCTTATTGAACTCGTAATCACTCGTTTC
AG

DOMAIN 2G-3 (3rd part of domain g)

GGACATATTGCTCATCGGAATGTGGATACATCTCGATCTCCGAGAGACATGCTGTTCAATGACCCC
GAACACGGGTCAGAATCATTCTTCTATAGACAGGTTCTCTTGGCTCTAGAACAGACAGACTTCTGC
CAATTTGAAGTTCAGTTTGAAATAACACACAATGCAATCCACTCTTGGACTGGAGGACATACTCCA
TATGGAATGTCATCACTGGAATATACAGCATATGATCCACTCTTTTATCTCCACCATTCCAACACT
GATCGTATCTGGGCCATCTGGCAGGCACTCCAGAAATACAGAGGTTTTCAATACAACGCAGCTCAT
TGCGATATCCAGGTTCTGAAACAACCTCTTAAACCATTCAGCGAGTCCAGGAATCCAAACCCAGTC
ACCAGAGCCAATTCTAGGGCAGTCGATTCATTTGATTATGAGAGACTCAATTATCAATATGACACA
CTTACCTTCCACGGACATTCTATCTCAGAACTTGATGCCATGCTTCAAGAGAGAAAGAAGGAAGAG
AGAACATTTGCAGCCTTCCTGTTGCACGGATTTGGCGCCAGTGCTGATGTTTCGTTTGATGTCTGC
ACACCTGATGGTCATTGTGCCTTTGCTGGAACCTTCGCGGTACTTGGTGGGGAGCTTGAGATGCCC
TGGTCCTTTGAAAGATTGTTCCGTTACGATATCACAAAGGTTCTCAAGCAGATGAATCTTCACTAT
GATTCTGAGTTCCACTTTGAGTTGAAGATTGTTGGCACAGATGGAACAGAACTGCCATCGGATCGT
ATCAAGAGCCCTACCATTGAACACCATGGAGGAG

INTRON 2G/2H (SEQ ID NO:155)

GTATGTTTTGAGATCCACATAATCTTCTACCCTGTCTCATTTCTAATGCTCTTCAATACACAATTT
ATATAGCCTTTGAGCTTCAGATGTATTACGGACAGGCATTACAGTATACATGTAATATGGTTTTCT
GCTATTTGCAAAAATTGTGTCCTATCTCTGTTCAGATCATCATGGCGGTGACACCTAG

DOMAIN 2H (SEQ ID NO:159)

GTCACGATCACAGTGAACGTCACGATGGATTTTTCAGGAAGGAAGTCGGTTCCCTGTCCCTGGATG
AAGCCAATGACCTTAAAAATGCACTGTACAAGCTGCAGAATGATCAGGGTCCCAATGGATATGAAT
CAATAGCCGGTTACCATGGCTATCCATTCCTCTGCCCTGAACATGGTGAAGACCAGTACGCATGCT
GTGTCCACGGAATGCCTGTATTTCCACATTGGCACAGACTTCATACAATCCAGTTTGAGAGAGCTC
TCAAAGAACATGGTTCTCATTTGGGTCTGCCATACTGGGACTGGAC

Fig. 11a

Primary structure of the KLH2 protein

DOMAIN B

GLPYWDWTMPMSHLPELATSETYLDPVTGETKNNPFHHAQVAFENGVTSRNPDAKLFMKPTYGDHT
YLFDSMIYAFEQEDFCDFEVQYELTHNAIHAWVGGSEKYSMSSLHYTAFDPIFYLHHSNVDRLWAI
WQALQIRRGKSYKAHCASSQEREPLKPFAFSSPLNNNEKTYHNSVPTNVYDYVGVLHYRYDDLQFG
GMTMSELEEYIHKQTQHDRTFAGFFLSYIGTSASVDIFINREGHDKYKVGSFVVLGGSKEMKWGFD
RMYKYEITEALKTLNVAVDDGFSITVEITDVDGSPPSADLIPPPAIIFDVVR

DOMAIN C

ADAKDFGHSRKIRKAVDSLTVEEQTSLRRAMADLQDDKTSGGFQQIAAFHGEPKWCPSPEAEKKFA
CCVHGMAVFPHWHRLLTVQGENALRKHGFTGGLPYWDWTRPMSALPHFVADPTYNDSVSSLEEDNP
WYHGHIDSVGHDTTRAVRDDLYQSPGFGHYTDIAKQVLLAFEQDDFCDFEVQFEIAHNFIHALVGG
NEPYSMSSLRYTTYDPIFFLHRSNTDRLWAIWQALQKYRGKPYNTANCAIASMRKPLQPFGLDSVI
NPDDETREHSVPFRVFDYKNNFDYEYESLAFNGLSIAQLDRELQRRKSHDRVFAGFLLHEIGQSAL
VKFYVCKHNVSDCDHYAGEFYILGDEAEMPWRYDRVYKYEITQQLHDLDLHVGDNFFLKYEAFDLN
GGSLGGSIFSQPSVIFEPAA

DOMAIN D

GSHQADEYREAVTSASHIRKNIRDLSEGEIESIRSAFLQIQKEGIYENIAKFHGKPGLCEHDGHPV
ACCVHGMPTFPHWHRLYVLQVENALLERGSAVAVPYWDWTEKADSLPSLINDATYFNSRSQTFDPN
PFFRGHIAFENAVTSRDPQPELWDNKDFYENVMLALEQDNFCDFEIQLELIHNALHSRLGGRAKYS
LSSLDYTAFDPVFFLHHANVDRIWAIWQDLQRYRKKPYNEADCAVNEMRKPLQPFNNPELNSDSMT
LKHNLPQDSFDYQNRFRYQYDNLQFNHFSIQKLDQTIQARKQHDRVFAGFILHNIGTSAVVDIYIC
VEQGGEQNCKTKAGSFTILGGETEMPFHFDRLYKFDITSALHKLGVPLDGHGFDIKVDVRAVNGSH
LDQHILNEPSLLFVPGERKNIYY

DOMAIN E

DGLSQHNLVRKEVSSLTTLEKHFLRKALKNMQADDSPDGYQAIASFHALPPLCPSPSAAHRHACCL
HGMATFPQWHRLYTVQFEDSLKRHGSIVGLPYWDWLKPQSALPDLVTQETYEHLFSHKTFPNPFLK
ANIEFEGEGVTTERDVDAEHLFAKGNLVYNNWFCNQALYALEQENYCDFEIQFEILHNGIHSWVGG
SKTHSIGHLHYASYDPLFYIHHSQTDRIWAIWQALQEHRGLSGKEAHCALEQMKDPLKPFSFGSPY
NLNKRTQEFSKPEDTFDYHRFGYEYDSLEFVGMSVSSLHNYIKQQQEADRVFAGFLLKGFGQSASV
SFDICRPDQSCQEAGYFSVLGGSSEMPWQFDRLYKYDITKTLKDMKLRYDDTFTIKVHIKDIAGAE
LDSDLIPTPSVLLEEGK

DOMAIN F

HGINVRHVGRNRIRMELSELTERDLASLKSAMRSLQADDGVNGYQAIASFHGLPASCHDDEGHEIA
CCIHGMPVFPHWHRLYTLQMDMALLSHGSAVAIPYWDWTKPISKLPDLFTSPEYYDPWRDAVVNNP
FAKGYIKSEDAYTVRDPQDILYHLQDETGTSVLLDQTLLALEQTDFCDFEVQFEVVHNAIHYLVGG
RQVYALSSQHYASYDPAFFIHHSFVDKIWAVWQALQKKRKRPYHKADCALNMMTKPMRPFAHDFNH
NGFTKMHAVPNTLFDFQDLFYTYDNLEIAGMNVNQLEAEINRRKSQTRVFAGFLLHGIGRSADVRF
WICKTADDCHASGMIFILGGSKEMHWAYDRNFKYDITQALKAQSIHPEDVFDTDAPFFIKVEVHGV
NKTALPSSAIPAPTIIYSAGE

Fig. 11b

DOMAIN G

DHIAGSGVRKDVTSLTASEIENLRHALQSVMDDDGPNGFQAIAAYHGSPPMCHMPDGRDVACCTHG
MASFPHWHRLFVKQMEDALAAHGAHIGIPYWDWTSAFSHLPALVTDHEHNPFHHGHIAHRNVDTSR
SPRDMLFNDPEHGSESFFYRQVLLALEQTDFCQFEVQFEITHNAIHSWTGGHTPYGMSSLEYTAYD
PLFYLHHSNTDRIWAIWQALQKYRGFQYNAAHCDIQVLKQPLKPFSESRNPNPVTRANSRAVDSFD
YERLNYQYDTLTFHGHSISELDAMLQERKKEERTFAAFLLHGFGASADVSFDVCTPDGHCAFAGTF
AVLGGELEMPWSFERLFRYDITKVLKQMNLHYDSEFHFELKIVGTDGTELPSDRIKSPTIEHHGG

DOMAIN H (SEQ ID NO:158)

GHDHSERHDGFFRKEVGSLSLDEANDLKNALYKLQNDQGPNGYESIAGYHGYPFLCPEHGEDQYAC
CVHGMPVFPHWHRLHTIQFERALKEHGSHLGLPYWDW

NUCLEIC ACID MOLECULE COMPRISING A NUCLEIC ACID SEQUENCE WHICH CODES FOR A HAEMOCYANIN, AND COMPRISING AT LEAST ONE INTRON SEQUENCE

CROSS-REFERENCE TO RELATED APPLICATIONS

This application claims benefit of PCT application PCT/EP00/08129 filed 21 Aug. 2000 that claimed benefit of German application No. 199 39 578.0 filed 20 Aug. 1999.

BACKGROUND OF THE INVENTION

The present invention relates to a nucleic acid molecule comprising a nucleic acid sequence which codes for a haemocyanin, a haemocyanin domain or a fragment with the immunological properties of at least one domain of haemocyanin, and comprising at least one intron sequence, constructs which comprise such molecules, host cells which comprise the nucleic acid sequences or the constructs, processes for the preparation of haemocyanin polypeptides, and recombinant haemocyanin polypeptides.

Haemocyanin is a blue copper protein which occurs in a freely dissolved form in the blood of numerous molluscs and arthropods and transports oxygen. Of the molluscs, the cephalopods, chitons, most gastropods and some bivalves contain haemocyanin. Among the arthropods, haemocyanin is typical of arachnids, xiphosurans, malacostracan crustaceans and *Scutigera*. Numerous species of insects contain proteins which are derived from haemocyanin. Haemocyanins are present in the extracellular medium and float in the haemolymph.

While arthropod haemocyanin has a maximum diameter of 25 nm under an electron microscope and a subunit has a molecular weight of 75,000 Da, mollusc cyanins are much larger. Thus e.g. the haemocyanin of *Megathura* has a diameter of 35 nm and is composed of 2 subunits. Each subunit has a molecular weight of approx. 400,000 Da and is divided into eight oxygen-binding domains, each of which has a molecular weight of approx. 50,000. The domains differ immunologically. These domains can be liberated from the subunit by limited proteolysis.

The haemocyanin of gastropods visible under an electron microscope has a molecular weight of approx. 8 million Da and is a di-decamer. In contrast to this, the haemocyanin of cephalopods is arranged as an isolated decamer, which also differs significantly from the haemocyanin of gastropods in the quaternary structure.

The haemocyanin of the Californian keyhole limpet *Megathura crenulata* is of particular immunological interest. The haemocyanin is therefore also called keyhole limpet haemocyanin (KLH). Haemocyanins are very potent antigens. Immunization of a vertebrate leads to a non-specific activation of the immune system which to date is not very well understood. By the general activation of the immune system, it is then possible also to achieve an immune reaction to other foreign structures which have previously been tolerated. KLH is used above all as a hapten carrier in order thus to achieve the formation of antibodies against the hapten.

In addition to *Megathura crenulata*, the abalone *Haliotis tuberculata* also belongs to the Archaegastropoda group, which is relatively old in respect of evolution. It is known that *Haliotis* also produces haemocyanin.

KLH is a mixture of two different haemocyanins, which are called KLH1 and KLH2. The subunit of KLH1 is a 390 kDa polypeptide which consists of eight globular domains called 1 a to 1 h according to their sequence in the subunit. On the other hand, KLH2 has a molecular weight of 350 kDa and according to the most recent data also contains 8 domains, called 2 a to 2 h. In vivo every type of subunit forms homo-oligomers, while no hetero-oligomers have been observed.

Amino-terminal, internal and carboxy-terminal domains have been obtained by limited proteolysis and crossed immunoelectrophoresis of the subunit of KLH1 and KLH2, and their amino-terminal sequences has been determined (Söhngen et al., Eur. J. Biochem. 248 (1997), 602–614; Gebauer et al., Zoology 98(1994), 51–68). However, the resulting sequences do not allow designing of sequence-specific primers and/or probes which promise success for hybridization with genomic DNA. Although both KLH types have been known since 1991 and 1994 respectively, it has so far not been possible to clarify the primary structure.

At the DNA level, in respect of molluscs only the cDNA sequence of the haemocyanin subunit from the cephalopod *Octopus dofleini* is so far known (Miller et al., J. Mol. Biol. 278 (1998), 827–842). *Octopus dofleini* is phylogenetically very far removed from the archaegastropods. A haemocyanin gene sequence from molluscs is so far not known at all.

As described by Miller at al. supra, it is difficult both to isolate a single functional domain (functional unit=domain; also called functional domain) and to obtain tissue which is suitable for purification of mRNA for cDNA sequencing.

There is a further difficulty in the analysis of the haemocyanin from *Megathura crenulata* in that the test animals must have reached an age of 4 to 8 years for haemolymph to be taken from them in the first place. After the haemolymph has been taken, haemocyanin is not subsequently produced in these animals. It is not yet known how haemocyanin synthesis could be stimulated. Furthermore, culture of *Megathura* is extremely expensive, since special flow basins are required for this.

BRIEF SUMMARY OF THE INVENTION

It is therefore an object of the present invention to provide means and ways in order to be able to produce haemocyanin and/or domains thereof in a sufficient amount and inexpensively. This includes the further object of providing a process with which this haemocyanin can be prepared.

This object is achieved according to the invention by a nucleic acid molecule comprising a nucleic acid sequence which codes for a haemocyanin, a haemocyanin domain or a functional fragment thereof with the immunological properties of at least one domain of a haemocyanin, and comprising at least one intron sequence, the nucleic acid sequence being selected from (a) nucleic acid sequences which are selected from the group consisting of the DNA sequences shown below or the corresponding RNA sequences or which contain these:
SEQ ID NO:1 (HtH1 domain a+signal peptide),
SEQ ID NO:2 (HtH1 domain b),
SEQ ID NO:3 (HtH1 domain c),
SEQ ID NO:4 (HtH1 domain d),
SEQ ID NO:5 (HtH1 domain e),
SEQ ID NO:6 (HtH1 domain f),
SEQ ID NO:7 (HtH1 domain g),
SEQ ID NO: 8 (HtH1 domain h),
SEQ ID NO:9 (partial HtH2 domain b),
SEQ ID NO:10 (HtH2 domain c), SEQ ID NO:11 (HtH2 domain d),
SEQ ID NO:12 (HtH2 domain e),
SEQ ID NO:13 (HtH2 domain f),
SEQ ID NO:14 (HtH2 domain g),
SEQ ID NO:15 (HtH2 domain h),
SEQ ID NO:16 (partial KLH1 domain b),
SEQ ID NO:17 (KLH1 domain c),
SEQ ID NO:18 (KLH1 domain d),
SEQ ID NO:19 (partial KLH1 domain e),
SEQ ID NO:20 (KLH2 domain b),
SEQ ID NO:21 (KLH2 domain c),
SEQ ID NO:22 (partial KLH2 domain d),
SEQ ID NO:23 (KLH2 domain g),
SEQ ID NO:24 (partial KLH2 domain h),
SEQ ID NO:49 (HtH1 domain a'+signal peptide),
SEQ ID NO:50 (partial HtH2 domain a),
SEQ ID NO:51 (HtH2 domain b'),
SEQ ID NO:52 (HtH2 domain d'),
SEQ ID NO:53 (HtH2 domain e'),
SEQ ID NO:54 (KLH1 domain e'),
SEQ ID NO:55 (KLH1 domain f),
SEQ ID NO:56 (KLH1 domain g),
SEQ ID NO:57 (KLH2 domain b'),
SEQ ID NO:58 (KLH2 domain c'),
SEQ ID NO:59 (KLH2 domain d'),
SEQ ID NO:60 (KLH1 domain e),
SEQ ID NO:61 (KLH2 domain f),
SEQ ID NO:62 (KLH2 domain g'),
SEQ ID NO:80 (HtH1 domain a"+signal peptide),
SEQ ID NO:81 (HtH1 domain b"),
SEQ ID NO:82 (HtH1 domain c"),
SEQ ID NO:83 (HtH1 domain d"),
SEQ ID NO:84 (HtH1 domain e"),
SEQ ID NO:85 (HtH1 domain f'),
SEQ ID NO:86 (HtH1 domain g"),
SEQ ID NO:87 (HtH1 domain h"),
SEQ ID NO:88 (partial HtH2 domain a"),
SEQ ID NO:89 (HtH2 domain b"),
SEQ ID NO:90 (HtH2 domain c"),
SEQ ID NO:91 (HtH2 domain d"),
SEQ ID NO:92 (HtH2 domain e"),
SEQ ID NO:93 (HtH2 domain f'),
SEQ ID NO:94 (HtH2 domain g"),
SEQ ID NO:95 (HtH2 domain h"),
SEQ ID NO:96 (partial KLH1 domain b"),
SEQ ID NO:97 (KLH1 domain c"),
SEQ ID NO:98 (KLH1 domain d"),
SEQ ID NO:99 (KLH1 domain e"),
SEQ ID NO:100 (KLH1 domain f'),
SEQ ID NO:101 (KLH1 domain g"),
SEQ ID NO:102 (KLH2 domain b"),
SEQ ID NO:103 (KLH2 domain c"),
SEQ ID NO:104 (KLH2 domain d"),
SEQ ID NO:105 (KLH2 domain e"),
SEQ ID NO:106 (KLH2 domain f'),
SEQ ID NO:107 (KLH2 domain g"),
SEQ ID NO:108 (partial KLH2 domain h"),
SEQ ID NO:157 (complete HtH2 domain a), (b) nucleic acid sequences which hybridize with the counter-strand of a nucleic acid sequence according to (a) and code for a polypeptide which has the immunological properties of at least one domain of a haemocyanin;

(c) nucleic acid sequences which on the basis of the genetic code are degenerated to the DNA sequences defined under (a) and (b) and code for a polypeptide which has the immunological properties of at least one domain of a haemocyanin;

(d) nucleic acid sequences which hybridize with one of the nucleic acid sequences described under (a) to (c) and the counter-strand of which codes for a polypeptide which has the immunological properties of at least one domain of a haemocyanin;

(e) nucleic acid sequences which are at least 60% homologous to one of the nucleic acid sequences described under (a);

(f) variants of the sequences described under (a) to (e), the variants containing additions, deletions, insertions or inversions and coding for a polypeptide which has the immunological properties of at least one domain of haemocyanin; and (g) combinations of several of the DNA sequences described under (a) to (f).

Preferably, the intron sequence is selected from the following sequences:

(i) nucleic acid sequences which are selected from the group consisting of the DNA sequences shown below or the corresponding RNA sequences or which contain these:

SEQ ID NO:109 (HtH1 intron 1S-1/1S-2),
SEQ ID NO:110 (HtH1 intron 1S-2/1A-1),
SEQ ID NO:111 (HtH1 intron 1A-1/1A-2),
SEQ ID NO:112 (HtH1 intron 1A-2/1A-3),
SEQ ID NO:113 (HtH1 intron 1A-3/1A-4),
SEQ ID NO:114 (HtH1 intron 1A-4/1B),
SEQ ID NO:115 (HtH1 intron 1B/1C),
SEQ ID NO:116 (HtH1 intron 1C/1 D),
SEQ ID NO:117 (HtH1 intron 1D/1 E),
SEQ ID NO:118 (HtH1 intron 1E/1F-1),
SEQ ID NO:119 (HtH1 intron 1F-1/1F-2),
SEQ ID NO:120 (HtH1 intron 1F-2/1G-1),
SEQ ID NO:121 (HtH1 intron 1F-1/G-2),
SEQ ID NO:122 (HtH1 intron 1G-2/1G-3),
SEQ ID NO:123 (HtH1 intron 1G-3/1H),
SEQ ID NO:124 (intron in the 3'UTR of HtH1),
SEQ ID NO:125 (HtH2 intron 2A-1/2A-2),
SEQ ID NO:126 (HtH2 intron 2A-1/2A-3),
SEQ ID NO:127 (HtH2 intron 2A-1/2A-4),
SEQ ID NO:128 (HtH2 intron 2A4/2B),
SEQ ID NO:129 (HtH2 intron 2B/2C),
SEQ ID NO:130 (HtH2 intron 2C/2D),
SEQ ID NO:131 (HtH2 intron 2D/2E),
SEQ ID NO:132 (HtH2 intron 2E/2F-1),
SEQ ID NO:133 (HtH2 intron 2F-1/2F-2),
SEQ ID NO:134 (HtH2 intron 2F-2/2GF-1),
SEQ ID NO:135 (HtH2 intron 2G-1/2G-2),
SEQ ID NO:136 (HtH2 intron 2G-2/2G-3),
SEQ ID NO:137 (HtH2 intron 2G-3/2H),
SEQ ID NO:138 (intron in the 3'UTR of HtH2),
SEQ ID NO:139 (KLH1 intron 1B/1C),
SEQ ID NO:140 (KLH1 intron 1C/1D),
SEQ ID NO:141 (KLH1 intron 1D/1E),
SEQ ID NO:142 (KLH1 intron 1E/1F),
SEQ ID NO:143 (KLH1 intron 1F-1/1F-2),
SEQ ID NO:144 (KLH1 intron 1F-2/1G-1),
SEQ ID NO:145 (KLH1 intron 1G-1/1G-2),
SEQ ID NO:146 (KLH1 intron 1G-2/1G-3),
SEQ ID NO:147 (KLH2 intron 2B/2C),
SEQ ID NO:148 (KLH2 intron 2C/2D),
SEQ ID NO:149 (KLH2 intron 2D/2E),
SEQ ID NO:150 (KLH2 intron 2E/2F),
SEQ ID NO:151 (KLH2 intron 2F),
SEQ ID NO:152 (KLH2 intron 2F-2/2G),
SEQ ID NO:153 (KLH2 intron 2G-1/2G-2),
SEQ ID NO:154 (KLH2 intron 2G-2/2G-3),
SEQ ID NO:155 (KLH2 intron 2G/2H);

(ii) nucleic acid sequences which hybridize with the counter-strand of a nucleic acid sequence according to (i);

(iii) nucleic acid sequences which are at least 60% homologous to one of the nucleic acid sequences described under (i);

(iv) variants of the sequences described under (i) to (iii), the variants containing additions, deletions, insertions or inversions with respect to the sequences described under (i) to (iii); and (v) combinations of several of the DNA sequences described under (i) to (iv).

Some terms are explained in more detail below in order to clarify how they are to be understood in connection with the present application.

The term "haemocyanin" as used below in the description includes complete haemocyanin, haemocyanin domains and/or fragments, haemocyanin mutants and fusion proteins. In respect of fusion proteins, these include, in particular, those in which the fusion comprises haemocyanin and antigens.

"Domains" are understood as meaning functional partial sequences of the haemocyanin subunits which can be separated from one another, for example, by limited proteolysis. They can furthermore have different immunological properties.

The "immunological properties of at least one domain of haemocyanin" means the property of a polypeptide of inducing, in the same manner as at least one domain of haemocyanin, an immunological response of the recipient immunized with the polypeptide. "Immunological response" here is understood as meaning T and/or B cell responses to haemocyanin epitopes, such as, for example, an antibody production. The immunological reaction can be observed, for example, by immunization of a mammal, such as e.g. a mouse, a rat or a rabbit, with the corresponding polypeptide and comparison of the immune response to the polypeptide used for the immunization with the immune response to natural haemocyanins.

The term "intron sequence" refers either to a sequence interrupting an eukaryotic gene or to the corresponding sequence in the RNA transcript. The intron sequence(s) and the coding sequence(s) are transcribed together; the intron transcript or transcripts are then deleted to obtain the functional RNA.

According to the invention, the term "antigen" includes both haptens and weak and potent antigens. Haptens are characterized in that they are substances of low molecular weight (less than 4,000 Da), but without being coupled to a carrier molecule are not capable of inducing an immunological reaction. Weak antigens are substances which can themselves already induce an immunological reaction and of which the potential to be able to induce an immunological reaction can be increased further by coupling with a carrier molecule at the protein and/or DNA level.

"His tag" means a sequence of at least 6 histidine amino acids which, by corresponding cloning and fusion with an expressible sequence, leads to a fusion protein which has at least 6 His residues on the $NH_2$ terminus and can easily be purified by complexing with an $Ni^{2+}$ column.

"Cloning" is intended to include all cloning methods known in the prior art which could be employed here but which are not all described in detail because they belong to the obvious hand tools of the skilled person.

"Variants" of a nucleic acid sequences include additions, deletions, insertions or inversions and code for a polypeptide which has the immunological properties of at least one domain of a haemocyanin. Variants can be synthetic or natural. Allelic variants are an example of natural variants.

"Recombinant expression in a suitable host cell" is to be understood as meaning all the expression methods known in the prior art in known expression systems which could be employed here but which are not all described in detail because they belong to the obvious hand tools of the skilled person.

The nucleic acid sequence contained in the nucleic acid molecule according to the invention can be genomic DNA, cDNA or synthetic DNA, synthetic DNA sequences also being understood as meaning those which comprise modified internucleoside bonds. The nucleic acid sequences can furthermore be RNA sequences, which may be necessary e.g. for expression by means of recombinant vector systems. The nucleic acid sequences according to (b) are obtainable, for example, by using a detectably marked probe which corresponds to one of the sequences described under (a) or a fragment, or a counter-strand thereof for screening cDNA/genomic DNA libraries from molluscs or arthropods. The mRNA on which the cDNA library is based is preferably to be obtained from mollusc tissues which express haemocyanin to a particularly high degree, such as e.g. mantle tissue from gastropods and branchial gland tissue from cephalopods.

Positive genomic DNA clones are identified by standard methods. Cf. Maniatis et al., Molecular Cloning (1989) Cold Spring Harbor Laboratory Press.

In a preferred embodiment, the hybridization described under (b), (d) or (ii) is carried out under stringent conditions. Stringent hybridization conditions are e.g. 68° C. overnight in 0.5×SSC; 1% blocking reagent (Boehringer Mannheim); 0.1% sodium lauryl sarcosinate and subsequent washing with 2×SSC; 0.1% SDS.

In a preferred embodiment, nucleic acid molecules comprising a nucleic acid sequence which is at least 60% homologous to one of the nucleic acid sequences described under (a) are provided. Nucleic acid sequences which are at least 80% homologous to one of the nucleic acid sequences described under (a) are preferred. Nucleic acid sequences which are at least 90% homologous to one of the nucleic acid sequences described under (a) are particularly preferred. In particular, the nucleic acid sequences are at least 95% homologous to one of the nucleic acid sequences described under (a).

In a further preferred embodiment, nucleic acid sequences comprising at least one intron sequence which is at least 60% homologous to one of the nucleic acid sequences described under (i) are provided. Intron sequence(s) which are at least 80% homologous to one of the nucleic acid sequences described under (i) are preferred. Intron sequence(s) which are at least 90% homologous to one of the nucleic acid sequences described under (i) are particularly preferred. In particular, the intron sequence(s) are at least 95% to one of the nucleic acid sequences described under (i).

According to the invention, the term "homology" means homology at the DNA level, which can be determined by known methods, e.g. computer-assisted sequence comparisons (Basic local alignment search tool, S. F. Altschul et al., J. Mol. Biol. 215 (1990), 403–410).

The term "homology" known to the skilled person describes the degree to which two or more nucleic acid molecules are related, this being determined by the concordance between the sequences. The percentage of "homology" is obtained from the percentage of identical regions in two or more sequences, taking into account gaps or other sequence peculiarities.

The homology of nucleic acid molecules which are related to one another can be determined with the aid of known methods. As a rule, special computer programs with algorithms which take account of the particular requirements are employed.

Preferred methods for the determination of homology initially produce the greatest concordance between the sequences analysed. Computer programs for determination of the homology between two sequences include, but are not limited to, the GCG program package, including GAP (Devereux, J., et al., Nucleic Acids Research 12 (12): 387 (1984); Genetics Computer Group University of Wisconsin, Madison, (WI)); BLASTP, BLASTN and FASTA (Altschul, S. et al., J. Mol. Biol. 215:403410 (1990)). The BLASTX program can be obtained from the National Centre for Biotechnology Information (NCBI) and from other sources (BLAST Handbook, Altschul S., et al., NCB NLM NIH Bethesda Md. 20894; Altschul, S., et al., J. Mol. Biol. 215:403410 (1990)). The known Smith Waterman algorithm can also be used for determining homologies.

Preferred parameters for the comparison of nucleic acid sequences include the following:

| | |
|---|---|
| Algorithm: | Needleman and Wunsch, J. Mol. Biol 48:443–453 (1970) |
| Comparison matrix: | Concordance (matches) = +10<br>Non-concordance (mismatch) = 0 |
| Gap penalty: | 50 |
| Gap length penalty: | 3 |

The GAP program is also suitable for use with the above parameters. The above parameters are the default parameters for nucleic acid sequence comparisons.

Further algorithms, gap opening penalties, gap extension penalties and comparison matrices by way of example, including those mentioned in the Program Handbook, Wisconsin Package, version 9, September 1997, can be used. The choice depends on the comparison to be made and furthermore on whether the comparison is to be made between sequence pairs, in which case GAP or Best Fit are preferred, or between a sequence and a comprehensive sequence databank, in which case FASTA or BLAST are preferred.

A concordance of 60% determined with the abovementioned algorithm is designated 60% homology in the context of this application. The same applies accordingly to higher degrees of homology.

In a preferred embodiment, the DNA sequence according to the invention is a combination of several of the DNA sequences described under (a) to (f) and at least one intron sequence, and can be obtained by fusion and optionally cloning, which are known to the skilled person. These combinations are of particular interest, since the encoded polypeptides are particularly immunogenic. Combinations which contain several or all of the domains in the sequence (a to h) which occurs naturally in the subunit are particularly preferred. Embodiments in which, after deletion of the intron sequence(s), the nucleic acid sequences which code for the domains are coupled to one another directly in frame are particularly preferred.

Constructs which comprise the nucleic acid molecules according to the invention are furthermore provided. In a preferred embodiment, the construct according to the invention comprises a promoter which is suitable for expression, the nucleic acid sequence being under the control of the promoter. The choice of promoter depends on the expression system used for expression. Generally, constitutive promoters are preferred, but inducible promoters, such as e.g. the metallothionein promoter, are also possible.

In a further preferred embodiment, the construct furthermore comprises an antigen-coding nucleic acid sequence which is bonded directly to the haemocyanin nucleic acid according to the invention. The antigen-coding sequence can be located both 5' and 3' relative to the haemocyanin sequence or also on both ends. It either follows the haemocyanin sequence directly in the same reading frame, or is coupled to it by a nucleic acid linker, the reading frame being preserved. By fusion of the antigen-coding sequence with the haemocyanin sequence the formation of a fusion protein in which the antigen-coding sequence is bonded covalently to the haemocyanin sequence is intended. The antigen according to the invention is a medically relevant antigen, which is selected, for example, from: tumour antigens, virus antigens and antigens of bacterial or parasitic pathogens. Tumour antigens can be, for example, Rb and p53. The virus antigens preferably originate from immunologically relevant viruses, such as e.g. influenza virus, hepatitis virus and HIV. Pathogen antigens are, inter alia, those from mammalian pathogens, in particular organisms which are pathogenic to humans, such as e.g. *Plasmodium*. Bacterial antigens can originate e.g. from *Klebsiella, Pseudomonas, E. coli, Vibrio cholerae, Chlamydia, Streptococci* or *Staphylococci*.

In another preferred embodiment, the construct furthermore comprises at least a part of a vector, in particular regulatory regions, the vector being selected from: bacteriophages, such as λ derivatives, adenoviruses, vaccinia viruses, baculoviruses, SV40 viruses and retroviruses, preferably MoMuLV (Moloney murine leukaemia virus).

A construct which additionally comprises a His tag-coding DNA sequence, which, when expressed, leads to the formation of a fusion protein with a His tag on the $NH_2$ terminus of the haemocyanin, facilitating purification of the protein on a nickel column by chelate formation, is furthermore preferred.

The invention furthermore provides host cells which contain the construct and which are suitable for expression of the construct. Numerous prokaryotic and eukaryotic expression systems are known in the prior art, the host cells being selected, for example, from prokaryotic cells, such as *E. coli* or *B. subtilis*, from eukaryotic cells, such as yeast cells, plant cells, insect cells and mammalian cells, e.g. CHO cells, COS cells or HeLa cells, and derivatives thereof. For example certain CHO production lines of which the glycosylation patterns are altered compared with CHO cells are known in the prior art. The haemocyanins obtained using glycosylation-deficient or glycosylation-reduced host cells possibly have additional epitopes which are otherwise not accessible to the immune system of the recipient in the case of complete glycosylation, so that haemocyanins with a reduced glycosylation under certain circumstances have an increased immunogenicity. From plant cells transformed with the construct according to the invention it is possible to produce transgenic plants or plant cell cultures which produce haemocyanin polypeptides, for example tobacco, potato, tomato, sugar beet, soya bean, coffee, pea, bean, rape, cotton, rice or maize plants or plant cell cultures.

The present invention also relates to a process for the preparation of a haemocyanin polypeptide. For this, the nucleic acid molecule according to the invention and/or the construct is expressed in a suitable host cell and the protein is isolated from the host cell or the medium by means of conventional processes.

Numerous processes for expression of DNA sequences are known to the skilled person; compare Recombinant Gene Expression Protocols in Methods in Molecular Biology, volume 62, Humana Press Totowa N.J. (1995). The expression can be both constitutive and inducible, inducers such as, for example, IPTG and $Zn^{2+}$ being known to the skilled person. If a His tag has been fused on to the $NH_2$ terminus of the haemocyanin, the haemocyanin prepared can be purified by chelate formation on a nickel column. Processes for the purification of haemocyanin, in particular KLH, are to be found in Harris et al., Micron 26 (1995), 201–212. The haemocyanin is preferably purified by ion exchange chromatography and/or gel filtration chromatography. The procedure for these measures is known to the skilled person.

In another preferred embodiment, the haemocyanin prepared according to the invention is modified. The modifications include di-, oligo- and polymerization of the monomeric starting substance, for example by crosslinking, e.g. by means of dicyclohexylcarbodiimide or pegylation or association (self assembly). The di-, oligo- and polymers prepared in this way can be separated from one another by gel filtration. The formation of decamers, didecamers or multidecamers is intended in particular. Further modifications include side chain modifications, for example of ϵ-amino-lysine residues of the haemocyanin, or amino- or carboxy-terminal modifications. Modification of the haemocyanin by covalent bonding to an antigen is particularly preferred, it being possible for the antigen to be reacted stoichiometrically or non-stoichiometrically with the haemocyanin. The antigen is preferably selected from tumour antigens, virus antigens and pathogen antigens, as mentioned above. Further modifications include post-translational events, e.g. glycosylation or partial or complete deglycosylation of the protein.

In a preferred embodiment, the haemocyanin obtained by recombinant expression in prokaryotes or glycosylation-deficient eukaryotes is non-glycosylated. Haemocyanin which is glycosylated by recombinant expression in eukaryotes which are capable of glycosylation, such as yeast cells, plant cells, insect cells or mammalian cells, such as CHO cells or HeLa cells, is also possible according to the invention.

Haemocyanin polypeptides which comprise an amino acid sequence, the amino acid sequence being coded by one or more of the nucleic acid molecules according to the invention, are provided in another embodiment, Haemocyanin polypeptides which comprise at least one amino acid sequence selected from the following group:

SEQ ID NO:25 (HtH1 domain a+signal peptide),
SEQ ID NO:26 (HtH1 domain b),
SEQ ID NO:27 (HtH1 domain c),
SEQ ID NO:28 (HtH1 domain d),
SEQ ID NO:29 (HtH1 domain e),
SEQ ID NO:30 (HtH1 domain f),
SEQ ID NO:31 (HtH1 domain g),
SEQ ID NO:32 (HtH1 domain h),
SEQ ID NO:33 (partial HtH2 domain b),
SEQ ID NO:34 (HtH2 domain c),
SEQ ID NO:35 (HtH2 domain d),
SEQ ID NO:36 (HtH2 domain e),
SEQ ID NO:37 (HtH2 domain f),
SEQ ID NO:38 (HtH2 domain g),
SEQ ID NO:39 (HtH2 domain h),
SEQ ID NO:40 (partial KLH1 domain b),
SEQ ID NO:41 (KLH1 domain c),
SEQ ID NO:42 (partial KLH1 domain d),
SEQ ID NO:43 (partial KLH1 domain e),
SEQ ID NO:44 (KLH2 domain b),
SEQ ID NO:45 (KLH2 domain c),
SEQ ID NO:46 (partial KLH2 domain d),
SEQ ID NO:47 (KLH2 domain g),
SEQ ID NO:48 (partial KLH2 domain h),
SEQ ID NO:63 (HtH1 domain a'+signal peptide),
SEQ ID NO:64 (HtH1 domain h'),
SEQ ID NO:65 (partial HtH2 domain a),
SEQ ID NO:156 (complete HtH2 domain a),
SEQ ID NO:66 (HtH2 domain b'),
SEQ ID NO:67 (HtH2 domain d'),
SEQ ID NO:68 (HtH2 domain e'),
SEQ ID NO:69 (partial KLH1 domain b'),
SEQ ID NO:70 (KLH1 domain e'),
SEQ ID NO:71 (KLH1 domain f),
SEQ ID NO:72 (KLH1 domain g),
SEQ ID NO:73 (KLH1 domain h),
SEQ ID NO:74 (KLH2 domain b'),
SEQ ID NO:75 (KLH2 domain c'),
SEQ ID NO:76 (KLH2 domain d'),
SEQ ID NO:77 (KLH2 domain e),
SEQ ID NO:78 (KLH2 domain f),
SEQ ID NO:79 (KLH2 domain g'),
SEQ ID NO:158 (partial KLH2 domain h), or a fragment of one of these sequences which has the immunological properties of at least one domain of haemocyanin are preferred.

The invention also includes haemocyanin polypeptides of which the sequence shows at least 60% or 70%, preferably at least 80%, particularly preferably at least 90% or 95% homology to one of the amino acid sequences according to SEQ ID NO:25 to 48 and SEQ ID NO:63 to 79 over a partial region of at least 90 amino acids.

In this connection, the expression "at least 70%, preferably at least 80%, particularly preferably at least 90% homology" relates to concordance at the amino acid sequence level, which can be determined by known methods, e.g. computer-assisted sequence comparisons (Basic local alignment search tool, S. F. Altschul et al., J. Mol. Biol. 215 (1990), 403–410).

The term "homology" known to the skilled person describes here the degree to which two or more polypeptide molecules are related, this being determined by the concordance between the sequences, concordance being understood as meaning both identical concordance and conservative amino acid exchange. The percentage of "homology" is obtained from the percentage of regions in concordance in two or more sequences, taking into account gaps or other sequence peculiarities.

The expression "conservative amino acid exchange" relates to an exchange of an amino acid residue for another amino acid residue, where the exchange does not lead to a change in polarity or charge. An example of a conservative amino acid exchange is the exchange of a non-polar amino acid residue for another non-polar amino acid residue.

The homology of polypeptide molecules which are related to one another can be determined with the aid of known methods. As a rule, special computer programs with algorithms which take account of the particular requirements are employed. Preferred methods for the determination of homology initially produce the greatest concordance between the sequences analysed. Computer programs for determination of the homology between two sequences include, but are not limited to, the GCG program package, including GAP (Devereux, J., et al., Nucleic Acids Research 12 (12): 387 (1984); Genetics Computer Group University of Wisconsin, Madison, (WI)); BLASTP, BLASTN and FASTA (Altschul, S. et al., J. Molec. Biol 215:403/410 (1990)). The BLAST X program can be obtained from the National Centre for Biotechnology Information (NCBI) and from other sources (BLAST Handbook, Altschul S., et al., NCB NLM NIH Bethesda Md. 20894; Altschul, S., et al., J. Mol. 215:403/410 (1990)). The known Smith Waterman algorithm can also be used for determining homology.

Preferred parameters for the sequence comparison include the following:

| | |
|---|---|
| Algorithm: | Needleman and Wunsch, J. Mol. Biol 48:443–453 (1970) |
| Comparison matrix: | BLOSUM 62 of Henikoff and Henikoff, Proc. Natl. Acad. Sci. USA 89:10915-10919 (1992) |
| Gap penalty: | 12 |
| Gap length penalty: | 4 |
| Similarity threshold: | 0 |

The GAP program is also suitable for use with the above parameters. The above parameters are the standard parameters (default parameters) for amino acid sequence comparisons where gaps at the ends do not reduce the homology value. If sequences are very short compared with the reference sequence, it may furthermore be necessary to increase the expected value to up to 100,000 and where appropriate to reduce the word size down to 2.

Further algorithms, gap opening penalties, gap extension penalties and comparison matrices by way of example, including those mentioned in the Programm-Handbuch, Wisconsin-Paket [Program Handbook, Wisconsin Package], version 9, September 1997, can be used. The choice depends on the comparison to be made and furthermore on whether the comparison is to be made between sequence pairs, in which case GAP or best fit are preferred, or between a sequence and a comprehensive sequence database, in which case FASTA or BLAST are preferred.

A concordance of 60% determined with the above mentioned algorithm is designated 60% homology in the context of this Application. The same applies accordingly to higher degrees of homology.

In another embodiment, the invention provides haemocyanin polypeptides which are obtainable by the recombinant preparation method or modifications thereof.

Preferred haemocyanin polypeptides are those which comprise each of the sequences SEQ ID NO: 25 to 32, it being possible for the sequence with SEQ ID NO:25 to be replaced by SEQ ID NO:63 and/or SEQ ID NO:32 to be replaced by SEQ ID NO:64.

Haemocyanin polypeptides which are also preferred are those which comprise either the sequences SEQ ID NO: 33 to 39 or the sequences SEQ ID NO:65, 66, 34–39, it being possible for SEQ ID NO:35 to be replaced by SEQ ID NO:67 and/or SEQ ID NO:36 to be replaced by SEQ ID NO:68. These haemocyanin polypeptides are particularly preferably haemocyanin 1 or 2 from Haliotis tuberculata.

Haemocyanin 1 from Haliotis tuberculata, which has an apparent molecular weight of 370 kDa in SDS-PAGE under reducing conditions, is particularly preferred. Haemocyanin 2 from *Haliotis tuberculata*, which has an apparent molecular weight of 370 kDa in SDS-PAGE under reducing conditions, is furthermore particularly preferred. The haemocyanins are obtainable from whole haemocyanin from *Haliotis tuberculata* by the selective dissociation process described in the examples.

Haemocyanin polypeptides which are furthermore preferred are those which comprise each of the sequences SEQ ID NO: 40 to 43 or the sequences SEQ ID NO:40 to 43 and SEQ ID NO:71 to 73, it being possible in each case for the sequence with SEQ ID NO:40 to be replaced by SEQ ID NO:66 and/or SEQ ID NO:43 to be replaced by SEQ ID NO:70. Haemocyanin polypeptides which are also preferred are those which comprise either each of the sequences SEQ ID NO: 44 to 48 or the sequences SEQ ID NO:44 to 46, 77, 78, 47, 48, it being possible in each case for the sequence with SEQ ID NO:44 to be replaced by SEQ ID NO:74, SEQ ID NO:45 to be replaced by SEQ ID NO:75, SEQ ID NO:46 to be replaced by SEQ ID NO:76 and/or SEQ ID NO:47 to be replaced by SEQ ID NO:79.

These haemocyanin polypeptides are particularly preferably complete haemocyanin 1 (KLH1) or 2 (KLH2) from *Megathura crenulata.*

Non-glycosylated and glycosylated haemocyanin polypeptide obtainable by expression in host cells which are capable or incapable of glycosylation is furthermore provided. Depending on the envisaged use of the haemocyanin polypeptide, the glycosylation pattern of yeast, in particular methylotrophic yeast, of plant cells or of COS or HeLa cells can be preferred.

The invention furthermore relates to pharmaceutical compositions which comprise the nucleic acid molecules according to the invention and physiologically tolerated additives known in the prior art. The pharmaceutical compositions are preferably employed for non-specific immunostimulation in the form of a gene therapy, haemocyanin polypeptides being expressed after transformation with a suitable vector and serving to antigenize the tissue.

In particular, the invention provides the use of a nucleic acid molecule according to the invention which is bonded to an antigen-coding DNA sequence for specific immunization against this antigen. Without being bound to this theory, the immunization here is based on non-specific stimulation of the immune system by haemocyanin polypeptide epitopes and more extensive specific immunization by recognition of antigen epitopes by the immune system.

Such an immunization is particularly valuable in respect of pathogen antigens, and especially in respect of tumour antigens. The usability of the pharmaceutical composition according to the invention for treatment of tumour diseases also results from the cross-reactivity of the haemocyanin-specific antibodies with carbohydrate residues, which occur on the surface of tumours, such as e.g. the Thomsen-Friedenreich antigen, which occurs in the majority of human tumours, such as epithelial carcinomas, ovarian carcinoma, colorectal carcinoma, mammary carcinoma, bronchial carcinoma and bladder carcinoma.

The pharmaceutical compositions according to the invention can furthermore be employed for treatment of parasitic diseases, such as schistosomiasis, and for prevention of cocaine abuse.

Pharmaceutical compositions which comprise a haemocyanin polypeptide according to the invention in combination with one or more physiologically tolerated additives are provided as a further embodiment of the present invention. As already mentioned above, such a haemocyanin polypeptide can consist of a complete haemocyanin subunit, of one or more domains and of one or more fragments of such domains, provided that these fragments still have the immunological properties of at least one domain of a haemocyanin. Such a pharmaceutical composition is suitable e.g. as an antiparasitic composition, antivirus composition or antitumour composition due to either the non-specific immunostimulation, which is to be attributed solely to the haemocyanin, or due to the specific immune reaction to antigens associated with the haemocyanin. It can thus be employed e.g. for treatment of schistosomiasis, epithelial carcinomas, ovarian carcinoma, colorectal carcinoma, mammary carcinoma, bronchial carcinoma and bladder carcinomas, but is also suitable for treatment of high blood pressure. The treatment of high blood pressure is achieved by carrying out an immunization with the aid of haemocyanin-β-adrenergic receptor peptide constructs and/or fusion proteins.

In another embodiment, the pharmaceutical compositions according to the invention are used as vaccines. They can thus make a valuable contribution to the prophylaxis of diseases caused by known pathogens. This applies in particular to pharmaceutical compositions in which a haemocyanin polypeptide is coupled to a virus, virus constituent, killed bacteria, bacteria constituents, in particular surface proteins from virus or bacteria envelopes, DNA, DNA constituents, inorganic or organic molecules, e.g. carbohydrates, peptides and/or glycoproteins.

According to another preferred embodiment, the pharmaceutical composition according to the invention is used for prevention of cocaine abuse.

Liposomes are particularly suitable for administration both of the nucleic acid molecules according to the invention and of the haemocyanin polypeptides. The present invention accordingly relates to liposomes which comprise a nucleic acid molecule according to the invention, a construct according to the invention or a haemocyanin polypeptide according to the invention.

Various methods for the preparation of liposomes which can be used for pharmaceutical purposes are known to the skilled person. The selectivity of the liposomes comprising the nucleic acid molecules or haemocyanin polypeptides according to the invention can be increased by the additional incorporation into the liposome of cell recognition molecules, which bind selectively to target cells. Receptor ligands which bind to receptors of the target cells or, especially in the case of tumours, antibodies directed against surface antigens of the particular target cells envisaged are particularly suitable for this.

The haemocyanin polypeptides according to the invention are furthermore envisaged as carrier molecules for medicaments, such as e.g. cytostatics. The increase in the molecular weight prolongs the physiological half-life of the medicaments considerably since the loss due to ultrafiltration in the kidneys is significantly reduced.

The vaccines are formulated by methods known to the skilled person; in some embodiments the additional use of adjuvants, such as e.g. Freund's adjuvant or polysaccharides, is envisaged.

The invention furthermore provides antibodies which react specifically with the haemocyanin polypeptide according to the invention and are obtainable by immunization of a test animal with a haemocyanin polypeptide. Polyclonal antibodies can be obtained by immunization, for example, of rabbits and subsequent isolation of antisera. Monoclonal antibodies can be obtained by standard methods by immunization of e.g. mice, isolation and immortalization of the spleen cells and cloning of the hybridomas which produce antibodies specific for haemocyanin.

A screening method for identification of tumour-specific DNA in a cell is furthermore provided, this comprising the steps:

a) bringing cell DNA and/or cell protein into contact with a probe comprising the nucleic acid molecule according to the invention and/or the antibody according to the invention and
b) detecting the specific binding.

The tumour to be detected is preferably a bladder carcinoma, epithelial carcinoma, ovarian carcinoma, mammary carcinoma, bronchial carcinoma or colorectal carcinoma.

It is intended to illustrate the invention with the following figures and examples, but not to limit this in any way. Further embodiments, which are also included, are accessible to the skilled person on the basis of the description and the examples.

BRIEF DESCRIPTION OF THE SEVERAL VIEWS OF THE DRAWING(S)

FIG. 1 shows the characterization and purification of *Haliotis tuberculata* haemocyanin (HtH):

(a) Electron microscopy of negatively stained whole HtH, which has been purified by ultracentrifugation of cell-free haemolymph;
(b) SDS polyacrylamide gel electrophoresis (7.5% polyacrylamide) of HtH1 compared with KLH (MW 370 kDa);
(c) Native polyacrylamide gel electrophoresis (5% polyacrylamide) of the HtH subunit preparation, the anode being at the lower edge;
(d) Crossed immunoelectrophoresis of the two HtH subunits using anti-HtH antibodies from the rabbit;
(e) Electron microscopy of the remaining HtH1 didecamers (white arrows) after selective dissociation of HtH2 (black arrows);
(f) Elution profile of the gel filtration chromatography (Biogel A15m) in the presence of ammonium molybdate/polyethylene glycol solution (pH 5.9) after selective dissociation of HtH2 into its subunit and subsequent concentration of HtH1 by ultracentrifugation;
(g) Native polyacrylamide gel electrophoresis (6.5% polyacrylamide) of HtH1 and HtH2 subunits purified by gel chromatography compared with the starting material;
(h,i) Crossed immunoelectrophoresis of chromatographically purified HtH subunits; and
(j,m) Crossed immunoelectrophoresis of the purified HtH subunits using anti-KLH antibodies from the rabbit which are specific for KLH1 and KLH2.

FIG. 2 shows the analysis of the subunit organization of HtH1, anti-HtH1 antibodies from the rabbit having been used for the immunoelectrophoresis and the anode being on the left-hand side;

(a) Crossed immunoelectrophoresis after limited proteolysis of HtH1 with the aid of elastase;
(b) SDS polyacrylamide gel electrophoresis (7.5% polyacrylamide) of the elastase-cleaved HtH1 subunit;
(c,d,g–j,l,n,p) Crossed immunoelectrophoresis of the elastase cleavage products of the HtH1 subunit;
(e) Crossed immunoelectrophoresis after limited proteolysis of HtH1 with the aid of V8 protease;
(f) SDS polyacrylamide gel electrophoresis (7.5% polyacrylamide) of the V8 protease-cleaved HtH1 subunit;
(k,m,o) Crossed immunoelectrophoresis after limited proteolysis of HtH1 with the aid of the three stated proteases.

FIG. 4 shows the genomic sequence of the HtH1 gene.

FIG. 5 shows the primary structure deduced for the HtH1 protein.

FIG. 6 shows the genomic sequence of the HtH2 gene.

FIG. 7 shows the primary structure deduced for the HtH2 protein.

FIG. 8 shows the genomic sequence of the KLH1 gene.

FIG. 9 shows the primary structure deduced for the KLH1 protein.

FIG. 10 shows the genomic sequence of the KLH2 gene.

FIG. 11 shows the primary structure deduced for the KLH2 protein.

DETAILED DESCRIPTION OF THE INVENTION

Examples

Material and Methods

Figures 1A, 1B, 1C, 1D, 1E, 1F:
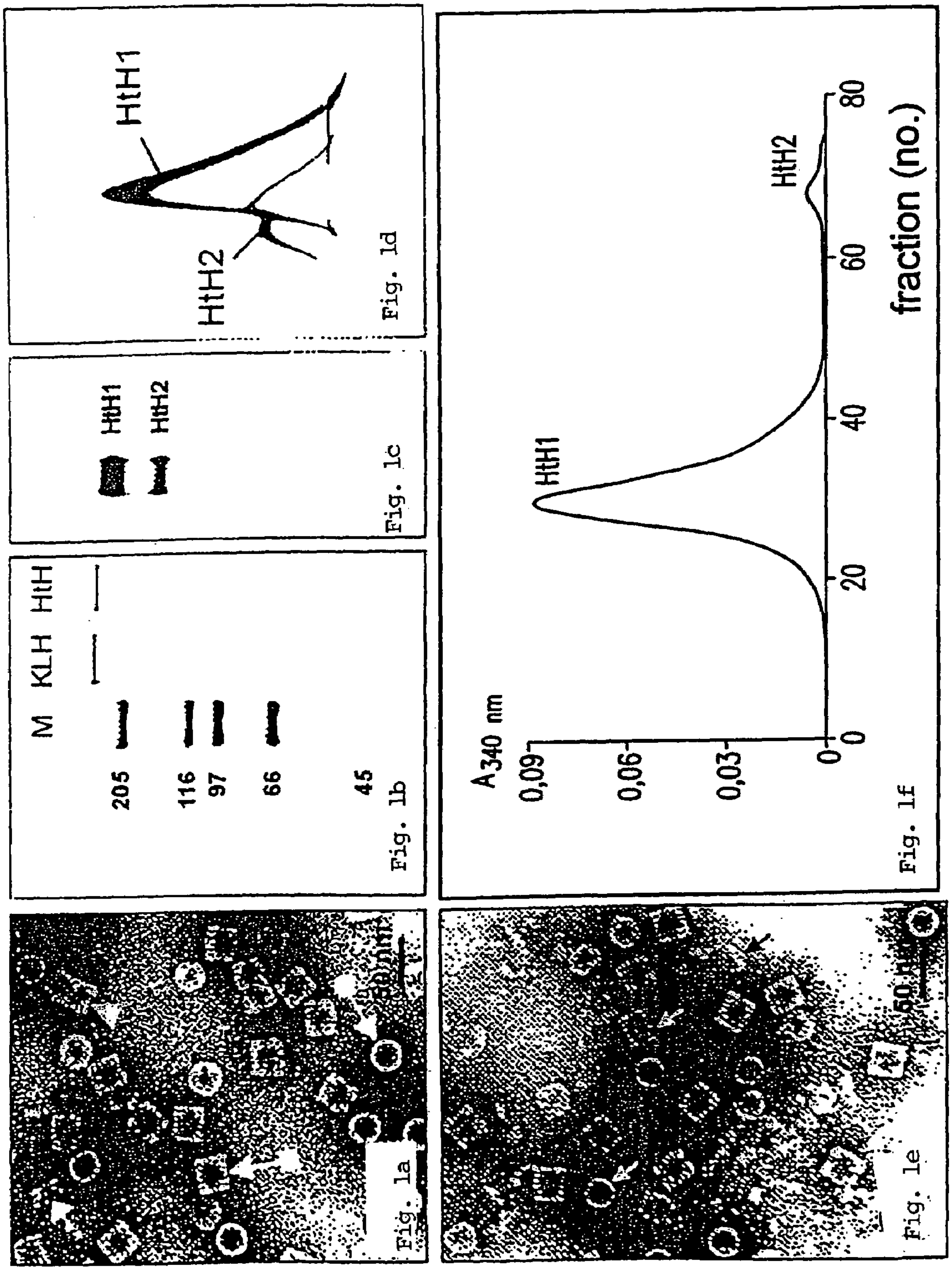

1. Preparation of the Haemolymph and Isolation of Haemocyanin

Individuals of the European abalone *Haliotis tuberculata* from the French Atlantic coast region were provided by S.M.E.L (Blainville sur Mer, France) and Biosyn (Fellbach, Germany). The animals were kept in a 300 l sea-water aquarium at 17° C. and fed with brown algae. For removal of the haemolymph, the abalones were placed on ice in a closed plastic bag. After one hour, large volumes of haemolymph had been secreted through their skin. It emerged that the haemocyanin obtained by this process is identical to the haemocyanin which could be collected by cutting a hollow in the foot of cooled-down sea snails using a scalpel blade. The blood cells were separated from the haemolymph by centrifugation at 800 g for 30 min at 4° C. The whole haemocyanin was then immediately sedimented by preparative ultracentrifugation at 30,000 g for 4 hours at 4° C. The supernatant was discarded and the blue haemocyanin pellet was suspended overnight in "stabilization buffer" (0.05 M Tris, 5 mM $CaCl_2$, 5 mM $MgCl_2$, 0.15 M NaCl, 1 mM PMSF, pH 7.4) and stored at 4° C.

Using the process described by Harris et al., 1995, supra, intact HtH1 was obtained from the whole HtH by selective dissociation of HtH2 in ammonium molybdate/polyethylene glycol (1%/0.2%) solution, pH 5.9 and subsequent ultracentrifugation. The partly purified HtH1 pellet formed was dissolved and purified to homogeneity by gel filtration on a Biogel A15m device. The last step resulted in small amounts of purified HtH2. Native HtH1 and HtH2 was dissociated quantitatively into the subunits by dialysis against "dissociation buffer" (0.13 M glycine/NaOH, pH 9.6) at 4° C. overnight; the presence of EDTA was not necessary. 1 mM PMSF was added at each stage of the purification to inhibit proteolysis.

2. Electron Microscopy

Conventional "negative staining" was carried out by the individual drop method (Harris and Horne in Harris, J. R. (editors) Electron microscopy in biology, (1991), IRL Press Oxford, p. 203–228). Carbon carrier films were initially subjected to glow discharge for 20 seconds to render them hydrophilic and adsorptive for the protein. The protein samples are allowed to adsorb on to the carbon films for 60 seconds. The buffer salts are then removed by sequential washing with four successive 20 µl drops of water.

Finally, the gratings are negatively stained with a 20 µl drop of 5% aqueous ammonium molybdate containing 1% trehalose (pH 7.0) and left to dry at room temperature. A Zeiss EM 900 transmission electron microscope is used for the electron microscopy analysis.

3. Polyacrylamide Gel Electrophoresis and Immunoelectrophoresis

SDS polyacrylamide gel electrophoresis (SDS-PAGE) was carried out by the method of Laemmli (Nature 227 (1970), 670–685). An alkaline system according to Markl et al. (1979) J. Comp. Physiol. 133 B, 167–175 with a 0.33 M Tris/borate, pH 9.6 as the gel buffer and 0.065 M Tris/borate, pH 9.6 as the electrode buffer was used for the native PAGE. Crossed and "crossed-line" immunoelectrophoresis (1E) were carried out in accordance with Weeke (Scand. J. Immunol. 2 (1973), Suppl. 1, 47–56) or Kroll (Scand. J. Immunol. 2, Suppl. 1 (1973), 79–81). Rabbit antibodies against dissociated whole HtH and purified HtH1 were produced by Charles River Deutschland (Kisslegg, Germany). The immunization process was carried out in accordance with Marki and Winter (J. Comp. Physiol. 159B (1989), 139–151).

4. Limited Proteolysis and Isolation of the Fragments

The limited proteolysis was carried out at 37° C. in 0.13 M glycine/NaOH, pH 9.6 by addition of one of the following enzymes (Sigma, Deisenhofen, Germany), which were dissolved in 0.1 M $NH_4HCO_3$, pH 8.0: *Staphylococcus aureus* V8 protease type XVII (8400), papain type II from papaya milk (P-3125), bovine pancreas elastase type IV (E-0258), chymotrypsin and trypsin. The haemocyanin concentration was between 1 and 10 mg/ml. The final concentration of the enzyme was 2% (weight/weight). The proteolysis was ended after 5 hours by freezing to −20° C. The HPLC process was carried out on a device from Applied Biosystems (BAI, Bensheim, Germany) equipped with a model 1000S Diode Array detector. The proteolytic fragments were introduced on to a small Mono-Q anion exchanger column (Pharmacia, Freiburg, Germany), which had been equilibrated with 0.02 M Tris/HCl, pH 8.0, and were eluted with a linear sodium chloride gradient (0.0 M–0.5 M CaCl) in the same buffer at a flow rate of 1 ml/min. Alternatively, the proteolytic fragments were isolated by cutting out the bands from native PAGE gels (Markl et al., 1979) J. Comp. Physiol. 133 B, 167–175, after they had first been inversely stained with the Roti-White system (Roth, Karlsruhe, Germany) in accordance with Fernandez-Patron et al. (1995) Anal. Biochem. 224, 203–211. For subsequent cleavage with a second enzyme, the fragments isolated were first dialysed overnight against 0.13 M glycine/NaOH, pH 9.6 to remove NaCl.

5. Amino Acid Sequence Analysis

The proteins obtained by the HPLC process were denatured in SDS-containing sample buffer and separated by SDS-PAGE (Laemmli, 1970, supra; 7.5% polyacrylamide). To prevent blocking of the $NH_2$ terminus, 0.6% (weight/weight) thioglycollic acid was added to the cathode buffer (Walsh et al., Biochemistry 27 (1988), 6867–6876). The protein bands were transferred by electro-transfer to ProBlot membranes (Applied Biosystems, Germany) in a vertical blotting chamber (25 mM borate buffer, pH 8.8, containing 2 mM EDTA; 10 min/100 mA, 15 min/200 mA, 12 h/300 mA). Detection of the individual polypeptides on the membranes was carried out with Ponceau S stain. The polypeptide bands of interest were cut out and sequenced in a 477A protein sequencing device from Applied Biosystems. The amounts of polypeptides applied to the sequencing device were in the lower pmol range.

6. cDNA Cloning and Sequence Analysis

A lambda-cDNA expression library was established from poly($A^+$)—RNA from Haliotis mantle tissue using the vector Lambda ZAP Express® in accordance with the manufacturer's instructions (Stratagene, Heidelberg, Germany). The clones were isolated using HtH-specific rabbit antibodies. The nucleotide sequencing was carried out on both strands using the Taq Dye deoxy Terminator® system. The sequences were arranged with the software CLUSTAL W (1.7)® and TREEVIEW® (Thompson et al., Nucl. Acids Res. 22 (1994), 4673–4680).

Example 1

Isolation of HtH and Separation of Two Different Types (HtH1 and HtH2)

The haemolymph was obtained from adult abalones. The blood cells were removed by centrifugation and the haemocyanin was then sedimented by ultracentrifugation. The blue haemocyanin pellet was dissolved again in "stabilization buffer" (pH 7.4) and examined by electron microscopy (FIG. 1*a*). It comprised mainly typical di-decamers, accompanied by a small content of decamers and tridecamers. Denaturing in 2% SDS in the presence of reducing substances and subsequent SDS-PAGE separation resulted in a single band, which corresponded to the polypeptide with an apparent molecular weight of 370 kDa, which is only slightly below the apparent subunit weight of KLH (FIG. 1*b*). Complete dissociation of the oligomers and of the di-decamers into the native polypeptides (subunits) was achieved by overnight dialysis of HtH against "dissociation buffer" (pH 9.6). The native PAGE method, which was used on these samples, showed a main and a secondary component (FIG. 1*c*). Crossed immunoelectrophoresis (crossed IE) using polyclonal rabbit antibodies generated against purified whole HtH showed two components which are immunologically different but show the classical reaction of being partly immunologically identical (FIG. 1*d*). Their preparative isolation (FIGS. 1*e–i*) showed that they are subunits of two different HtH types, called HtH1 and HtH2, and the patterns of the native PAGE and crossed IE methods could be assigned to each individually (FIG. 1*c, d*).

Figures 1G, 1H, 1I, 1J, 1K, 1L, 1M:
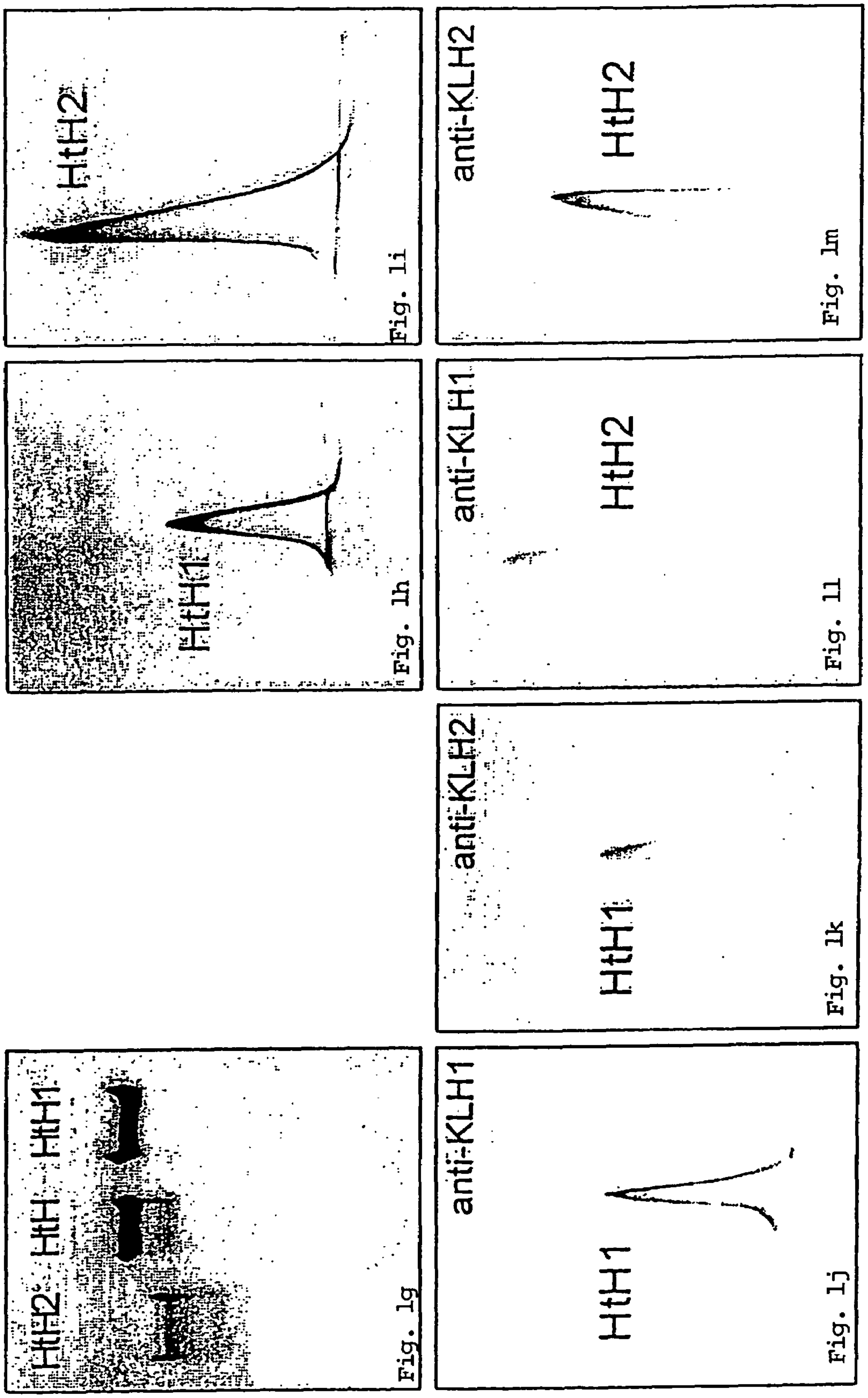

The separation of HtH1 and HtH2 was carried out by the method of selective dissociation according to Harris et al., 1995, supra. In ammonium molybdate/polyethylene glycol, HtH1 in the oligomer state (di-decamer) was completely stable, while HtH2 dissociated completely into the subunits (FIG. 1*e*). This allowed quantitative sedimentation of HtH1 in an ultracentrifuge, while the majority of the HtH2 remained in the supernatant. Large amounts of HtH1 were purified to homogeneity from the redissolved pellet by gel filtration chromatography, which also resulted in small amounts of pure HtH2 (FIG. 1*f*). The fractions were investigated by native PAGE (FIG. 1*g*) and crossed IE (FIG. 1*h, i*). The process of selective dissociation of HtH2 removed all the tri-decamer from the samples, which suggests that the latter are built up from HtH2, but not from HtH1 (FIG. 1*e*). The selective dissociation behaviour of HtH2 and also the ability to form aggregates which are larger than in vivo di-decamers correspond to the properties of KLH2. Conversely, the stability of HtH1 under these conditions and its inability to assemble into aggregates larger than di-decamers resemble the behaviour of KLH1. This feature of being related is demonstrated further by the reaction of anti-KLH1 and anti-KLH2 antibodies against the two HtH types (FIG. 1*j–m*).

Example 2

Analysis of the Organization of the HtH1 Subunit

Figures 2A, 2B, 2C, 2D, 2E, 2F, 2G, 2H:
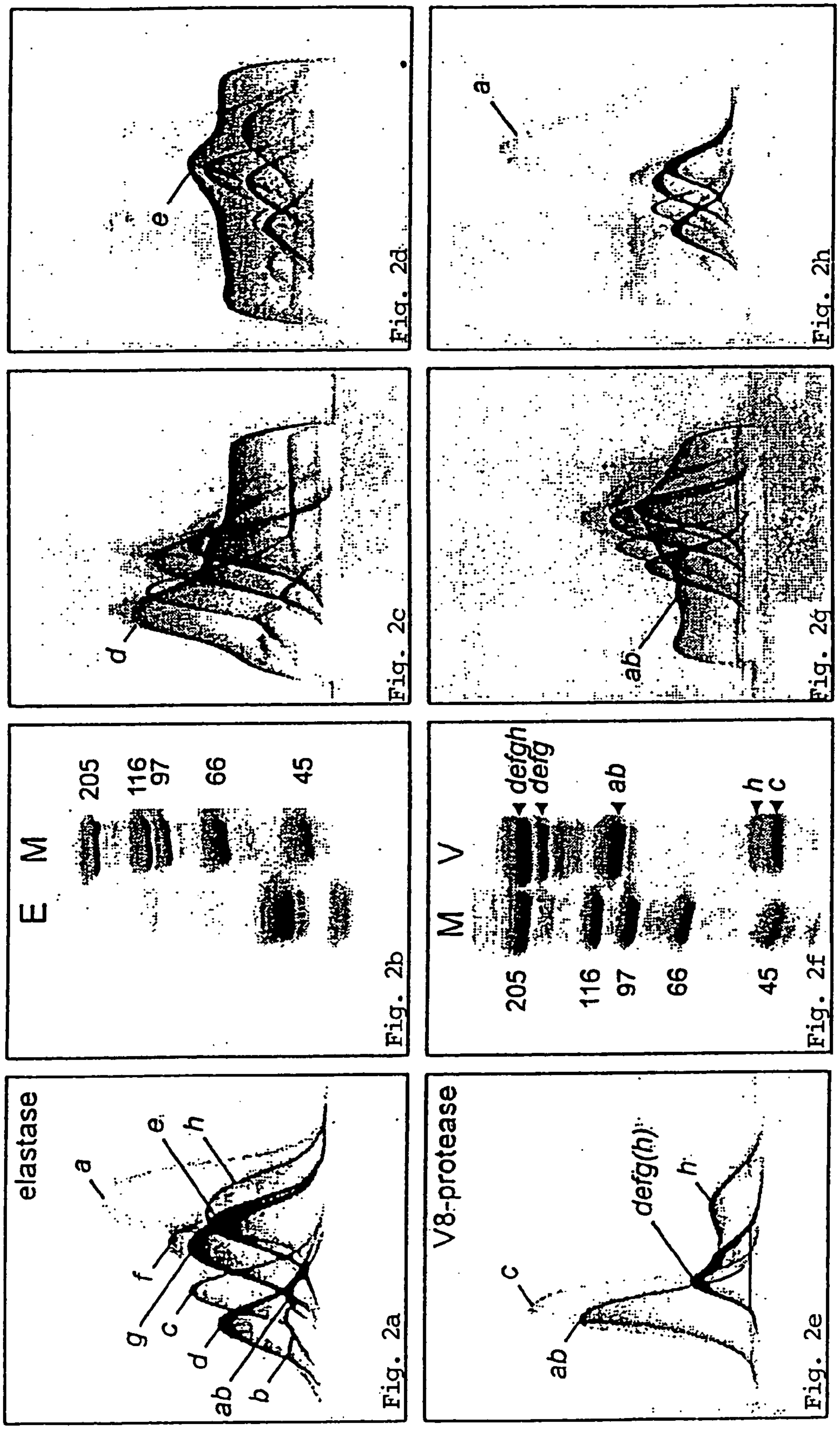

The eight functional units (FUs, often called "functional domains") which form a mollusc haemocyanin subunit differ in primary structure and show no immunological cross-reactivity, as emerged from crossed IE. In the case of the purified HtH1 subunit (FIG. 1*g, h*), small concentrations of five different proteases (elastase, V8 protease, papain, trypsin and chymotrypsin) which had cleaved the peptide bonds between adjacent FUs of KLH1 and KLH2 were used (Gebauer et al., 1994, supra, Söhngen et al., 1997, supra). The cleavage products were investigated by crossed IE and SDS-PAGE (FIG. 2). Elastase treatment produces eight individual FUs, deduced from the number of different immunoprecipitation peaks in the crossed IE (FIG. 2*a*) and with the apparent molecular weight of approx. 50 kDa of the main portion of the cleavage products in SDS-PAGE (FIG. 2*b*). A further precipitation peak was recognized as FU dimer, which was formed by incomplete cleavage of the segment ab (FIG. 2*a*). By an HPLC process with a Mono-Q column (FIG. 3*a*), two of the elastase cleavage products were obtained in a sufficient purity to allow their clear assignment to two of the eight precipitation peaks (FIG. 2*c, d*) by "crossed-line IE". The other four proteases had different cleavage patterns, which comprised mixtures of individual FUs and larger fragments containing two, three or more FUs (e.g. FIG. 2*e, f*). Many of them were concentrated to a sufficient amount by the HPLC process (FIGS. 3*b–e*) to allow their identification in their corresponding SDS-PAGE and crossed IE patterns. A number of these components were sequenced N-terminally by blot transfer of SDS gels on ProBlot® membranes (Table 1). The results were compared with the N-terminal sequences which had been obtained from the apparently orthologous protein in Megathura crenulata, KLH1 (Table I), the complete FU arrangement of which is available (Söhngen et al., 1997, supra; cf. FIG. 5*b*). The result of the entire batch led to the determination of the complete FU arrangement within the HtH1 subunit (FIG. 2*a*).

Figures 2I, 2J, 2K, 2L, 2M, 2N, 2O, 2P:
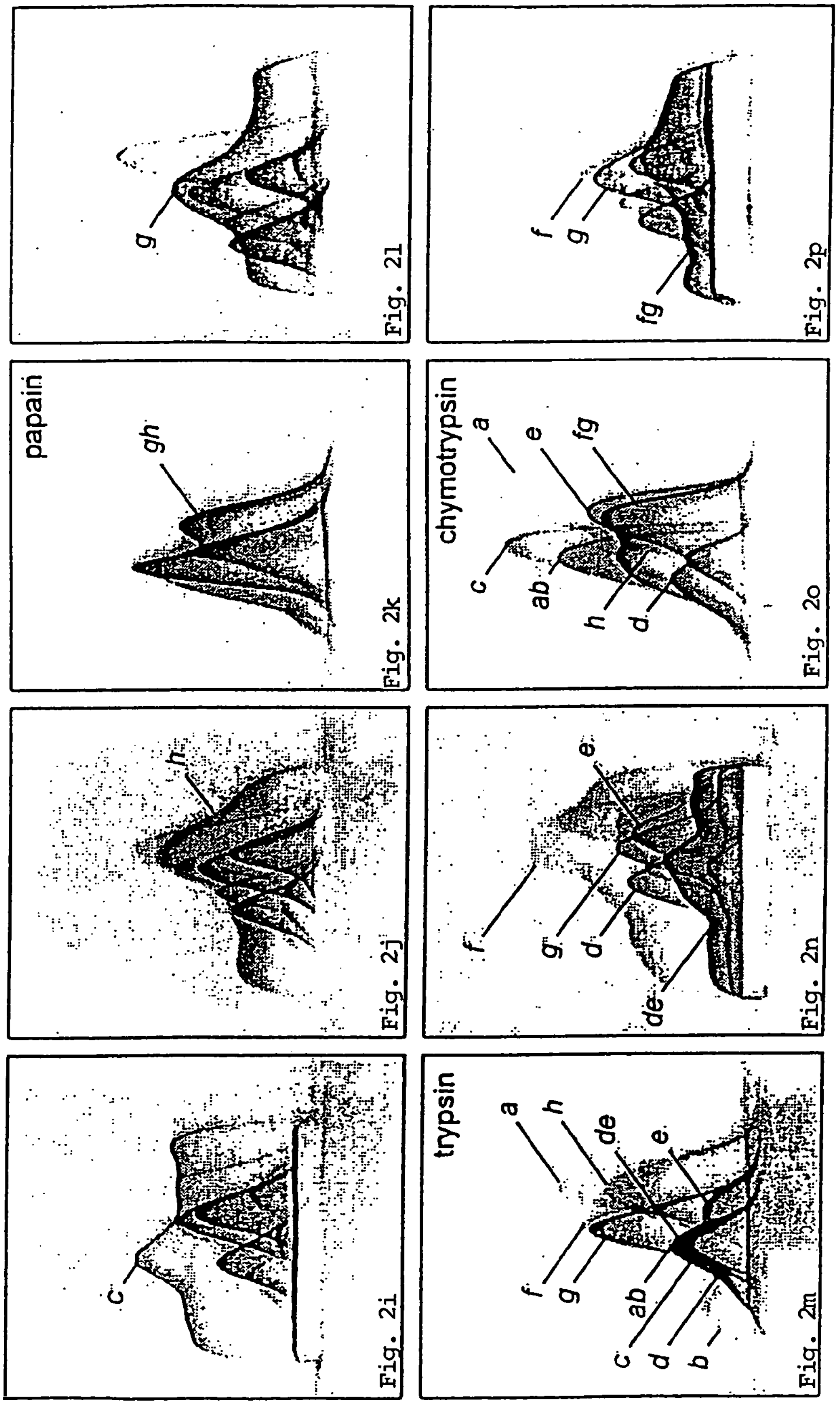
Figure 3A:
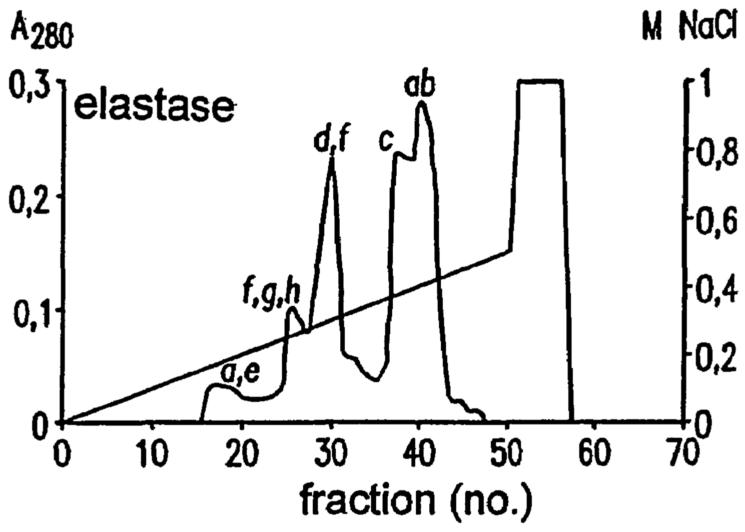
FIG. 3 shows the separation of proteolytic cleavage products of the subunit HtH1 with the aid of HPLC.
Figure 3B:
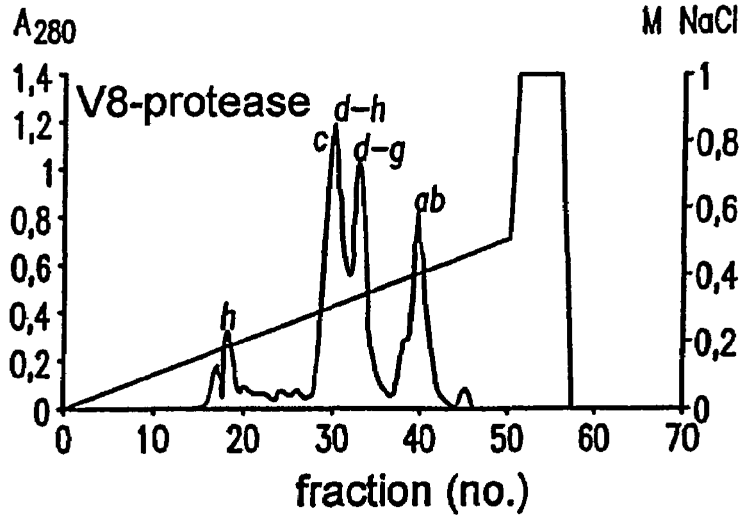
Figure 3C:
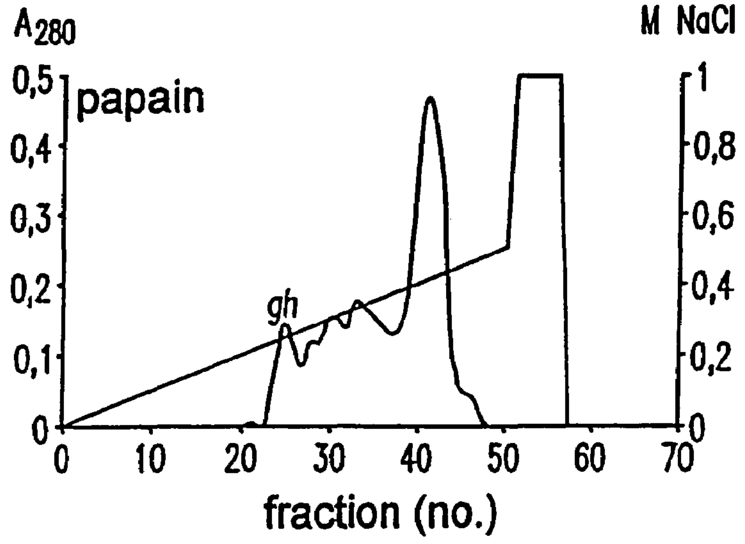

In particular, cleavage of the HtH1 subunit (1-abcdefgh) with V8 protease resulted in four precipitation peaks in the crossed IE (FIG. 2*e*). The SDS-PAGE showed five different fragments (FIG. 2*f*): 220 kDa (5 FUs), 185 kDa (4 FUs), 100 kDa (2 FUs), 55 kDa (1 FU) and 46 kDa (1 FU). The 100 kDa fragment was isolated by the HPLC method (FIG. 3*b*) and identified by N-terminal sequencing as 1-ab, since the sequence was identical to that of the intact subunit (Table I). In the "crossed-line" IE process, 1-ab fused with three precipitation peaks of the elastase cleavage pattern. On the basis of the evaluation, they represent fragments 1-ab, 1-a and 1-b (FIG. 2*g*). However, it remained unclear which peak represents 1-a and which 1-b. In a second step, the 1-ab purified by HPLC was cleaved by elastase into its component FUs, from which one could be eluted by the native PAGE gel strip method and was assigned to the elastase pattern by the "crossed-line" IE method (FIG. 2*h*) and sequenced N-terminally. This component had the same N-terminal sequence as the whole subunit and was therefore identical to 1-a. The second FU of the 100 kDa fragment is thus 1-b (FIG. 2*a*; Table I). HPLC-purified 1-c and 1-h were also obtained (FIG. 3*b*), identified by N-terminal sequence similarities with the corresponding FUs in KLH1 (Table I) and assigned by the "crossed-line" IE method to their corresponding precipitation peaks in the elastase pattern (FIG. 2*i, j*). 1-a, 1-b, 1-c and 1-h were furthermore identified (FIG. 2*a*). Using papain for subunit cleavage, five different peaks were obtained in the crossed IE method (FIG. 2*k*). A 100 kDa fragment (2 FUs) was purified from such a sample by the HPLC method (FIG. 3*c*), and, according to the "crossed-line" IE method, contained the FU 1-h already identified and one of the four FUs still not identified and therefore must be 1-gh (FIGS. 2*k*, 3*c*). In fact, this fragment had an N-terminal sequence which showed similarities with KLH1-g (Table I). For further confirmation, the HPLC-purified fragment 1-gh was cleaved into its constituent FUs with elastase, from which 1-g was purified and identified by N-terminal sequencing. It was assigned to its peak in the elastase cleavage patter by the "crossed-line" IE method (FIG. 21).

Figure 3D:
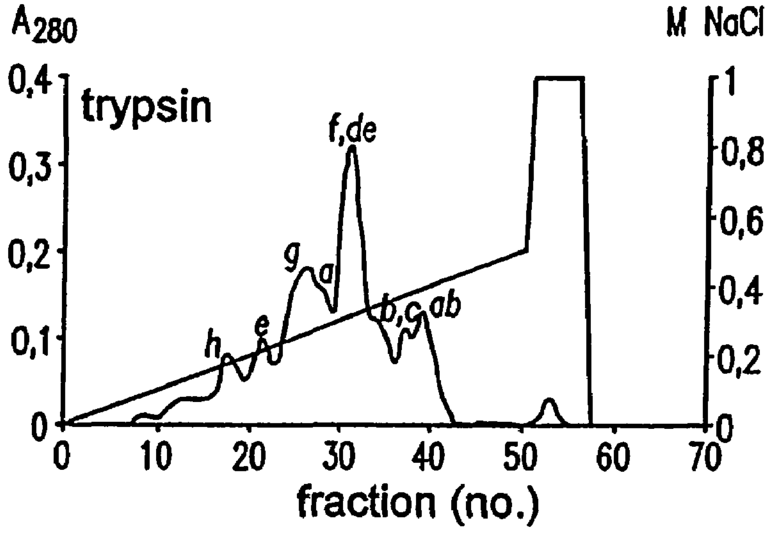
Figure 3E:
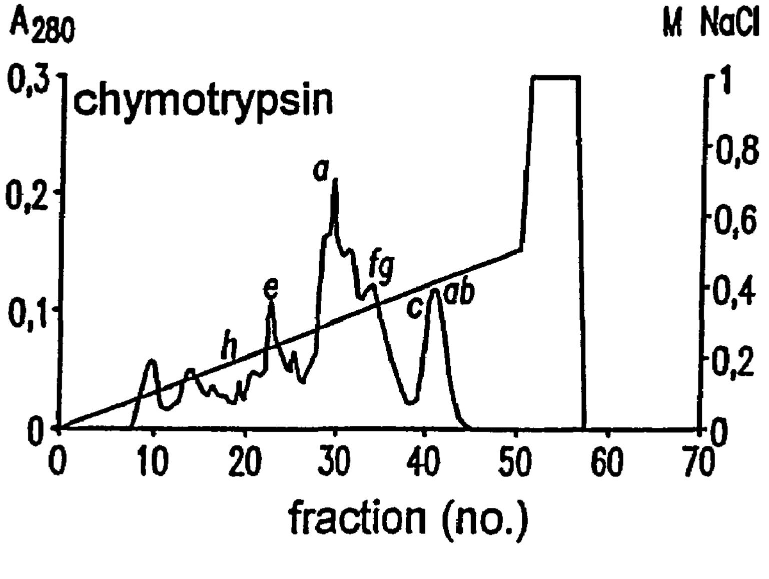

The 220 kDa fragment from the V8 protease cleavage (FIG. 2*e, f*) was purified by HPLC (FIG. 3*b*) and in the "crossed-line" IE method fused with 1-h, 1-g and three peaks of the elastase cleavage pattern which have not yet been identified. The 185 kDa fragment was furthermore obtained in a sufficient purity (FIG. 2*e, f*; 3*b*), and it was shown that it comprised the same components with the exception of 1-h. This suggested that the 22 kDa and the 185 kDa fragment are 1-defgh and 1-defg respectively. In fact, the N-terminal sequence was practically identical and furthermore showed similarity with KLH1-d (Table I). Cleavage of the HtH1 subunit with trypsin resulted in a large number of components in the molecular weight range of one or two FUs (FIG. 2*m*). Several of the components were concentrated in HPLC fractions (FIG. 3*d*). A 100 kDa fragment proved to be particularly useful since it had the same N-terminal sequence as the fragment 1-defg from the v8 protease cleavage (Table 1); the 100 kDa fragment should therefore be 1-de. In the "crossed-line" IE method, this component fused with two of the three FU peaks of the elastase cleavage pattern not yet identified (FIG. 2*n*), which should therefore be 1-d and 1-e, and thus left a single possibility for 1-f. The "crossed-line" IE method also showed that FU 1-f was furthermore present in the 1-de fraction (FIG. 2*n*). The identification of 1-f was confirmed by cleavage of the subunit with chymotrypsin (FIG. 20) and a subsequent HPLC process (FIG. 3*e*). This cleavage gave, inter alia, a 95 kDa fragment (2 FUs) which fused with 1-g and a second peak (FIG. 2*p*) in the "crossed-line" IE method and could therefore be either 1-gh (which could be ruled out since 1-h had already been identified) or 1-fg (which seems appropriate on the basis of the further peak in question, which was identical to the remaining candidate). In fact, this fragment showed a new N-terminal sequence which is similar to KLH1-f in a certain manner. The last problem was now to assign the two remaining FU peaks to 1-d and 1-e. This was achieved using HPLC-isolated FUs from samples in which the subunit had been cleaved with elastase. (FIG. 2*c, d*; 3*a*). The more acidic component in the crossed IE method was deduced as 1-d from its N-terminal sequence, which is identical to that of 1-defgh (FIG. 2*c*, Table I), while the more basic component of the 1-d/1-g pair had a new N-terminal sequence (Table I) and therefore had to be 1-e (FIG. 2*a*). The structure of the functional units of subunit HtH1 was thus clarified.

Example 3

Comparison of the molecular weights and N-terminal sequences of the biochemically isolated functional units (FUs) from HtH1 and KLH1. The various FUs, each with an intact binuclear copper-binding site, were liberated from their larger unit as globular segments by limited proteolysis; cf. the section "Isolation and analysis of the units from HtH1". The KLH1 data were obtained from Söhngen et al., supra. The assignment as an actual unit was done on the basis of the molecular weight and the immunological properties (cf. FIG. 2). The unusually low molecular weight of isolated HtH1-d could means that a large peptide was split off C-terminally.

TABLE 1

| Functional unit | Weight (kDa) | N-terminal sequence |
|---|---|---|
| HtH1-a | 53 | DNVVRKDVSHLTDDEVQ |
| KLH1-a | 50 | ENLVRKDVERL |
| HtH1-b | 48 | ? |
| KLH1-b | 45 | ? |
| HtH1-c | 46 | FEDEKHSLRIRKNVDSLTPEENTNERLR |
| KLH1-c | 45 | KVPRSRLIRKNVDRLTPSE |
| HtH1-d | 40 | VEEVTGASHIRKNLNDLNTGEM |
| KLH1-d | 50 | EVTSANRIRKNIENLS |
| HtH1-e | 49 | ILDHDHEEEILVRKNIIDLSP |
| KLH1-e | 50 | ? |
| HtH1-f | 50 | KLNSRKHTPNRVRHELSSLSSRDIASLKA |
| KLH1-f | 45 | HHLSXNKVRHDLSTL |
| HtH1-g | 45 | DHQSGSIAGSGVRKDVNTLTKAETDNLRE |
| KLH1-g | 45 | SSMAGHFVRKDINTLTP |
| HtH1-h | 55 | DEHHDDRLADVLIRKEVDFLSLQEANAIKD |
| KLH1-h | 60 | HEDHHEDILVRKNIHSL |

Example 4

Cloning of Haemocyanin cDNA

1. For cloning the cDNA of haemocyanin, mRNA was isolated from the mantle tissue of the particular mollusc. The first cDNA strand was obtained by reverse transcription with Oligo(dT) as a primer. The second strand was obtained conventional synthesis with random primers. The cDNA obtained in this way was cloned in a lambda expression vector to form a cDNA expression library. Using an anti-haemocyanin antibody, the library was searched under suitable conditions, positive clones being obtained. These positive clones were isolated, sequenced and characterized.
2. A cDNA probe was prepared from the N-terminal region of a positive clone obtained, and the cDNA library was searched with this. The positive clones obtained were in turn isolated, sequenced and characterized.
3. To obtain sequences arranged still further to 5', another expression library was established from cDNA, this being obtained with the aid of a combination of haemocyanin-specific and "random" primers. This cDNA library was searched with cDNA probes which correspond to the "N-terminal" regions of the positive clones obtained under (2.). The positive clones obtained were isolated, sequenced and characterized.

Example 5

Cloning of Haemocyanin Genes

Genomic DNA was isolated by standard methods. The PCR reaction was carried out with the aid of haemocyanin-specific primers in order to amplify the gene sections of the haemocyanins of interest. The amplification products obtained were cloned in a suitable vector (for example pGem T or pGem T easy (Promega, Mannheim) sequenced and characterized.

Example 6

Recombinant Expression of Haemocyanin

A PCR reaction was carried out with a cDNA clone which contains the coding sequence for HtH-1 d in order to amplify specifically the coding sequence of the domain 1 d. Synthetically prepared oligonucleotides were used as primers. Primer 1 (upstream) comprises six nucleotides of the end of the domain HtH-1c, an SacI cleavage site and 12 nucleotides of the end of the domain HtH-1 d. Primer 2 (downstream) comprises six nucleotides of the start of the domain HtH-1 e, an SalI cleavage site and an HtH1-d-specific sequence.

| | | |
|---|---|---|
| PCR conditions: | 2 min | 95° C. |
| | 30 sec | 95° C. |
| | 30 sec | 55° C. |

-continued

| | | |
|---|---|---|
| | 1 min | 72° C. |
| | 35 cycles | |
| | 10 min | 72° C. |

The amplification product was cloned in the pGEM T easy PCR cloning vector (Promega) in XL-1 Blue (Stratagene). After isolation of the recombinant plasmid and restriction with SacI and SalI, the cDNA of domain 1d could be isolated. The expression vector pQE30 (Qiagen) was also restricted with the corresponding enzymes.

The ligation was then carried out between the HtH-1d-cDNA (restricted with SacI and SalI) and pQE (restricted with SacI and SalI). Directed cloning of the cDNA which codes for HtH-1d in an expression vector is thus possible. The expression of HtH1-d in pQE in XL-1 Blue is carried out in accordance with the manufacturer's instructions. The expression of further HtH 1, HtH2 or KLH 1 or KLH2 domains can be carried out analogously.

The invention claimed is:

1. An isolated haemocyanin polypeptide comprising at least one amino acid sequence recombinantly expressed in a suitable host cell and selected from the following group:

SEQ ID NO:44 (KLH2 domain b),
SEQ ID NO:45 (KLH2 domain c),
SEQ ID NO:46 (partial KLH2 domain d),
SEQ ID NO:47 (KLH2 domain g),
SEQ ID NO:48 (partial KLH2 domain h),
SEQ ID NO:74 (KLH2 domain b'),
SEQ ID NO:75 (KLH2 domain c'),
SEQ ID NO:76 (KLH2 domain d'),
SEQ ID NO:77 (KLH2 domain e),
SEQ ID NO:78 (KLH2 domain f),
SEQ ID NO:79 (KLH2 domain g'), and
SEQ ID NO:158 (partial KLH2 domain h), or a sequence that shows at least 90% identity to one of the amino acid sequences according to SEQ ID NOs 44–48, 74–79 and 158 over a partial region of 90 amino acids, wherein the glycosylation pattern is different from naturally occurring KLH from *Megathura crenulata*.

2. The recombinant haemocyanin polypeptide according to claim 1, characterized in that the haemocyanin polypeptide comprises either the sequences SEQ ID NO: 44 to 48 or the sequences SEQ ID NO:44 to 46, 77, 78, 47, 48 and is KLH2 from *Megathura crenulata*, it being possible in each case for the sequence with SEQ ID NO:44 to be replaced by SEQ ID NO:74, SEQ ID NO:45 to be replaced by SEQ ID NO:75, SEQ ID NO:46 to be replaced by SEQ ID NO:76 and/or SEQ ID NO:47 to be replaced by SEQ ID NO:79.

3. The recombinant haemocyanin polypeptide according to claim 1, characterized in that it is bonded covalently to viruses, virus constituents, bacteria, bacteria constituents, DNA, DNA constituents, inorganic or organic molecules, such as carbohydrates, peptides and/or glycoproteins.

4. The recombinant haemocyanin polypeptide according to claim 1, characterized in that the haemocyanin polypeptide is non-glycosylated.

5. The recombinant haemocyanin polypeptide according to claim 1, characterized in that the haemocyanin polypeptide is glycosylated.

6. A pharmaceutical composition, comprising a haemocyanin polypeptide according to claim 1 and physiologically tolerated additives.

* * * * *

SEQUENCE LISTING

```
<160> NUMBER OF SEQ ID NOS: 239

<210> SEQ ID NO 1
<211> LENGTH: 1269
<212> TYPE: DNA
<213> ORGANISM: Haliotis tuberculata

<400> SEQUENCE: 1

ggcttgttca gtttctactc gtcgcccttg tggcgggggc tggagcagac aacgtcgtca     60

gaaaggacgt gagtcacctc acggatgacg aggtgcaagc tctccacggc gccctccatg    120

acgtcactgc atctacaggg cctctgagtt tcgaagacat aacatcttac catgccgcac    180

cagcgtcgtg tgactacaag ggacggaaga tcgcctgctg tgtccacggt atgcccagtt    240

tccccttctg gcacagggca tatgtcgtcc aagccgagcg ggcactgttg tccaaacgga    300

agactgtcgg aatgccttac tgggactgga cgcaaacgct gactcactta ccatctcttg    360

tgactgaacc catctacatt gacagtaaag gtggaaaggc tcaaaccaac tactggtacc    420

gcggcgagat agcgttcatc aataagaaga ctgcgcgagc tgtagatgat cgcctattcg    480

agaaggtgga gcctggtcac tacacacatc ttatggagac tgtcctcgac gctctcgaac    540

aggacgaatt ctgtaaattt gaaatccagt tcgagttggc tcataatgct atccattact    600

tggttggcgg taaatttgaa tattcaatgt caaacttgga atacacctcc tacgacccca    660

tcttcttcct ccaccactcc aacgttgacc gcctcttcgc catctggcag cgtcttcagg    720

aactgcgagg aaagaatccc aatgcaatgg actgtgcaca tgaactcgct caccagcaac    780

tccaaccctt caacagggac agcaatccag tccagctcac aaaggaccac tcgacacctg    840

ctgacctctt tgattacaaa caacttggat acagctacga cagcttaaac ctgaatggaa    900

tgacgccaga acagctgaaa acagaactag acgaacgcca ctccaaagaa cgtgcgtttg    960

caagcttccg actcagtggc tttgggggtt ctgccaacgt tgttgtctat gcatgtgtcc   1020

ctgatgatga tccacgcagt gatgactact gcgagaaagc aggcgacttc ttcattcttg   1080

gggtcaaag cgaaatgccg tggagattct acagaccctt cttctatgat gtaactgaag   1140

cggtacatca ccttggagtc ccgctaagtg gccactacta tgtgaaaaca gaactcttca   1200
```

-continued

```
gcgtgaatgg cacagcactt tcacctgatc ttcttcctca accaactgtt gcctaccgac   1260

ctgggaaag                                                            1269


<210> SEQ ID NO 2
<211> LENGTH: 1257
<212> TYPE: DNA
<213> ORGANISM: Haliotis tuberculata

<400> SEQUENCE: 2

gtcaccttga cccacctgtg catcatcgcc acgatgacga tcttattgtt cgaaaaaata     60

tagatcattt gactcgtgaa gaggaatacg agctaaggat ggctctggag agattccagg    120

ccgacacatc cgttgatggg taccaggcta cagtagagta ccatggcctt cctgctcgtt    180

gtccacgacc agatgcaaaa gtcaggttcg cctgttgtat gcatggcatg gcatccttcc    240

ctcactggca ccggctgttc gttacccagg tggaagatgc tcttgtacgg cgtggatcgc    300

ctatcggtgt tccttattgg gactggacaa aacctatgac tcaccttcca gacttggcat    360

caaatgagac gtacgtagac ccgtatggac atacacatca taatccattc ttcaatgcaa    420

atatatcttt tgaggaggga caccatcaca cgagcaggat gatagattcg aaactgtttg    480

ccccagtcgc ttttggggag cattcccatc tgtttgatgg aatcctgtac gcatttgagc    540

aggaagattt ctgcgacttt gagattcagt ttgagttagt ccataattct attcatgcgt    600

ggataggcgg ttccgaagat tactccatgg ccaccctgca ttacacagcc tttgacccca    660

ttttctacct tcatcattcc aatgtcgatc gtctatgggc aatctggcaa gctcttcaaa    720

tcaggagaca caagccatat caagcccact gtgcacagtc tgtggaacag ttgccaatga    780

agccatttgc tttcccatca cctcttaaca acaacgagaa gacacatagt cattcagtcc    840

cgactgacat ttatgactac gaggaagtgc tgcactacag ctacgatgat ctaacgtttg    900

gtgggatgaa ccttgaagaa atagaagaag ctatacatct cagacaacag catgaacgag    960

tcttcgcggg atttctcctt gctggaatag gaacatctgc acttgttgac attttcataa   1020

ataaaccggg gaaccaacca ctcaaagctg gagatattgc cattcttggt ggtgccaagg   1080

aaatgccttg ggcgtttgac cgcttgtata aggtcgaaat aactgactca ttgaagacac   1140

tttctctcga tgtcgatgga gattatgaag tcacttttaa aattcatgat atgcacggaa   1200

acgctcttga tacggacctg attccacacg cagcagttgt ttctgagcca gctcacc      1257


<210> SEQ ID NO 3
<211> LENGTH: 1242
<212> TYPE: DNA
<213> ORGANISM: Haliotis tuberculata

<400> SEQUENCE: 3

ctacctttga ggatgaaaag cacagcttac gaatcagaaa aaatgtcgac agcttgactc     60

ctgaagaaac aaatgaactg cgtaaagccc tggagcttct tgaaaatgat catactgcag    120

gtggattcaa tcagcttggc gccttccatg gagagcctaa atggtgccct aatcctgaag    180

cggagcacaa ggttgcatgc tgtgttcatg gcatggctgt tttccctcat tggcacaggc    240

ttcttgctct ccaggcggag aatgctctta gaaagcatgg gtacagtggt gctctaccat    300

actgggattg gactcgcccc ctttcccaac ttcctgatct ggttagtcat gagcagtata    360

cagatccttc cgaccatcac gtgaagcata acccgtggtt caatggccac atcgatacag    420

taaatcagga taccaccaga agcgtacggg aggatcttta tcaacaacct gaatttggac    480

atttcacgga tattgctcaa caagtcctct tagcattaga acaagatgac ttctgttcgt    540
```

-continued

```
ttgaagtgca gtatgagatt tcccataatt ttatccatgc acttgtagga ggaaccgacg    600

cttatggcat ggcatcgctg agatatacag catacgatcc aatctttttc ttgcatcatt    660

caaacaccga caggatctgg gctatttggc aatccctgca aaaatacaga ggcaaaccgt    720

acaacactgc caactgcgcc atagaatcta tgagaaggcc cctgcaacca tttggactaa    780

gcagtgccat taaccctgac agaatcacca gagagcatgc tatcccgttt gatgtcttca    840

actatagaga taaccttcat tacgtatatg ataccctgga atttaatggt ttgtcgattt    900

cacaacttga tagagagctg gaaaaaatca agagtcacga aagagtattt gctggattct    960

tgctgtcggg gattaaaaaa tctgctcttg tgaaattcga agtttgtact ccacctgata   1020

attgtcataa agcaggggag ttttatctac tcggggacga aaacgagatg gcttgggcct   1080

atgaccgact tttcaagtat gatattactc aggttctgga agcaaaccat ctacacttct   1140

atgatcatct cttcattcgc tacgaagtct ttgatcttaa aggagtgagt ttgggaactg   1200

acctgttcca cactgcaaat gtggtacatg attccggcac ag                      1242
```

<210> SEQ ID NO 4
<211> LENGTH: 1239
<212> TYPE: DNA
<213> ORGANISM: Haliotis tuberculata

<400> SEQUENCE: 4

```
gcacccgtga tcgtgataac tacgttgaag aagttactgg ggccagtcat atcaggaaga     60

atttgaacga cctcaatacc ggagaaatgg aaagccttag agctgctttc ctgcatattc    120

aggacgacgg aacatatgaa tctattgccc agtaccatgg caaaccaggc aaatgtcaat    180

tgaatgatca taatattgcg tgttgtgtcc atggtatgcc taccttcccc cagtggcaca    240

gactgtatgt ggttcaggtg gagaatgctc tcctaaacag gggatctggt gtggctgttc    300

cttactggga gtggactgct cccatagacc atctacctca tttcattgat gatgcaacat    360

acttcaattc ccgacaacag cggtacgacc ctaacccttt cttcagggga aaggttactt    420

ttgaaaacgc agtcacaaca agggacccac aagccgggct cttcaactca gattatatgt    480

atgagaatgt tttacttgca ctggagcagg aaaattattg tgactttgaa attcagtttg    540

agcttgttca taacgcactt cattccatgc tgggaggtaa agggcagtac tccatgtcct    600

ccctggacta ttctgcgttt gatcccgtct tcttcctaca tcatgccaac acggacagac    660

tgtgggcaat ctggcaggaa ctacaaagat tccgagaact gccttatgaa gaagcgaact    720

gtgcaatcaa cctcatgcat caaccactga agccgttcag tgatccacat gagaatcacg    780

acaatgtcac tttgaaatac tcaaaaccac aggacggatt cgactaccag aaccacttcg    840

gatacaagta tgacaacctt gagttccatc acttatctat cccaagtctt gatgctaccc    900

tgaagcaaag gagaaatcac gacagagtgt ttgcgggctt ccttcttcat aacataggaa    960

cttctgctga cataactatc tacatatgtc tgcctgacgg acggcgtggc aatgactgca   1020

gtcatgaggc gggaacattc tatatcctcg gaggcgaaac agagatgcct tttatctttg   1080

accgtttgta taaatttgaa atcaccaaac cactgcaaca gttaggagtc aagctgcatg   1140

gtggagtttt cgaactggag cttgagatca aggcatacaa cggttcctat ctggatcccc   1200

ataccttga tccaactatc atctttgaac ctggaacag                           1239
```

<210> SEQ ID NO 5
<211> LENGTH: 1260
<212> TYPE: DNA
<213> ORGANISM: Haliotis tuberculata -continued

<400> SEQUENCE: 5

```
atacccatat cttggaccac gaccatgagg aagagatact tgtcaggaag aatataattg     60
atttgagccc aagggagagg gtttctctag tcaaagcttt gcaaagaatg aagaatgatc    120
gctccgctga tgggtaccaa gccattgcct ctttccatgc cctgccacca ctctgtccca    180
atccatctgc agctcaccgt tatgcttgct gtgtccatgg catggctaca tttccccagt    240
ggcacagact gtacactgtt caggttcagg atgccctgag gagacatggt tcacttgttg    300
gtattcctta ctgggactgg acaaaaccag tcaacgagtt acccgagctt ctttcttcag    360
caacatttta tcatccaatc cggaatatta atatttcaaa tccattcctc ggggctgaca    420
tagaatttga aggaccgggc gttcatacag agaggcacat aaatactgag cgcctgtttc    480
acagtgggga tcatgacgga taccacaact ggttcttcga aactgttctc tttgctttgg    540
aacaggaaga ttactgcgat tttgaaatac aatttgagat agcccataat ggcatccaca    600
catggattgg tggaagcgca gtatatggca tgggacacct tcactatgca tcatatgatc    660
caattttcta catccaccat tcacagacgg acagaatatg ggctatttgg caagagctgc    720
agaagtacag ggtctatct ggttcggaag caaactgtgc cattgaacat atgagaacac     780
ccttgaagcc tttcagcttt gggccaccct acaatttgaa tagtcatacg caagaatatt    840
caaagcctga ggacacgttt gactataaga agtttggata cagatatgat agtctggaat    900
tggaggggcg atcaatttct cgcattgatg aacttatcca gcagagacag gagaaagaca    960
gaacttttgc agggttcctc cttaaaggtt ttggtacatc cgcatctgtg tcattgcaag   1020
tttgcagagt tgatcacacc tgtaaagatg cgggctattt cactattctg ggaggatcag   1080
ccgaaatgcc atgggcattc gacaggcttt ataagtatga cattactaaa actcttcacg   1140
acatgaacct gaggcacgag gacactttct ctatagacgt aactatcacg tcttacaatg   1200
gaacagtact ctcgggagac ctcattcaga cgccctccat tatatttgta cctggacgcc   1260
```

<210> SEQ ID NO 6
<211> LENGTH: 1251
<212> TYPE: DNA
<213> ORGANISM: Haliotis tuberculata

<400> SEQUENCE: 6

```
ataaactcaa ctcacggaaa catacaccta acagagtccg ccatgagcta agtagcctta     60
gttcccgtga catagcaagc ttgaaggcag ctttgacaag ccttcaacat gataatggga    120
ctgatggtta tcaagctatt gctgccttcc atggcgttcc tgcgcagtgc cacgagccat    180
ctggacgtga gatcgcctgt tgcatccacg gcatggcgac gtttcctcac tggcaccggt    240
tgtacactct gcagttggag caagcgctgc gcagacacgg gtccagtgtt gctgttccat    300
actgggactg gaccaagcca atcaccgaac tgccacacat tctgacagac ggagaatatt    360
atgacgtttg gcaaaatgcc gtcttggcca atccgtttgc aagaggttat gtgaaaatta    420
aagatgcatt tacggtgaga aatgtccagg aaagtctgtt caaaatgtca agttttggaa    480
agcactcgct tctgtttgac caggctttgt tggctcttga acaaactgac tactgtgact    540
tcgaagttca gtttgaagtg atgcataaca cgatccatta tctcgtagga gggcgtcaaa    600
cgtacgcctt ctcctctctc gagtattcct catacgatcc aatcttcttt attcaccact    660
cgtttgttga caaaatatgg gctgtatggc aagaactgca aagcaggaga catctacagt    720
ttagaacagc tgattgtgct gtgggcctca tgggtcaggc aatgaggcct ttcaacaagg    780
atttcaacca caactcgttc accaagaagc acgcagtccc taatacagta tttgattatg    840
```

-continued aagatcttgg ctataactat gacaaccttg aaatcagtgg tttaaactta aatgagatcg 900
aggcgttaat agcaaaacgc aagtcacatg ctagagtctt tgctgggttc ctgttgtttg 960
gattaggaac ttcggctgat atacatctgg aaatttgcaa gacatcggaa aactgccatg 1020
atgctggtgt gattttcatc cttggaggtt ctgcagagat gcattgggca tacaaccgcc 1080
tctacaagta tgacattaca gaagcattgc aggaatttga catcaaccct gaagatgttt 1140
tccatgctga tgaaccattt ttcctgaggc tgtcggttgt tgctgtgaat ggaactgtca 1200
ttccatcgtc tcatcttcac cagccaacga taatctatga accaggcgaa g 1251

<210> SEQ ID NO 7
<211> LENGTH: 1209
<212> TYPE: DNA
<213> ORGANISM: Haliotis tuberculata

<400> SEQUENCE: 7
atcaccatga cgaccatcag tcgggaagca tagcaggatc cggggtccgc aaggacgtga 60
acaccttgac taaggctgag accgacaacc tgagggaggc gctgtggggt gtcatggcag 120
accacggtcc caatggcttt caagctattg ctgctttcca tggaaaacca gctttgtgtc 180
ccatgcctga tggccacaac tactcatgtt gtactcacgg catggctacc ttcccacact 240
ggcatcgcct ctacaccaag cagatggagg atgcaatgag ggcgcatggg tctcatgtcg 300
gcctgcccta ctgggactgg actgctgcct tcacccacct gccaacactg gtcaccgaca 360
cggacaacaa ccccttccaa catggacaca ttgattatct caatgtcagc acaactcgat 420
ctccccgaga catgctgttc aacgaccccg agcatggatc agagtcgttc ttctacagac 480
aagtcctctt agctctggaa caaactgatt tctgcaaatt cgaagttcag tttgagataa 540
cccacaatgc catccattcc tggacaggtg gccacagccc ctacggaatg tccactctcg 600
acttcactgc ctacgatcct ctcttctggc ttcaccactc caacaccgac agaatctggg 660
ctgtctggca agctttgcaa gaatacagag gacttccata caaccatgcc aattgtgaga 720
tccaggcaat gaaaacgccc ctgaggcctt tcagtgacga tatcaaccac aacccagtca 780
caaaggctaa cgcgaagcca ttagatgtgt tcgagtataa tcggttgagc ttccagtacg 840
acaacctcat cttccatgga tacagtattc cggaacttga tcgcgtgctt gaagaaagaa 900
aggaggagga cagaatattt gctgccttcc ttctcagtgg aatcaagcgt agtgctgatg 960
tagtgttcga catatgccag ccagaacacg aatgtgtgtt cgcagggact tttgcgattt 1020
tgggagggga gctagaaatg ccctggtcct tcgacagact gttccgctat gatatcacca 1080
aggtgatgaa gcagctacac ctgaggcatg actctgactt taccttcagg gtgaagattg 1140
tcggcaccga cgaccacgag cttccttcag acagtgtcaa agcaccaact attgaatttg 1200
aaccgggcg 1209

<210> SEQ ID NO 8
<211> LENGTH: 1535
<212> TYPE: DNA
<213> ORGANISM: Haliotis tuberculata

<400> SEQUENCE: 8
tgcacagagg cggaaaccac gaagatgaac accatgatga cagactcgca gatgtcctga 60
tcaggaaaga agttgacttc ctctccctgc aagaggccaa cgcaattaag gatgcactgt 120
acaagctcca gaatgacgac agtaaagggg gctttgaggc catagctggc tatcacgggt 180
atcctaatat gtgtccagaa agaggtaccg acaagtatcc ctgctgtgtc cacggaatgc 240

-continued

```
ccgtgttccc ccactggcac cgcctgcata ccattcagat ggagagagct ctgaaaaacc    300

atggctctcc aatgggcatt ccttactggg attggacaaa gaagatgtcg agtcttccat    360

ctttctttgg agattccagc aacaacaacc ctttctacaa atattacatc cggggcgtgc    420

agcacgaaac aaccagggac attaatcaga gactctttaa tcaaaccaag tttggtgaat    480

ttgattacct atattaccta actctgcaag tcctggagga aaactcgtac tgtgactttg    540

aagttcagta tgagatcctc cataacgccg tccactcctg gcttggagga actggaaagt    600

attccatgtc taccctggag cattcggcct ttgaccctgt cttcatgatt caccactcga    660

gtttggatag aatctggatc ctttggcaga agttgcaaaa gataagaatg aagccttact    720

acgcattgga ttgtgctggc gacagactta tgaaagaccc cctgcatccc ttcaactacg    780

aaaccgttaa tgaagatgaa ttcacccgca tcaactcttt cccaagcata ctgtttgacc    840

actacaggtt caactatgaa tacgataaca tgagaatcag ggtcaggac atacatgaac    900

ttgaagaggt aattcaggaa ttaagaaaca aagatcgcat atttgctggt tttgttttgt    960

cgggcttacg gatatcagct acagtgaaag tattcattca ttcgaaaaac gatacaagtc   1020

acgaagaata tgcaggagaa tttgcagttt tgggaggtga gaaggagatg ccgtgggcat   1080

atgaaagaat gctgaaattg gacatctccg atgctgtaca caagcttcac gtgaaagatg   1140

aagacatccg ttttagagtg gttgttactg cctacaacgg tgacgttgtt accaccaggc   1200

tgtctcagcc attcatcgtc caccgtccag cccatgtggc tcacgacatc ttggtaatcc   1260

cagtaggtgc gggccatgac cttccgccta aagtcgtagt aaagagcggc accaaagtcg   1320

agtttacacc aatagattcg tcggtgaaca aagcaatggt ggagctgggc agctatactg   1380

ctatggctaa atgcatcgtt ccccctttct cttaccacgg ctttgaactg gacaaagtct   1440

acagcgtcga tcacggagac tactacattg ctgcaggtac ccacgcgttg tgtgagcaga   1500

acctcaggct ccacatccac gtggaacacg agtag                              1535
```

<210> SEQ ID NO 9
<211> LENGTH: 1003
<212> TYPE: DNA
<213> ORGANISM: Haliotis tuberculata

<400> SEQUENCE: 9

```
cacagactgt tcgtcaccca ggtggaagat gctctgatca ggcgaggatc gcctataggg     60

gtcccctact gggactggac tcagcctatg gcgcatctcc caggacttgc agacaacgcc    120

acctatagag atcccatcag cggggacagc agacacaacc ccttccacga tgttgaagtt    180

gcctttgaaa atggacgtac agaacgtcac ccagatagta gattgtttga acaaccttta    240

tttggcaaac atacgcgtct cttcgacagt atagtctatg cttttgagca ggaggacttc    300

tgcgattttg aagttcaatt tgagatgacc cataataata ttcacgcctg gattggtggc    360

ggcgagaagt attccatgtc ttctctacac tacacagcct tcgaccctat cttctacctt    420

cgtcactcca acactgaccg gctctgggca atttggcaag cgttgcagat acgaagaaac    480

aggccttaca aggctcattg tgcttggtct gaggaacgcc agcctctcaa acctttcgcc    540

ttcagttccc cactgaacaa caacgaaaaa acctacgaaa actcggtgcc caccaacgtt    600

tacgactacg aaggagtcct tggctatact tatgatgacc tcaacttcgg gggcatggac    660

ctgggtcagc ttgaggaata catccagagg cagagacaga gagacaggac ctttgctggt    720

ttctttctgt cacatattgg tacatcagcg aatgttgaaa tcattataga ccatgggact    780

cttcatacct ccgtgggcac gtttgctgtt cttggcggag agaaggagat gaaatgggga    840
```

-continued

```
tttgaccgtt tgtacaaata tgagattaca gatgaactga ggcaacttaa tctccgtgct     900

gatgatgttt tcagcatctc tgttaaagta actgatgttg atggcagtga gctgtcctct     960

gaactcatcc catctgctgc tatcatcttc gaacgaagcc ata                      1003
```

<210> SEQ ID NO 10
<211> LENGTH: 1251
<212> TYPE: DNA
<213> ORGANISM: Haliotis tuberculata

<400> SEQUENCE: 10

```
ttgaccatca ggacccgcat catgacacaa tcattaggaa aaatgttgat aatcttacac      60

ccgaggaaat taattctctg aggcgggcaa tggcagacct tcaatcagac aaaaccgccg     120

gtggattcca gcaaattgct gcttttcacg gggaacccaa atggtgccca agtcccgatg     180

ctgagaagaa gttctcctgc tgtgtccatg gaatggctgt cttccctcac tggcacagac     240

tcctgaccgt gcaaggcgag aatgccctga gaaagcatgg atgtctcgga gctctcccct     300

actgggactg gactcggccc ctgtctcacc tacctgattt ggttttggta agtagcagaa     360

ctacaccgat gccatattcc accgtggaag cccgaaaccc ctggtacagc ggccatattg     420

atacagttgg tgttgacaca acaagaagcg tccgtcaaga actgtatgaa gctcctggat     480

ttggccatta tactggggtc gctaagcaag tgcttctggc tttggagcag gatgacttct     540

gtgattttga agtccagttt gagatagctc acaatttcat tcacgctctt gtcggcggaa     600

gcgagccata tggtatggcg tcactccgtt acactactta tgatccaatt ttctacctcc     660

atcattctaa cactgacaga ctctgggcta tatggcaggc tctacaaaag tacaggggca     720

aaccttacaa ttccgccaac tgcgccattg cttctatgag aaaacccccta caaccctttg     780

gtctgactga tgagatcaac ccggatgatg agacaagaca gcatgctgtt cctttcagtg     840

tctttgatta caagaacaac ttcaattatg aatatgacac ccttgacttc aacggactat     900

caatctccca gctggaccgt gaactgtcac ggagaaagtc tcatgacaga gtatttgccg     960

gatttttgct gcatggtatt cagcagtctg cactagttaa attctttgtc tgcaaatcag    1020

atgatgactg tgaccactat gctggtgaat tctacatcct tggtgatgaa gctgaaatgc    1080

catggggcta tgatcgtctt tacaaatatg agatcactga gcagctcaat gccctggatc    1140

tacacatcgg agatagattc ttcatcagat acgaagcgtt tgatcttcat ggtacaagtc    1200

ttggaagcaa catcttcccc aaaccttctg tcatacatga cgaaggggca g             1251
```

<210> SEQ ID NO 11
<211> LENGTH: 1244
<212> TYPE: DNA
<213> ORGANISM: Haliotis tuberculata

<400> SEQUENCE: 11

```
gtcaccatca ggctgacgag tacgacgaag ttgtaactgc tgcaagccac atcagaaaga      60

atttaaaaga tctgtcaaag ggagaagtag agagcctaag gtctgccttc ctgcaacttc     120

agaacgacgg agtctatgag aatattgcca agttccacgg caagcctggg ttgtgtgatg     180

ataacggtcg caaggttgcc tgttgtgtcc atggaatgcc caccttcccc cagtggcaca     240

ggctctatgt cctccaggtg gagaatgctt tgctggagag aggatctgcc gtctctgtgc     300

catactggga ctggactgaa acatttacag agctgccatc tttgattgct gaggctacct     360

atttcaattc ccgtcaacaa acgtttgacc ctaatccttt cttcagaggt aaaatcagtt     420

ttgagaatgc tgttacaaca cgtgatcccc agcctgagct gtacgttaac aggtactact     480
```

-continued

```
accaaaacgt catgttggtt tttgaacagg acaactactg cgacttcgag atacagtttg    540

agatggttca caatgttctc catgcttggc ttggtggaag agctacttat tctatttctt    600

ctcttgatta ttctgcattc gaccctgtgt ttttccttca ccatgcgaac acagatagat    660

tgtgggccat ctggcaggag ctgcagaggt acaggaagaa gccatacaat gaagcggatt    720

gtgccattaa cctaatgcgc aaacctctac atcccttcga caacagtgat ctcaatcatg    780

atcctgtaac ctttaaatac tcaaaaccca ctgatggctt tgactaccag aacaactttg    840

gatacaagta tgacaacctt gagttcaatc atttcagtat tcccaggctt gaagaaatca    900

ttcgtattag acaacgtcaa gatcgtgtgt ttgcaggatt cctccttcac aacattggga    960

catccgcaac tgttgagata ttcgtctgtg tccctaccac cagcggtgag caaaactgtg   1020

aaaacaaagc cggaacattt gccgtactcg gaggagaaac agagatggcg tttcattttg   1080

acagactcta caggtttgac atcagtgaaa cactgaggga cctcggcata cagctggaca   1140

gccatgactt tgacctcagc atcaagattc aaggagtaaa tggatcctac cttgatccac   1200

acatcctgcc agagccatcc ttgatttttg tgcctggttc aagt                    1244
```

```
<210> SEQ ID NO 12
<211> LENGTH: 1255
<212> TYPE: DNA
<213> ORGANISM: Haliotis tuberculata

<400> SEQUENCE: 12

tctttcctgc gtcctgatgg gcattcagat gacatccttg tgagaaaaga agtgaacagc     60

ctgacaacca gggagactgc atctctgatc catgctctga aaagtatgca ggaagaccat    120

tcacctgacg ggttccaagc cattgcctct ttccatgctc tgccaccact ctgcccttca    180

ccatctgcag ctcaccgtta tgcttgctgt gtccacggca tggctacatt tccccagtgg    240

cacagattgt acactgtaca gttccaggat gcactgagga gacatggagc tacggtaggt    300

gtaccgtatt gggattggct gcgaccgcag tctcacctac cagagcttgt caccatggag    360

acataccatg atatttggag taacagagat ttccccaatc ctttctacca agccaatatt    420

gagtttgaag gagaaaacat tacaacagag agagaagtca ttgcagacaa actttttgtc    480

aaaggtggac acgtttttga taaactggtt cttcaaacaa gccatcctag cgctgagcag    540

gaaaactact gtgactttga gattcagttt gaaattcttc acaacggcgt tcacacgtgg    600

gtcggaggca gtcgtaccta ctctatcgga catcttcatt acgcattcta cgaccctctt    660

ttctaccttc accatttcca gacagaccgt atttgggcaa tctggcaaga actccaggaa    720

cagagagggc tctcgggtga tgaggctcac tgtgctctcg agcaaatgag agaaccattg    780

aagcctttca gcttcggcgc tccttataac tggaatcagc tcacacagga tttctcccga    840

cccgaggaca ccttcgacta caggaagttt ggttatgaat atgacaattt agaattcctg    900

ggaatgtcag ttgctgaact ggatcaatac attattgaac atcaagaaaa tgatagagta    960

ttcgctgggt tcctgttgag tggattcgga ggttccgcat cagttaattt ccaggtttgt   1020

agagctgatt ccacatgtca ggatgctggg tacttcaccg ttcttggtgg cagtgctgag   1080

atggcgtggg catttgacag gctttacaaa tatgacatta ctgaaactct ggagaaaatg   1140

caccttcgat atgatgatga cttcacaatc tctgtcagtc tgaccgccaa caacggaact   1200

gtcctgagca gcagtctaat cccaacaccg agtgtcatat tccagcgggg acatc        1255
```

-continued

<210> SEQ ID NO 13
<211> LENGTH: 1248
<212> TYPE: DNA
<213> ORGANISM: Haliotis tuberculata

<400> SEQUENCE: 13
gtgacataaa taccaggagc atgtcaccga accgtgttcg ccgtgagctg agcgatctgt 60
ctgcgaggga cctgtctagt ctcaagtctg ctctgcgaga cctacaggag gatgatggcc 120
ccaacggata ccaggctctt gcagccttcc atgggctacc agcaggctgc catgatagcc 180
ggggaaatga gatcgcatgt tgcattcacg ggatgccgac cttcccccag tggcacagac 240
tgtacaccct gcagttggag atggctctga ggagacatgg atcatctgtc gccatcccct 300
actgggactg gacaaagcct atctccgaac tcccctcgct cttcaccagc cctgagtatt 360
atgacccatg gcatgatgct gtggtaaaca acccattctc caaaggtttt gtcaaatttg 420
caaataccta cacagtaaga gacccacagg agatgctgtt ccagctttgt gaacatggag 480
agtcaatcct ctatgagcaa actcttcttg ctcttgagca aaccgactac tgtgattttg 540
aggtacagtt tgaggtcctc cataacgtga tccactacct tgttggtgga cgtcagacct 600
acgcattgtc ttctctgcat tatgcctcct acgacccatt cttctttata caccattcct 660
ttgtggataa gatgtgggta gtatggcaag ctcttcaaaa gaggaggaaa cttccataca 720
agcgagctga ctgtgctgtc aacctaatga ctaaaccaat gaggccattt gactccgata 780
tgaatcagaa cccattcaca aagatgcacg cagttcccaa cacactctat gactacgaga 840
cactgtacta cagctacgat aatctcgaaa taggtggcag gaatctcgac cagcttcagg 900
ctgaaattga cagaagcaga agccacgatc gcgtttttgc tggattcttg cttcgtggaa 960
tcggaacttc tgctgatgtc aggttttgga tttgtagaaa tgaaaatgac tgccacaggg 1020
gtggaataat tttcatctta ggtggagcca aggaaatgcc atggtcattt gacagaaact 1080
tcaagtttga tatcacccat gtactcgaga atgctggcat tagcccagag gacgtgtttg 1140
atgctgagga gccattttat atcaaggttg agatccatgc tgttaacaag accatgatac 1200
cgtcgtctgt gatcccagcc ccaactatca tctattctcc tggggaag 1248

<210> SEQ ID NO 14
<211> LENGTH: 1207
<212> TYPE: DNA
<213> ORGANISM: Haliotis tuberculata

<400> SEQUENCE: 14
gtcgcgctgc tgacagtgcg cactctgcca acattgctgg ctctggggtg aggaaggacg 60
tcacgaccct cactgtgtct gagaccgaga acctaagaca ggctcttcaa ggtgtcatcg 120
atgatactgg tcccaatggt taccaagcaa tagcatcctt ccacggaagt cctccaatgt 180
gcgagatgaa cggccgcaag gttgcctgtt gtgctcacgg tatggcctcc ttcccacact 240
ggcacagact gtatgtgaag cagatggaag atgccctggc tgaccacggg tcacatatcg 300
gcatccctta ctgggactgg acaactgcct tcacagagtt acccgccctt gtcacagact 360
ccgagaacaa tcccttccat gagggtcgca ttgatcatct cggtgtaacc acgtcacgtt 420
cccccagaga catgctgttt aacgacccag agcaaggatc agagtcgttc ttctatagac 480
aagtcctcct ggctttggag cagactgact actgccagtt cgaagtccag tttgagctga 540
cccacaacgc cattcactcc tggacaggtg gacgtagccc ttacggaatg tcgaccctcg 600
agttcacagc ctacgatcct ctcttctggc ttcaccactc caacaccgac agaatctggg 660

-continued ctgtctggca agcactgcag aaataccgag gactcccata caacgaagca cactgtgaaa 720
tccaggttct gaaacagccc ttgaggccat tcaacgatga catcaaccac aatccaatca 780
ccaagactaa tgccaggcct atcgattcat ttgattatga gaggtttaac tatcagtatg 840
acacccttag cttccatggt aagagcatcc ctgaactgaa tgacctgctc gaggaaagaa 900
aaagagaaga gagaacattt gctgccttcc ttcttcgtgg aatcggttgc agtgctgatg 960
tcgtctttga catctgccgg cccaatggtg actgtgtctt tgcaggaacc tttgctgtgc 1020
tgggagggga gctagaaatg ccttggtcct tcgacagact gttccgctat gacatcacca 1080
gagtcatgaa tcagctccat ctccagtatg attcagattt cagtttcagg gtgaagcttg 1140
ttgccaccaa tggcactgag ctttcatcag accttctcaa gtcaccaaca attgaacatg 1200
aacttgg 1207

<210> SEQ ID NO 15
<211> LENGTH: 1546
<212> TYPE: DNA
<213> ORGANISM: Haliotis tuberculata
<220> FEATURE:
<221> NAME/KEY: misc_feature
<222> LOCATION: (1273)..(1273)
<223> OTHER INFORMATION: “n” is a, g, c, or t, including c or t

<400> SEQUENCE: 15
agcccacaga ggaccagttg aagaaacaga agtcactcgc caacatactg acggcaatgc 60
acactttcat cgtaaggaag ttgattcgct gtccctggat gaagcaaaca acttgaagaa 120
tgccctttac aagctacaga acgaccacag tctaacggga tacgaagcaa tctctggtta 180
ccatggatac cccaatctgt gtccggaaga aggcgatgac aaaatacccc tgctgcgtcc 240
ccggatgggc atctttcctt actggcacag actcttgacc attcaactgg aaagagctct 300
tgagcacaat ggtgcactgc ttggtgttcc ttactgggac tggaacaagg acctgtcgtc 360
actgccggcg ttcttctccg actccagcaa caacaatccc tacttcaagt accacatcgc 420
cggtgttggt cacgacaccg tcagagagcc aactagtctt atatataacc agccccaaat 480
ccatggttat gattatctct attacctagc attgaccacg cttgaagaaa acaattactg 540
ggactttgag gttcagtatg agatcctcca caacgccgtc cactcctggc ttggaggatc 600
ccagaagtat tccatgtcta ccctggagta ttcggccttt gaccctgtct ttatgatcct 660
tcactcgggt ctagacagac tttggatcat ctggcaagaa cttcagaaga tcaggagaaa 720
gccctacaac ttcgctaaat gtgcttatca tatgatggaa gagccactgg cgcccttcag 780
ctatccatct atcaaccagg acgagttcac ccgtgccaac tccaagcctt ctacagtttt 840
tgacagccat aagttcggct accattacga taacctgaat gttagaggtc acagcatcca 900
agaactcaac acaatcatca atgacttgag aaacacagac agaatctacg caggatttgt 960
tttgtcaggc atcggtacgt ctgctagtgt caagatctat ctccgaacag atgacaatga 1020
cgaagaagtt ggaactttca ctgtcctggg aggagagagg gaaatgccat gggcctacga 1080
gcgagttttc aagtatgaca tcacagaggt tgcagataga cttaaaatta agttatgggg 1140
acacccttta acttccggaa ctggagatca catccttacg aatggaatcg gtggtaaaca 1200
agagcctacc caaatccttt catcatctac agacctgcca atcatgacta cgatgttctt 1260
gttatcccag tanggaagaa accttcacat ccctcccaaa gttgtcgtca agaaaggcac 1320
ccgcatcgag ttccacccag tcgatgattc agttacgaga ccagttgttg atcttggaag 1380
ctacactgca ctcttcaact gtgtggtacc accgttcaca taccacggat tcgaactgaa 1440

-continued

```
ccacgtctat tctgtcaagc ctggtgacta ctatgttact ggacccacga gagacctttg   1500

ccagaatgca gatgtcagga ttcatatcca tgttgaggat gagtaa                  1546
```

<210> SEQ ID NO 16
<211> LENGTH: 967
<212> TYPE: DNA
<213> ORGANISM: Megathura crenulata

<400> SEQUENCE: 16

```
ggcctaccgt actgggactg gactgaaccc atgacacaca ttccgggtct ggcaggaaac     60

aaaacttatg tggattctca tggtgcatcc cacacaaatc cttttcatag ttcagtgatt    120

gcatttgaag aaaatgctcc ccacaccaaa agacaaatag atcaaagact ctttaaaccc    180

gctacctttg gacaccacac agacctgttc aaccagattt tgtatgcctt tgaacaagaa    240

gattactgtg actttgaagt ccaatttgag attacccata acacgattca cgcttggaca    300

ggaggaagcg aacatttctc aatgtcgtcc ctacattaca cagctttcga tcctttgttt    360

tactttcacc attctaacgt tgatcgtctt tgggccgttt ggcaagcctt acagatgaga    420

cggcataaac cctacagggc ccactgcgcc atatctctgg aacatatgca tctgaaacca    480

ttcgcctttt catctcccct taacaataac gaaaagactc atgccaatgc catgccaaac    540

aagatctacg actatgaaaa tgtcctccat tacacatacg aagatttaac atttggaggc    600

atctctctgg aaaacataga aaagatgatc cacgaaaacc agcaagaaga cagaatatat    660

gccggttttc tcctggctgg catacgtact tcagcaaatg ttgatatctt cattaaaact    720

accgattccg tgcaacataa ggctggaaca tttgcagtgc tcggtggaag caaggaaatg    780

aagtggggat ttgatcgcgt tttcaagttt gacatcacgc acgttttgaa agatctcgat    840

ctcactgctg atggcgattt cgaagttact gttgacatca ctgaagtcga tggaactaaa    900

cttgcatcca gtcttattcc acatgcttct gtcattcgtg agcatgcacg tggtaagctg    960

aatagag                                                              967
```

<210> SEQ ID NO 17
<211> LENGTH: 1242
<212> TYPE: DNA
<213> ORGANISM: Megathura crenulata

<400> SEQUENCE: 17

```
ttaaatttga caaagtgcca aggagtcgtc ttattcgaaa aaatgtagac cgtttgagcc     60

ccgaggagat gaatgaactt cgtaaagccc tagccttact gaaagaggac aaaagtgccg    120

gtggatttca gcagcttggt gcattccatg gggagccaaa atggtgtcct agtcccgaag    180

catctaaaaa atttgcctgc tgtgttcacg gcatgtctgt gttccctcac tggcatcgac    240

tgttgacggt tcagagtgaa aatgctttga gacgacatgg ctacgatgga gctttgccgt    300

actgggattg gacctctcct cttaatcacc ttcccgaact ggcagatcat gagaagtacg    360

tcgaccctga agatggggta gagaagcata acccttggtt cgatggtcat atagatacag    420

tcgacaaaac aacaacaaga agtgttcaga ataaactctt cgaacagcct gagtttggtc    480

attatacaag cattgccaaa caagtactgc tagcgttgga acaggacaat ttctgtgact    540

ttgaaatcca atatgagatt gcccataact acatccatgc acttgtagga ggcgctcagc    600

cttatggtat ggcatcgctt cgctacactg cttttgatcc actattctac ttgcatcact    660

ctaatacaga tcgtatatgg gcaatatggc aggctttaca gaagtacaga ggaaaaccgt    720

acaacgttgc taactgtgct gttacatcga tgagagaacc tttgcaacca tttggcctct    780
```

-continued

```
ctgccaatat caacacagac catgtaacca aggagcattc agtgccattc aacgtttttg    840

attacaagac caatttcaat tatgaatatg acactttgga atttaacggt ctctcaatct    900

ctcagttgaa taaaaagctc gaagcgataa agagccaaga caggttcttt gcaggcttcc    960

tgttatctgg tttcaagaaa tcatctcttg ttaaattcaa tatttgcacc gatagcagca   1020

actgtcaccc cgctggagag ttttaccttc tgggtgatga aaacgagatg ccatgggcat   1080

acgatagagt cttcaaatat gacataaccg aaaaactcca cgatctaaag ctgcatgcag   1140

aagaccactt ctacattgac tatgaagtat ttgaccttaa accagcaagc ctgggaaaag   1200

atttgttcaa gcagccttca gtcattcatg aaccaagaat ag                       1242
```

<210> SEQ ID NO 18
<211> LENGTH: 1236
<212> TYPE: DNA
<213> ORGANISM: Megathura crenulata

<400> SEQUENCE: 18

```
gtcaccatga aggcgaagta tatcaagctg aagtaacttc tgccaaccgt attcgaaaaa     60

acattgaaaa tctgagcctt ggtgaactcg aaagtctgag agctgccttc ctggaaattg    120

aaaacgatgg aacttacgaa tcaatagcta aattccatgg tagccctggt ttgtgccagt    180

taaatggtaa ccccatctct tgttgtgtcc atggcatgcc aactttccct cactggcaca    240

gactgtacgt ggttgtcgtt gagaatgccc tcctgaaaaa aggatcatct gtagctgttc    300

cctattggga ctggacaaaa cgaatcgaac atttacctca cctgatttca gacgccactt    360

actacaattc caggcaacat cactatgaga caaacccatt ccatcatggc aaaatcacac    420

acgagaatga aatcactact agggatccca aggacagcct cttccattca gactactttt    480

acgagcaggt cctttacgcc ttggagcagg ataacttctg tgatttcgag attcagttgg    540

agatattaca caatgcattg cattctttac ttggtggcaa aggtaaatat tccatgtcaa    600

accttgatta cgctgctttt gatcctgtgt tcttccttca tcacgcaacg actgacagaa    660

tctgggcaat ctggcaagac cttcagaggt tccgaaaacg gccataccga gaagcgaatt    720

gcgctatcca attgatgcac acgccactcc agccgtttga taagagcgac aacaatgacg    780

aggcaacgaa aacgcatgcc actccacatg atggttttga atatcaaaac agctttggtt    840

atgcttacga taatctggaa ctgaatcact actcgattcc tcagcttgat cacatgctgc    900

aagaaagaaa aaggcatgac agagtattcg ctggcttcct ccttcacaat attggaacat    960

ctgccgatgg ccatgtattt gtatgtctcc caactgggga acacacgaag gactgcagtc   1020

atgaggctgg tatgttctcc atcttaggcg gtcaaacgga gatgtccttt gtatttgaca   1080

gactttacaa acttgacata actaaagcct tgaaaaagaa cggtgtgcac ctgcaagggg   1140

atttcgatct ggaaattgag attacggctg tgaatggatc tcatctagac agtcatgtca   1200

tccactctcc cactatactg tttgaggccg gaacag                             1236
```

<210> SEQ ID NO 19
<211> LENGTH: 241
<212> TYPE: DNA
<213> ORGANISM: Megathura crenulata

<400> SEQUENCE: 19

```
attctgccca cacagatgat ggacacactg aaccagtgat gattcgcaaa gatatcacac     60

aattggacaa gcgtcaacaa ctgtcactgg tgaaagccct cgagtccatg aaagccgacc    120

attcatctga tgggttccag gcaatcgctt ccttccatgc tcttcctcct ctttgtccat    180
```

-continued

```
caccagctgc ttcaaagagg tttgcgtgct gcgtccatgg catgccaacc ttcccgcaat    240

g                                                                     241
```

<210> SEQ ID NO 20
<211> LENGTH: 949
<212> TYPE: DNA
<213> ORGANISM: Megathura crenulata

<400> SEQUENCE: 20

```
ggcctgccct actgggattg gaccatgcca atgagtcatt tgccagaact ggctacaagt     60

gagacctacc tcgatccagt tactggggaa actaaaaaca accctttcca tcacgcccaa    120

gtggcgtttg aaaatggtgt aacaagcagg aatcctgatg ccaaactttt tatgaaacca    180

acttacggag accacactta cctcttcgac agcatgatct acgcatttga gcaggaagac    240

ttctgcgact ttgaagtcca atatgagctc acgcataatg caatacatgc atgggttgga    300

ggcagtgaaa agtattcaat gtcttctctt cactacactg cttttgatcc tatattttac    360

ctccatcact caaatgttga tcgtctctgg gccatttggc aagctcttca aatcaggaga    420

ggcaagtctt acaaggccca ctgcgcctcg tctcaagaaa gagaaccatt aaagcctttt    480

gcattcagtt ccccactgaa caacaacgag aaaacgtacc acaactctgt ccccactaac    540

gtttatgact atgtgggagt tttgcactat cgatatgatg accttcagtt tggcggtatg    600

accatgtcag aacttgagga atatattcac aagcagacac aacatgatag aacctttgca    660

ggattcttcc tttcatatat tggaacatca gcaagcgtag atatcttcat caatcgagaa    720

ggtcatgata aatacaaagt gggaagtttt gtagtacttg gtggatccaa agaaatgaaa    780

tggggctttg atagaatgta caagtatgag atcactgagg ctctgaagac gctgaatgtt    840

gcagtggatg atgggttcag cattactgtt gagatcaccg atgttgatgg atctccccca    900

tctgcagatc tcattccacc tcctgctata atctttgaac gtggtcatg                949
```

<210> SEQ ID NO 21
<211> LENGTH: 760
<212> TYPE: DNA
<213> ORGANISM: Megathura crenulata

<400> SEQUENCE: 21

```
ctgatgccaa agactttggc catagcagaa aaatcaggaa agccgttgat tctctgacag     60

tcgaagaaca aacttcgttg aggcgagcta tggcagatct acaggacgac aaaacatcag    120

gggtttcca gcagattgca gcattccacg gagaaccaaa atggtgtcca agccccgaag    180

cggagaaaaa atttgcatgc tgtgttcatg gaatggctgt tttccctcac tggcacagat    240

tgctgacagt tcaaggagaa aatgctctga ggaaacatgg ctttactggt ggactgccct    300

actgggactg gactcgatca atgagcgccc ttccacattt tgttgctgat cctacttaca    360

atgatgctat ttccagccag gaagaagata acccatggca tcatggtcac atagactctg    420

ttgggcatga tactacaaga gatgtgcgtg atgatcttta tcaatctcct ggtttcggtc    480

actacacaga tattgcacaa caagtccttc tggcctttga gcaggacagt ttctgtgatt    540

ttgaggtaca atttgaaatt gcccataatt tcatacatgc actgattggt ggtaacgaac    600

catacagtat gtcatctttg aggtatacta catacgatcc aatcttcttc ttgcaccact    660

ccagtacaga ccgactttgg gccatctggc aagcaatcac tagtgcggcc gcctgcaggt    720

cgaccataag ggagagctcc caacgcgttg gatgcaatct                          760
```

-continued

<210> SEQ ID NO 22
<211> LENGTH: 323
<212> TYPE: DNA
<213> ORGANISM: Megathura crenulata

<400> SEQUENCE: 22
gttcacacca ggctgatgaa tatcgtgagg cagtaacaag cgctagccac ataagaaaaa 60
atatccggga cctctcagag ggagaaattg agagcatcag atctgctttc ctccaaattc 120
aaaaagaggg tatatatgaa aacattgcaa agttccatgg aaaaccagga ctttgtgaac 180
atgatggaca tcctgttgct tgttgtgtcc atggcatgcc cacctttccc cactggcaca 240
gactgtacgt tcttcaggtg gagaatgcgc tcttagaacg agggtctgca gttgctgttc 300
cttactggga ctggacccta cct 323

<210> SEQ ID NO 23
<211> LENGTH: 988
<212> TYPE: DNA
<213> ORGANISM: Megathura crenulata

<400> SEQUENCE: 23
atggctgtgt ttccgcactg gcacagactg tttgtgaaac agatggagga cgcacttgct 60
gctcatggag ctcatattgg cataccatac tgggattgga caagtgcgtt tagtcatctg 120
cccgccctag tgactgacca cgagaacaat cccttccacc acggccatat tggtcatctg 180
aatgtggata catctcgatc tccaagagac atgctgttta atgatcctga acaaggctca 240
gaatcattct tctacagaca ggttctcttg actctagaac agacagactt ctgccaattt 300
gaagttcagt ttgaacttac acacaatgcc atccactctt ggactggagg acatactcca 360
tatggaatgt catcactgga atatacagca tatgatccac tcttttatct ccaccattcc 420
aacactgatc gtatctgggc catctggcag gcactccaga aatatagagg tcttccatac 480
aacgcagctc actgcgatat ccaagttctg aaacaacctc ttaaaccatt cagcgagtcc 540
aggaatccaa acccagtcac cagagccaat tctagggccg ttgattcatt tgattatgag 600
aaattcaatt atcaatatga cacacttacc ttccacggac tttctatccc agaacttgat 660
gccatgcttc aagagagaaa gaaggaagag agaacatttg cagccttcct gttgcacgga 720
tttggcgcca gtgctgatgt ttcgtttgat gtctgcacac ctgatggtca ttgtgccttt 780
gctggaacct tcgcggtact tggtggggag cttgagatgc cctggtcctt tgaaagattg 840
ttccgttacg atatcacaaa ggttctcaag cagatgaatc ttcactatga ttctgagttc 900
cactttgagt tgaagattgt tggcacagat ggaacagaac tgccatcgga tcgtatcaag 960
agccctacca ttgaacacca tggaggag 988

<210> SEQ ID NO 24
<211> LENGTH: 310
<212> TYPE: DNA
<213> ORGANISM: Megathura crenulata

<400> SEQUENCE: 24
gtcacgatca cagtgaacgt cacgatggat ttttcaggaa ggaagtcggt tccctgtccc 60
tggatgaagc caatgacctt aaaaatgcac tgtacaagct gcagaatgat cagggtccca 120
atggatatga atcaatagcc ggttaccatg gctatccatt cctctgccct gaacatggtg 180
aagaccagta cgcatgctgt gtccacggaa tgcctgtatt tccacattgg cacagacttc 240

-continued atacaatcca gtttgagaga gctctcaaag aacatggttc tcatttgggt ctgccatact 300
gggactggac 310

<210> SEQ ID NO 25
<211> LENGTH: 422
<212> TYPE: PRT
<213> ORGANISM: Haliotis tuberculata
<220> FEATURE:
<221> NAME/KEY: SIGNAL
<222> LOCATION: (1)..(15)

<400> SEQUENCE: 25

Leu Val Gln Phe Leu Leu Val Ala Leu Val Ala Gly Ala Gly Ala Asp
1 5 10 15

Asn Val Val Arg Lys Asp Val Ser His Leu Thr Asp Asp Glu Val Gln
20 25 30

Ala Leu His Gly Ala Leu His Asp Val Thr Ala Ser Thr Gly Pro Leu
35 40 45

Ser Phe Glu Asp Ile Thr Ser Tyr His Ala Ala Pro Ala Ser Cys Asp
50 55 60

Tyr Lys Gly Arg Lys Ile Ala Cys Cys Val His Gly Met Pro Ser Phe
65 70 75 80

Pro Phe Trp His Arg Ala Tyr Val Val Gln Ala Glu Arg Ala Leu Leu
85 90 95

Ser Lys Arg Lys Thr Val Gly Met Pro Tyr Trp Asp Trp Thr Gln Thr
100 105 110

Leu Thr His Leu Pro Ser Leu Val Thr Glu Pro Ile Tyr Ile Asp Ser
115 120 125

Lys Gly Gly Lys Ala Gln Thr Asn Tyr Trp Tyr Arg Gly Glu Ile Ala
130 135 140

Phe Ile Asn Lys Lys Thr Ala Arg Ala Val Asp Asp Arg Leu Phe Glu
145 150 155 160

Lys Val Glu Pro Gly His Tyr Thr His Leu Met Glu Thr Val Leu Asp
165 170 175

Ala Leu Glu Gln Asp Glu Phe Cys Lys Phe Glu Ile Gln Phe Glu Leu
180 185 190

Ala His Asn Ala Ile His Tyr Leu Val Gly Gly Lys Phe Glu Tyr Ser
195 200 205

Met Ser Asn Leu Glu Tyr Thr Ser Tyr Asp Pro Ile Phe Phe Leu His
210 215 220

His Ser Asn Val Asp Arg Leu Phe Ala Ile Trp Gln Arg Leu Gln Glu
225 230 235 240

Leu Arg Gly Lys Asn Pro Asn Ala Met Asp Cys Ala His Glu Leu Ala
245 250 255

His Gln Gln Leu Gln Pro Phe Asn Arg Asp Ser Asn Pro Val Gln Leu
260 265 270

Thr Lys Asp His Ser Thr Pro Ala Asp Leu Phe Asp Tyr Lys Gln Leu
275 280 285

Gly Tyr Ser Tyr Asp Ser Leu Asn Leu Asn Gly Met Thr Pro Glu Gln
290 295 300

Leu Lys Thr Glu Leu Asp Glu Arg His Ser Lys Glu Arg Ala Phe Ala
305 310 315 320

Ser Phe Arg Leu Ser Gly Phe Gly Gly Ser Ala Asn Val Val Val Tyr
325 330 335

-continued

```
Ala Cys Val Pro Asp Asp Asp Pro Arg Ser Asp Asp Tyr Cys Glu Lys
            340                 345                 350

Ala Gly Asp Phe Phe Ile Leu Gly Gly Gln Ser Glu Met Pro Trp Arg
        355                 360                 365

Phe Tyr Arg Pro Phe Phe Tyr Asp Val Thr Glu Ala Val His His Leu
    370                 375                 380

Gly Val Pro Leu Ser Gly His Tyr Tyr Val Lys Thr Glu Leu Phe Ser
385                 390                 395                 400

Val Asn Gly Thr Ala Leu Ser Pro Asp Leu Leu Pro Gln Pro Thr Val
                405                 410                 415

Ala Tyr Arg Pro Gly Lys
            420


<210> SEQ ID NO 26
<211> LENGTH: 419
<212> TYPE: PRT
<213> ORGANISM: Haliotis tuberculata

<400> SEQUENCE: 26

Gly His Leu Asp Pro Pro Val His His Arg His Asp Asp Asp Leu Ile
  1               5                  10                  15

Val Arg Lys Asn Ile Asp His Leu Thr Arg Glu Glu Glu Tyr Glu Leu
            20                  25                  30

Arg Met Ala Leu Glu Arg Phe Gln Ala Asp Thr Ser Val Asp Gly Tyr
        35                  40                  45

Gln Ala Thr Val Glu Tyr His Gly Leu Pro Ala Arg Cys Pro Arg Pro
    50                  55                  60

Asp Ala Lys Val Arg Phe Ala Cys Cys Met His Gly Met Ala Ser Phe
 65                  70                  75                  80

Pro His Trp His Arg Leu Phe Val Thr Gln Val Glu Asp Ala Leu Val
                85                  90                  95

Arg Arg Gly Ser Pro Ile Gly Val Pro Tyr Trp Asp Trp Thr Lys Pro
            100                 105                 110

Met Thr His Leu Pro Asp Leu Ala Ser Asn Glu Thr Tyr Val Asp Pro
        115                 120                 125

Tyr Gly His Thr His His Asn Pro Phe Phe Asn Ala Asn Ile Ser Phe
    130                 135                 140

Glu Glu Gly His His His Thr Ser Arg Met Ile Asp Ser Lys Leu Phe
145                 150                 155                 160

Ala Pro Val Ala Phe Gly Glu His Ser His Leu Phe Asp Gly Ile Leu
                165                 170                 175

Tyr Ala Phe Glu Gln Glu Asp Phe Cys Asp Phe Glu Ile Gln Phe Glu
            180                 185                 190

Leu Val His Asn Ser Ile His Ala Trp Ile Gly Gly Ser Glu Asp Tyr
        195                 200                 205

Ser Met Ala Thr Leu His Tyr Thr Ala Phe Asp Pro Ile Phe Tyr Leu
    210                 215                 220

His His Ser Asn Val Asp Arg Leu Trp Ala Ile Trp Gln Ala Leu Gln
225                 230                 235                 240

Ile Arg Arg His Lys Pro Tyr Gln Ala His Cys Ala Gln Ser Val Glu
                245                 250                 255

Gln Leu Pro Met Lys Pro Phe Ala Phe Pro Ser Pro Leu Asn Asn Asn
            260                 265                 270

Glu Lys Thr His Ser His Ser Val Pro Thr Asp Ile Tyr Asp Tyr Glu
        275                 280                 285
```

-continued

```
Glu Val Leu His Tyr Ser Tyr Asp Asp Leu Thr Phe Gly Gly Met Asn
    290                 295                 300

Leu Glu Glu Ile Glu Glu Ala Ile His Leu Arg Gln Gln His Glu Arg
305                 310                 315                 320

Val Phe Ala Gly Phe Leu Leu Ala Gly Ile Gly Thr Ser Ala Leu Val
                325                 330                 335

Asp Ile Phe Ile Asn Lys Pro Gly Asn Gln Pro Leu Lys Ala Gly Asp
            340                 345                 350

Ile Ala Ile Leu Gly Gly Ala Lys Glu Met Pro Trp Ala Phe Asp Arg
        355                 360                 365

Leu Tyr Lys Val Glu Ile Thr Asp Ser Leu Lys Thr Leu Ser Leu Asp
    370                 375                 380

Val Asp Gly Asp Tyr Glu Val Thr Phe Lys Ile His Asp Met His Gly
385                 390                 395                 400

Asn Ala Leu Asp Thr Asp Leu Ile Pro His Ala Ala Val Val Ser Glu
                405                 410                 415

Pro Ala His


<210> SEQ ID NO 27
<211> LENGTH: 414
<212> TYPE: PRT
<213> ORGANISM: Haliotis tuberculata

<400> SEQUENCE: 27

Pro Thr Phe Glu Asp Glu Lys His Ser Leu Arg Ile Arg Lys Asn Val
  1               5                  10                  15

Asp Ser Leu Thr Pro Glu Glu Thr Asn Glu Leu Arg Lys Ala Leu Glu
            20                  25                  30

Leu Leu Glu Asn Asp His Thr Ala Gly Gly Phe Asn Gln Leu Gly Ala
        35                  40                  45

Phe His Gly Glu Pro Lys Trp Cys Pro Asn Pro Glu Ala Glu His Lys
     50                  55                  60

Val Ala Cys Cys Val His Gly Met Ala Val Phe Pro His Trp His Arg
 65                  70                  75                  80

Leu Leu Ala Leu Gln Ala Glu Asn Ala Leu Arg Lys His Gly Tyr Ser
                 85                  90                  95

Gly Ala Leu Pro Tyr Trp Asp Trp Thr Arg Pro Leu Ser Gln Leu Pro
            100                 105                 110

Asp Leu Val Ser His Glu Gln Tyr Thr Asp Pro Ser Asp His His Val
        115                 120                 125

Lys His Asn Pro Trp Phe Asn Gly His Ile Asp Thr Val Asn Gln Asp
    130                 135                 140

Thr Thr Arg Ser Val Arg Glu Asp Leu Tyr Gln Gln Pro Glu Phe Gly
145                 150                 155                 160

His Phe Thr Asp Ile Ala Gln Gln Val Leu Leu Ala Leu Glu Gln Asp
                165                 170                 175

Asp Phe Cys Ser Phe Glu Val Gln Tyr Glu Ile Ser His Asn Phe Ile
            180                 185                 190

His Ala Leu Val Gly Gly Thr Asp Ala Tyr Gly Met Ala Ser Leu Arg
        195                 200                 205

Tyr Thr Ala Tyr Asp Pro Ile Phe Phe Leu His His Ser Asn Thr Asp
    210                 215                 220

Arg Ile Trp Ala Ile Trp Gln Ser Leu Gln Lys Tyr Arg Gly Lys Pro
225                 230                 235                 240
```

-continued

```
Tyr Asn Thr Ala Asn Cys Ala Ile Glu Ser Met Arg Arg Pro Leu Gln
                245                 250                 255

Pro Phe Gly Leu Ser Ser Ala Ile Asn Pro Asp Arg Ile Thr Arg Glu
            260                 265                 270

His Ala Ile Pro Phe Asp Val Phe Asn Tyr Arg Asp Asn Leu His Tyr
        275                 280                 285

Val Tyr Asp Thr Leu Glu Phe Asn Gly Leu Ser Ile Ser Gln Leu Asp
    290                 295                 300

Arg Glu Leu Glu Lys Ile Lys Ser His Glu Arg Val Phe Ala Gly Phe
305                 310                 315                 320

Leu Leu Ser Gly Ile Lys Lys Ser Ala Leu Val Lys Phe Glu Val Cys
                325                 330                 335

Thr Pro Pro Asp Asn Cys His Lys Ala Gly Glu Phe Tyr Leu Leu Gly
            340                 345                 350

Asp Glu Asn Glu Met Ala Trp Ala Tyr Asp Arg Leu Phe Lys Tyr Asp
        355                 360                 365

Ile Thr Gln Val Leu Glu Ala Asn His Leu His Phe Tyr Asp His Leu
    370                 375                 380

Phe Ile Arg Tyr Glu Val Phe Asp Leu Lys Gly Val Ser Leu Gly Thr
385                 390                 395                 400

Asp Leu Phe His Thr Ala Asn Val Val His Asp Ser Gly Thr
                405                 410


<210> SEQ ID NO 28
<211> LENGTH: 413
<212> TYPE: PRT
<213> ORGANISM: Haliotis tuberculata

<400> SEQUENCE: 28

Gly Thr Arg Asp Arg Asp Asn Tyr Val Glu Glu Val Thr Gly Ala Ser
  1               5                  10                  15

His Ile Arg Lys Asn Leu Asn Asp Leu Asn Thr Gly Glu Met Glu Ser
            20                  25                  30

Leu Arg Ala Ala Phe Leu His Ile Gln Asp Asp Gly Thr Tyr Glu Ser
        35                  40                  45

Ile Ala Gln Tyr His Gly Lys Pro Gly Lys Cys Gln Leu Asn Asp His
     50                  55                  60

Asn Ile Ala Cys Cys Val His Gly Met Pro Thr Phe Pro Gln Trp His
 65                  70                  75                  80

Arg Leu Tyr Val Val Gln Val Glu Asn Ala Leu Leu Asn Arg Gly Ser
                 85                  90                  95

Gly Val Ala Val Pro Tyr Trp Glu Trp Thr Ala Pro Ile Asp His Leu
            100                 105                 110

Pro His Phe Ile Asp Asp Ala Thr Tyr Phe Asn Ser Arg Gln Gln Arg
        115                 120                 125

Tyr Asp Pro Asn Pro Phe Phe Arg Gly Lys Val Thr Phe Glu Asn Ala
    130                 135                 140

Val Thr Thr Arg Asp Pro Gln Ala Gly Leu Phe Asn Ser Asp Tyr Met
145                 150                 155                 160

Tyr Glu Asn Val Leu Leu Ala Leu Glu Gln Glu Asn Tyr Cys Asp Phe
                165                 170                 175

Glu Ile Gln Phe Glu Leu Val His Asn Ala Leu His Ser Met Leu Gly
            180                 185                 190

Gly Lys Gly Gln Tyr Ser Met Ser Ser Leu Asp Tyr Ser Ala Phe Asp
        195                 200                 205
```

-continued

Pro Val Phe Phe Leu His His Ala Asn Thr Asp Arg Leu Trp Ala Ile
    210                 215                 220

Trp Gln Glu Leu Gln Arg Phe Arg Glu Leu Pro Tyr Glu Glu Ala Asn
225                 230                 235                 240

Cys Ala Ile Asn Leu Met His Gln Pro Leu Lys Pro Phe Ser Asp Pro
                245                 250                 255

His Glu Asn His Asp Asn Val Thr Leu Lys Tyr Ser Lys Pro Gln Asp
            260                 265                 270

Gly Phe Asp Tyr Gln Asn His Phe Gly Tyr Lys Tyr Asp Asn Leu Glu
        275                 280                 285

Phe His His Leu Ser Ile Pro Ser Leu Asp Ala Thr Leu Lys Gln Arg
    290                 295                 300

Arg Asn His Asp Arg Val Phe Ala Gly Phe Leu Leu His Asn Ile Gly
305                 310                 315                 320

Thr Ser Ala Asp Ile Thr Ile Tyr Ile Cys Leu Pro Asp Gly Arg Arg
                325                 330                 335

Gly Asn Asp Cys Ser His Glu Ala Gly Thr Phe Tyr Ile Leu Gly Gly
            340                 345                 350

Glu Thr Glu Met Pro Phe Ile Phe Asp Arg Leu Tyr Lys Phe Glu Ile
        355                 360                 365

Thr Lys Pro Leu Gln Gln Leu Gly Val Lys Leu His Gly Gly Val Phe
    370                 375                 380

Glu Leu Glu Leu Glu Ile Lys Ala Tyr Asn Gly Ser Tyr Leu Asp Pro
385                 390                 395                 400

His Thr Phe Asp Pro Thr Ile Ile Phe Glu Pro Gly Thr
                405                 410

<210> SEQ ID NO 29
<211> LENGTH: 420
<212> TYPE: PRT
<213> ORGANISM: Haliotis tuberculata

<400> SEQUENCE: 29

Asp Thr His Ile Leu Asp His Asp His Glu Glu Glu Ile Leu Val Arg
  1               5                  10                  15

Lys Asn Ile Ile Asp Leu Ser Pro Arg Glu Arg Val Ser Leu Val Lys
            20                  25                  30

Ala Leu Gln Arg Met Lys Asn Asp Arg Ser Ala Asp Gly Tyr Gln Ala
        35                  40                  45

Ile Ala Ser Phe His Ala Leu Pro Pro Leu Cys Pro Asn Pro Ser Ala
     50                  55                  60

Ala His Arg Tyr Ala Cys Cys Val His Gly Met Ala Thr Phe Pro Gln
 65                  70                  75                  80

Trp His Arg Leu Tyr Thr Val Gln Val Gln Asp Ala Leu Arg Arg His
                 85                  90                  95

Gly Ser Leu Val Gly Ile Pro Tyr Trp Asp Trp Thr Lys Pro Val Asn
            100                 105                 110

Glu Leu Pro Glu Leu Leu Ser Ser Ala Thr Phe Tyr His Pro Ile Arg
        115                 120                 125

Asn Ile Asn Ile Ser Asn Pro Phe Leu Gly Ala Asp Ile Glu Phe Glu
    130                 135                 140

Gly Pro Gly Val His Thr Glu Arg His Ile Asn Thr Glu Arg Leu Phe
145                 150                 155                 160

His Ser Gly Asp His Asp Gly Tyr His Asn Trp Phe Phe Glu Thr Val
                165                 170                 175

-continued

```
Leu Phe Ala Leu Glu Gln Glu Asp Tyr Cys Asp Phe Glu Ile Gln Phe
            180                 185                 190

Glu Ile Ala His Asn Gly Ile His Thr Trp Ile Gly Gly Ser Ala Val
        195                 200                 205

Tyr Gly Met Gly His Leu His Tyr Ala Ser Tyr Asp Pro Ile Phe Tyr
    210                 215                 220

Ile His His Ser Gln Thr Asp Arg Ile Trp Ala Ile Trp Gln Glu Leu
225                 230                 235                 240

Gln Lys Tyr Arg Gly Leu Ser Gly Ser Glu Ala Asn Cys Ala Ile Glu
                245                 250                 255

His Met Arg Thr Pro Leu Lys Pro Phe Ser Phe Gly Pro Pro Tyr Asn
            260                 265                 270

Leu Asn Ser His Thr Gln Glu Tyr Ser Lys Pro Glu Asp Thr Phe Asp
        275                 280                 285

Tyr Lys Lys Phe Gly Tyr Arg Tyr Asp Ser Leu Glu Leu Glu Gly Arg
    290                 295                 300

Ser Ile Ser Arg Ile Asp Glu Leu Ile Gln Gln Arg Gln Glu Lys Asp
305                 310                 315                 320

Arg Thr Phe Ala Gly Phe Leu Leu Lys Gly Phe Gly Thr Ser Ala Ser
                325                 330                 335

Val Ser Leu Gln Val Cys Arg Val Asp His Thr Cys Lys Asp Ala Gly
            340                 345                 350

Tyr Phe Thr Ile Leu Gly Gly Ser Ala Glu Met Pro Trp Ala Phe Asp
        355                 360                 365

Arg Leu Tyr Lys Tyr Asp Ile Thr Lys Thr Leu His Asp Met Asn Leu
    370                 375                 380

Arg His Glu Asp Thr Phe Ser Ile Asp Val Thr Ile Thr Ser Tyr Asn
385                 390                 395                 400

Gly Thr Val Leu Ser Gly Asp Leu Ile Gln Thr Pro Ser Ile Ile Phe
                405                 410                 415

Val Pro Gly Arg
            420


<210> SEQ ID NO 30
<211> LENGTH: 417
<212> TYPE: PRT
<213> ORGANISM: Haliotis tuberculata

<400> SEQUENCE: 30

His Lys Leu Asn Ser Arg Lys His Thr Pro Asn Arg Val Arg His Glu
  1               5                  10                  15

Leu Ser Ser Leu Ser Ser Arg Asp Ile Ala Ser Leu Lys Ala Ala Leu
            20                  25                  30

Thr Ser Leu Gln His Asp Asn Gly Thr Asp Gly Tyr Gln Ala Ile Ala
        35                  40                  45

Ala Phe His Gly Val Pro Ala Gln Cys His Glu Pro Ser Gly Arg Glu
     50                  55                  60

Ile Ala Cys Cys Ile His Gly Met Ala Thr Phe Pro His Trp His Arg
 65                  70                  75                  80

Leu Tyr Thr Leu Gln Leu Glu Gln Ala Leu Arg Arg His Gly Ser Ser
                 85                  90                  95

Val Ala Val Pro Tyr Trp Asp Trp Thr Lys Pro Ile Thr Glu Leu Pro
            100                 105                 110

His Ile Leu Thr Asp Gly Glu Tyr Tyr Asp Val Trp Gln Asn Ala Val
        115                 120                 125
```

-continued

```
Leu Ala Asn Pro Phe Ala Arg Gly Tyr Val Lys Ile Lys Asp Ala Phe
    130                 135                 140

Thr Val Arg Asn Val Gln Glu Ser Leu Phe Lys Met Ser Ser Phe Gly
145                 150                 155                 160

Lys His Ser Leu Leu Phe Asp Gln Ala Leu Leu Ala Leu Glu Gln Thr
                165                 170                 175

Asp Tyr Cys Asp Phe Glu Val Gln Phe Glu Val Met His Asn Thr Ile
            180                 185                 190

His Tyr Leu Val Gly Gly Arg Gln Thr Tyr Ala Phe Ser Ser Leu Glu
        195                 200                 205

Tyr Ser Ser Tyr Asp Pro Ile Phe Phe Ile His His Ser Phe Val Asp
    210                 215                 220

Lys Ile Trp Ala Val Trp Gln Glu Leu Gln Ser Arg Arg His Leu Gln
225                 230                 235                 240

Phe Arg Thr Ala Asp Cys Ala Val Gly Leu Met Gly Gln Ala Met Arg
                245                 250                 255

Pro Phe Asn Lys Asp Phe Asn His Asn Ser Phe Thr Lys Lys His Ala
            260                 265                 270

Val Pro Asn Thr Val Phe Asp Tyr Glu Asp Leu Gly Tyr Asn Tyr Asp
        275                 280                 285

Asn Leu Glu Ile Ser Gly Leu Asn Leu Asn Glu Ile Glu Ala Leu Ile
    290                 295                 300

Ala Lys Arg Lys Ser His Ala Arg Val Phe Ala Gly Phe Leu Leu Phe
305                 310                 315                 320

Gly Leu Gly Thr Ser Ala Asp Ile His Leu Glu Ile Cys Lys Thr Ser
                325                 330                 335

Glu Asn Cys His Asp Ala Gly Val Ile Phe Ile Leu Gly Gly Ser Ala
            340                 345                 350

Glu Met His Trp Ala Tyr Asn Arg Leu Tyr Lys Tyr Asp Ile Thr Glu
        355                 360                 365

Ala Leu Gln Glu Phe Asp Ile Asn Pro Glu Asp Val Phe His Ala Asp
    370                 375                 380

Glu Pro Phe Phe Leu Arg Leu Ser Val Val Ala Val Asn Gly Thr Val
385                 390                 395                 400

Ile Pro Ser Ser His Leu His Gln Pro Thr Ile Ile Tyr Glu Pro Gly
                405                 410                 415

Glu


<210> SEQ ID NO 31
<211> LENGTH: 403
<212> TYPE: PRT
<213> ORGANISM: Haliotis tuberculata

<400> SEQUENCE: 31

Asp His His Asp Asp His Gln Ser Gly Ser Ile Ala Gly Ser Gly Val
  1               5                  10                  15

Arg Lys Asp Val Asn Thr Leu Thr Lys Ala Glu Thr Asp Asn Leu Arg
            20                  25                  30

Glu Ala Leu Trp Gly Val Met Ala Asp His Gly Pro Asn Gly Phe Gln
        35                  40                  45

Ala Ile Ala Ala Phe His Gly Lys Pro Ala Leu Cys Pro Met Pro Asp
     50                  55                  60

Gly His Asn Tyr Ser Cys Cys Thr His Gly Met Ala Thr Phe Pro His
 65                  70                  75                  80
```

-continued

```
Trp His Arg Leu Tyr Thr Lys Gln Met Glu Asp Ala Met Arg Ala His
                 85                  90                  95

Gly Ser His Val Gly Leu Pro Tyr Trp Asp Trp Thr Ala Ala Phe Thr
            100                 105                 110

His Leu Pro Thr Leu Val Thr Asp Thr Asp Asn Asn Pro Phe Gln His
        115                 120                 125

Gly His Ile Asp Tyr Leu Asn Val Ser Thr Thr Arg Ser Pro Arg Asp
    130                 135                 140

Met Leu Phe Asn Asp Pro Glu His Gly Ser Glu Ser Phe Phe Tyr Arg
145                 150                 155                 160

Gln Val Leu Leu Ala Leu Glu Gln Thr Asp Phe Cys Lys Phe Glu Val
                165                 170                 175

Gln Phe Glu Ile Thr His Asn Ala Ile His Ser Trp Thr Gly Gly His
            180                 185                 190

Ser Pro Tyr Gly Met Ser Thr Leu Asp Phe Thr Ala Tyr Asp Pro Leu
        195                 200                 205

Phe Trp Leu His His Ser Asn Thr Asp Arg Ile Trp Ala Val Trp Gln
    210                 215                 220

Ala Leu Gln Glu Tyr Arg Gly Leu Pro Tyr Asn His Ala Asn Cys Glu
225                 230                 235                 240

Ile Gln Ala Met Lys Thr Pro Leu Arg Pro Phe Ser Asp Asp Ile Asn
                245                 250                 255

His Asn Pro Val Thr Lys Ala Asn Ala Lys Pro Leu Asp Val Phe Glu
            260                 265                 270

Tyr Asn Arg Leu Ser Phe Gln Tyr Asp Asn Leu Ile Phe His Gly Tyr
        275                 280                 285

Ser Ile Pro Glu Leu Asp Arg Val Leu Glu Glu Arg Lys Glu Glu Asp
    290                 295                 300

Arg Ile Phe Ala Ala Phe Leu Leu Ser Gly Ile Lys Arg Ser Ala Asp
305                 310                 315                 320

Val Val Phe Asp Ile Cys Gln Pro Glu His Glu Cys Val Phe Ala Gly
                325                 330                 335

Thr Phe Ala Ile Leu Gly Gly Glu Leu Glu Met Pro Trp Ser Phe Asp
            340                 345                 350

Arg Leu Phe Arg Tyr Asp Ile Thr Lys Val Met Lys Gln Leu His Leu
        355                 360                 365

Arg His Asp Ser Asp Phe Thr Phe Arg Val Lys Ile Val Gly Thr Asp
    370                 375                 380

Asp His Glu Leu Pro Ser Asp Ser Val Lys Ala Pro Thr Ile Glu Phe
385                 390                 395                 400

Glu Pro Gly


<210> SEQ ID NO 32
<211> LENGTH: 511
<212> TYPE: PRT
<213> ORGANISM: Haliotis tuberculata

<400> SEQUENCE: 32

Val His Arg Gly Gly Asn His Glu Asp Glu His His Asp Asp Arg Leu
  1               5                  10                  15

Ala Asp Val Leu Ile Arg Lys Glu Val Asp Phe Leu Ser Leu Gln Glu
            20                  25                  30

Ala Asn Ala Ile Lys Asp Ala Leu Tyr Lys Leu Gln Asn Asp Asp Ser
        35                  40                  45
```

-continued

```
Lys Gly Gly Phe Glu Ala Ile Ala Gly Tyr His Gly Tyr Pro Asn Met
     50                  55                  60

Cys Pro Glu Arg Gly Thr Asp Lys Tyr Pro Cys Cys Val His Gly Met
 65                  70                  75                  80

Pro Val Phe Pro His Trp His Arg Leu His Thr Ile Gln Met Glu Arg
                 85                  90                  95

Ala Leu Lys Asn His Gly Ser Pro Met Gly Ile Pro Tyr Trp Asp Trp
            100                 105                 110

Thr Lys Lys Met Ser Ser Leu Pro Ser Phe Phe Gly Asp Ser Ser Asn
        115                 120                 125

Asn Asn Pro Phe Tyr Lys Tyr Tyr Ile Arg Gly Val Gln His Glu Thr
    130                 135                 140

Thr Arg Asp Val Asn Gln Arg Leu Phe Asn Gln Thr Lys Phe Gly Glu
145                 150                 155                 160

Phe Asp Tyr Leu Tyr Tyr Leu Thr Leu Gln Val Leu Glu Glu Asn Ser
                165                 170                 175

Tyr Cys Asp Phe Glu Val Gln Tyr Glu Ile Leu His Asn Ala Val His
            180                 185                 190

Ser Trp Leu Gly Gly Thr Gly Gln Tyr Ser Met Ser Thr Leu Glu Tyr
        195                 200                 205

Ser Ala Phe Asp Pro Val Phe Met Ile His His Ser Ser Leu Asp Arg
    210                 215                 220

Ile Trp Ile Leu Trp Gln Lys Leu Gln Lys Ile Arg Met Lys Pro Tyr
225                 230                 235                 240

Tyr Ala Leu Asp Cys Ala Gly Asp Arg Leu Met Lys Asp Pro Leu His
                245                 250                 255

Pro Phe Asn Tyr Glu Thr Val Asn Glu Asp Glu Phe Thr Arg Ile Asn
            260                 265                 270

Ser Phe Pro Ser Ile Leu Phe Asp His Tyr Arg Phe Asn Tyr Glu Tyr
        275                 280                 285

Asp Asn Met Arg Ile Arg Gly Gln Asp Ile His Glu Leu Glu Glu Val
    290                 295                 300

Ile Gln Glu Leu Arg Asn Lys Asp Arg Ile Phe Ala Gly Phe Val Leu
305                 310                 315                 320

Ser Gly Leu Arg Ile Ser Ala Thr Val Lys Val Phe Ile His Ser Lys
                325                 330                 335

Asn Asp Thr Ser His Glu Glu Tyr Ala Gly Glu Phe Ala Val Leu Gly
            340                 345                 350

Gly Glu Lys Glu Met Pro Trp Ala Tyr Glu Arg Met Leu Lys Leu Asp
        355                 360                 365

Ile Ser Asp Ala Val His Lys Leu His Val Lys Asp Glu Asp Ile Arg
    370                 375                 380

Phe Arg Val Val Val Thr Ala Tyr Asn Gly Asp Val Val Thr Thr Arg
385                 390                 395                 400

Leu Ser Gln Pro Phe Ile Val His Arg Pro Ala His Val Ala His Asp
                405                 410                 415

Ile Leu Val Ile Pro Val Gly Ala Gly His Asp Leu Pro Pro Lys Val
            420                 425                 430

Val Val Lys Ser Gly Thr Lys Val Glu Phe Thr Pro Ile Asp Ser Ser
        435                 440                 445

Val Asn Lys Ala Met Val Glu Leu Gly Ser Tyr Thr Ala Met Ala Lys
    450                 455                 460
```

-continued

```
Cys Ile Val Pro Pro Phe Ser Tyr His Gly Phe Glu Leu Asp Lys Val
465                 470                 475                 480

Tyr Ser Val Asp His Gly Asp Tyr Tyr Ile Ala Ala Gly Thr His Ala
                485                 490                 495

Leu Cys Glu Gln Asn Leu Arg Leu His Ile His Val Glu His Glu
            500                 505                 510


<210> SEQ ID NO 33
<211> LENGTH: 334
<212> TYPE: PRT
<213> ORGANISM: Haliotis tuberculata

<400> SEQUENCE: 33

His Arg Leu Phe Val Thr Gln Val Glu Asp Ala Leu Ile Arg Arg Gly
  1               5                  10                  15

Ser Pro Ile Gly Val Pro Tyr Trp Asp Trp Thr Gln Pro Met Ala His
             20                  25                  30

Leu Pro Gly Leu Ala Asp Asn Ala Thr Tyr Arg Asp Pro Ile Ser Gly
         35                  40                  45

Asp Ser Arg His Asn Pro Phe His Asp Val Glu Val Ala Phe Glu Asn
     50                  55                  60

Gly Arg Thr Glu Arg His Pro Asp Ser Arg Leu Phe Glu Gln Pro Leu
 65                  70                  75                  80

Phe Gly Lys His Thr Arg Leu Phe Asp Ser Ile Val Tyr Ala Phe Glu
                 85                  90                  95

Gln Glu Asp Phe Cys Asp Phe Glu Val Gln Phe Glu Met Thr His Asn
            100                 105                 110

Asn Ile His Ala Trp Ile Gly Gly Gly Glu Lys Tyr Ser Met Ser Ser
        115                 120                 125

Leu His Tyr Thr Ala Phe Asp Pro Ile Phe Tyr Leu Arg His Ser Asn
    130                 135                 140

Thr Asp Arg Leu Trp Ala Ile Trp Gln Ala Leu Gln Ile Arg Arg Asn
145                 150                 155                 160

Arg Pro Tyr Lys Ala His Cys Ala Trp Ser Glu Glu Arg Gln Pro Leu
                165                 170                 175

Lys Pro Phe Ala Phe Ser Ser Pro Leu Asn Asn Asn Glu Lys Thr Tyr
            180                 185                 190

Glu Asn Ser Val Pro Thr Asn Val Tyr Asp Tyr Glu Gly Val Leu Gly
        195                 200                 205

Tyr Thr Tyr Asp Asp Leu Asn Phe Gly Gly Met Asp Leu Gly Gln Leu
    210                 215                 220

Glu Glu Tyr Ile Gln Arg Gln Arg Gln Arg Asp Arg Thr Phe Ala Gly
225                 230                 235                 240

Phe Phe Leu Ser His Ile Gly Thr Ser Ala Asn Val Glu Ile Ile Ile
                245                 250                 255

Asp His Gly Thr Leu His Thr Ser Val Gly Thr Phe Ala Val Leu Gly
            260                 265                 270

Gly Glu Lys Glu Met Lys Trp Gly Phe Asp Arg Leu Tyr Lys Tyr Glu
        275                 280                 285

Ile Thr Asp Glu Leu Arg Gln Leu Asn Leu Arg Ala Asp Asp Val Phe
    290                 295                 300

Ser Ile Ser Val Lys Val Thr Asp Val Asp Gly Ser Glu Leu Ser Ser
305                 310                 315                 320

Glu Leu Ile Pro Ser Ala Ala Ile Ile Phe Glu Arg Ser His
                325                 330
```

-continued

<210> SEQ ID NO 34
<211> LENGTH: 417
<212> TYPE: PRT
<213> ORGANISM: Haliotis tuberculata

<400> SEQUENCE: 34

```
Ile Asp His Gln Asp Pro His His Asp Thr Ile Ile Arg Lys Asn Val
  1               5                  10                  15

Asp Asn Leu Thr Pro Glu Glu Ile Asn Ser Leu Arg Arg Ala Met Ala
             20                  25                  30

Asp Leu Gln Ser Asp Lys Thr Ala Gly Gly Phe Gln Gln Ile Ala Ala
         35                  40                  45

Phe His Gly Glu Pro Lys Trp Cys Pro Ser Pro Asp Ala Glu Lys Lys
     50                  55                  60

Phe Ser Cys Cys Val His Gly Met Ala Val Phe Pro His Trp His Arg
 65                  70                  75                  80

Leu Leu Thr Val Gln Gly Glu Asn Ala Leu Arg Lys His Gly Cys Leu
                 85                  90                  95

Gly Ala Leu Pro Tyr Trp Asp Trp Thr Arg Pro Leu Ser His Leu Pro
            100                 105                 110

Asp Leu Val Leu Val Ser Ser Arg Thr Thr Pro Met Pro Tyr Ser Thr
        115                 120                 125

Val Glu Ala Arg Asn Pro Trp Tyr Ser Gly His Ile Asp Thr Val Gly
    130                 135                 140

Val Asp Thr Thr Arg Ser Val Arg Gln Glu Leu Tyr Glu Ala Pro Gly
145                 150                 155                 160

Phe Gly His Tyr Thr Gly Val Ala Lys Gln Val Leu Leu Ala Leu Glu
                165                 170                 175

Gln Asp Asp Phe Cys Asp Phe Glu Val Gln Phe Glu Ile Ala His Asn
            180                 185                 190

Phe Ile His Ala Leu Val Gly Gly Ser Glu Pro Tyr Gly Met Ala Ser
        195                 200                 205

Leu Arg Tyr Thr Thr Tyr Asp Pro Ile Phe Tyr Leu His His Ser Asn
    210                 215                 220

Thr Asp Arg Leu Trp Ala Ile Trp Gln Ala Leu Gln Lys Tyr Arg Gly
225                 230                 235                 240

Lys Pro Tyr Asn Ser Ala Asn Cys Ala Ile Ala Ser Met Arg Lys Pro
                245                 250                 255

Leu Gln Pro Phe Gly Leu Thr Asp Glu Ile Asn Pro Asp Asp Glu Thr
            260                 265                 270

Arg Gln His Ala Val Pro Phe Ser Val Phe Asp Tyr Lys Asn Asn Phe
        275                 280                 285

Asn Tyr Glu Tyr Asp Thr Leu Asp Phe Asn Gly Leu Ser Ile Ser Gln
    290                 295                 300

Leu Asp Arg Glu Leu Ser Arg Arg Lys Ser His Asp Arg Val Phe Ala
305                 310                 315                 320

Gly Phe Leu Leu His Gly Ile Gln Gln Ser Ala Leu Val Lys Phe Phe
                325                 330                 335

Val Cys Lys Ser Asp Asp Asp Cys Asp His Tyr Ala Gly Glu Phe Tyr
            340                 345                 350

Ile Leu Gly Asp Glu Ala Glu Met Pro Trp Gly Tyr Asp Arg Leu Tyr
        355                 360                 365

Lys Tyr Glu Ile Thr Glu Gln Leu Asn Ala Leu Asp Leu His Ile Gly
    370                 375                 380
```

-continued

```
Asp Arg Phe Phe Ile Arg Tyr Glu Ala Phe Asp Leu His Gly Thr Ser
385                 390                 395                 400

Leu Gly Ser Asn Ile Phe Pro Lys Pro Ser Val Ile His Asp Glu Gly
                405                 410                 415

Ala


<210> SEQ ID NO 35
<211> LENGTH: 415
<212> TYPE: PRT
<213> ORGANISM: Haliotis tuberculata

<400> SEQUENCE: 35

Gly His His Gln Ala Asp Glu Tyr Asp Glu Val Val Thr Ala Ala Ser
  1               5                  10                  15

His Ile Arg Lys Asn Leu Lys Asp Leu Ser Lys Gly Glu Val Glu Ser
             20                  25                  30

Leu Arg Ser Ala Phe Leu Gln Leu Gln Asn Asp Gly Val Tyr Glu Asn
         35                  40                  45

Ile Ala Lys Phe His Gly Lys Pro Gly Leu Cys Asp Asp Asn Gly Arg
     50                  55                  60

Lys Val Ala Cys Cys Val His Gly Met Pro Thr Phe Pro Gln Trp His
 65                  70                  75                  80

Arg Leu Tyr Val Leu Gln Val Glu Asn Ala Leu Leu Glu Arg Gly Ser
                 85                  90                  95

Ala Val Ser Val Pro Tyr Trp Asp Trp Thr Glu Thr Phe Thr Glu Leu
            100                 105                 110

Pro Ser Leu Ile Ala Glu Ala Thr Tyr Phe Asn Ser Arg Gln Gln Thr
        115                 120                 125

Phe Asp Pro Asn Pro Phe Phe Arg Gly Lys Ile Ser Phe Glu Asn Ala
    130                 135                 140

Val Thr Thr Arg Asp Pro Gln Pro Glu Leu Tyr Val Asn Arg Tyr Tyr
145                 150                 155                 160

Tyr Gln Asn Val Met Leu Val Phe Glu Gln Asp Asn Tyr Cys Asp Phe
                165                 170                 175

Glu Ile Gln Phe Glu Met Val His Asn Val Leu His Ala Trp Leu Gly
            180                 185                 190

Gly Arg Ala Thr Tyr Ser Ile Ser Ser Leu Asp Tyr Ser Ala Phe Asp
        195                 200                 205

Pro Val Phe Phe Leu His His Ala Asn Thr Asp Arg Leu Trp Ala Ile
    210                 215                 220

Trp Gln Glu Leu Gln Arg Tyr Arg Lys Lys Pro Tyr Asn Glu Ala Asp
225                 230                 235                 240

Cys Ala Ile Asn Leu Met Arg Lys Pro Leu His Pro Phe Asp Asn Ser
                245                 250                 255

Asp Leu Asn His Asp Pro Val Thr Phe Lys Tyr Ser Lys Pro Thr Asp
            260                 265                 270

Gly Phe Asp Tyr Gln Asn Asn Phe Gly Tyr Lys Tyr Asp Asn Leu Glu
        275                 280                 285

Phe Asn His Phe Ser Ile Pro Arg Leu Glu Glu Ile Ile Arg Ile Arg
    290                 295                 300

Gln Arg Gln Asp Arg Val Phe Ala Gly Phe Leu Leu His Asn Ile Gly
305                 310                 315                 320

Thr Ser Ala Thr Val Glu Ile Phe Val Cys Val Pro Thr Thr Ser Gly
                325                 330                 335
```

-continued

```
Glu Gln Asn Cys Glu Asn Lys Ala Gly Thr Phe Ala Val Leu Gly Gly
            340                 345                 350

Glu Thr Glu Met Ala Phe His Phe Asp Arg Leu Tyr Arg Phe Asp Ile
        355                 360                 365

Ser Glu Thr Leu Arg Asp Leu Gly Ile Gln Leu Asp Ser His Asp Phe
    370                 375                 380

Asp Leu Ser Ile Lys Ile Gln Gly Val Asn Gly Ser Tyr Leu Asp Pro
385                 390                 395                 400

His Ile Leu Pro Glu Pro Ser Leu Ile Phe Val Pro Gly Ser Ser
                405                 410                 415


<210> SEQ ID NO 36
<211> LENGTH: 418
<212> TYPE: PRT
<213> ORGANISM: Haliotis tuberculata

<400> SEQUENCE: 36

Ser Phe Leu Arg Pro Asp Gly His Ser Asp Asp Ile Leu Val Arg Lys
  1               5                  10                  15

Glu Val Asn Ser Leu Thr Thr Arg Glu Thr Ala Ser Leu Ile His Ala
            20                  25                  30

Leu Lys Ser Met Gln Glu Asp His Ser Pro Asp Gly Phe Gln Ala Ile
        35                  40                  45

Ala Ser Phe His Ala Leu Pro Pro Leu Cys Pro Ser Pro Ser Ala Ala
    50                  55                  60

His Arg Tyr Ala Cys Cys Val His Gly Met Ala Thr Phe Pro Gln Trp
65                  70                  75                  80

His Arg Leu Tyr Thr Val Gln Phe Gln Asp Ala Leu Arg Arg His Gly
                85                  90                  95

Ala Thr Val Gly Val Pro Tyr Trp Asp Trp Leu Arg Pro Gln Ser His
            100                 105                 110

Leu Pro Glu Leu Val Thr Met Glu Thr Tyr His Asp Ile Trp Ser Asn
        115                 120                 125

Arg Asp Phe Pro Asn Pro Phe Tyr Gln Ala Asn Ile Glu Phe Glu Gly
    130                 135                 140

Glu Asn Ile Thr Thr Glu Arg Glu Val Ile Ala Asp Lys Leu Phe Val
145                 150                 155                 160

Lys Gly Gly His Val Phe Asp Lys Leu Val Leu Gln Thr Ser His Pro
                165                 170                 175

Ser Ala Glu Gln Glu Asn Tyr Cys Asp Phe Glu Ile Gln Phe Glu Ile
            180                 185                 190

Leu His Asn Gly Val His Thr Trp Val Gly Gly Ser Arg Thr Tyr Ser
        195                 200                 205

Ile Gly His Leu His Tyr Ala Phe Tyr Asp Pro Leu Phe Tyr Leu His
    210                 215                 220

His Phe Gln Thr Asp Arg Ile Trp Ala Ile Trp Gln Glu Leu Gln Glu
225                 230                 235                 240

Gln Arg Gly Leu Ser Gly Asp Glu Ala His Cys Ala Leu Glu Gln Met
                245                 250                 255

Arg Glu Pro Leu Lys Pro Phe Ser Phe Gly Ala Pro Tyr Asn Trp Asn
            260                 265                 270

Gln Leu Thr Gln Asp Phe Ser Arg Pro Glu Asp Thr Phe Asp Tyr Arg
        275                 280                 285

Lys Phe Gly Tyr Glu Tyr Asp Asn Leu Glu Phe Leu Gly Met Ser Val
    290                 295                 300
```

-continued

```
Ala Glu Leu Asp Gln Tyr Ile Ile Glu His Gln Glu Asn Asp Arg Val
305                 310                 315                 320

Phe Ala Gly Phe Leu Leu Ser Gly Phe Gly Gly Ser Ala Ser Val Asn
                325                 330                 335

Phe Gln Val Cys Arg Ala Asp Ser Thr Cys Gln Asp Ala Gly Tyr Phe
            340                 345                 350

Thr Val Leu Gly Gly Ser Ala Glu Met Ala Trp Ala Phe Asp Arg Leu
        355                 360                 365

Tyr Lys Tyr Asp Ile Thr Glu Thr Leu Glu Lys Met His Leu Arg Tyr
    370                 375                 380

Asp Asp Asp Phe Thr Ile Ser Val Ser Leu Thr Ala Asn Asn Gly Thr
385                 390                 395                 400

Val Leu Ser Ser Ser Leu Ile Pro Thr Pro Ser Val Ile Phe Gln Arg
                405                 410                 415

Gly His


<210> SEQ ID NO 37
<211> LENGTH: 416
<212> TYPE: PRT
<213> ORGANISM: Haliotis tuberculata

<400> SEQUENCE: 37

Arg Asp Ile Asn Thr Arg Ser Met Ser Pro Asn Arg Val Arg Arg Glu
  1               5                  10                  15

Leu Ser Asp Leu Ser Ala Arg Asp Leu Ser Ser Leu Lys Ser Ala Leu
             20                  25                  30

Arg Asp Leu Gln Glu Asp Asp Gly Pro Asn Gly Tyr Gln Ala Leu Ala
         35                  40                  45

Ala Phe His Gly Leu Pro Ala Gly Cys His Asp Ser Arg Gly Asn Glu
     50                  55                  60

Ile Ala Cys Cys Ile His Gly Met Pro Thr Phe Pro Gln Trp His Arg
 65                  70                  75                  80

Leu Tyr Thr Leu Gln Leu Glu Met Ala Leu Arg Arg His Gly Ser Ser
                 85                  90                  95

Val Ala Ile Pro Tyr Trp Asp Trp Thr Lys Pro Ile Ser Glu Leu Pro
            100                 105                 110

Ser Leu Phe Thr Ser Pro Glu Tyr Tyr Asp Pro Trp His Asp Ala Val
        115                 120                 125

Val Asn Asn Pro Phe Ser Lys Gly Phe Val Lys Phe Ala Asn Thr Tyr
    130                 135                 140

Thr Val Arg Asp Pro Gln Glu Met Leu Phe Gln Leu Cys Glu His Gly
145                 150                 155                 160

Glu Ser Ile Leu Tyr Glu Gln Thr Leu Leu Ala Leu Glu Gln Thr Asp
                165                 170                 175

Tyr Cys Asp Phe Glu Val Gln Phe Glu Val Leu His Asn Val Ile His
            180                 185                 190

Tyr Leu Val Gly Gly Arg Gln Thr Tyr Ala Leu Ser Ser Leu His Tyr
        195                 200                 205

Ala Ser Tyr Asp Pro Phe Phe Phe Ile His His Ser Phe Val Asp Lys
    210                 215                 220

Met Trp Val Val Trp Gln Ala Leu Gln Lys Arg Arg Lys Leu Pro Tyr
225                 230                 235                 240

Lys Arg Ala Asp Cys Ala Val Asn Leu Met Thr Lys Pro Met Arg Pro
                245                 250                 255
```

-continued

Phe Asp Ser Asp Met Asn Gln Asn Pro Phe Thr Lys Met His Ala Val
260 265 270

Pro Asn Thr Leu Tyr Asp Tyr Glu Thr Leu Tyr Tyr Ser Tyr Asp Asn
275 280 285

Leu Glu Ile Gly Gly Arg Asn Leu Asp Gln Leu Gln Ala Glu Ile Asp
290 295 300

Arg Ser Arg Ser His Asp Arg Val Phe Ala Gly Phe Leu Leu Arg Gly
305 310 315 320

Ile Gly Thr Ser Ala Asp Val Arg Phe Trp Ile Cys Arg Asn Glu Asn
325 330 335

Asp Cys His Arg Gly Gly Ile Ile Phe Ile Leu Gly Gly Ala Lys Glu
340 345 350

Met Pro Trp Ser Phe Asp Arg Asn Phe Lys Phe Asp Ile Thr His Val
355 360 365

Leu Glu Asn Ala Gly Ile Ser Pro Glu Asp Val Phe Asp Ala Glu Glu
370 375 380

Pro Phe Tyr Ile Lys Val Glu Ile His Ala Val Asn Lys Thr Met Ile
385 390 395 400

Pro Ser Ser Val Ile Pro Ala Pro Thr Ile Ile Tyr Ser Pro Gly Glu
405 410 415

<210> SEQ ID NO 38
<211> LENGTH: 402
<212> TYPE: PRT
<213> ORGANISM: Haliotis tuberculata

<400> SEQUENCE: 38

Gly Arg Ala Ala Asp Ser Ala His Ser Ala Asn Ile Ala Gly Ser Gly
1 5 10 15

Val Arg Lys Asp Val Thr Thr Leu Thr Val Ser Glu Thr Glu Asn Leu
20 25 30

Arg Gln Ala Leu Gln Gly Val Ile Asp Asp Thr Gly Pro Asn Gly Tyr
35 40 45

Gln Ala Ile Ala Ser Phe His Gly Ser Pro Pro Met Cys Glu Met Asn
50 55 60

Gly Arg Lys Val Ala Cys Cys Ala His Gly Met Ala Ser Phe Pro His
65 70 75 80

Trp His Arg Leu Tyr Val Lys Gln Met Glu Asp Ala Leu Ala Asp His
85 90 95

Gly Ser His Ile Gly Ile Pro Tyr Trp Asp Trp Thr Thr Ala Phe Thr
100 105 110

Glu Leu Pro Ala Leu Val Thr Asp Ser Glu Asn Asn Pro Phe His Glu
115 120 125

Gly Arg Ile Asp His Leu Gly Val Thr Thr Ser Arg Ser Pro Arg Asp
130 135 140

Met Leu Phe Asn Asp Pro Glu Gln Gly Ser Glu Ser Phe Phe Tyr Arg
145 150 155 160

Gln Val Leu Leu Ala Leu Glu Gln Thr Asp Tyr Cys Gln Phe Glu Val
165 170 175

Gln Phe Glu Leu Thr His Asn Ala Ile His Ser Trp Thr Gly Gly Arg
180 185 190

Ser Pro Tyr Gly Met Ser Thr Leu Glu Phe Thr Ala Tyr Asp Pro Leu
195 200 205

Phe Trp Leu His His Ser Asn Thr Asp Arg Ile Trp Ala Val Trp Gln
210 215 220

-continued

```
Ala Leu Gln Lys Tyr Arg Gly Leu Pro Tyr Asn Glu Ala His Cys Glu
225                 230                 235                 240

Ile Gln Val Leu Lys Gln Pro Leu Arg Pro Phe Asn Asp Asp Ile Asn
                245                 250                 255

His Asn Pro Ile Thr Lys Thr Asn Ala Arg Pro Ile Asp Ser Phe Asp
            260                 265                 270

Tyr Glu Arg Phe Asn Tyr Gln Tyr Asp Thr Leu Ser Phe His Gly Lys
        275                 280                 285

Ser Ile Pro Glu Leu Asn Asp Leu Leu Glu Glu Arg Lys Arg Glu Glu
    290                 295                 300

Arg Thr Phe Ala Ala Phe Leu Leu Arg Gly Ile Gly Cys Ser Ala Asp
305                 310                 315                 320

Val Val Phe Asp Ile Cys Arg Pro Asn Gly Asp Cys Val Phe Ala Gly
                325                 330                 335

Thr Phe Ala Val Leu Gly Gly Glu Leu Glu Met Pro Trp Ser Phe Asp
            340                 345                 350

Arg Leu Phe Arg Tyr Asp Ile Thr Arg Val Met Asn Gln Leu His Leu
        355                 360                 365

Gln Tyr Asp Ser Asp Phe Ser Phe Arg Val Lys Leu Val Ala Thr Asn
    370                 375                 380

Gly Thr Glu Leu Ser Ser Asp Leu Leu Lys Ser Pro Thr Ile Glu His
385                 390                 395                 400

Glu Leu


<210> SEQ ID NO 39
<211> LENGTH: 515
<212> TYPE: PRT
<213> ORGANISM: Haliotis tuberculata
<220> FEATURE:
<221> NAME/KEY: misc_feature
<222> LOCATION: (425)..(425)
<223> OTHER INFORMATION: "Xaa" is any naturally-occurring amino acid
      residue, including Tyr

<400> SEQUENCE: 39

Gly Ala His Arg Gly Pro Val Glu Glu Thr Glu Val Thr Arg Gln His
  1               5                  10                  15

Thr Asp Gly Asn Ala His Phe His Arg Lys Glu Val Asp Ser Leu Ser
             20                  25                  30

Leu Asp Glu Ala Asn Asn Leu Lys Asn Ala Leu Tyr Lys Leu Gln Asn
         35                  40                  45

Asp His Ser Leu Thr Gly Tyr Glu Ala Ile Ser Gly Tyr His Gly Tyr
     50                  55                  60

Pro Asn Leu Cys Pro Glu Glu Gly Asp Asp Lys Ile Pro Leu Leu Arg
 65                  70                  75                  80

Pro Arg Met Gly Ile Phe Pro Tyr Trp His Arg Leu Leu Thr Ile Gln
                 85                  90                  95

Leu Glu Arg Ala Leu Glu His Asn Gly Ala Leu Leu Gly Val Pro Tyr
            100                 105                 110

Trp Asp Trp Asn Lys Asp Leu Ser Ser Leu Pro Ala Phe Phe Ser Asp
        115                 120                 125

Ser Ser Asn Asn Asn Pro Tyr Phe Lys Tyr His Ile Ala Gly Val Gly
    130                 135                 140

His Asp Thr Val Arg Glu Pro Thr Ser Leu Ile Tyr Asn Gln Pro Gln
145                 150                 155                 160
```

-continued

```
Ile His Gly Tyr Asp Tyr Leu Tyr Tyr Leu Ala Leu Thr Thr Leu Glu
                165                 170                 175

Glu Asn Asn Tyr Trp Asp Phe Glu Val Gln Tyr Glu Ile Leu His Asn
            180                 185                 190

Ala Val His Ser Trp Leu Gly Gly Ser Gln Lys Tyr Ser Met Ser Thr
        195                 200                 205

Leu Glu Tyr Ser Ala Phe Asp Pro Val Phe Met Ile Leu His Ser Gly
    210                 215                 220

Leu Asp Arg Leu Trp Ile Ile Trp Gln Glu Leu Gln Lys Ile Arg Arg
225                 230                 235                 240

Lys Pro Tyr Asn Phe Ala Lys Cys Ala Tyr His Met Met Glu Glu Pro
                245                 250                 255

Leu Ala Pro Phe Ser Tyr Pro Ser Ile Asn Gln Asp Glu Phe Thr Arg
            260                 265                 270

Ala Asn Ser Lys Pro Ser Thr Val Phe Asp Ser His Lys Phe Gly Tyr
        275                 280                 285

His Tyr Asp Asn Leu Asn Val Arg Gly His Ser Ile Gln Glu Leu Asn
    290                 295                 300

Thr Ile Ile Asn Asp Leu Arg Asn Thr Asp Arg Ile Tyr Ala Gly Phe
305                 310                 315                 320

Val Leu Ser Gly Ile Gly Thr Ser Ala Ser Val Lys Ile Tyr Leu Arg
                325                 330                 335

Thr Asp Asp Asn Asp Glu Glu Val Gly Thr Phe Thr Val Leu Gly Gly
            340                 345                 350

Glu Arg Glu Met Pro Trp Ala Tyr Glu Arg Val Phe Lys Tyr Asp Ile
        355                 360                 365

Thr Glu Val Ala Asp Arg Leu Lys Ile Lys Leu Trp Gly His Pro Leu
    370                 375                 380

Thr Ser Gly Thr Gly Asp His Ile Leu Thr Asn Gly Ile Gly Gly Lys
385                 390                 395                 400

Gln Glu Pro Thr Gln Ile Leu Ser Ser Ser Thr Asp Leu Pro Ile Met
                405                 410                 415

Thr Thr Met Phe Leu Leu Ser Gln Xaa Gly Arg Asn Leu His Ile Pro
            420                 425                 430

Pro Lys Val Val Val Lys Lys Gly Thr Arg Ile Glu Phe His Pro Val
        435                 440                 445

Asp Asp Ser Val Thr Arg Pro Val Val Asp Leu Gly Ser Tyr Thr Ala
    450                 455                 460

Leu Phe Asn Cys Val Val Pro Pro Phe Thr Tyr His Gly Phe Glu Leu
465                 470                 475                 480

Asn His Val Tyr Ser Val Lys Pro Gly Asp Tyr Tyr Val Thr Gly Pro
                485                 490                 495

Thr Arg Asp Leu Cys Gln Asn Ala Asp Val Arg Ile His Ile His Val
            500                 505                 510

Glu Asp Glu
        515
```

<210> SEQ ID NO 40
<211> LENGTH: 322
<212> TYPE: PRT
<213> ORGANISM: Megathura crenulata -continued

<400> SEQUENCE: 40

```
Gly Leu Pro Tyr Trp Asp Trp Thr Glu Pro Met Thr His Ile Pro Gly
  1               5                  10                  15

Leu Ala Gly Asn Lys Thr Tyr Val Asp Ser His Gly Ala Ser His Thr
             20                  25                  30

Asn Pro Phe His Ser Ser Val Ile Ala Phe Glu Glu Asn Ala Pro His
         35                  40                  45

Thr Lys Arg Gln Ile Asp Gln Arg Leu Phe Lys Pro Ala Thr Phe Gly
     50                  55                  60

His His Thr Asp Leu Phe Asn Gln Ile Leu Tyr Ala Phe Glu Gln Glu
 65                  70                  75                  80

Asp Tyr Cys Asp Phe Glu Val Gln Phe Glu Ile Thr His Asn Thr Ile
                 85                  90                  95

His Ala Trp Thr Gly Gly Ser Glu His Phe Ser Met Ser Ser Leu His
            100                 105                 110

Tyr Thr Ala Phe Asp Pro Leu Phe Tyr Phe His His Ser Asn Val Asp
        115                 120                 125

Arg Leu Trp Ala Val Trp Gln Ala Leu Gln Met Arg Arg His Lys Pro
    130                 135                 140

Tyr Arg Ala His Cys Ala Ile Ser Leu Glu His Met His Leu Lys Pro
145                 150                 155                 160

Phe Ala Phe Ser Ser Pro Leu Asn Asn Asn Glu Lys Thr His Ala Asn
                165                 170                 175

Ala Met Pro Asn Lys Ile Tyr Asp Tyr Glu Asn Val Leu His Tyr Thr
            180                 185                 190

Tyr Glu Asp Leu Thr Phe Gly Gly Ile Ser Leu Glu Asn Ile Glu Lys
        195                 200                 205

Met Ile His Glu Asn Gln Gln Glu Asp Arg Ile Tyr Ala Gly Phe Leu
    210                 215                 220

Leu Ala Gly Ile Arg Thr Ser Ala Asn Val Asp Ile Phe Ile Lys Thr
225                 230                 235                 240

Thr Asp Ser Val Gln His Lys Ala Gly Thr Phe Ala Val Leu Gly Gly
                245                 250                 255

Ser Lys Glu Met Lys Trp Gly Phe Asp Arg Val Phe Lys Phe Asp Ile
            260                 265                 270

Thr His Val Leu Lys Asp Leu Asp Leu Thr Ala Asp Gly Asp Phe Glu
        275                 280                 285

Val Thr Val Asp Ile Thr Glu Val Asp Gly Thr Lys Leu Ala Ser Ser
    290                 295                 300

Leu Ile Pro His Ala Ser Val Ile Arg Glu His Ala Arg Gly Lys Leu
305                 310                 315                 320

Asn Arg
```

<210> SEQ ID NO 41
<211> LENGTH: 414
<212> TYPE: PRT
<213> ORGANISM: Megathura crenulata

<400> SEQUENCE: 41

```
Val Lys Phe Asp Lys Val Pro Arg Ser Arg Leu Ile Arg Lys Asn Val
  1               5                  10                  15

Asp Arg Leu Ser Pro Glu Glu Met Asn Glu Leu Arg Lys Ala Leu Ala
             20                  25                  30
```

-continued

```
Leu Leu Lys Glu Asp Lys Ser Ala Gly Gly Phe Gln Gln Leu Gly Ala
        35                  40                  45

Phe His Gly Glu Pro Lys Trp Cys Pro Ser Pro Glu Ala Ser Lys Lys
    50                  55                  60

Phe Ala Cys Cys Val His Gly Met Ser Val Phe Pro His Trp His Arg
 65                 70                  75                      80

Leu Leu Thr Val Gln Ser Glu Asn Ala Leu Arg Arg His Gly Tyr Asp
                85                  90                  95

Gly Ala Leu Pro Tyr Trp Asp Trp Thr Ser Pro Leu Asn His Leu Pro
            100                 105                 110

Glu Leu Ala Asp His Glu Lys Tyr Val Asp Pro Glu Asp Gly Val Glu
        115                 120                 125

Lys His Asn Pro Trp Phe Asp Gly His Ile Asp Thr Val Asp Lys Thr
    130                 135                 140

Thr Thr Arg Ser Val Gln Asn Lys Leu Phe Glu Gln Pro Glu Phe Gly
145                 150                 155                 160

His Tyr Thr Ser Ile Ala Lys Gln Val Leu Leu Ala Leu Glu Gln Asp
                165                 170                 175

Asn Phe Cys Asp Phe Glu Ile Gln Tyr Glu Ile Ala His Asn Tyr Ile
            180                 185                 190

His Ala Leu Val Gly Gly Ala Gln Pro Tyr Gly Met Ala Ser Leu Arg
        195                 200                 205

Tyr Thr Ala Phe Asp Pro Leu Phe Tyr Leu His His Ser Asn Thr Asp
    210                 215                 220

Arg Ile Trp Ala Ile Trp Gln Ala Leu Gln Lys Tyr Arg Gly Lys Pro
225                 230                 235                 240

Tyr Asn Val Ala Asn Cys Ala Val Thr Ser Met Arg Glu Pro Leu Gln
                245                 250                 255

Pro Phe Gly Leu Ser Ala Asn Ile Asn Thr Asp His Val Thr Lys Glu
            260                 265                 270

His Ser Val Pro Phe Asn Val Phe Asp Tyr Lys Thr Asn Phe Asn Tyr
        275                 280                 285

Glu Tyr Asp Thr Leu Glu Phe Asn Gly Leu Ser Ile Ser Gln Leu Asn
    290                 295                 300

Lys Lys Leu Glu Ala Ile Lys Ser Gln Asp Arg Phe Phe Ala Gly Phe
305                 310                 315                 320

Leu Leu Ser Gly Phe Lys Lys Ser Ser Leu Val Lys Phe Asn Ile Cys
                325                 330                 335

Thr Asp Ser Ser Asn Cys His Pro Ala Gly Glu Phe Tyr Leu Leu Gly
            340                 345                 350

Asp Glu Asn Glu Met Pro Trp Ala Tyr Asp Arg Val Phe Lys Tyr Asp
        355                 360                 365

Ile Thr Glu Lys Leu His Asp Leu Lys Leu His Ala Glu Asp His Phe
    370                 375                 380

Tyr Ile Asp Tyr Glu Val Phe Asp Leu Lys Pro Ala Ser Leu Gly Lys
385                 390                 395                 400

Asp Leu Phe Lys Gln Pro Ser Val Ile His Glu Pro Arg Ile
                405                 410
```

<210> SEQ ID NO 42
<211> LENGTH: 411
<212> TYPE: PRT
<213> ORGANISM: Megathura crenulata -continued

<400> SEQUENCE: 42

```
Gly His His Glu Gly Glu Val Tyr Gln Ala Glu Val Thr Ser Ala Asn
  1               5                  10                  15

Arg Ile Arg Lys Asn Ile Glu Asn Leu Ser Leu Gly Glu Leu Glu Ser
             20                  25                  30

Leu Arg Ala Ala Phe Leu Glu Ile Glu Asn Asp Gly Thr Tyr Glu Ser
         35                  40                  45

Ile Ala Lys Phe His Gly Ser Pro Gly Leu Cys Gln Leu Asn Gly Asn
     50                  55                  60

Pro Ile Ser Cys Cys Val His Gly Met Pro Thr Phe Pro His Trp His
 65                  70                  75                  80

Arg Leu Tyr Val Val Val Val Glu Asn Ala Leu Leu Lys Lys Gly Ser
                 85                  90                  95

Ser Val Ala Val Pro Tyr Trp Asp Trp Thr Lys Arg Ile Glu His Leu
            100                 105                 110

Pro His Leu Ile Ser Asp Ala Thr Tyr Tyr Asn Ser Arg Gln His His
        115                 120                 125

Tyr Glu Thr Asn Pro Phe His His Gly Lys Ile Thr His Glu Asn Glu
    130                 135                 140

Ile Thr Thr Arg Asp Pro Lys Asp Ser Leu Phe His Ser Asp Tyr Phe
145                 150                 155                 160

Tyr Glu Gln Val Leu Tyr Ala Leu Glu Gln Asp Asn Phe Cys Asp Phe
                165                 170                 175

Glu Ile Gln Leu Glu Ile Leu His Asn Ala Leu His Ser Leu Leu Gly
            180                 185                 190

Gly Lys Gly Lys Tyr Ser Met Ser Asn Leu Asp Tyr Ala Ala Phe Asp
        195                 200                 205

Pro Val Phe Phe Leu His His Ala Thr Thr Asp Arg Ile Trp Ala Ile
    210                 215                 220

Trp Gln Asp Leu Gln Arg Phe Arg Lys Arg Pro Tyr Arg Glu Ala Asn
225                 230                 235                 240

Cys Ala Ile Gln Leu Met His Thr Pro Leu Gln Pro Phe Asp Lys Ser
                245                 250                 255

Asp Asn Asn Asp Glu Ala Thr Lys Thr His Ala Thr Pro His Asp Gly
            260                 265                 270

Phe Glu Tyr Gln Asn Ser Phe Gly Tyr Ala Tyr Asp Asn Leu Glu Leu
        275                 280                 285

Asn His Tyr Ser Ile Pro Gln Leu Asp His Met Leu Gln Glu Arg Lys
    290                 295                 300

Arg His Asp Arg Val Phe Ala Gly Phe Leu Leu His Asn Ile Gly Thr
305                 310                 315                 320

Ser Ala Asp Gly His Val Phe Val Cys Leu Pro Thr Gly Glu His Thr
                325                 330                 335

Lys Asp Cys Ser His Glu Ala Gly Met Phe Ser Ile Leu Gly Gly Gln
            340                 345                 350

Thr Glu Met Ser Phe Val Phe Asp Arg Leu Tyr Lys Leu Asp Ile Thr
        355                 360                 365

Lys Ala Leu Lys Lys Asn Gly Val His Leu Gln Gly Asp Phe Asp Leu
    370                 375                 380

Glu Ile Glu Ile Thr Ala Val Asn Gly Ser His Leu Asp Ser His Val
385                 390                 395                 400

Ile His Ser Pro Thr Ile Leu Phe Glu Ala Gly
                405                 410
```

-continued

<210> SEQ ID NO 43
<211> LENGTH: 111
<212> TYPE: PRT
<213> ORGANISM: Megathura crenulata

<400> SEQUENCE: 43

Asp Ser Ala His Thr Asp Asp Gly His Thr Glu Pro Val Met Ile Arg
1 5 10 15

Lys Asp Ile Thr Gln Leu Asp Lys Arg Gln Gln Leu Ser Leu Val Lys
20 25 30

Ala Leu Glu Ser Met Lys Ala Asp His Ser Ser Asp Gly Phe Gln Ala
35 40 45

Ile Ala Ser Phe His Ala Leu Pro Pro Leu Cys Pro Ser Pro Ala Ala
50 55 60

Ser Lys Arg Phe Ala Cys Cys Val His Gly Met Pro Thr Phe Pro Gln
65 70 75 80

Trp His Arg Leu Tyr Thr Val Gln Phe Gln Asp Ser Leu Arg Lys His
85 90 95

Gly Ala Val Val Gly Leu Pro Tyr Trp Asp Trp Thr Leu Pro Arg
100 105 110

<210> SEQ ID NO 44
<211> LENGTH: 317
<212> TYPE: PRT
<213> ORGANISM: Megathura crenulata

<400> SEQUENCE: 44

Gly Leu Pro Tyr Trp Asp Trp Thr Met Pro Met Ser His Leu Pro Glu
1 5 10 15

Leu Ala Thr Ser Glu Thr Tyr Leu Asp Pro Val Thr Gly Glu Thr Lys
20 25 30

Asn Asn Pro Phe His His Ala Gln Val Ala Phe Glu Asn Gly Val Thr
35 40 45

Ser Arg Asn Pro Asp Ala Lys Leu Phe Met Lys Pro Thr Tyr Gly Asp
50 55 60

His Thr Tyr Leu Phe Asp Ser Met Ile Tyr Ala Phe Glu Gln Glu Asp
65 70 75 80

Phe Cys Asp Phe Glu Val Gln Tyr Glu Leu Thr His Asn Ala Ile His
85 90 95

Ala Trp Val Gly Gly Ser Glu Lys Tyr Ser Met Ser Ser Leu His Tyr
100 105 110

Thr Ala Phe Asp Pro Ile Phe Tyr Leu His His Ser Asn Val Asp Arg
115 120 125

Leu Trp Ala Ile Trp Gln Ala Leu Gln Ile Arg Arg Gly Lys Ser Tyr
130 135 140

Lys Ala His Cys Ala Ser Ser Gln Glu Arg Glu Pro Leu Lys Pro Phe
145 150 155 160

Ala Phe Ser Ser Pro Leu Asn Asn Asn Glu Lys Thr Tyr His Asn Ser
165 170 175

Val Pro Thr Asn Val Tyr Asp Tyr Val Gly Val Leu His Tyr Arg Tyr
180 185 190

Asp Asp Leu Gln Phe Gly Gly Met Thr Met Ser Glu Leu Glu Glu Tyr
195 200 205

Ile His Lys Gln Thr Gln His Asp Arg Thr Phe Ala Gly Phe Phe Leu
210 215 220

-continued

```
Ser Tyr Ile Gly Thr Ser Ala Ser Val Asp Ile Phe Ile Asn Arg Glu
225                 230                 235                 240

Gly His Asp Lys Tyr Lys Val Gly Ser Phe Val Val Leu Gly Gly Ser
                245                 250                 255

Lys Glu Met Lys Trp Gly Phe Asp Arg Met Tyr Lys Tyr Glu Ile Thr
            260                 265                 270

Glu Ala Leu Lys Thr Leu Asn Val Ala Val Asp Asp Gly Phe Ser Ile
        275                 280                 285

Thr Val Glu Ile Thr Asp Val Asp Gly Ser Pro Pro Ser Ala Asp Leu
    290                 295                 300

Ile Pro Pro Pro Ala Ile Ile Phe Glu Arg Gly His Ala
305                 310                 315
```

<210> SEQ ID NO 45
<211> LENGTH: 411
<212> TYPE: PRT
<213> ORGANISM: Megathura crenulata

<400> SEQUENCE: 45

```
Asp Ala Lys Asp Phe Gly His Ser Arg Lys Ile Arg Lys Ala Val Asp
  1               5                  10                  15

Ser Leu Thr Val Glu Glu Gln Thr Ser Leu Arg Arg Ala Met Ala Asp
             20                  25                  30

Leu Gln Asp Asp Lys Thr Ser Gly Gly Phe Gln Gln Ile Ala Ala Phe
         35                  40                  45

His Gly Glu Pro Lys Trp Cys Pro Ser Pro Glu Ala Glu Lys Lys Phe
     50                  55                  60

Ala Cys Cys Val His Gly Met Ala Val Phe Pro His Trp His Arg Leu
 65                  70                  75                  80

Leu Thr Val Gln Gly Glu Asn Ala Leu Arg Lys His Gly Phe Thr Gly
                 85                  90                  95

Gly Leu Pro Tyr Trp Asp Trp Thr Arg Ser Met Ser Ala Leu Pro His
            100                 105                 110

Phe Val Ala Asp Pro Thr Tyr Asn Asp Ala Ile Ser Ser Gln Glu Glu
        115                 120                 125

Asp Asn Pro Trp His His Gly His Ile Asp Ser Val Gly His Asp Thr
    130                 135                 140

Thr Arg Asp Val Arg Asp Asp Leu Tyr Gln Ser Pro Gly Phe Gly His
145                 150                 155                 160

Tyr Thr Asp Ile Ala Gln Gln Val Leu Leu Ala Phe Glu Gln Asp Ser
                165                 170                 175

Phe Cys Asp Phe Glu Val Gln Phe Glu Ile Ala His Asn Phe Ile His
            180                 185                 190

Ala Leu Ile Gly Gly Asn Glu Pro Tyr Ser Met Ser Ser Leu Arg Tyr
        195                 200                 205

Thr Thr Tyr Asp Pro Ile Phe Phe Leu His His Ser Ser Thr Asp Arg
    210                 215                 220

Leu Trp Ala Ile Trp Gln Ala Leu Gln Lys Tyr Arg Gly Lys Pro Tyr
225                 230                 235                 240

Asn Thr Ala Asn Cys Ala Ile Ala Ser Met Arg Lys Pro Leu Gln Pro
                245                 250                 255

Phe Gly Leu Asp Ser Val Ile Asn Pro Asp Asp Glu Thr Arg Glu His
            260                 265                 270

Ser Val Pro Phe Arg Val Phe Asp Tyr Lys Asn Asn Phe Asp Tyr Glu
        275                 280                 285
```

-continued

```
Tyr Glu Ser Leu Ala Phe Asn Gly Leu Ser Ile Ala Gln Leu Asp Arg
    290                 295                 300

Glu Leu Gln Arg Arg Lys Ser His Asp Arg Val Phe Ala Gly Phe Leu
305                 310                 315                 320

Leu His Glu Ile Gly Gln Ser Ala Lys His Asn Val Ser Asp Cys Asp
                325                 330                 335

His Tyr Ala Gly Glu Phe Tyr Ile Leu Gly Asp Glu Ala Glu Met Pro
            340                 345                 350

Trp Arg Tyr Asp Arg Val Tyr Lys Tyr Glu Ile Thr Gln Gln Leu His
        355                 360                 365

Asp Leu Asp Leu His Val Gly Asp Asn Phe Phe Leu Lys Tyr Glu Ala
    370                 375                 380

Phe Asp Leu Asn Gly Gly Ser Leu Gly Gly Ser Ile Phe Ser Gln Pro
385                 390                 395                 400

Ser Val Ile Phe Glu Pro Ala Ala Gly Met Phe
                405                 410


<210> SEQ ID NO 46
<211> LENGTH: 109
<212> TYPE: PRT
<213> ORGANISM: Megathura crenulata

<400> SEQUENCE: 46

Gly Ser His Gln Ala Asp Glu Tyr Arg Glu Ala Val Thr Ser Ala Ser
  1               5                  10                  15

His Ile Arg Lys Asn Ile Arg Asp Leu Ser Glu Gly Glu Ile Glu Ser
             20                  25                  30

Ile Arg Ser Ala Phe Leu Gln Ile Gln Lys Glu Gly Ile Tyr Glu Asn
         35                  40                  45

Ile Ala Lys Phe His Gly Lys Pro Gly Leu Cys Glu His Asp Gly His
     50                  55                  60

Pro Val Ala Cys Cys Val His Gly Met Pro Thr Phe Pro His Trp His
 65                  70                  75                  80

Arg Leu Tyr Val Leu Gln Val Glu Asn Ala Leu Leu Glu Arg Gly Ser
                 85                  90                  95

Ala Val Ala Val Pro Tyr Trp Asp Trp Thr Leu Pro Arg
            100                 105


<210> SEQ ID NO 47
<211> LENGTH: 329
<212> TYPE: PRT
<213> ORGANISM: Megathura crenulata

<400> SEQUENCE: 47

Met Ala Val Phe Pro His Trp His Arg Leu Phe Val Lys Gln Met Glu
  1               5                  10                  15

Asp Ala Leu Ala Ala His Gly Ala His Ile Gly Ile Pro Tyr Trp Asp
             20                  25                  30

Trp Thr Ser Ala Phe Ser His Leu Pro Ala Leu Val Thr Asp His Glu
         35                  40                  45

Asn Asn Pro Phe His His Gly His Ile Gly His Leu Asn Val Asp Thr
     50                  55                  60

Ser Arg Ser Pro Arg Asp Met Leu Phe Asn Asp Pro Glu Gln Gly Ser
 65                  70                  75                  80

Glu Ser Phe Phe Tyr Arg Gln Val Leu Leu Thr Leu Glu Gln Thr Asp
                 85                  90                  95
```

-continued

```
Phe Cys Gln Phe Glu Val Gln Phe Glu Leu Thr His Asn Ala Ile His
            100                 105                 110

Ser Trp Thr Gly Gly His Thr Pro Tyr Gly Met Ser Ser Leu Glu Tyr
        115                 120                 125

Thr Ala Tyr Asp Pro Leu Phe Tyr Leu His His Ser Asn Thr Asp Arg
    130                 135                 140

Ile Trp Ala Ile Trp Gln Ala Leu Gln Lys Tyr Arg Gly Leu Pro Tyr
145                 150                 155                 160

Asn Ala Ala His Cys Asp Ile Gln Val Leu Lys Gln Pro Leu Lys Pro
                165                 170                 175

Phe Ser Glu Ser Arg Asn Pro Asn Pro Val Thr Arg Ala Asn Ser Arg
            180                 185                 190

Ala Val Asp Ser Phe Asp Tyr Glu Lys Phe Asn Tyr Gln Tyr Asp Thr
        195                 200                 205

Leu Thr Phe His Gly Leu Ser Ile Pro Glu Leu Asp Ala Met Leu Gln
    210                 215                 220

Glu Arg Lys Lys Glu Glu Arg Thr Phe Ala Ala Phe Leu Leu His Gly
225                 230                 235                 240

Phe Gly Ala Ser Ala Asp Val Ser Phe Asp Val Cys Thr Pro Asp Gly
                245                 250                 255

His Cys Ala Phe Ala Gly Thr Phe Ala Val Leu Gly Gly Glu Leu Glu
            260                 265                 270

Met Pro Trp Ser Phe Glu Arg Leu Phe Arg Tyr Asp Ile Thr Lys Val
        275                 280                 285

Leu Lys Gln Met Asn Leu His Tyr Asp Ser Glu Phe His Phe Glu Leu
    290                 295                 300

Lys Ile Val Gly Thr Asp Gly Thr Glu Leu Pro Ser Asp Arg Ile Lys
305                 310                 315                 320

Ser Pro Thr Ile Glu His His Gly Gly
                325


<210> SEQ ID NO 48
<211> LENGTH: 103
<212> TYPE: PRT
<213> ORGANISM: Megathura crenulata

<400> SEQUENCE: 48

Gly His Asp His Ser Glu Arg His Asp Gly Phe Phe Arg Lys Glu Val
  1               5                  10                  15

Gly Ser Leu Ser Leu Asp Glu Ala Asn Asp Leu Lys Asn Ala Leu Tyr
             20                  25                  30

Lys Leu Gln Asn Asp Gln Gly Pro Asn Gly Tyr Glu Ser Ile Ala Gly
         35                  40                  45

Tyr His Gly Tyr Pro Phe Leu Cys Pro Glu His Gly Glu Asp Gln Tyr
     50                  55                  60

Ala Cys Cys Val His Gly Met Pro Val Phe Pro His Trp His Arg Leu
 65                  70                  75                  80

His Thr Ile Gln Phe Glu Arg Ala Leu Lys Glu His Gly Ser His Leu
                 85                  90                  95

Gly Leu Pro Tyr Trp Asp Trp
            100


<210> SEQ ID NO 49
<211> LENGTH: 1269
<212> TYPE: DNA
<213> ORGANISM: Haliotis tuberculata
```

-continued

<400> SEQUENCE: 49

```
ggcttgttca gtttctactc gtcgcccttg tggtgggggc tggagcagac aacgtcgtca     60
gaaaggacgt gagtcacctc acggatgacg aggtgcaagc tctccacggc gccctccatg    120
acgtcactgc atctacaggg cctctgagtt tcgaagacat aacatcttac catgccgcac    180
cagcgtcgtg tgactacaag ggacggaaga tcgcctgctg tgtccacggt atgcccagtt    240
tccccttctg gcacagggca tatgtcgtcc aagccgagcg ggcactgttg tccaaacgga    300
agactgtcgg aatgccttac tgggactgga cgcaaacgct gactcactta ccatctcttg    360
tgactgaacc catctacatt gacagtaaag gtggaaaggc tcaaaccaac tactggtacc    420
gcggcgagat agcgttcatc aataagaaga ctgcgcgagc tgtagatgat cgcctattcg    480
agaaggtgga gcctggtcac tacacacatc ttatggagac tgtcctcgac gctctcgaac    540
aggacgaatt ctgtaaattt gaaatccagt tcgagttggc tcataatgct atccattact    600
tggttggcgg taaatttgaa tattcaatgt caaacttgga atacacctcc tacgacccca    660
tcttcttcct ccaccactcc aacgttgacc gcctcttcgc catctggcag cgtcttcagg    720
aactgcgagg aaagaatccc aatgcaatgg actgtgcaca tgaactcgct caccagcaac    780
tccaaccctt caacagggac agcaatccag tccagctcac aaaggaccac tcgacacctg    840
ctgacctctt tgattacaaa caacttggat acagctacga cagcttaaac ctgaatggaa    900
tgacgccaga acagctgaaa acagaactag acgaacgcca ctccaaagaa cgtgcgtttg    960
caagcttccg actcagtggc tttggggggtt ctgccaacgt tgttgtctat gcatgtgtcc   1020
ctgatgatga tccacgcagt gatgactact gcgagaaagc aggcgacttc ttcattcttg   1080
ggggtcaaag cgaaatgccg tggagattct acagaccctt cttctatgat gtaactgaag   1140
cggtacatca ccttggagtc ccgctaagtg gccactacta tgtgaaaaca gaactcttca   1200
gcgtgaatgg cacagcactt tcacctgatc ttcttcctca accaactgtt gcctaccgac   1260
ctgggaaag                                                            1269
```

<210> SEQ ID NO 50
<211> LENGTH: 569
<212> TYPE: DNA
<213> ORGANISM: Haliotis tuberculata

<400> SEQUENCE: 50

```
ggtcttccgt actgggactg gacgcagcat ctgactcaac tcccagatct ggtgtcagac     60
cccttgtttg tcgacccgga aggaggaaag gcccatgaca acgcatggta tcgtggaaac    120
atcaagtttg agaataagaa gactgcaaga gctgttgacg atcgcctttt cgagaaggtt    180
ggaccaggag agaatacccg actctttgaa ggaattctcg atgctcttga acaggatgaa    240
ttctgcaact tcgagatcca gtttgagttg gctcacaacg ctatccacta cctggttggc    300
ggccgtcaca cgtactccat gtctcatctc gagttacacc ctcctacgac cccctcttct    360
tcctccatca ctccaacacc ggaccgcatc ttcgccatct gggaacgtct tcaggtactc    420
agaggaaagg accccaacac cgccgactgc gcacacaacc tcatccatga gcccatggaa    480
ccgttccgtc gggactcgaa ccctcttgac ctcaccaggg aaaactccaa accaattgac    540
agctttgatt atgcccacct tggctacca                                      569
```

<210> SEQ ID NO 51
<211> LENGTH: 1246
<212> TYPE: DNA
<213> ORGANISM: Haliotis tuberculata -continued

<400> SEQUENCE: 51

```
gttacagagg ccccagctcc ctcctcggat gctcacctcg ccgtcaggaa ggatatcaac     60
catctgacac gcgaggaggt gtacgagctg cgcagagcta tggagagatt ccaggccgac    120
acatccgttg atgggtacca ggctacggtt gagtatcacg gcttacctgc tcgatgtcca    180
ttccccgagg ccacaaatag gttcgcctgt tgcatccacg gcatggcgac attccctcat    240
tggcacagac tgttcgtcac ccaggtggaa gatgctctga tcaggcgagg atcgcctata    300
ggggtcccct actgggactg gactcagcct atggcgcatc tcccaggact tgcagacaac    360
gccacctata gagatcccat cagcggggac agcagacaca acccctteca cgatgttgaa    420
gttgcctttg aaaatggacg tacagaacgt cacccagata gtagattgtt tgaacaacct    480
ttatttggca aacatacgcg tctcttcgac agtatagtct atgcttttga gcaggaggac    540
ttctgcgatt ttgaagttca atttgagatg acccataata atattcacgc ctggattggt    600
ggcggcgaga agtattccat gtcttctcta cactacacag ccttcgaccc tatcttctac    660
cttcgtcact ccaacactga ccggctctgg gcaatttggc aagcgttgca gatacgaaga    720
aacaggcctt acaaggctca ttgtgcttgg tctgaggaac gccagcctct caaacctttc    780
gccttcagtt ccccactgaa caacaacgaa aaaacctacg aaaactcggt gcccaccaac    840
gtttacgact acgaaggagt ccttggctat acttatgatg acctcaactt cgggggcatg    900
gacctgggtc agcttgagga atacatccag aggcagagac agagagacag gacctttgct    960
ggtttctttc tgtcacatat tggtacatca gcgaatgttg aaatcattat agaccatggg   1020
actcttcata cctccgtggg cacgtttgct gttcttggcg gagagaagga gatgaaatgg   1080
ggatttgacc gtttgtacaa atatgagatt acagatgaac tgaggcaact taatctccgt   1140
gctgatgatg ttttcagcat ctctgttaaa gtaactgatg ttgatggcag tgagctgtcc   1200
tctgaactca tcccatctgc tgctatcatc ttcgaacgaa gccata                  1246
```

<210> SEQ ID NO 52
<211> LENGTH: 1242
<212> TYPE: DNA
<213> ORGANISM: Haliotis tuberculata

<400> SEQUENCE: 52

```
gtcaccatca ggctgacgag tacgacgaag ttgtaactgc tgcaagccac atcagaaaga     60
atttaaaaga tctgtcaaag ggagaagtag agagcctaag gtctgccttc ctgcaacttc    120
agaacgacgg agtctatgag aatattgcca agttccacgg caagcctggg ttgtgtgatg    180
ataacggtcg caaggttgcc tgttgtgtcc atggaatgcc caccttcccc cagtggcaca    240
ggctctatgt cctccaggtg gagaatgctt tgctggagag aggatctgcc gtctctgtgc    300
catactggga ctggactgaa acatttacag agctgccatc tttgattgct gaggctacct    360
atttcaattc ccgtcaacaa acgtttgacc ctaatccttt cttcagaggt aaaatcagtt    420
ttgagaatgc tgttacaaca cgtgatcccc agcctgagct gtacgttaac aggtactact    480
accaaaacgt catgttggtt tttgaacagg acaactactg cgacttcgag atacagtttg    540
agatggttca caatgttctc catgcttggc ttggtggaag agctacttat tctatttctt    600
ctcttgatta ttctgcattc gaccctgtgt ttttccttca ccatgcgaac acagatagat    660
tgtgggccat ctggcaggag ctgcagaggt acaggaagaa gccatacaat gaagcggatt    720
gtgccattaa cctaatgcgc aaacctctac atcccttcga caacagtgat ctcaatcatg    780
atcctgtaac ctttaaatac tcaaaaccca ctgatggctt tgactaccag aacaactttg    840
```

-continued

```
gatacaagta tgacaacctt gagttcaatc atttcagtat tcccaggctt gaagaaatca    900
ttcgtattag acaacgtcaa gatcgtgtgt ttgcaggatt cctccttcac aacattggga    960
catccgcaac tgttgagata ttcgtctgtg tccctaccac cagcggtgag caaaactgtg   1020
aaaacaaagc cggaacattt gccgtactcg gaggagaaac agagatggcg tttcattttg   1080
acagactcta caggtttgac atcagtgaaa cactgaggga cctcggcata cagctggaca   1140
gccatgactt tgacctcagc atcaagattc aaggagtaaa tggatcctac cttgatccac   1200
acatcctgcc agagccatcc ttgatttttg tgcctggttc aa                      1242
```

<210> SEQ ID NO 53
<211> LENGTH: 1257
<212> TYPE: DNA
<213> ORGANISM: Haliotis tuberculata

<400> SEQUENCE: 53

```
gttctttcct gcgtcctgat gggcattcag atgacatcct tgtgagaaaa gaagtgaaca     60
gcctgacaac cagggagact gcatctctga tccatgctct gaaaagtatg caggaagacc    120
attcacctga cgggttccaa gccattgcct ctttccatgc tctgccacca ctctgccctt    180
caccatctgc agctcaccgt tatgcttgct gtgtccacgg catggctaca tttccccagt    240
ggcacagatt gtacactgta cagttccagg atgcactgag gagacatgga gctacggtag    300
gtgtaccgta ttgggattgg ctgcgaccgc agtctcacct accagagctt gtcaccatgg    360
agacatacca tgatatttgg agtaacagag atttccccaa tcctttctac caagccaata    420
ttgagtttga aggagaaaac attacaacag agagagaagt cattgcagac aaactttttg    480
tcaaaggtgg acacgttttt gataaactgg ttcttcaaac aagccatcct agcgctgagc    540
aggaaaacta ctgtgacttt gagattcagt ttgaaattct tcacaacggc gttcacacgt    600
gggtcggagg cagtcgtacc tactctatcg gacatcttca ttacgcattc tacgaccctc    660
ttttctacct tcaccatttc cagacagacc gtatttgggc aatctggcaa gaactccagg    720
aacagagagg gctctcgggt gatgaggctc actgtgctct cgagcaaatg agagaaccat    780
tgaagccttt cagcttcggc gctccttata actggaatca gctcacacag gatttctccc    840
gacccgagga caccttcgac tacaggaagt ttggttatga atatgacaat ttagaattcc    900
tgggaatgtc agttgctgaa ctggatcaat acattattga acatcaagaa aatgatagag    960
tattcgctgg gttcctgttg agtggattcg gaggttccgc atcagttaat ttccaggttt   1020
gtagagctga ttccacatgt caggatgctg ggtacttcac cgttcttggt ggcagtgctg   1080
agatggcgtg ggcatttgac aggctttaca aatatgacat tactgaaact ctggagaaaa   1140
tgcaccttcg atatgatgat gacttcacaa tctctgtcag tctgaccgcc aacaacggaa   1200
ctgtcctgag cagcagtcta atcccaacac cgagtgtcat attccagcgg ggacatc      1257
```

<210> SEQ ID NO 54
<211> LENGTH: 1257
<212> TYPE: DNA
<213> ORGANISM: Megathura crenulata

<400> SEQUENCE: 54

```
attctgccca cacagatgat ggacacactg aaccagtgat gattcgcaaa gatatcacac     60
aattggacaa gcgtcaacaa ctgtcactgg tgaaagccct cgagtccatg aaagccgacc    120
attcatctga tgggttccag gcaatcgctt ccttccatgc tcttcctcct ctttgtccat    180
caccagctgc ttcaaagagg tttgcgtgct gcgtccatgg catggcaacg ttcccacaat    240
```

-continued

```
ggcaccgtct gtacacagtc caattccaag attctctcag aaaacatggt gcagtcgttg    300

gacttccgta ctgggactgg accctacctc gttctgaatt accagagctc ctgaccgtct    360

caactattca tgacccggag acaggcagag atataccaaa tccatttatt ggttctaaaa    420

tagagtttga aggagaaaac gtacatacta aaagagatat caatagggat cgtctcttcc    480

agggatcaac aaaaacacat cataactggt ttattgagca agcactgctt gctcttgaac    540

aaaccaacta ctgcgacttc gaggttcagt ttgaaattat gcataatggt gttcatacct    600

gggttggagg caaggagccc tatggaattg gccatctgca ttatgcttcc tatgatccac    660

ttttctacat ccatcactcc caaactgatc gtatttgggc tatatggcaa tcgttgcagc    720

gtttcagagg actttctgga tctgaggcta actgtgctgt aaatctcatg aaaactcctc    780

tgaagccttt cagctttgga gcaccatata atcttaatga tcacacgcat gatttctcaa    840

agcctgaaga tacattcgac taccaaaagt ttggatacat atatgacact ctggaatttg    900

cagggtggtc aattcgtggc attgaccata ttgtccgtaa caggcaggaa cattcaaggg    960

tctttgccgg attcttgctt gaaggatttg gcacctctgc cactgtcgat ttccaggtct   1020

gtcgcacagc gggagactgt gaagatgcag ggtacttcac cgtgttggga ggtgaaaaag   1080

aaatgccttg ggcctttgat cggctttaca agtacgacat aacagaaacc ttagacaaga   1140

tgaaccttcg acatgacgaa atcttccaga ttgaagtaac cattacatcc tacgatggaa   1200

ctgtactcga tagtggcctt attcccacac cgtcaatcat ctatgatcct gctcatc      1257
```

<210> SEQ ID NO 55
<211> LENGTH: 1254
<212> TYPE: DNA
<213> ORGANISM: Megathura crenulata

<400> SEQUENCE: 55

```
atgatattag ttcgcaccac ctgtcgctca acaaggttcg tcatgatctg agtacactga     60

gtgagcgaga tattggaagc cttaaatatg ctttgagcag cttgcaggca gatacctcag    120

cagatggttt tgctgccatt gcatccttcc atggtctgcc tgccaaatgt aatgacagcc    180

acaataacga ggtggcatgc tgtatccatg gaatgcctac attcccccac tggcacagac    240

tctacaccct ccaatttgag caagctctaa gaagacatgg ctctagtgta gcagtaccct    300

actgggactg gacaaagcca atacataata ttccacatct gttcacagac aaagaatact    360

acgatgtctg gagaaataaa gtaatgccaa atccatttgc ccgagggtat gtcccctcac    420

acgatacata cacggtaaga gacgtccaag aaggcctgtt ccacctgaca tcaacgggtg    480

aacactcagc gcttctgaat caagctcttt tggcgctgga acagcacgac tactgcgatt    540

ttgcagtcca gtttgaagtc atgcacaaca caatccatta cctagtggga ggacctcaag    600

tctattcttt gtcatccctt cattatgctt catatgatcc gatcttcttc atacaccact    660

cctttgtaga caaggtttgg gctgtctggc aggctcttca agaaaagaga ggccttccat    720

cagaccgtgc tgactgcgct gttagtctga tgactcagaa catgaggcct ttccattacg    780

aaattaacca taaccagttc accaagaaac atgcagttcc aaatgatgtt ttcaagtacg    840

aactcctggg ttacagatac gacaatctgg aaatcggtgg catgaatttg catgaaattg    900

aaaaggaaat caaagacaaa cagcaccatg tgagagtgtt tgcagggttc ctccttcacg    960

gaattagaac ctcagctgat gtccaattcc agatttgtaa aacatcagaa gattgtcacc   1020

atggaggcca aatcttcgtt cttgggggga ctaaagagat ggcctgggct tataaccgtt   1080

tattcaagta cgatattacc catgctcttc atgacgcaca catcactcca gaagacgtat   1140
```

-continued

```
tccatccctc tgaaccattc ttcatcaagg tgtcagtgac agccgtcaac ggaacagttc   1200

ttccggcttc aatcctgcat gcaccaacca ttatctatga acctggtctc ggtg         1254


<210> SEQ ID NO 56
<211> LENGTH: 509
<212> TYPE: DNA
<213> ORGANISM: Megathura crenulata

<400> SEQUENCE: 56

accatcacga agatcatcat tcttcttcta tggctggaca tggtgtcaga aaggaaatca     60

acacacttac cactgcagag gtggacaatc tcaaagatgc catgagagcc gtcatggcag    120

accacggtcc aaatggatac caggctatag cagcgttcca tggaaaccca ccaatgtgcc    180

ctatgccaga tggaaagaat tactcgtgtt gtacacatgg catggctact ttcccccact    240

ggcacagact gtacacaaaa cagatggaag atgccttgac cgcccatggt gccagagtcg    300

gccttcctta ctgggacggg acaactgcct ttacagcttt gccaactttt gtcacagatg    360

aagaggacaa tcctttccat catggtcaca tagactattt gggagtggat acaactcggt    420

cgccccgaga caagttgttc aatgatccag agcgaggatc agaatcgttc ttctacaggc    480

aggttctctt ggctttggag cagacagat                                      509


<210> SEQ ID NO 57
<211> LENGTH: 943
<212> TYPE: DNA
<213> ORGANISM: Megathura crenulata

<400> SEQUENCE: 57

ggcctgccct actgggattg gaccatgcca atgagtcatt tgccagaact ggctacaagt     60

gagacctacc tcgatccagt tactggggaa actaaaaaca accctttcca tcacgcccaa    120

gtggcgtttg aaaatggtgt aacaagcagg aatcctgatg ccaaactttt tatgaaacca    180

acttacggag accacactta cctcttcgac agcatgatct acgcatttga gcaggaagac    240

ttctgcgact ttgaagtcca atatgagctc acgcataatg caatacatgc atgggttgga    300

ggcagtgaaa agtattcaat gtcttctctt cactacactg cttttgatcc tatattttac    360

ctccatcact caaatgttga tcgtctctgg gccatttggc aagctcttca aatcaggaga    420

ggcaagtctt acaaggccca ctgcgcctcg tctcaagaaa gagaaccatt aaagcctttt    480

gcattcagtt ccccactgaa caacaacgag aaaacgtacc acaactctgt ccccactaac    540

gtttatgact atgtgggagt tttgcactat cgatatgatg accttcagtt tggcggtatg    600

accatgtcag aacttgagga atatattcac aagcagacac aacatgatag aacctttgca    660

ggattcttcc tttcatatat tggaacatca gcaagcgtag atatcttcat caatcgagaa    720

ggtcatgata aatacaaagt gggaagtttt gtagtacttg gtggatccaa agaaatgaaa    780

tggggctttg atagaatgta caagtatgag atcactgagg ctctgaagac gctgaatgtt    840

gcagtggatg atgggttcag cattactgtt gagatcaccg atgttgatgg atctcccccca    900

tctgcagatc tcattccacc tcctgctata atctttgaac gtg                      943


<210> SEQ ID NO 58
<211> LENGTH: 1248
<212> TYPE: DNA
<213> ORGANISM: Megathura crenulata
```

-continued

<400> SEQUENCE: 58
ctgatgccaa agactttggc catagcagaa aaatcaggaa agccgttgat tctctgacag 60
tcgaagaaca aacttcgttg aggcgagcta tggcagatct acaggacgac aaaacatcag 120
ggggtttcca gcagattgca gcattccacg gagaaccaaa atggtgtcca agccccgaag 180
cggagaaaaa atttgcatgc tgtgttcatg gaatggctgt tttccctcac tggcacagat 240
tgctgacagt tcaaggagaa aatgctctga ggaaacatgg ctttactggt ggactgccct 300
actgggactg gactcgatca atgagcgccc ttccacattt tgttgctgat cctacttaca 360
atgatgctat ttccagccag gaagaagata acccatggca tcatggtcac atagactctg 420
ttgggcatga tactacaaga gatgtgcgtg atgatcttta tcaatctcct ggtttcggtc 480
actacacaga tattgcaaaa caagtccttc tggcctttga gcaggacgat ttctgtgatt 540
ttgaggtaca atttgaaatt gcccataatt tcatacatgc tctggttggt ggtaacgaac 600
catacagtat gtcatctttg aggtatacta catacgatcc aatcttcttc ttgcaccgct 660
ccaatacaga ccgactttgg gccatttggc aagctttgca aaaataccgg gggaaaccat 720
acaacactgc aaactgtgcc attgcatcca tgagaaaacc acttcagcca tttggtcttg 780
atagtgtcat aaatccagat gacgaaactc gtgaacattc ggttcctttc cgagtcttcg 840
actacaagaa caacttcgac tatgagtatg agagcctggc atttaatggt ctgtctattg 900
cccaactgga ccgagagttg cagagaagaa agtcacatga cagagtcttt gcaggattcc 960
ttcttcatga aattggacag tctgcactcg tgaaattcta cgtttgcaaa cacaatgtat 1020
ctgactgtga ccattatgct ggagaattct acattttggg agatgaagct gagatgcctt 1080
ggaggtatga ccgtgtgtac aagtacgaga taacacagca gctgcacgat ttagatctac 1140
atgttggaga taatttcttc cttaaatatg aagcctttga tctgaatggc ggaagtcttg 1200
gtggaagtat cttttctcag ccttcggtga ttttcgagcc agctgcag 1248

<210> SEQ ID NO 59
<211> LENGTH: 1257
<212> TYPE: DNA
<213> ORGANISM: Megathura crenulata

<400> SEQUENCE: 59
gttcacacca ggctgatgaa tatcgtgagg cagtaacaag cgctagccac ataagaaaaa 60
atatccggga cctctcagag ggagaaattg agagcatcag atctgctttc ctccaaattc 120
aaaaagaggg tatatatgaa aacattgcaa agttccatgg aaaaccagga ctttgtgaac 180
atgatggaca tcctgttgct tgttgtgtcc atggcatgcc cacctttccc cactggcaca 240
gactgtacgt tcttcaggtg gagaatgcgc tcttagaacg agggtctgca gttgctgttc 300
cttactggga ctggaccgag aaagctgact ctctgccatc attaatcaat gatgcaactt 360
atttcaattc acgatcccag acctttgatc ctaatccttt cttcagggga catattgcct 420
tcgagaatgc tgtgacgtcc agagatcctc agccagaact atgggacaat aaggacttct 480
acgagaatgt catgctggct cttgagcaag acaacttctg tgactttgag attcagcttg 540
agctgataca caacgccctt cattctagac ttggaggaag ggctaaatac tccctttcgt 600
ctcttgatta taccgcattt gatcctgtat ttttccttca ccatgcaaac gttgacagaa 660
tctgggccat ctggcaggac ttgcagagat atagaaagaa accatacaat gaggctgact 720
gcgcagtcaa cgagatgcgt aaacctcttc aaccatttaa taacccagaa cttaacagtg 780
attccatgac gcttaaacac aacctcccac aagacagttt tgattatcaa aaccgcttca 840

-continued

```
ggtaccaata tgataacctt caatttaacc acttcagcat acaaaagcta gaccaaacta    900

ttcaggctag aaaacaacac gacagagttt ttgctggctt tattcttcac aacattggga    960

catctgctgt tgtagatatt tatatttgcg ttgaacaagg aggagaacaa aactgcaaga   1020

caaaggcggg ttccttcacg attctggggg gagaaacaga aatgccattc cactttgacc   1080

gcttgtacaa atttgacata acgtctgctc tgcataaact tggtgttccc ttggacggac   1140

atggattcga catcaaagtt gacgtcagag ctgtcaatgg atcgcatctt gatcaacaca   1200

tcctcaacga accgagtctg ctttttgttc ctggtgaacg taagaatata tattatg      1257
```

<210> SEQ ID NO 60
<211> LENGTH: 1239
<212> TYPE: DNA
<213> ORGANISM: Megathura crenulata

<400> SEQUENCE: 60

```
atgggctttc acaacataat cttgtgcgaa aagaagtaag ctctcttaca acactggaga     60

aacatttttt gaggaaagct ctcaagaaca tgcaagcaga tgattctcca gacggatatc    120

aagctattgc ttctttccac gctttgcctc ctctttgtcc aagtccatct gctgcacata    180

gacacgcttg ttgcctccat ggtatggcta ccttccctca gtggcacaga ctctacacag    240

ttcagttcga agattctttg aaacgacatg gttctattgt cggacttcca tattgggatt    300

ggctgaaacc gcagtctgca ctccctgatt tggtgacaca ggagacatac gagcacctgt    360

tttcacacaa aaccttccca aatccgttcc tcaaggcaaa tatagaattt gagggagagg    420

gagtaacaac agagagggat gttgatgctg aacacctctt tgcaaaagga aatctggttt    480

acaacaactg gttttgcaat caggcactat atgcactaga acaagaaaat tactgtgact    540

ttgaaataca gttcgaaatt ttgcataatg gaattcattc atgggttgga ggatcaaaga    600

cccattcaat aggtcatctt cattacgcat catacgatcc actgttctat atccaccatt    660

cgcagacaga tcgcatttgg gctatctggc aagctctcca ggagcacaga ggtctttcag    720

ggaaggaagc acactgcgcc ctggagcaaa tgaaagaccc tctcaaacct ttcagctttg    780

gaagtcccta taatttgaac aaacgcactc aagagttctc caagcctgaa gacacatttg    840

attatcaccg attcgggtat gagtatgatt ccctcgaatt tgttggcatg tctgtttcaa    900

gtttacataa ctatataaaa caacaacagg aagctgatag agtcttcgca ggattccttc    960

ttaaaggatt tggacaatca gcatccgtat cgtttgatat ctgcagacca gaccagagtt   1020

gccaagaagc tggatacttc tcagttctcg gtggaagttc agaaatgccg tggcagtttg   1080

acaggcttta caagtacgac attacaaaaa cgttgaaaga catgaaactg cgatacgatg   1140

acacatttac catcaaggtt cacataaagg atatagctgg agctgagttg gacagcgatc   1200

tgattccaac tccttctgtt ctccttgaag aaggaaagc                          1239
```

<210> SEQ ID NO 61
<211> LENGTH: 1251
<212> TYPE: DNA
<213> ORGANISM: Haliotis tuberculata

<400> SEQUENCE: 61

```
atgggatcaa tgtacgtcac gttggtcgta atcggattcg tatggaacta tctgaactca     60

ccgagagaga tctcgccagc ctgaaatctg caatgaggtc tctacaagct gacgatgggg    120

tgaacggtta tcaagccatt gcatcattcc acggtctccc ggcttcttgt catgatgatg    180

agggacatga gattgcctgt tgtatccacg gaatgccagt attcccacac tggcacaggc    240
```

-continued

```
tttacaccct gcaaatggac atggctctgt tatctcacgg atctgctgtt gctattccat    300
actgggactg gaccaaacct atcagcaaac tgcctgatct cttcaccagc cctgaatatt    360
acgatccttg gagggatgca gttgtcaata atccatttgc taaaggctac attaaatccg    420
aggacgctta cacggttagg gatcctcagg acattttgta ccacttgcag gacgaaacgg    480
gaacatctgt tttgttagat caaactcttt tagccttaga gcagacagat ttctgtgatt    540
ttgaggttca atttgaggtc gtccataatg ctattcacta cttggtgggt ggtcgacaag    600
tttatgctct ttcttctcaa cactatgctt catatgaccc agccttcttt attcatcact    660
cctttgttga caaaatatgg gcagtctggc aagctctgca aaagaagaga aagcgtccct    720
atcataaagc ggattgtgct cttaacatga tgaccaaacc aatgcgacca tttgcacacg    780
atttcaatca caatggattc acaaaaatgc acgcagtccc caacactcta tttgactttc    840
aggacctttt ctacacgtat gacaacttag aaattgctgg catgaatgtt aatcagttgg    900
aagcggaaat caaccggcga aaaagccaaa caagagtctt tgccgggttc cttctacatg    960
gcattggaag atcagctgat gtacgatttt ggatttgcaa gacagctgac gactgccacg   1020
catctggcat gatctttatc ttaggaggtt ctaaagagat gcactgggcc tatgacagga   1080
actttaaata cgacatcacc caagctttga aggctcagtc catacaccct gaagatgtgt   1140
ttgacactga tgctcctttc ttcattaaag tggaggtcca tggtgtaaac aagactgctc   1200
tcccatcttc agctatccca gcacctacta taatctactc agctggtgaa g            1251
```

```
<210> SEQ ID NO 62
<211> LENGTH: 1185
<212> TYPE: DNA
<213> ORGANISM: Haliotis tuberculata
<220> FEATURE:
<221> NAME/KEY: misc_feature
<222> LOCATION: (163)..(163)
<223> OTHER INFORMATION: “n” is a, g, c, or t, including c

<400> SEQUENCE: 62

atcatattgc tggcagtgga gtcaggaaag acgtgacgtc tcttaccgca tctgagatag     60
agaacctgag gcatgctctg caaagcgtga tggatgatga tggacccaat ggattccagg    120
caattgctgc ttatcacgga agtcctccca tgtgtcacat gcntgatggt agagacgttg    180
catgttgtac tcatggaatg gcatctttcc ctcactggca cagactgttt gtgaaacaga    240
tggaggatgc actggctgcg catggagctc acattggcat accatactgg gattggacaa    300
gtgcgtttag tcatctgcct gccctagtga ctgaccacga gcacaatccc ttccaccacg    360
gacatattgc tcatcggaat gtggatacat ctcgatctcc gagagacatg ctgttcaatg    420
accccgaaca cgggtcagaa tcattcttct atagacaggt tctcttggct ctagaacaga    480
cagacttctg ccaatttgaa gttcagtttg aaataacaca caatgcaatc cactcttgga    540
ctggaggaca tactccatat ggaatgtcat cactggaata tacagcatat gatccactct    600
tttatctcca ccattccaac actgatcgta tctgggccat ctggcaggca ctccagaaat    660
acagaggttt tcaatacaac gcagctcatt gcgatatcca ggttctgaaa caacctctta    720
aaccattcag cgagtccagg aatccaaacc cagtcaccag agccaattct agggcagtcg    780
attcatttga ttatgagaga ctcaattatc aatatgacac acttaccttc cacggacatt    840
ctatctcaga acttgatgcc atgcttcaag agagaaagaa ggaagagaga acatttgcag    900
ccttcctgtt gcacggattt ggcgccagtg ctgatgtttc gtttgatgtc tgcacacctg    960
atggtcattg tgcctttgct ggaaccttcg cggtacttgg tggggagctt gagatgccct   1020
```

-continued

```
ggtcctttga aagattgttc cgttacgata tcacaaaggt tctcaagcag atgaatcttc   1080

actatgattc tgagttccac tttgagttga agattgttgg cacagatgga acagaactgc   1140

catcggatcg tatcaagagc cctaccattg aacaccatgg aggag                   1185


<210> SEQ ID NO 63
<211> LENGTH: 422
<212> TYPE: PRT
<213> ORGANISM: Haliotis tuberculata
<220> FEATURE:
<221> NAME/KEY: SIGNAL
<222> LOCATION: (1)..(15)

<400> SEQUENCE: 63

Leu Val Gln Phe Leu Leu Val Ala Leu Val Val Gly Ala Gly Ala Asp
  1               5                  10                  15

Asn Val Val Arg Lys Asp Val Ser His Leu Thr Asp Asp Glu Val Gln
             20                  25                  30

Ala Leu His Gly Ala Leu His Asp Val Thr Ala Ser Thr Gly Pro Leu
         35                  40                  45

Ser Phe Glu Asp Ile Thr Ser Tyr His Ala Ala Pro Ala Ser Cys Asp
     50                  55                  60

Tyr Lys Gly Arg Lys Ile Ala Cys Cys Val His Gly Met Pro Ser Phe
 65                  70                  75                  80

Pro Phe Trp His Arg Ala Tyr Val Val Gln Ala Glu Arg Ala Leu Leu
                 85                  90                  95

Ser Lys Arg Lys Thr Val Gly Met Pro Tyr Trp Asp Trp Thr Gln Thr
            100                 105                 110

Leu Thr His Leu Pro Ser Leu Val Thr Glu Pro Ile Tyr Ile Asp Ser
        115                 120                 125

Lys Gly Gly Lys Ala Gln Thr Asn Tyr Trp Tyr Arg Gly Glu Ile Ala
    130                 135                 140

Phe Ile Asn Lys Lys Thr Ala Arg Ala Val Asp Asp Arg Leu Phe Glu
145                 150                 155                 160

Lys Val Glu Pro Gly His Tyr Thr His Leu Met Glu Thr Val Leu Asp
                165                 170                 175

Ala Leu Glu Gln Asp Glu Phe Cys Lys Phe Glu Ile Gln Phe Glu Leu
            180                 185                 190

Ala His Asn Ala Ile His Tyr Leu Val Gly Gly Lys Phe Glu Tyr Ser
        195                 200                 205

Met Ser Asn Leu Glu Tyr Thr Ser Tyr Asp Pro Ile Phe Phe Leu His
    210                 215                 220

His Ser Asn Val Asp Arg Leu Phe Ala Ile Trp Gln Arg Leu Gln Glu
225                 230                 235                 240

Leu Arg Gly Lys Asn Pro Asn Ala Met Asp Cys Ala His Glu Leu Ala
                245                 250                 255

His Gln Gln Leu Gln Pro Phe Asn Arg Asp Ser Asn Pro Val Gln Leu
            260                 265                 270

Thr Lys Asp His Ser Thr Pro Ala Asp Leu Phe Asp Tyr Lys Gln Leu
        275                 280                 285

Gly Tyr Ser Tyr Asp Ser Leu Asn Leu Asn Gly Met Thr Pro Glu Gln
    290                 295                 300

Leu Lys Thr Glu Leu Asp Glu Arg His Ser Lys Glu Arg Ala Phe Ala
305                 310                 315                 320

Ser Phe Arg Leu Ser Gly Phe Gly Gly Ser Ala Asn Val Val Val Tyr
                325                 330                 335
```

-continued

```
Ala Cys Val Pro Asp Asp Asp Pro Arg Ser Asp Asp Tyr Cys Glu Lys
            340                 345                 350

Ala Gly Asp Phe Phe Ile Leu Gly Gly Gln Ser Glu Met Pro Trp Arg
        355                 360                 365

Phe Tyr Arg Pro Phe Phe Tyr Asp Val Thr Glu Ala Val His His Leu
    370                 375                 380

Gly Val Pro Leu Ser Gly His Tyr Tyr Val Lys Thr Glu Leu Phe Ser
385                 390                 395                 400

Val Asn Gly Thr Ala Leu Ser Pro Asp Leu Leu Pro Gln Pro Thr Val
                405                 410                 415

Ala Tyr Arg Pro Gly Lys
            420


<210> SEQ ID NO 64
<211> LENGTH: 511
<212> TYPE: PRT
<213> ORGANISM: Haliotis tuberculata

<400> SEQUENCE: 64

Val His Arg Gly Gly Asn His Glu Asp Glu His His Asp Asp Arg Leu
  1               5                  10                  15

Ala Asp Val Leu Ile Arg Lys Glu Val Asp Phe Leu Ser Leu Gln Glu
             20                  25                  30

Ala Asn Ala Ile Lys Asp Ala Leu Tyr Lys Leu Gln Asn Asp Asp Ser
         35                  40                  45

Lys Gly Gly Phe Glu Ala Ile Ala Gly Tyr His Gly Tyr Pro Asn Met
     50                  55                  60

Cys Pro Glu Arg Gly Thr Asp Lys Tyr Pro Cys Cys Val His Gly Met
 65                  70                  75                  80

Pro Val Phe Pro His Trp His Arg Leu His Thr Ile Gln Met Glu Arg
                 85                  90                  95

Ala Leu Lys Asn His Gly Ser Pro Met Gly Ile Pro Tyr Trp Asp Trp
            100                 105                 110

Thr Lys Lys Met Ser Ser Leu Pro Ser Phe Phe Gly Asp Ser Ser Asn
        115                 120                 125

Asn Asn Pro Phe Tyr Lys Tyr Tyr Ile Arg Gly Val Gln His Glu Thr
    130                 135                 140

Thr Arg Asp Val Asn Gln Arg Leu Phe Asn Gln Thr Lys Phe Gly Glu
145                 150                 155                 160

Phe Asp Tyr Leu Tyr Tyr Leu Thr Leu Gln Val Leu Glu Glu Asn Ser
                165                 170                 175

Tyr Cys Asp Phe Glu Val Gln Tyr Glu Ile Leu His Asn Ala Val His
            180                 185                 190

Ser Trp Leu Gly Gly Thr Gly Gln Tyr Ser Met Ser Thr Leu Glu His
        195                 200                 205

Ser Ala Phe Asp Pro Val Phe Met Ile His His Ser Ser Leu Asp Arg
    210                 215                 220

Ile Trp Ile Leu Trp Gln Lys Leu Gln Lys Ile Arg Met Lys Pro Tyr
225                 230                 235                 240

Tyr Ala Leu Asp Cys Ala Gly Asp Arg Leu Met Lys Asp Pro Leu His
                245                 250                 255

Pro Phe Asn Tyr Glu Thr Val Asn Glu Asp Glu Phe Thr Arg Ile Asn
            260                 265                 270

Ser Phe Pro Ser Ile Leu Phe Asp His Tyr Arg Phe Asn Tyr Glu Tyr
        275                 280                 285
```

-continued

```
Asp Asn Met Arg Ile Arg Gly Gln Asp Ile His Glu Leu Glu Glu Val
    290                 295                 300

Ile Gln Glu Leu Arg Asn Lys Asp Arg Ile Phe Ala Gly Phe Val Leu
305                 310                 315                 320

Ser Gly Leu Arg Ile Ser Ala Thr Val Lys Val Phe Ile His Ser Lys
                325                 330                 335

Asn Asp Thr Ser His Glu Glu Tyr Ala Gly Glu Phe Ala Val Leu Gly
            340                 345                 350

Gly Glu Lys Glu Met Pro Trp Ala Tyr Glu Arg Met Leu Lys Leu Asp
        355                 360                 365

Ile Ser Asp Ala Val His Lys Leu His Val Lys Asp Glu Asp Ile Arg
    370                 375                 380

Phe Arg Val Val Val Thr Ala Tyr Asn Gly Asp Val Val Thr Thr Arg
385                 390                 395                 400

Leu Ser Gln Pro Phe Ile Val His Arg Pro Ala His Val Ala His Asp
                405                 410                 415

Ile Leu Val Ile Pro Val Gly Ala Gly His Asp Leu Pro Pro Lys Val
            420                 425                 430

Val Val Lys Ser Gly Thr Lys Val Glu Phe Thr Pro Ile Asp Ser Ser
        435                 440                 445

Val Asn Lys Ala Met Val Glu Leu Gly Ser Tyr Thr Ala Met Ala Lys
    450                 455                 460

Cys Ile Val Pro Pro Phe Ser Tyr His Gly Phe Glu Leu Asp Lys Val
465                 470                 475                 480

Tyr Ser Val Asp His Gly Asp Tyr Tyr Ile Ala Ala Gly Thr His Ala
                485                 490                 495

Leu Cys Glu Gln Asn Leu Arg Leu His Ile His Val Glu His Glu
            500                 505                 510


<210> SEQ ID NO 65
<211> LENGTH: 197
<212> TYPE: PRT
<213> ORGANISM: Haliotis tuberculata

<400> SEQUENCE: 65

Gly Leu Pro Tyr Trp Asp Trp Thr Gln His Leu Thr Gln Leu Pro Asp
  1               5                  10                  15

Leu Val Ser Asp Pro Leu Phe Val Asp Pro Glu Gly Gly Lys Ala His
             20                  25                  30

Asp Asn Ala Trp Tyr Arg Gly Asn Ile Lys Phe Glu Asn Lys Lys Thr
         35                  40                  45

Ala Arg Ala Val Asp Asp Arg Leu Phe Glu Lys Val Gly Pro Gly Glu
     50                  55                  60

Asn Thr Arg Leu Phe Glu Gly Ile Leu Asp Ala Leu Glu Gln Asp Glu
 65                  70                  75                  80

Phe Cys Asn Phe Glu Ile Gln Phe Glu Leu Ala His Asn Ala Ile His
                 85                  90                  95

Tyr Leu Val Gly Gly Arg His Thr Tyr Ser Met Ser His Leu Glu Tyr
            100                 105                 110

Thr Ser Tyr Asp Pro Leu Phe Phe Leu His His Ser Asn Pro Asp Arg
        115                 120                 125

Ile Phe Ala Ile Trp Glu Arg Leu Gln Val Leu Arg Gly Lys Asp Pro
    130                 135                 140

Asn Thr Ala Asp Cys Ala His Asn Leu Ile His Glu Pro Met Glu Pro
145                 150                 155                 160
```

-continued

```
Phe Arg Arg His Glu Pro Met Glu Pro Phe Arg Arg Asp Ser Asn Pro
                165                 170                 175

Leu Asp Leu Thr Arg Glu Asn Ser Lys Pro Ile Asp Ser Phe Asp Tyr
            180                 185                 190

Ala His Leu Gly Tyr
        195


<210> SEQ ID NO 66
<211> LENGTH: 415
<212> TYPE: PRT
<213> ORGANISM: Haliotis tuberculata

<400> SEQUENCE: 66

Val Thr Glu Ala Pro Ala Pro Ser Ser Asp Ala His Leu Ala Val Arg
  1               5                  10                  15

Lys Asp Ile Asn His Leu Thr Arg Glu Glu Val Tyr Glu Leu Arg Arg
            20                  25                  30

Ala Met Glu Arg Phe Gln Ala Asp Thr Ser Val Asp Gly Tyr Gln Ala
        35                  40                  45

Thr Val Glu Tyr His Gly Leu Pro Ala Arg Cys Pro Phe Pro Glu Ala
    50                  55                  60

Thr Asn Arg Phe Ala Cys Cys Ile His Gly Met Ala Thr Phe Pro His
65                  70                  75                  80

Trp His Arg Leu Phe Val Thr Gln Val Glu Asp Ala Leu Ile Arg Arg
                85                  90                  95

Gly Ser Pro Ile Gly Val Pro Tyr Trp Asp Trp Thr Gln Pro Met Ala
            100                 105                 110

His Leu Pro Gly Leu Ala Asp Asn Ala Thr Tyr Arg Asp Pro Ile Ser
        115                 120                 125

Gly Asp Ser Arg His Asn Pro Phe His Asp Val Glu Val Ala Phe Glu
    130                 135                 140

Asn Gly Arg Thr Glu Arg His Pro Asp Ser Arg Leu Phe Glu Gln Pro
145                 150                 155                 160

Leu Phe Gly Lys His Thr Arg Leu Phe Asp Ser Ile Val Tyr Ala Phe
                165                 170                 175

Glu Gln Glu Asp Phe Cys Asp Phe Glu Val Gln Phe Glu Met Thr His
            180                 185                 190

Asn Asn Ile His Ala Trp Ile Gly Gly Gly Glu Lys Tyr Ser Met Ser
        195                 200                 205

Ser Leu His Tyr Thr Ala Phe Asp Pro Ile Phe Tyr Leu Arg His Ser
    210                 215                 220

Asn Thr Asp Arg Leu Trp Ala Ile Trp Gln Ala Leu Gln Ile Arg Arg
225                 230                 235                 240

Asn Arg Pro Tyr Lys Ala His Cys Ala Trp Ser Glu Glu Arg Gln Pro
                245                 250                 255

Leu Lys Pro Phe Ala Phe Ser Ser Pro Leu Asn Asn Asn Glu Lys Thr
            260                 265                 270

Tyr Glu Asn Ser Val Pro Thr Asn Val Tyr Asp Tyr Glu Gly Val Leu
        275                 280                 285

Gly Tyr Thr Tyr Asp Asp Leu Asn Phe Gly Gly Met Asp Leu Gly Gln
    290                 295                 300

Leu Glu Glu Tyr Ile Gln Arg Gln Arg Gln Arg Asp Arg Thr Phe Ala
305                 310                 315                 320

Gly Phe Phe Leu Ser His Ile Gly Thr Ser Ala Asn Val Glu Ile Ile
                325                 330                 335
```

-continued

```
Ile Asp His Gly Thr Leu His Thr Ser Val Gly Thr Phe Ala Val Leu
            340                 345                 350

Gly Gly Glu Lys Glu Met Lys Trp Gly Phe Asp Arg Leu Tyr Lys Tyr
        355                 360                 365

Glu Ile Thr Asp Glu Leu Arg Gln Leu Asn Leu Arg Ala Asp Asp Val
    370                 375                 380

Phe Ser Ile Ser Val Lys Val Thr Asp Val Asp Gly Ser Glu Leu Ser
385                 390                 395                 400

Ser Glu Leu Ile Pro Ser Ala Ala Ile Ile Phe Glu Arg Ser His
                405                 410                 415


<210> SEQ ID NO 67
<211> LENGTH: 414
<212> TYPE: PRT
<213> ORGANISM: Haliotis tuberculata

<400> SEQUENCE: 67

Gly His His Gln Ala Asp Glu Tyr Asp Glu Val Val Thr Ala Ala Ser
  1               5                  10                  15

His Ile Arg Lys Asn Leu Lys Asp Leu Ser Lys Gly Glu Val Glu Ser
             20                  25                  30

Leu Arg Ser Ala Phe Leu Gln Leu Gln Asn Asp Gly Val Tyr Glu Asn
         35                  40                  45

Ile Ala Lys Phe His Gly Lys Pro Gly Leu Cys Asp Asp Asn Gly Arg
     50                  55                  60

Lys Val Ala Cys Cys Val His Gly Met Pro Thr Phe Pro Gln Trp His
 65                  70                  75                  80

Arg Leu Tyr Val Leu Gln Val Glu Asn Ala Leu Leu Glu Arg Gly Ser
                 85                  90                  95

Ala Val Ser Val Pro Tyr Trp Asp Trp Thr Glu Thr Phe Thr Glu Leu
            100                 105                 110

Pro Ser Leu Ile Ala Glu Ala Thr Tyr Phe Asn Ser Arg Gln Gln Thr
        115                 120                 125

Phe Asp Pro Asn Pro Phe Phe Arg Gly Lys Ile Ser Phe Glu Asn Ala
    130                 135                 140

Val Thr Thr Arg Asp Pro Gln Pro Glu Leu Tyr Val Asn Arg Tyr Tyr
145                 150                 155                 160

Tyr Gln Asn Val Met Leu Val Phe Glu Gln Asp Asn Tyr Cys Asp Phe
                165                 170                 175

Glu Ile Gln Phe Glu Met Val His Asn Val Leu His Ala Trp Leu Gly
            180                 185                 190

Gly Arg Ala Thr Tyr Ser Ile Ser Ser Leu Asp Tyr Ser Ala Phe Asp
        195                 200                 205

Pro Val Phe Phe Leu His His Ala Asn Thr Asp Arg Leu Trp Ala Ile
    210                 215                 220

Trp Gln Glu Leu Gln Arg Tyr Arg Lys Lys Pro Tyr Asn Glu Ala Asp
225                 230                 235                 240

Cys Ala Ile Asn Leu Met Arg Lys Pro Leu His Pro Phe Asp Asn Ser
                245                 250                 255

Asp Leu Asn His Asp Pro Val Thr Phe Lys Tyr Ser Lys Pro Thr Asp
            260                 265                 270

Gly Phe Asp Tyr Gln Asn Asn Phe Gly Tyr Lys Tyr Asp Asn Leu Glu
        275                 280                 285

Phe Asn His Phe Ser Ile Pro Arg Leu Glu Glu Ile Ile Arg Ile Arg
    290                 295                 300
```

-continued

```
Gln Arg Gln Asp Arg Val Phe Ala Gly Phe Leu Leu His Asn Ile Gly
305                 310                 315                 320

Thr Ser Ala Thr Val Glu Ile Phe Val Cys Val Pro Thr Thr Ser Gly
                325                 330                 335

Glu Gln Asn Cys Glu Asn Lys Ala Gly Thr Phe Ala Val Leu Gly Gly
            340                 345                 350

Glu Thr Glu Met Ala Phe His Phe Asp Arg Leu Tyr Arg Phe Asp Ile
        355                 360                 365

Ser Glu Thr Leu Arg Asp Leu Gly Ile Gln Leu Asp Ser His Asp Phe
    370                 375                 380

Asp Leu Ser Ile Lys Ile Gln Gly Val Asn Gly Ser Tyr Leu Asp Pro
385                 390                 395                 400

His Ile Leu Pro Glu Pro Ser Leu Ile Phe Val Pro Gly Ser
                405                 410


<210> SEQ ID NO 68
<211> LENGTH: 419
<212> TYPE: PRT
<213> ORGANISM: Haliotis tuberculata

<400> SEQUENCE: 68

Ser Ser Phe Leu Arg Pro Asp Gly His Ser Asp Asp Ile Leu Val Arg
  1               5                  10                  15

Lys Glu Val Asn Ser Leu Thr Thr Arg Glu Thr Ala Ser Leu Ile His
            20                  25                  30

Ala Leu Lys Ser Met Gln Glu Asp His Ser Pro Asp Gly Phe Gln Ala
        35                  40                  45

Ile Ala Ser Phe His Ala Leu Pro Pro Leu Cys Pro Ser Pro Ser Ala
    50                  55                  60

Ala His Arg Tyr Ala Cys Cys Val His Gly Met Ala Thr Phe Pro Gln
 65                  70                  75                  80

Trp His Arg Leu Tyr Thr Val Gln Phe Gln Asp Ala Leu Arg Arg His
                 85                  90                  95

Gly Ala Thr Val Gly Val Pro Tyr Trp Asp Trp Leu Arg Pro Gln Ser
            100                 105                 110

His Leu Pro Glu Leu Val Thr Met Glu Thr Tyr His Asp Ile Trp Ser
        115                 120                 125

Asn Arg Asp Phe Pro Asn Pro Phe Tyr Gln Ala Asn Ile Glu Phe Glu
    130                 135                 140

Gly Glu Asn Ile Thr Thr Glu Arg Glu Val Ile Ala Asp Lys Leu Phe
145                 150                 155                 160

Val Lys Gly Gly His Val Phe Asp Lys Leu Val Leu Gln Thr Ser His
                165                 170                 175

Pro Ser Ala Glu Gln Glu Asn Tyr Cys Asp Phe Glu Ile Gln Phe Glu
            180                 185                 190

Ile Leu His Asn Gly Val His Thr Trp Val Gly Gly Ser Arg Thr Tyr
        195                 200                 205

Ser Ile Gly His Leu His Tyr Ala Phe Tyr Asp Pro Leu Phe Tyr Leu
    210                 215                 220

His His Phe Gln Thr Asp Arg Ile Trp Ala Ile Trp Gln Glu Leu Gln
225                 230                 235                 240

Glu Gln Arg Gly Leu Ser Gly Asp Glu Ala His Cys Ala Leu Glu Gln
                245                 250                 255

Met Arg Glu Pro Leu Lys Pro Phe Ser Phe Gly Ala Pro Tyr Asn Trp
            260                 265                 270
```

-continued

```
Asn Gln Leu Thr Gln Asp Phe Ser Arg Pro Glu Asp Thr Phe Asp Tyr
        275                 280                 285

Arg Lys Phe Gly Tyr Glu Tyr Asp Asn Leu Glu Phe Leu Gly Met Ser
    290                 295                 300

Val Ala Glu Leu Asp Gln Tyr Ile Ile Glu His Gln Glu Asn Asp Arg
305                 310                 315                 320

Val Phe Ala Gly Phe Leu Leu Ser Gly Phe Gly Gly Ser Ala Ser Val
                325                 330                 335

Asn Phe Gln Val Cys Arg Ala Asp Ser Thr Cys Gln Asp Ala Gly Tyr
            340                 345                 350

Phe Thr Val Leu Gly Gly Ser Ala Glu Met Ala Trp Ala Phe Asp Arg
        355                 360                 365

Leu Tyr Lys Tyr Asp Ile Thr Glu Thr Leu Glu Lys Met His Leu Arg
    370                 375                 380

Tyr Asp Asp Asp Phe Thr Ile Ser Val Ser Leu Thr Ala Asn Asn Gly
385                 390                 395                 400

Thr Val Leu Ser Ser Ser Leu Ile Pro Thr Pro Ser Val Ile Phe Gln
                405                 410                 415

Arg Gly His


<210> SEQ ID NO 69
<211> LENGTH: 378
<212> TYPE: PRT
<213> ORGANISM: Megathura crenulata

<400> SEQUENCE: 69

Arg Tyr Gln Ala Thr Ala Glu Tyr His Gly Leu Pro Ala Arg Cys Pro
  1               5                  10                  15

Arg Pro Asp Ala Lys Asp Arg Tyr Ala Cys Cys Val His Gly Met Pro
             20                  25                  30

Ile Phe Pro His Trp His Arg Leu Phe Val Thr Gln Val Glu Asp Ala
         35                  40                  45

Leu Val Gly Arg Gly Ala Thr Ile Gly Ile Pro Tyr Trp Asp Trp Thr
     50                  55                  60

Glu Pro Met Thr His Ile Pro Gly Leu Ala Gly Asn Lys Thr Tyr Val
 65                  70                  75                  80

Asp Ser His Gly Ala Ser His Thr Asn Pro Phe His Ser Ser Val Ile
                 85                  90                  95

Ala Phe Glu Glu Asn Ala Pro His Thr Lys Arg Gln Ile Asp Gln Arg
            100                 105                 110

Leu Phe Lys Pro Ala Thr Phe Gly His His Thr Asp Leu Phe Asn Gln
        115                 120                 125

Ile Leu Tyr Ala Phe Glu Gln Glu Asp Tyr Cys Asp Phe Glu Val Gln
    130                 135                 140

Phe Glu Ile Thr His Asn Thr Ile His Ala Trp Thr Gly Gly Ser Glu
145                 150                 155                 160

His Phe Ser Met Ser Ser Leu His Tyr Thr Ala Phe Asp Pro Leu Phe
                165                 170                 175

Tyr Phe His His Ser Asn Val Asp Arg Leu Trp Ala Val Trp Gln Ala
            180                 185                 190

Leu Gln Met Arg Arg His Lys Pro Tyr Arg Ala His Cys Ala Ile Ser
        195                 200                 205

Leu Glu His Met His Leu Lys Pro Phe Ala Phe Ser Ser Pro Leu Asn
    210                 215                 220
```

-continued

```
Asn Asn Glu Lys Thr His Ala Asn Ala Met Pro Asn Lys Ile Tyr Asp
225                 230                 235                 240

Tyr Glu Asn Val Leu His Tyr Thr Tyr Glu Asp Leu Thr Phe Gly Gly
                245                 250                 255

Ile Ser Leu Glu Asn Ile Glu Lys Met Ile His Glu Asn Gln Gln Glu
            260                 265                 270

Asp Arg Ile Tyr Ala Gly Phe Leu Leu Ala Gly Ile Arg Thr Ser Ala
        275                 280                 285

Asn Val Asp Ile Phe Ile Lys Thr Thr Asp Ser Val Gln His Lys Ala
    290                 295                 300

Gly Thr Phe Ala Val Leu Gly Gly Ser Lys Glu Met Lys Trp Gly Phe
305                 310                 315                 320

Asp Arg Val Phe Lys Phe Asp Ile Thr His Val Leu Lys Asp Leu Asp
                325                 330                 335

Leu Thr Ala Asp Gly Asp Phe Glu Val Thr Val Asp Ile Thr Glu Val
            340                 345                 350

Asp Gly Thr Lys Leu Ala Ser Ser Leu Ile Pro His Ala Ser Val Ile
        355                 360                 365

Arg Glu His Ala Arg Gly Lys Leu Asn Arg
    370                 375
```

<210> SEQ ID NO 70
<211> LENGTH: 419
<212> TYPE: PRT
<213> ORGANISM: Megathura crenulata

<400> SEQUENCE: 70

```
Asp Ser Ala His Thr Asp Asp Gly His Thr Glu Pro Val Met Ile Arg
  1               5                  10                  15

Lys Asp Ile Thr Gln Leu Asp Lys Arg Gln Gln Leu Ser Leu Val Lys
            20                  25                  30

Ala Leu Glu Ser Met Lys Ala Asp His Ser Ser Asp Gly Phe Gln Ala
        35                  40                  45

Ile Ala Ser Phe His Ala Leu Pro Pro Leu Cys Pro Ser Pro Ala Ala
    50                  55                  60

Ser Lys Arg Phe Ala Cys Cys Val His Gly Met Ala Thr Phe Pro Gln
 65                  70                  75                  80

Trp His Arg Leu Tyr Thr Val Gln Phe Gln Asp Ser Leu Arg Lys His
                85                  90                  95

Gly Ala Val Val Gly Leu Pro Tyr Trp Asp Trp Thr Leu Pro Arg Ser
            100                 105                 110

Glu Leu Pro Glu Leu Leu Thr Val Ser Thr Ile His Asp Pro Glu Thr
        115                 120                 125

Gly Arg Asp Ile Pro Asn Pro Phe Ile Gly Ser Lys Ile Glu Phe Glu
    130                 135                 140

Gly Glu Asn Val His Thr Lys Arg Asp Ile Asn Arg Asp Arg Leu Phe
145                 150                 155                 160

Gln Gly Ser Thr Lys Thr His His Asn Trp Phe Ile Glu Gln Ala Leu
                165                 170                 175

Leu Ala Leu Glu Gln Thr Asn Tyr Cys Asp Phe Glu Val Gln Phe Glu
            180                 185                 190

Ile Met His Asn Gly Val His Thr Trp Val Gly Gly Lys Glu Pro Tyr
        195                 200                 205

Gly Ile Gly His Leu His Tyr Ala Ser Tyr Asp Pro Leu Phe Tyr Ile
    210                 215                 220
```

-continued

```
His His Ser Gln Thr Asp Arg Ile Trp Ala Ile Trp Gln Ser Leu Gln
225                 230                 235                 240

Arg Phe Arg Gly Leu Ser Gly Ser Glu Ala Asn Cys Ala Val Asn Leu
                245                 250                 255

Met Lys Thr Pro Leu Lys Pro Phe Ser Phe Gly Ala Pro Tyr Asn Leu
            260                 265                 270

Asn Asp His Thr His Asp Phe Ser Lys Pro Glu Asp Thr Phe Asp Tyr
        275                 280                 285

Gln Lys Phe Gly Tyr Ile Tyr Asp Thr Leu Glu Phe Ala Gly Trp Ser
    290                 295                 300

Ile Arg Gly Ile Asp His Ile Val Arg Asn Arg Gln Glu His Ser Arg
305                 310                 315                 320

Val Phe Ala Gly Phe Leu Leu Glu Gly Phe Gly Thr Ser Ala Thr Val
                325                 330                 335

Asp Phe Gln Val Cys Arg Thr Ala Gly Asp Cys Glu Asp Ala Gly Tyr
            340                 345                 350

Phe Thr Val Leu Gly Gly Glu Lys Glu Met Pro Trp Ala Phe Asp Arg
        355                 360                 365

Leu Tyr Lys Tyr Asp Ile Thr Glu Thr Leu Asp Lys Met Asn Leu Arg
    370                 375                 380

His Asp Glu Ile Phe Gln Ile Glu Val Thr Ile Thr Ser Tyr Asp Gly
385                 390                 395                 400

Thr Val Leu Asp Ser Gly Leu Ile Pro Thr Pro Ser Ile Ile Tyr Asp
                405                 410                 415

Pro Ala His


<210> SEQ ID NO 71
<211> LENGTH: 418
<212> TYPE: PRT
<213> ORGANISM: Megathura crenulata

<400> SEQUENCE: 71

His Asp Ile Ser Ser His His Leu Ser Leu Asn Lys Val Arg His Asp
  1               5                  10                  15

Leu Ser Thr Leu Ser Glu Arg Asp Ile Gly Ser Leu Lys Tyr Ala Leu
            20                  25                  30

Ser Ser Leu Gln Ala Asp Thr Ser Ala Asp Gly Phe Ala Ala Ile Ala
        35                  40                  45

Ser Phe His Gly Leu Pro Ala Lys Cys Asn Asp Ser His Asn Asn Glu
     50                  55                  60

Val Ala Cys Cys Ile His Gly Met Pro Thr Phe Pro His Trp His Arg
 65                  70                  75                  80

Leu Tyr Thr Leu Gln Phe Glu Gln Ala Leu Arg Arg His Gly Ser Ser
                 85                  90                  95

Val Ala Val Pro Tyr Trp Asp Trp Thr Lys Pro Ile His Asn Ile Pro
            100                 105                 110

His Leu Phe Thr Asp Lys Glu Tyr Tyr Asp Val Trp Arg Asn Lys Val
        115                 120                 125

Met Pro Asn Pro Phe Ala Arg Gly Tyr Val Pro Ser His Asp Thr Tyr
    130                 135                 140

Thr Val Arg Asp Val Gln Glu Gly Leu Phe His Leu Thr Ser Thr Gly
145                 150                 155                 160

Glu His Ser Ala Leu Leu Asn Gln Ala Leu Leu Ala Leu Glu Gln His
                165                 170                 175
```

-continued

```
Asp Tyr Cys Asp Phe Ala Val Gln Phe Glu Val Met His Asn Thr Ile
            180                 185                 190

His Tyr Leu Val Gly Gly Pro Gln Val Tyr Ser Leu Ser Ser Leu His
        195                 200                 205

Tyr Ala Ser Tyr Asp Pro Ile Phe Phe Ile His His Ser Phe Val Asp
    210                 215                 220

Lys Val Trp Ala Val Trp Gln Ala Leu Gln Glu Lys Arg Gly Leu Pro
225                 230                 235                 240

Ser Asp Arg Ala Asp Cys Ala Val Ser Leu Met Thr Gln Asn Met Arg
                245                 250                 255

Pro Phe His Tyr Glu Ile Asn His Asn Gln Phe Thr Lys Lys His Ala
            260                 265                 270

Val Pro Asn Asp Val Phe Lys Tyr Glu Leu Leu Gly Tyr Arg Tyr Asp
        275                 280                 285

Asn Leu Glu Ile Gly Gly Met Asn Leu His Glu Ile Glu Lys Glu Ile
    290                 295                 300

Lys Asp Lys Gln His His Val Arg Val Phe Ala Gly Phe Leu Leu His
305                 310                 315                 320

Gly Ile Arg Thr Ser Ala Asp Val Gln Phe Gln Ile Cys Lys Thr Ser
                325                 330                 335

Glu Asp Cys His His Gly Gly Gln Ile Phe Val Leu Gly Gly Thr Lys
            340                 345                 350

Glu Met Ala Trp Ala Tyr Asn Arg Leu Phe Lys Tyr Asp Ile Thr His
        355                 360                 365

Ala Leu His Asp Ala His Ile Thr Pro Glu Asp Val Phe His Pro Ser
    370                 375                 380

Glu Pro Phe Phe Ile Lys Val Ser Val Thr Ala Val Asn Gly Thr Val
385                 390                 395                 400

Leu Pro Ala Ser Ile Leu His Ala Pro Thr Ile Ile Tyr Glu Pro Gly
                405                 410                 415

Leu Gly


<210> SEQ ID NO 72
<211> LENGTH: 241
<212> TYPE: PRT
<213> ORGANISM: Megathura crenulata

<400> SEQUENCE: 72

Asp His His Glu Asp His His Ser Ser Ser Met Ala Gly His Gly Val
  1               5                  10                  15

Arg Lys Glu Ile Asn Thr Leu Thr Thr Ala Glu Val Asp Asn Leu Lys
            20                  25                  30

Asp Ala Met Arg Ala Val Met Ala Asp His Gly Pro Asn Gly Tyr Gln
         35                  40                  45

Ala Ile Ala Ala Phe His Gly Asn Pro Pro Met Cys Pro Met Pro Asp
     50                  55                  60

Gly Lys Asn Tyr Ser Cys Cys Thr His Gly Met Ala Thr Phe Pro His
 65                  70                  75                  80

Trp His Arg Leu Tyr Thr Lys Gln Met Glu Asp Ala Leu Thr Ala His
                 85                  90                  95

Gly Ala Arg Val Gly Leu Pro Tyr Trp Asp Gly Thr Thr Ala Phe Thr
            100                 105                 110

Ala Leu Pro Thr Phe Val Thr Asp Glu Glu Asp Asn Pro Phe His His
        115                 120                 125
```

-continued

```
Gly His Ile Asp Tyr Leu Gly Val Asp Thr Thr Arg Ser Pro Arg Asp
    130                 135                 140

Lys Leu Phe Asn Asp Pro Glu Arg Gly Ser Glu Ser Phe Phe Tyr Arg
145                 150                 155                 160

Gln Val Leu Leu Ala Leu Glu Gln Thr Asp Phe Cys Gln Phe Glu Val
                165                 170                 175

Gln Phe Glu Ile Thr His Asn Ala Ile His Ser Trp Thr Gly Gly Leu
            180                 185                 190

Thr Pro Tyr Gly Met Ser Thr Leu Glu Tyr Thr Thr Tyr Asp Pro Leu
        195                 200                 205

Phe Trp Leu His His Ala Asn Thr Asp Arg Ile Trp Ala Ile Trp Gln
    210                 215                 220

Ala Leu Gln Glu Tyr Arg Gly Leu Pro Tyr Asp His Ala Asn Cys Glu
225                 230                 235                 240

Ile
```

<210> SEQ ID NO 73
<211> LENGTH: 98
<212> TYPE: PRT
<213> ORGANISM: Megathura crenulata

<400> SEQUENCE: 73

```
Lys His His Glu Lys His His Glu Asp His His Glu Asp Ile Leu Val
  1               5                  10                  15

Arg Lys Asn Ile His Ser Leu Ser His His Glu Ala Glu Glu Leu Arg
             20                  25                  30

Asp Ala Leu Tyr Lys Leu Gln Asn Asp Glu Ser His Gly Gly Tyr Glu
         35                  40                  45

His Ile Ala Gly Phe His Gly Tyr Pro Asn Leu Cys Pro Glu Lys Gly
     50                  55                  60

Asp Glu Lys Tyr Pro Cys Cys Val His Gly Met Ser Ile Phe Pro His
 65                  70                  75                  80

Trp His Arg Leu His Thr Ile Gln Leu Glu Arg Ala Leu Lys Lys His
                 85                  90                  95

Gly Ser
```

<210> SEQ ID NO 74
<211> LENGTH: 314
<212> TYPE: PRT
<213> ORGANISM: Megathura crenulata

<400> SEQUENCE: 74

```
Gly Leu Pro Tyr Trp Asp Trp Thr Met Pro Met Ser His Leu Pro Glu
  1               5                  10                  15

Leu Ala Thr Ser Glu Thr Tyr Leu Asp Pro Val Thr Gly Glu Thr Lys
             20                  25                  30

Asn Asn Pro Phe His His Ala Gln Val Ala Phe Glu Asn Gly Val Thr
         35                  40                  45

Ser Arg Asn Pro Asp Ala Lys Leu Phe Met Lys Pro Thr Tyr Gly Asp
     50                  55                  60

His Thr Tyr Leu Phe Asp Ser Met Ile Tyr Ala Phe Glu Gln Glu Asp
 65                  70                  75                  80

Phe Cys Asp Phe Glu Val Gln Tyr Glu Leu Thr His Asn Ala Ile His
                 85                  90                  95

Ala Trp Val Gly Gly Ser Glu Lys Tyr Ser Met Ser Ser Leu His Tyr
            100                 105                 110
```

-continued

Thr Ala Phe Asp Pro Ile Phe Tyr Leu His His Ser Asn Val Asp Arg
115 120 125

Leu Trp Ala Ile Trp Gln Ala Leu Gln Ile Arg Arg Gly Lys Ser Tyr
130 135 140

Lys Ala His Cys Ala Ser Ser Gln Glu Arg Glu Pro Leu Lys Pro Phe
145 150 155 160

Ala Phe Ser Ser Pro Leu Asn Asn Asn Glu Lys Thr Tyr His Asn Ser
165 170 175

Val Pro Thr Asn Val Tyr Asp Tyr Val Gly Val Leu His Tyr Arg Tyr
180 185 190

Asp Asp Leu Gln Phe Gly Gly Met Thr Met Ser Glu Leu Glu Glu Tyr
195 200 205

Ile His Lys Gln Thr Gln His Asp Arg Thr Phe Ala Gly Phe Phe Leu
210 215 220

Ser Tyr Ile Gly Thr Ser Ala Ser Val Asp Ile Phe Ile Asn Arg Glu
225 230 235 240

Gly His Asp Lys Tyr Lys Val Gly Ser Phe Val Val Leu Gly Gly Ser
245 250 255

Lys Glu Met Lys Trp Gly Phe Asp Arg Met Tyr Lys Tyr Glu Ile Thr
260 265 270

Glu Ala Leu Lys Thr Leu Asn Val Ala Val Asp Asp Gly Phe Ser Ile
275 280 285

Thr Val Glu Ile Thr Asp Val Asp Gly Ser Pro Pro Ser Ala Asp Leu
290 295 300

Ile Pro Pro Pro Ala Ile Ile Phe Glu Arg
305 310

<210> SEQ ID NO 75
<211> LENGTH: 416
<212> TYPE: PRT
<213> ORGANISM: Megathura crenulata

<400> SEQUENCE: 75

Ala Asp Ala Lys Asp Phe Gly His Ser Arg Lys Ile Arg Lys Ala Val
1 5 10 15

Asp Ser Leu Thr Val Glu Glu Gln Thr Ser Leu Arg Arg Ala Met Ala
20 25 30

Asp Leu Gln Asp Asp Lys Thr Ser Gly Gly Phe Gln Gln Ile Ala Ala
35 40 45

Phe His Gly Glu Pro Lys Trp Cys Pro Ser Pro Glu Ala Glu Lys Lys
50 55 60

Phe Ala Cys Cys Val His Gly Met Ala Val Phe Pro His Trp His Arg
65 70 75 80

Leu Leu Thr Val Gln Gly Glu Asn Ala Leu Arg Lys His Gly Phe Thr
85 90 95

Gly Gly Leu Pro Tyr Trp Asp Trp Thr Arg Ser Met Ser Ala Leu Pro
100 105 110

His Phe Val Ala Asp Pro Thr Tyr Asn Asp Ala Ile Ser Ser Gln Glu
115 120 125

Glu Asp Asn Pro Trp His His Gly His Ile Asp Ser Val Gly His Asp
130 135 140

Thr Thr Arg Asp Val Arg Asp Asp Leu Tyr Gln Ser Pro Gly Phe Gly
145 150 155 160

His Tyr Thr Asp Ile Ala Lys Gln Val Leu Leu Ala Phe Glu Gln Asp
165 170 175

-continued

Asp Phe Cys Asp Phe Glu Val Gln Phe Glu Ile Ala His Asn Phe Ile
180 185 190

His Ala Leu Val Gly Gly Asn Glu Pro Tyr Ser Met Ser Ser Leu Arg
195 200 205

Tyr Thr Thr Tyr Asp Pro Ile Phe Phe Leu His Arg Ser Asn Thr Asp
210 215 220

Arg Leu Trp Ala Ile Trp Gln Ala Leu Gln Lys Tyr Arg Gly Lys Pro
225 230 235 240

Tyr Asn Thr Ala Asn Cys Ala Ile Ala Ser Met Arg Lys Pro Leu Gln
245 250 255

Pro Phe Gly Leu Asp Ser Val Ile Asn Pro Asp Asp Glu Thr Arg Glu
260 265 270

His Ser Val Pro Phe Arg Val Phe Asp Tyr Lys Asn Asn Phe Asp Tyr
275 280 285

Glu Tyr Glu Ser Leu Ala Phe Asn Gly Leu Ser Ile Ala Gln Leu Asp
290 295 300

Arg Glu Leu Gln Arg Arg Lys Ser His Asp Arg Val Phe Ala Gly Phe
305 310 315 320

Leu Leu His Glu Ile Gly Gln Ser Ala Leu Val Lys Phe Tyr Val Cys
325 330 335

Lys His Asn Val Ser Asp Cys Asp His Tyr Ala Gly Glu Phe Tyr Ile
340 345 350

Leu Gly Asp Glu Ala Glu Met Pro Trp Arg Tyr Asp Arg Val Tyr Lys
355 360 365

Tyr Glu Ile Thr Gln Gln Leu His Asp Leu Asp Leu His Val Gly Asp
370 375 380

Asn Phe Phe Leu Lys Tyr Glu Ala Phe Asp Leu Asn Gly Gly Ser Leu
385 390 395 400

Gly Gly Ser Ile Phe Ser Gln Pro Ser Val Ile Phe Glu Pro Ala Ala
405 410 415

<210> SEQ ID NO 76
<211> LENGTH: 419
<212> TYPE: PRT
<213> ORGANISM: Megathura crenulata

<400> SEQUENCE: 76

Gly Ser His Gln Ala Asp Glu Tyr Arg Glu Ala Val Thr Ser Ala Ser
1 5 10 15

His Ile Arg Lys Asn Ile Arg Asp Leu Ser Glu Gly Glu Ile Glu Ser
20 25 30

Ile Arg Ser Ala Phe Leu Gln Ile Gln Lys Glu Gly Ile Tyr Glu Asn
35 40 45

Ile Ala Lys Phe His Gly Lys Pro Gly Leu Cys Glu His Asp Gly His
50 55 60

Pro Val Ala Cys Cys Val His Gly Met Pro Thr Phe Pro His Trp His
65 70 75 80

Arg Leu Tyr Val Leu Gln Val Glu Asn Ala Leu Leu Glu Arg Gly Ser
85 90 95

Ala Val Ala Val Pro Tyr Trp Asp Trp Thr Glu Lys Ala Asp Ser Leu
100 105 110

Pro Ser Leu Ile Asn Asp Ala Thr Tyr Phe Asn Ser Arg Ser Gln Thr
115 120 125

Phe Asp Pro Asn Pro Phe Phe Arg Gly His Ile Ala Phe Glu Asn Ala
130 135 140

-continued

```
Val Thr Ser Arg Asp Pro Gln Pro Glu Leu Trp Asp Asn Lys Asp Phe
145                 150                 155                 160

Tyr Glu Asn Val Met Leu Ala Leu Glu Gln Asp Asn Phe Cys Asp Phe
                165                 170                 175

Glu Ile Gln Leu Glu Leu Ile His Asn Ala Leu His Ser Arg Leu Gly
            180                 185                 190

Gly Arg Ala Lys Tyr Ser Leu Ser Ser Leu Asp Tyr Thr Ala Phe Asp
        195                 200                 205

Pro Val Phe Phe Leu His His Ala Asn Val Asp Arg Ile Trp Ala Ile
    210                 215                 220

Trp Gln Asp Leu Gln Arg Tyr Arg Lys Lys Pro Tyr Asn Glu Ala Asp
225                 230                 235                 240

Cys Ala Val Asn Glu Met Arg Lys Pro Leu Gln Pro Phe Asn Asn Pro
                245                 250                 255

Glu Leu Asn Ser Asp Ser Met Thr Leu Lys His Asn Leu Pro Gln Asp
            260                 265                 270

Ser Phe Asp Tyr Gln Asn Arg Phe Arg Tyr Gln Tyr Asp Asn Leu Gln
        275                 280                 285

Phe Asn His Phe Ser Ile Gln Lys Leu Asp Gln Thr Ile Gln Ala Arg
    290                 295                 300

Lys Gln His Asp Arg Val Phe Ala Gly Phe Ile Leu His Asn Ile Gly
305                 310                 315                 320

Thr Ser Ala Val Val Asp Ile Tyr Ile Cys Val Glu Gln Gly Gly Glu
                325                 330                 335

Gln Asn Cys Lys Thr Lys Ala Gly Ser Phe Thr Ile Leu Gly Gly Glu
            340                 345                 350

Thr Glu Met Pro Phe His Phe Asp Arg Leu Tyr Lys Phe Asp Ile Thr
        355                 360                 365

Ser Ala Leu His Lys Leu Gly Val Pro Leu Asp Gly His Gly Phe Asp
    370                 375                 380

Ile Lys Val Asp Val Arg Ala Val Asn Gly Ser His Leu Asp Gln His
385                 390                 395                 400

Ile Leu Asn Glu Pro Ser Leu Leu Phe Val Pro Gly Glu Arg Lys Asn
                405                 410                 415

Ile Tyr Tyr


<210> SEQ ID NO 77
<211> LENGTH: 413
<212> TYPE: PRT
<213> ORGANISM: Megathura crenulata

<400> SEQUENCE: 77

Asp Gly Leu Ser Gln His Asn Leu Val Arg Lys Glu Val Ser Ser Leu
  1               5                  10                  15

Thr Thr Leu Glu Lys His Phe Leu Arg Lys Ala Leu Lys Asn Met Gln
             20                  25                  30

Ala Asp Asp Ser Pro Asp Gly Tyr Gln Ala Ile Ala Ser Phe His Ala
         35                  40                  45

Leu Pro Pro Leu Cys Pro Ser Pro Ser Ala Ala His Arg His Ala Cys
     50                  55                  60

Cys Leu His Gly Met Ala Thr Phe Pro Gln Trp His Arg Leu Tyr Thr
 65                  70                  75                  80

Val Gln Phe Glu Asp Ser Leu Lys Arg His Gly Ser Ile Val Gly Leu
                 85                  90                  95
```

-continued

```
Pro Tyr Trp Asp Trp Leu Lys Pro Gln Ser Ala Leu Pro Asp Leu Val
            100                 105                 110

Thr Gln Glu Thr Tyr Glu His Leu Phe Ser His Lys Thr Phe Pro Asn
        115                 120                 125

Pro Phe Leu Lys Ala Asn Ile Glu Phe Glu Gly Glu Gly Val Thr Thr
    130                 135                 140

Glu Arg Asp Val Asp Ala Glu His Leu Phe Ala Lys Gly Asn Leu Val
145                 150                 155                 160

Tyr Asn Asn Trp Phe Cys Asn Gln Ala Leu Tyr Ala Leu Glu Gln Glu
                165                 170                 175

Asn Tyr Cys Asp Phe Glu Ile Gln Phe Glu Ile Leu His Asn Gly Ile
            180                 185                 190

His Ser Trp Val Gly Gly Ser Lys Thr His Ser Ile Gly His Leu His
        195                 200                 205

Tyr Ala Ser Tyr Asp Pro Leu Phe Tyr Ile His His Ser Gln Thr Asp
    210                 215                 220

Arg Ile Trp Ala Ile Trp Gln Ala Leu Gln Glu His Arg Gly Leu Ser
225                 230                 235                 240

Gly Lys Glu Ala His Cys Ala Leu Glu Gln Met Lys Asp Pro Leu Lys
                245                 250                 255

Pro Phe Ser Phe Gly Ser Pro Tyr Asn Leu Asn Lys Arg Thr Gln Glu
            260                 265                 270

Phe Ser Lys Pro Glu Asp Thr Phe Asp Tyr His Arg Phe Gly Tyr Glu
        275                 280                 285

Tyr Asp Ser Leu Glu Phe Val Gly Met Ser Val Ser Ser Leu His Asn
    290                 295                 300

Tyr Ile Lys Gln Gln Gln Glu Ala Asp Arg Val Phe Ala Gly Phe Leu
305                 310                 315                 320

Leu Lys Gly Phe Gly Gln Ser Ala Ser Val Ser Phe Asp Ile Cys Arg
                325                 330                 335

Pro Asp Gln Ser Cys Gln Glu Ala Gly Tyr Phe Ser Val Leu Gly Gly
            340                 345                 350

Ser Ser Glu Met Pro Trp Gln Phe Asp Arg Leu Tyr Lys Tyr Asp Ile
        355                 360                 365

Thr Lys Thr Leu Lys Asp Met Lys Leu Arg Tyr Asp Asp Thr Phe Thr
    370                 375                 380

Ile Lys Val His Ile Lys Asp Ile Ala Gly Ala Glu Leu Asp Ser Asp
385                 390                 395                 400

Leu Ile Pro Thr Pro Ser Val Leu Leu Glu Glu Gly Lys
                405                 410


<210> SEQ ID NO 78
<211> LENGTH: 417
<212> TYPE: PRT
<213> ORGANISM: Megathura crenulata

<400> SEQUENCE: 78

His Gly Ile Asn Val Arg His Val Gly Arg Asn Arg Ile Arg Met Glu
  1               5                  10                  15

Leu Ser Glu Leu Thr Glu Arg Asp Leu Ala Ser Leu Lys Ser Ala Met
             20                  25                  30

Arg Ser Leu Gln Ala Asp Asp Gly Val Asn Gly Tyr Gln Ala Ile Ala
         35                  40                  45

Ser Phe His Gly Leu Pro Ala Ser Cys His Asp Asp Glu Gly His Glu
     50                  55                  60
```

-continued

```
Ile Ala Cys Cys Ile His Gly Met Pro Val Phe Pro His Trp His Arg
 65                  70                  75                  80

Leu Tyr Thr Leu Gln Met Asp Met Ala Leu Leu Ser His Gly Ser Ala
                 85                  90                  95

Val Ala Ile Pro Tyr Trp Asp Trp Thr Lys Pro Ile Ser Lys Leu Pro
            100                 105                 110

Asp Leu Phe Thr Ser Pro Glu Tyr Tyr Asp Pro Trp Arg Asp Ala Val
        115                 120                 125

Val Asn Asn Pro Phe Ala Lys Gly Tyr Ile Lys Ser Glu Asp Ala Tyr
    130                 135                 140

Thr Val Arg Asp Pro Gln Asp Ile Leu Tyr His Leu Gln Asp Glu Thr
145                 150                 155                 160

Gly Thr Ser Val Leu Leu Asp Gln Thr Leu Leu Ala Leu Glu Gln Thr
                165                 170                 175

Asp Phe Cys Asp Phe Glu Val Gln Phe Glu Val Val His Asn Ala Ile
            180                 185                 190

His Tyr Leu Val Gly Gly Arg Gln Val Tyr Ala Leu Ser Ser Gln His
        195                 200                 205

Tyr Ala Ser Tyr Asp Pro Ala Phe Phe Ile His His Ser Phe Val Asp
    210                 215                 220

Lys Ile Trp Ala Val Trp Gln Ala Leu Gln Lys Lys Arg Lys Arg Pro
225                 230                 235                 240

Tyr His Lys Ala Asp Cys Ala Leu Asn Met Met Thr Lys Pro Met Arg
                245                 250                 255

Pro Phe Ala His Asp Phe Asn His Asn Gly Phe Thr Lys Met His Ala
            260                 265                 270

Val Pro Asn Thr Leu Phe Asp Phe Gln Asp Leu Phe Tyr Thr Tyr Asp
        275                 280                 285

Asn Leu Glu Ile Ala Gly Met Asn Val Asn Gln Leu Glu Ala Glu Ile
    290                 295                 300

Asn Arg Arg Lys Ser Gln Thr Arg Val Phe Ala Gly Phe Leu Leu His
305                 310                 315                 320

Gly Ile Gly Arg Ser Ala Asp Val Arg Phe Trp Ile Cys Lys Thr Ala
                325                 330                 335

Asp Asp Cys His Ala Ser Gly Met Ile Phe Ile Leu Gly Gly Ser Lys
            340                 345                 350

Glu Met His Trp Ala Tyr Asp Arg Asn Phe Lys Tyr Asp Ile Thr Gln
        355                 360                 365

Ala Leu Lys Ala Gln Ser Ile His Pro Glu Asp Val Phe Asp Thr Asp
    370                 375                 380

Ala Pro Phe Phe Ile Lys Val Glu Val His Gly Val Asn Lys Thr Ala
385                 390                 395                 400

Leu Pro Ser Ser Ala Ile Pro Ala Pro Thr Ile Ile Tyr Ser Ala Gly
                405                 410                 415

Glu
```

<210> SEQ ID NO 79
<211> LENGTH: 395
<212> TYPE: PRT
<213> ORGANISM: Megathura crenulata
<220> FEATURE:
<221> NAME/KEY: misc_feature
<222> LOCATION: (55)..(55)
<223> OTHER INFORMATION: “Xaa” is any naturally-occurring amino acid
      residue including Pro, Leu, His and Arg -continued

<400> SEQUENCE: 79

```
Asp His Ile Ala Gly Ser Gly Val Arg Lys Asp Val Thr Ser Leu Thr
  1               5                  10                  15

Ala Ser Glu Ile Glu Asn Leu Arg His Ala Leu Gln Ser Val Met Asp
             20                  25                  30

Asp Asp Gly Pro Asn Gly Phe Gln Ala Ile Ala Ala Tyr His Gly Ser
         35                  40                  45

Pro Pro Met Cys His Met Xaa Asp Gly Arg Asp Val Ala Cys Cys Thr
     50                  55                  60

His Gly Met Ala Ser Phe Pro His Trp His Arg Leu Phe Val Lys Gln
 65                  70                  75                  80

Met Glu Asp Ala Leu Ala Ala His Gly Ala His Ile Gly Ile Pro Tyr
                 85                  90                  95

Trp Asp Trp Thr Ser Ala Phe Ser His Leu Pro Ala Leu Val Thr Asp
            100                 105                 110

His Glu His Asn Pro Phe His His Gly His Ile Ala His Arg Asn Val
        115                 120                 125

Asp Thr Ser Arg Ser Pro Arg Asp Met Leu Phe Asn Asp Pro Glu His
    130                 135                 140

Gly Ser Glu Ser Phe Phe Tyr Arg Gln Val Leu Leu Ala Leu Glu Gln
145                 150                 155                 160

Thr Asp Phe Cys Gln Phe Glu Val Gln Phe Glu Ile Thr His Asn Ala
                165                 170                 175

Ile His Ser Trp Thr Gly Gly His Thr Pro Tyr Gly Met Ser Ser Leu
            180                 185                 190

Glu Tyr Thr Ala Tyr Asp Pro Leu Phe Tyr Leu His His Ser Asn Thr
        195                 200                 205

Asp Arg Ile Trp Ala Ile Trp Gln Ala Leu Gln Lys Tyr Arg Gly Phe
    210                 215                 220

Gln Tyr Asn Ala Ala His Cys Asp Ile Gln Val Leu Lys Gln Pro Leu
225                 230                 235                 240

Lys Pro Phe Ser Glu Ser Arg Asn Pro Asn Pro Val Thr Arg Ala Asn
                245                 250                 255

Ser Arg Ala Val Asp Ser Phe Asp Tyr Glu Arg Leu Asn Tyr Gln Tyr
            260                 265                 270

Asp Thr Leu Thr Phe His Gly His Ser Ile Ser Glu Leu Asp Ala Met
        275                 280                 285

Leu Gln Glu Arg Lys Lys Glu Glu Arg Thr Phe Ala Ala Phe Leu Leu
    290                 295                 300

His Gly Phe Gly Ala Ser Ala Asp Val Ser Phe Asp Val Cys Thr Pro
305                 310                 315                 320

Asp Gly His Cys Ala Phe Ala Gly Thr Phe Ala Val Leu Gly Gly Glu
                325                 330                 335

Leu Glu Met Pro Trp Ser Phe Glu Arg Leu Phe Arg Tyr Asp Ile Thr
            340                 345                 350

Lys Val Leu Lys Gln Met Asn Leu His Tyr Asp Ser Glu Phe His Phe
        355                 360                 365

Glu Leu Lys Ile Val Gly Thr Asp Gly Thr Glu Leu Pro Ser Asp Arg
    370                 375                 380

Ile Lys Ser Pro Thr Ile Glu His His Gly Gly
385                 390                 395
```

-continued

<210> SEQ ID NO 80
<211> LENGTH: 1266
<212> TYPE: DNA
<213> ORGANISM: Haliotis tuberculata

<400> SEQUENCE: 80

```
cttgttcagt ttctactcgt cgcccttgtg gtgggggctg gagcagacaa cgtcgtcaga     60
aaggacgtga gtcacctcac ggatgacgag gtgcaagctc tccacggcgc cctccatgac    120
gtcactgcat ctacagggcc tctgagtttc gaagacataa catcttacca tgccgcacca    180
gcgtcgtgtg actacaaggg acggaagatc gcctgctgtg tccacggtat gcccagtttc    240
cccttctggc acagggcata tgtcgtccaa gccgagcggg cactgttgtc caaacggaag    300
actgtcggaa tgccttactg ggactggacg caaacgctga ctcacttacc atctcttgtg    360
actgaaccca tctacattga cagtaaaggt ggaaaggctc aaaccaacta ctggtaccgc    420
ggcgagatag cgttcatcaa taagaagact gcgcgagctg tagatgatcg cctattcgag    480
aaggtggagc ctggtcacta cacacatctt atggagactg tcctcgacgc tctcgaacag    540
gacgaattct gtaaatttga aatccagttc gagttggctc ataatgctat ccattacttg    600
gttggcggta aatttgaata ttcaatgtca aacttggaat acacctccta cgaccccatc    660
ttcttcctcc accactccaa cgttgaccgc ctcttcgcca tctggcagcg tcttcaggaa    720
ctgcgaggaa agaatcccaa tgcaatggac tgtgcacatg aactcgctca ccagcaactc    780
caacccttca acagggacag caatccagtc cagctcacaa aggaccactc gacacctgct    840
gacctctttg attacaaaca acttggatac agctacgaca gcttaaacct gaatggaatg    900
acgccagaac agctgaaaac agaactagac gaacgccact ccaaagaacg tgcgtttgca    960
agcttccgac tcagtggctt tggggggttct gccaacgttg ttgtctatgc atgtgtccct   1020
gatgatgatc cacgcagtga tgactactgc gagaaagcag gcgacttctt cattcttggg   1080
ggtcaaagcg aaatgccgtg gagattctac agacccttct tctatgatgt aactgaagcg   1140
gtacatcacc ttggagtccc gctaagtggc cactactatg tgaaaacaga actcttcagc   1200
gtgaatggca cagcactttc acctgatctt cttcctcaac caactgttgc ctaccgacct   1260
gggaaa                                                               1266
```

<210> SEQ ID NO 81
<211> LENGTH: 1257
<212> TYPE: DNA
<213> ORGANISM: Haliotis tuberculata

<400> SEQUENCE: 81

```
ggtcaccttg acccacctgt gcatcatcgc cacgatgacg atcttattgt tcgaaaaaat     60
atagatcatt tgactcgtga agaggaatac gagctaagga tggctctgga gagattccag    120
gccgacacat ccgttgatgg gtaccaggct acagtagagt accatggcct tcctgctcgt    180
tgtccacgac cagatgcaaa agtcaggttc gcctgttgta tgcatggcat ggcatccttc    240
cctcactggc accggctgtt cgttacccag gtggaagatg ctcttgtacg gcgtggatcg    300
cctatcggtg ttccttattg ggactggaca aaacctatga ctcaccttcc agacttggca    360
tcaaatgaga cgtacgtaga cccgtatgga catacacatc ataatccatt cttcaatgca    420
aatatatctt ttgaggaggg acaccatcac acgagcagga tgatagattc gaaactgttt    480
gccccagtcg cttttgggga gcattcccat ctgtttgatg gaatcctgta cgcatttgag    540
caggaagatt tctgcgactt tgagattcag tttgagttag tccataattc tattcatgcg    600
```

-continued

```
tggataggcg gttccgaaga ttactccatg gccaccctgc attacacagc ctttgacccc    660

attttctacc ttcatcattc caatgtcgat cgtctatggg caatctggca agctcttcaa    720

atcaggagac acaagccata tcaagcccac tgtgcacagt ctgtggaaca gttgccaatg    780

aagccatttg ctttcccatc acctcttaac aacaacgaga agacacatag tcattcagtc    840

ccgactgaca tttatgacta cgaggaagtg ctgcactaca gctacgatga tctaacgttt    900

ggtgggatga accttgaaga aatagaagaa gctatacatc tcagacaaca gcatgaacga    960

gtcttcgcgg gatttctcct tgctggaata ggaacatctg cacttgttga cattttcata   1020

aataaaccgg ggaaccaacc actcaaagct ggagatattg ccattcttgg tggtgccaag   1080

gaaatgcctt gggcgtttga ccgcttgtat aaggtcgaaa taactgactc attgaagaca   1140

ctttctctcg atgtcgatgg agattatgaa gtcactttta aaattcatga tatgcacgga   1200

aacgctcttg atacggacct gattccacac gcagcagttg tttctgagcc agctcac      1257
```

<210> SEQ ID NO 82
<211> LENGTH: 1242
<212> TYPE: DNA
<213> ORGANISM: Haliotis tuberculata

<400> SEQUENCE: 82

```
cctacctttg aggatgaaaa gcacagctta cgaatcagaa aaaatgtcga cagcttgact     60

cctgaagaaa caaatgaact gcgtaaagcc ctggagcttc ttgaaaatga tcatactgca    120

ggtggattca atcagcttgg cgccttccat ggagagccta aatggtgccc taatcctgaa    180

gcggagcaca aggttgcatg ctgtgttcat ggcatggctg ttttccctca ttggcacagg    240

cttcttgctc tccaggcgga gaatgctctt agaaagcatg ggtacagtgg tgctctacca    300

tactgggatt ggactcgccc cctttcccaa cttcctgatc tggttagtca tgagcagtat    360

acagatcctt ccgaccatca cgtgaagcat aacccgtggt tcaatggcca catcgataca    420

gtaaatcagg ataccaccag aagcgtacgg gaggatcttt atcaacaacc tgaatttgga    480

catttcacgg atattgctca acaagtcctc ttagcattag aacaagatga cttctgttcg    540

tttgaagtgc agtatgagat ttcccataat tttatccatg cacttgtagg aggaaccgac    600

gcttatggca tggcatcgct gagatataca gcatacgatc caatcttttt cttgcatcat    660

tcaaacaccg acaggatctg ggctatttgg caatccctgc aaaaatacag aggcaaaccg    720

tacaacactg ccaactgcgc catagaatct atgagaaggc ccctgcaacc atttggacta    780

agcagtgcca ttaaccctga cagaatcacc agagagcatg ctatcccgtt tgatgtcttc    840

aactatagag ataaccttca ttacgtatat gataccctgg aatttaatgg tttgtcgatt    900

tcacaacttg atagagagct ggaaaaaatc aagagtcacg aaagagtatt tgctggattc    960

ttgctgtcgg ggattaaaaa atctgctctt gtgaaattcg aagtttgtac tccacctgat   1020

aattgtcata aagcagggga gttttatcta ctcggggacg aaaacgagat ggcttgggcc   1080

tatgaccgac ttttcaagta tgatattact caggttctgg aagcaaacca tctacacttc   1140

tatgatcatc tcttcattcg ctacgaagtc tttgatctta aaggagtgag tttgggaact   1200

gacctgttcc acactgcaaa tgtggtacat gattccggca ca                      1242
```

<210> SEQ ID NO 83
<211> LENGTH: 1239
<212> TYPE: DNA
<213> ORGANISM: Haliotis tuberculata -continued

<400> SEQUENCE: 83

```
ggcacccgtg atcgtgataa ctacgttgaa gaagttactg gggccagtca tatcaggaag      60
aatttgaacg acctcaatac cggagaaatg gaaagcctta gagctgcttt cctgcatatt     120
caggacgacg gaacatatga atctattgcc cagtaccatg gcaaaccagg caaatgtcaa     180
ttgaatgatc ataatattgc gtgttgtgtc catggtatgc ctaccttccc ccagtggcac     240
agactgtatg tggttcaggt ggagaatgct ctcctaaaca ggggatctgg tgtggctgtt     300
ccttactggg agtggactgc tcccatagac catctacctc atttcattga tgatgcaaca     360
tacttcaatt cccgacaaca gcggtacgac cctaaccctt tcttcagggg aaaggttact     420
tttgaaaacg cagtcacaac aagggaccca caagccgggc tcttcaactc agattatatg     480
tatgagaatg ttttacttgc actggagcag gaaaattatt gtgactttga aattcagttt     540
gagcttgttc ataacgcact tcattccatg ctgggaggta aagggcagta ctccatgtcc     600
tccctggact attctgcgtt tgatcccgtc ttcttcctac atcatgccaa cacggacaga     660
ctgtgggcaa tctggcagga actacaaaga ttccgagaac tgccttatga agaagcgaac     720
tgtgcaatca acctcatgca tcaaccactg aagccgttca gtgatccaca tgagaatcac     780
gacaatgtca ctttgaaata ctcaaaacca caggacggat tcgactacca gaaccacttc     840
ggatacaagt atgacaacct tgagttccat cacttatcta tcccaagtct tgatgctacc     900
ctgaagcaaa ggagaaatca cgacagagtg tttgcgggct tccttcttca taacatagga     960
acttctgctg acataactat ctacatatgt ctgcctgacg gacggcgtgg caatgactgc    1020
agtcatgagg cgggaacatt ctatatcctc ggaggcgaaa cagagatgcc ttttatcttt    1080
gaccgtttgt ataaatttga aatcaccaaa ccactgcaac agttaggagt caagctgcat    1140
ggtggagttt tcgaactgga gcttgagatc aaggcataca acggttccta tctggatccc    1200
catacctttg atccaactat catctttgaa cctggaaca                           1239
```

<210> SEQ ID NO 84
<211> LENGTH: 1260
<212> TYPE: DNA
<213> ORGANISM: Haliotis tuberculata

<400> SEQUENCE: 84

```
gatacccata tcttggacca cgaccatgag gaagagatac ttgtcaggaa gaatataatt      60
gatttgagcc caagggagag ggtttctcta gtcaaagctt tgcaaagaat gaagaatgat     120
cgctccgctg atgggtacca agccattgcc tctttccatg ccctgccacc actctgtccc     180
aatccatctg cagctcaccg ttatgcttgc tgtgtccatg gcatggctac atttccccag     240
tggcacagac tgtacactgt tcaggttcag gatgccctga ggagacatgg ttcacttgtt     300
ggtattcctt actgggactg gacaaaacca gtcaacgagt tacccgagct tctttcttca     360
gcaacatttt atcatccaat ccggaatatt aatatttcaa atccattcct cggggctgac     420
atagaatttg aaggaccggg cgttcataca gagaggcaca taaatactga gcgcctgttt     480
cacagtgggg atcatgacgg ataccacaac tggttcttcg aaactgttct ctttgctttg     540
gaacaggaag attactgcga ttttgaaata caatttgaga tagcccataa tggcatccac     600
acatggattg gtggaagcgc agtatatggc atgggacacc ttcactatgc atcatatgat     660
ccaattttct acatccacca ttcacagacg gacagaatat gggctatttg gcaagagctg     720
cagaagtaca ggggtctatc tggttcggaa gcaaactgtg ccattgaaca tatgagaaca     780
cccttgaagc ctttcagctt tggcccaccc tacaatttga atagtcatac gcaagaatat     840
```

-continued

```
tcaaagcctg aggacacgtt tgactataag aagtttggat acagatatga tagtctggaa    900

ttggaggggc gatcaatttc tcgcattgat gaacttatcc agcagagaca ggagaaagac    960

agaacttttg cagggttcct ccttaaaggt tttggtacat ccgcatctgt gtcattgcaa   1020

gtttgcagag ttgatcacac ctgtaaagat gcgggctatt tcactattct gggaggatca   1080

gccgaaatgc catgggcatt cgacaggctt tataagtatg acattactaa aactcttcac   1140

gacatgaacc tgaggcacga ggacactttc tctatagacg taactatcac gtcttacaat   1200

ggaacagtac tctcgggaga cctcattcag acgccctcca ttatatttgt acctggacgc   1260
```

<210> SEQ ID NO 85
<211> LENGTH: 1251
<212> TYPE: DNA
<213> ORGANISM: Haliotis tuberculata

<400> SEQUENCE: 85

```
cataaactca actcacggaa acatacacct aacagagtcc gccatgagct aagtagcctt     60

agttcccgtg acatagcaag cttgaaggca gctttgacaa gccttcaaca tgataatggg    120

actgatggtt atcaagctat tgctgccttc catggcgttc ctgcgcagtg ccacgagcca    180

tctggacgtg agatcgcctg ttgcatccac ggcatggcga cgtttcctca ctggcaccgg    240

ttgtacactc tgcagttgga gcaagcgctg cgcagacacg ggtccagtgt tgctgttcca    300

tactgggact ggaccaagcc aatcaccgaa ctgccacaca ttctgacaga cggagaatat    360

tatgacgttt ggcaaaatgc cgtcttggcc aatccgtttg caagaggtta tgtgaaaatt    420

aaagatgcat ttacggtgag aaatgtccag gaaagtctgt tcaaaatgtc aagttttgga    480

aagcactcgc ttctgtttga ccaggctttg ttggctcttg aacaaactga ctactgtgac    540

ttcgaagttc agtttgaagt gatgcataac acgatccatt atctcgtagg agggcgtcaa    600

acgtacgcct tctcctctct cgagtattcc tcatacgatc caatcttctt tattcaccac    660

tcgtttgttg acaaaatatg ggctgtatgg caagaactgc aaagcaggag acatctacag    720

tttagaacag ctgattgtgc tgtgggcctc atgggtcagg caatgaggcc tttcaacaag    780

gatttcaacc acaactcgtt caccaagaag cacgcagtcc ctaatacagt atttgattat    840

gaagatcttg gctataacta tgacaacctt gaaatcagtg gtttaaactt aaatgagatc    900

gaggcgttaa tagcaaaacg caagtcacat gctagagtct ttgctgggtt cctgttgttt    960

ggattaggaa cttcggctga tatacatctg gaaatttgca agacatcgga aaactgccat   1020

gatgctggtg tgattttcat ccttggaggt tctgcagaga tgcattgggc atacaaccgc   1080

ctctacaagt atgacattac agaagcattg caggaatttg acatcaaccc tgaagatgtt   1140

ttccatgctg atgaaccatt tttcctgagg ctgtcggttg ttgctgtgaa tggaactgtc   1200

attccatcgt ctcatcttca ccagccaacg ataatctatg aaccaggcga a             1251
```

<210> SEQ ID NO 86
<211> LENGTH: 1209
<212> TYPE: DNA
<213> ORGANISM: Haliotis tuberculata

<400> SEQUENCE: 86

```
gatcaccatg acgaccatca gtcgggaagc atagcaggat ccggggtccg caaggacgtg     60

aacaccttga ctaaggctga gaccgacaac ctgagggagg cgctgtgggg tgtcatggca    120

gaccacggtc ccaatggctt tcaagctatt gctgctttcc atggaaaacc agctttgtgt    180

cccatgcctg atggccacaa ctactcatgt tgtactcacg gcatggctac cttcccacac    240
```

-continued

```
tggcatcgcc tctacaccaa gcagatggag gatgcaatga gggcgcatgg gtctcatgtc    300
ggcctgccct actgggactg gactgctgcc ttcacccacc tgccaacact ggtcaccgac    360
acggacaaca accccttcca acatggacac attgattatc tcaatgtcag cacaactcga    420
tctccccgag acatgctgtt caacgacccc gagcatggat cagagtcgtt cttctacaga    480
caagtcctct tagctctgga acaaactgat ttctgcaaat tcgaagttca gtttgagata    540
acccacaatg ccatccattc ctggacaggt ggccacagcc cctacggaat gtccactctc    600
gacttcactg cctacgatcc tctcttctgg cttcaccact ccaacaccga cagaatctgg    660
gctgtctggc aagctttgca agaatacaga ggacttccat acaaccatgc caattgtgag    720
atccaggcaa tgaaaacgcc cctgaggcct ttcagtgacg atatcaacca caacccagtc    780
acaaaggcta acgcgaagcc attagatgtg ttcgagtata atcggttgag cttccagtac    840
gacaacctca tcttccatgg atacagtatt ccggaacttg atcgcgtgct tgaagaaaga    900
aaggaggagg acagaatatt tgctgccttc cttctcagtg gaatcaagcg tagtgctgat    960
gtagtgttcg acatatgcca gccagaacac gaatgtgtgt tcgcagggac ttttgcgatt   1020
ttgggagggg agctagaaat gccctggtcc ttcgacagac tgttccgcta tgatatcacc   1080
aaggtgatga agcagctaca cctgaggcat gactctgact ttaccttcag ggtgaagatt   1140
gtcggcaccg acgaccacga gcttccttca gacagtgtca aagcaccaac tattgaattt   1200
gaaccgggc                                                           1209
```

<210> SEQ ID NO 87
<211> LENGTH: 1536
<212> TYPE: DNA
<213> ORGANISM: Haliotis tuberculata

<400> SEQUENCE: 87

```
gtgcacagag gcggaaacca cgaagatgaa caccatgatg acagactcgc agatgtcctg     60
atcaggaaag aagttgactt cctctccctg caagaggcca acgcaattaa ggatgcactg    120
tacaagctcc agaatgacga cagtaaaggg ggctttgagg ccatagctgg ctatcacggg    180
tatcctaata tgtgtccaga aagaggtacc gacaagtatc cctgctgtgt ccacggaatg    240
cccgtgttcc cccactggca ccgcctgcat accattcaga tggagagagc tctgaaaaac    300
catggctctc caatgggcat tccttactgg gattggacaa agaagatgtc gagtcttcca    360
tctttctttg gagattccag caacaacaac cctttctaca aatattacat ccggggcgtg    420
cagcacgaaa caaccaggga cattaatcag agactcttta atcaaaccaa gtttggtgaa    480
tttgattacc tatattacct aactctgcaa gtcctggagg aaaactcgta ctgtgacttt    540
gaagttcagt atgagatcct ccataacgcc gtccactcct ggcttggagg aactggaaag    600
tattccatgt ctaccctgga gcattcggcc tttgaccctg tcttcatgat tcaccactcg    660
agtttggata gaatctggat cctttggcag aagttgcaaa agataagaat gaagccttac    720
tacgcattgg attgtgctgg cgacagactt atgaaagacc ccctgcatcc cttcaactac    780
gaaaccgtta atgaagatga attcacccgc atcaactctt tcccaagcat actgtttgac    840
cactacaggt tcaactatga atacgataac atgagaatca ggggtcagga catacatgaa    900
cttgaagagg taattcagga attaagaaac aaagatcgca tatttgctgg ttttgttttg    960
tcgggcttac ggatatcagc tacagtgaaa gtattcattc attcgaaaaa cgatacaagt   1020
cacgaagaat atgcaggaga atttgcagtt ttgggaggtg agaaggagat gccgtgggca   1080
tatgaaagaa tgctgaaatt ggacatctcc gatgctgtac acaagcttca cgtgaaagat   1140
```

-continued

```
gaagacatcc gttttagagt ggttgttact gcctacaacg gtgacgttgt taccaccagg   1200

ctgtctcagc cattcatcgt ccaccgtcca gcccatgtgg ctcacgacat cttggtaatc   1260

ccagtaggtg cgggccatga ccttccgcct aaagtcgtag taaagagcgg caccaaagtc   1320

gagtttacac caatagattc gtcggtgaac aaagcaatgg tggagctggg cagctatact   1380

gctatggcta aatgcatcgt tccccctttc tcttaccacg gctttgaact ggacaaagtc   1440

tacagcgtcg atcacggaga ctactacatt gctgcaggta cccacgcgtt gtgtgagcag   1500

aacctcaggc tccacatcca cgtggaacac gagtag                             1536
```

<210> SEQ ID NO 88
<211> LENGTH: 591
<212> TYPE: DNA
<213> ORGANISM: Haliotis tuberculata

<400> SEQUENCE: 88

```
ggtcttccgt actgggactg gacgcagcat ctgactcaac tcccagatct ggtgtcagac     60

cccttgtttg tcgacccgga aggaggaaag gcccatgaca acgcatggta tcgtggaaac    120

atcaagtttg agaataagaa gactgcaaga gctgttgacg atcgcctttt cgagaaggtt    180

ggaccaggag agaatacccg actctttgaa ggaattctcg atgctcttga acaggatgaa    240

ttctgcaact tcgagatcca gtttgagttg gctcacaacg ctatccacta cctggttggc    300

ggccgtcaca cgtactccat gtctcatctc gagtacacct cctacgaccc cctcttcttc    360

ctccatcact ccaacccgga ccgcatcttc gccatctggg aacgtcttca ggtactcaga    420

ggaaaggacc ccaacaccgc cgactgcgca cacaacctca tccatgagcc catggaaccg    480

ttccgtcggc atgagcccat ggaaccgttc cgtcgggact cgaaccctct tgacctcacc    540

agggaaaact ccaaaccaat tgacagcttt gattatgccc accttggcta c             591
```

<210> SEQ ID NO 89
<211> LENGTH: 1245
<212> TYPE: DNA
<213> ORGANISM: Haliotis tuberculata

<400> SEQUENCE: 89

```
gttacagagg ccccagctcc ctcctcggat gctcacctcg ccgtcaggaa ggatatcaac     60

catctgacac gcgaggaggt gtacgagctg cgcagagcta tggagagatt ccaggccgac    120

acatccgttg atgggtacca ggctacggtt gagtatcacg gcttacctgc tcgatgtcca    180

ttccccgagg ccacaaatag gttcgcctgt tgcatccacg gcatggcgac attccctcat    240

tggcacagac tgttcgtcac ccaggtggaa gatgctctga tcaggcgagg atcgcctata    300

ggggtcccct actgggactg gactcagcct atggcgcatc tcccaggact tgcagacaac    360

gccacctata gagatcccat cagcggggac agcagacaca accccttcca cgatgttgaa    420

gttgcctttg aaaatggacg tacagaacgt cacccagata gtagattgtt tgaacaacct    480

ttatttggca aacatacgcg tctcttcgac agtatagtct atgcttttga gcaggaggac    540

ttctgcgatt ttgaagttca atttgagatg acccataata atattcacgc ctggattggt    600

ggcggcgaga agtattccat gtcttctcta cactacacag ccttcgaccc tatcttctac    660

cttcgtcact ccaacactga ccggctctgg gcaatttggc aagcgttgca gatacgaaga    720

aacaggcctt acaaggctca ttgtgcttgg tctgaggaac gccagcctct caaacctttc    780

gccttcagtt ccccactgaa caacaacgaa aaaacctacg aaaactcggt gcccaccaac    840

gtttacgact acgaaggagt ccttggctat acttatgatg acctcaactt cgggggcatg    900
```

-continued

```
gacctgggtc agcttgagga atacatccag aggcagagac agagagacag gacctttgct    960

ggtttctttc tgtcacatat tggtacatca gcgaatgttg aaatcattat agaccatggg   1020

actcttcata cctccgtggg cacgtttgct gttcttggcg gagagaagga gatgaaatgg   1080

ggatttgacc gtttgtacaa atatgagatt acagatgaac tgaggcaact taatctccgt   1140

gctgatgatg ttttcagcat ctctgttaaa gtaactgatg ttgatggcag tgagctgtcc   1200

tctgaactca tcccatctgc tgctatcatc ttcgaacgaa gccat                    1245
```

<210> SEQ ID NO 90
<211> LENGTH: 1251
<212> TYPE: DNA
<213> ORGANISM: Haliotis tuberculata

<400> SEQUENCE: 90

```
attgaccatc aggacccgca tcatgacaca atcattagga aaaatgttga taatcttaca     60

cccgaggaaa ttaattctct gaggcgggca atggcagacc ttcaatcaga caaaaccgcc    120

ggtggattcc agcaaattgc tgcttttcac ggggaaccca aatggtgccc aagtcccgat    180

gctgagaaga agttctcctg ctgtgtccat ggaatggctg tcttccctca ctggcacaga    240

ctcctgaccg tgcaaggcga gaatgccctg agaaagcatg gatgtctcgg agctctcccc    300

tactgggact ggactcggcc cctgtctcac ctacctgatt tggttttggt aagtagcaga    360

actacaccga tgccatattc caccgtggaa gcccgaaacc cctggtacag cggccatatt    420

gatacagttg gtgttgacac aacaagaagc gtccgtcaag aactgtatga agctcctgga    480

tttggccatt atactggggt cgctaagcaa gtgcttctgg ctttggagca ggatgacttc    540

tgtgattttg aagtccagtt tgagatagct cacaatttca ttcacgctct tgtcggcgga    600

agcgagccat atggtatggc gtcactccgt tacactactt atgatccaat tttctacctc    660

catcattcta acactgacag actctgggct atatggcagg ctctacaaaa gtacaggggc    720

aaaccttaca attccgccaa ctgcgccatt gcttctatga gaaaacccct acaacccttt    780

ggtctgactg atgagatcaa cccggatgat gagacaagac agcatgctgt tcctttcagt    840

gtctttgatt acaagaacaa cttcaattat gaatatgaca cccttgactt caacggacta    900

tcaatctccc agctggaccg tgaactgtca cggagaaagt ctcatgacag agtatttgcc    960

ggatttttgc tgcatggtat tcagcagtct gcactagtta aattctttgt ctgcaaatca   1020

gatgatgact gtgaccacta tgctggtgaa ttctacatcc ttggtgatga agctgaaatg   1080

ccatggggct atgatcgtct ttacaaatat gagatcactg agcagctcaa tgccctggat   1140

ctacacatcg gagatagatt cttcatcaga tacgaagcgt ttgatcttca tggtacaagt   1200

cttggaagca acatcttccc caaaccttct gtcatacatg acgaaggggc a             1251
```

<210> SEQ ID NO 91
<211> LENGTH: 1242
<212> TYPE: DNA
<213> ORGANISM: Haliotis tuberculata

<400> SEQUENCE: 91

```
ggtcaccatc aggctgacga gtacgacgaa gttgtaactg ctgcaagcca catcagaaag     60

aatttaaaag atctgtcaaa gggagaagta gagagcctaa ggtctgcctt cctgcaactt    120

cagaacgacg gagtctatga gaatattgcc aagttccacg gcaagcctgg gttgtgtgat    180

gataacggtc gcaaggttgc ctgttgtgtc catggaatgc ccaccttccc ccagtggcac    240

aggctctatg tcctccaggt ggagaatgct ttgctggaga gaggatctgc cgtctctgtg    300
```

-continued

```
ccatactggg actggactga aacatttaca gagctgccat ctttgattgc tgaggctacc    360

tatttcaatt cccgtcaaca aacgtttgac cctaatcctt tcttcagagg taaaatcagt    420

tttgagaatg ctgttacaac acgtgatccc cagcctgagc tgtacgttaa caggtactac    480

taccaaaacg tcatgttggt ttttgaacag gacaactact gcgacttcga gatacagttt    540

gagatggttc acaatgttct ccatgcttgg cttggtggaa gagctactta ttctatttct    600

tctcttgatt attctgcatt cgaccctgtg tttttccttc accatgcgaa cacagataga    660

ttgtgggcca tctggcagga gctgcagagg tacaggaaga agccatacaa tgaagcggat    720

tgtgccatta acctaatgcg caaacctcta catcccttcg acaacagtga tctcaatcat    780

gatcctgtaa cctttaaata ctcaaaaccc actgatggct ttgactacca gaacaacttt    840

ggatacaagt atgacaacct tgagttcaat catttcagta ttcccaggct tgaagaaatc    900

attcgtatta gacaacgtca agatcgtgtg tttgcaggat tcctccttca caacattggg    960

acatccgcaa ctgttgagat attcgtctgt gtccctacca ccagcggtga gcaaaactgt   1020

gaaaacaaag ccggaacatt tgccgtactc ggaggagaaa cagagatggc gtttcatttt   1080

gacagactct acaggtttga catcagtgaa acactgaggg acctcggcat acagctggac   1140

agccatgact ttgacctcag catcaagatt caaggagtaa atggatccta ccttgatcca   1200

cacatcctgc cagagccatc cttgattttt gtgcctggtt ca                      1242
```

```
<210> SEQ ID NO 92
<211> LENGTH: 1257
<212> TYPE: DNA
<213> ORGANISM: Haliotis tuberculata

<400> SEQUENCE: 92

agttctttcc tgcgtcctga tgggcattca gatgacatcc ttgtgagaaa agaagtgaac     60

agcctgacaa ccagggagac tgcatctctg atccatgctc tgaaaagtat gcaggaagac    120

cattcacctg acgggttcca agccattgcc tctttccatg ctctgccacc actctgccct    180

tcaccatctg cagctcaccg ttatgcttgc tgtgtccacg gcatggctac atttccccag    240

tggcacagat tgtacactgt acagttccag gatgcactga ggagacatgg agctacggta    300

ggtgtaccgt attgggattg gctgcgaccg cagtctcacc taccagagct tgtcaccatg    360

gagacatacc atgatatttg gagtaacaga gatttcccca atcctttcta ccaagccaat    420

attgagtttg aaggagaaaa cattacaaca gagagagaag tcattgcaga caaacttttt    480

gtcaaaggtg gacacgtttt tgataaactg gttcttcaaa caagccatcc tagcgctgag    540

caggaaaact actgtgactt tgagattcag tttgaaattc ttcacaacgg cgttcacacg    600

tgggtcggag gcagtcgtac ctactctatc ggacatcttc attacgcatt ctacgaccct    660

cttttctacc ttcaccattt ccagacagac cgtatttggg caatctggca agaactccag    720

gaacagagag ggctctcggg tgatgaggct cactgtgctc tcgagcaaat gagagaacca    780

ttgaagcctt tcagcttcgg cgctccttat aactggaatc agctcacaca ggatttctcc    840

cgacccgagg acaccttcga ctacaggaag tttggttatg aatatgacaa tttagaattc    900

ctgggaatgt cagttgctga actggatcaa tacattattg aacatcaaga aaatgataga    960

gtattcgctg ggttcctgtt gagtggattc ggaggttccg catcagttaa tttccaggtt   1020

tgtagagctg attccacatg tcaggatgct gggtacttca ccgttcttgg tggcagtgct   1080

gagatggcgt gggcatttga caggctttac aaatatgaca ttactgaaac tctggagaaa   1140
```

-continued atgcaccttc gatatgatga tgacttcaca atctctgtca gtctgaccgc caacaacgga 1200
actgtcctga gcagcagtct aatcccaaca ccgagtgtca tattccagcg gggacat 1257

<210> SEQ ID NO 93
<211> LENGTH: 1248
<212> TYPE: DNA
<213> ORGANISM: Haliotis tuberculata

<400> SEQUENCE: 93
cgtgacataa ataccaggag catgtcaccg aaccgtgttc gccgtgagct gagcgatctg 60
tctgcgaggg acctgtctag tctcaagtct gctctgcgag acctacagga ggatgatggc 120
cccaacggat accaggctct tgcagccttc catgggctac cagcaggctg ccatgatagc 180
cggggaaatg agatcgcatg ttgcattcac gggatgccga ccttccccca gtggcacaga 240
ctgtacaccc tgcagttgga gatggctctg aggagacatg gatcatctgt cgccatcccc 300
tactgggact ggacaaagcc tatctccgaa ctcccctcgc tcttcaccag ccctgagtat 360
tatgacccat ggcatgatgc tgtggtaaac aacccattct ccaaaggttt tgtcaaattt 420
gcaaatacct acacagtaag agacccacag gagatgctgt tccagctttg tgaacatgga 480
gagtcaatcc tctatgagca aactcttctt gctcttgagc aaaccgacta ctgtgatttt 540
gaggtacagt ttgaggtcct ccataacgtg atccactacc ttgttggtgg acgtcagacc 600
tacgcattgt cttctctgca ttatgcctcc tacgacccat tcttctttat acaccattcc 660
tttgtggata agatgtgggt agtatggcaa gctcttcaaa agaggaggaa acttccatac 720
aagcgagctg actgtgctgt caacctaatg actaaaccaa tgaggccatt tgactccgat 780
atgaatcaga acccattcac aaagatgcac gcagttccca acacactcta tgactacgag 840
acactgtact acagctacga taatctcgaa ataggtggca ggaatctcga ccagcttcag 900
gctgaaattg acagaagcag aagccacgat cgcgtttttg ctggattctt gcttcgtgga 960
atcggaactt ctgctgatgt caggttttgg atttgtagaa atgaaaatga ctgccacagg 1020
ggtggaataa ttttcatctt aggtggagcc aaggaaatgc catggtcatt tgacagaaac 1080
ttcaagtttg atatcaccca tgtactcgag aatgctggca ttagcccaga ggacgtgttt 1140
gatgctgagg agccatttta tatcaaggtt gagatccatg ctgttaacaa gaccatgata 1200
ccgtcgtctg tgatcccagc cccaactatc atctattctc ctggggaa 1248

<210> SEQ ID NO 94
<211> LENGTH: 1206
<212> TYPE: DNA
<213> ORGANISM: Haliotis tuberculata

<400> SEQUENCE: 94
ggtcgcgctg ctgacagtgc gcactctgcc aacattgctg gctctggggt gaggaaggac 60
gtcacgaccc tcactgtgtc tgagaccgag aacctaagac aggctcttca aggtgtcatc 120
gatgatactg gtcccaatgg ttaccaagca atagcatcct tccacggaag tcctccaatg 180
tgcgagatga acggccgcaa ggttgcctgt tgtgctcacg gtatggcctc cttcccacac 240
tggcacagac tgtatgtgaa gcagatggaa gatgccctgg ctgaccacgg gtcacatatc 300
ggcatccctt actgggactg gacaactgcc ttcacagagt tacccgccct tgtcacagac 360
tccgagaaca atcccttcca tgagggtcgc attgatcatc tcggtgtaac cacgtcacgt 420
tcccccagag acatgctgtt taacgaccca gagcaaggat cagagtcgtt cttctataga 480
caagtcctcc tggctttgga gcagactgac tactgccagt tcgaagtcca gtttgagctg 540

-continued

```
acccacaacg ccattcactc ctggacaggt ggacgtagcc cttacggaat gtcgaccctc    600

gagttcacag cctacgatcc tctcttctgg cttcaccact ccaacaccga cagaatctgg    660

gctgtctggc aagcactgca gaaataccga ggactcccat acaacgaagc acactgtgaa    720

atccaggttc tgaaacagcc cttgaggcca ttcaacgatg acatcaacca caatccaatc    780

accaagacta atgccaggcc tatcgattca tttgattatg agaggtttaa ctatcagtat    840

gacaccctta gcttccatgg taagagcatc cctgaactga atgacctgct cgaggaaaga    900

aaaagagaag agagaacatt tgctgccttc cttcttcgtg gaatcggttg cagtgctgat    960

gtcgtctttg acatctgccg gcccaatggt gactgtgtct ttgcaggaac ctttgctgtg   1020

ctgggagggg agctagaaat gccttggtcc ttcgacagac tgttccgcta tgacatcacc   1080

agagtcatga atcagctcca tctccagtat gattcagatt tcagtttcag ggtgaagctt   1140

gttgccacca atggcactga gctttcatca gaccttctca agtcaccaac aattgaacat   1200

gaactt                                                              1206
```

```
<210> SEQ ID NO 95
<211> LENGTH: 1548
<212> TYPE: DNA
<213> ORGANISM: Haliotis tuberculata
<220> FEATURE:
<221> NAME/KEY: misc_feature
<222> LOCATION: (1275)..(1275)
<223> OTHER INFORMATION: "n" is a, g, c, or t, including c or t

<400> SEQUENCE: 95

ggagcccaca gaggaccagt tgaagaaaca gaagtcactc gccaacatac tgacggcaat     60

gcacactttc atcgtaagga agttgattcg ctgtccctgg atgaagcaaa caacttgaag    120

aatgcccttt acaagctaca gaacgaccac agtctaacgg gatacgaagc aatctctggt    180

taccatggat accccaatct gtgtccggaa gaaggcgatg acaaaatacc cctgctgcgt    240

ccccggatgg gcatctttcc ttactggcac agactcttga ccattcaact ggaaagagct    300

cttgagcaca atggtgcact gcttggtgtt ccttactggg actggaacaa ggacctgtcg    360

tcactgccgg cgttcttctc cgactccagc aacaacaatc cctacttcaa gtaccacatc    420

gccggtgttg gtcacgacac cgtcagagag ccaactagtc ttatatataa ccagccccaa    480

atccatggtt atgattatct ctattaccta gcattgacca cgcttgaaga aaacaattac    540

tgggactttg aggttcagta tgagatcctc cacaacgccg tccactcctg gcttggagga    600

tcccagaagt attccatgtc taccctggag tattcggcct ttgaccctgt ctttatgatc    660

cttcactcgg gtctagacag actttggatc atctggcaag aacttcagaa gatcaggaga    720

aagccctaca acttcgctaa atgtgcttat catatgatgg aagagccact ggcgcccttc    780

agctatccat ctatcaacca ggacgagttc acccgtgcca actccaagcc ttctacagtt    840

tttgacagcc ataagttcgg ctaccattac gataacctga atgttagagg tcacagcatc    900

caagaactca acacaatcat caatgacttg agaaacacag acagaatcta cgcaggattt    960

gttttgtcag gcatcggtac gtctgctagt gtcaagatct atctccgaac agatgacaat   1020

gacgaagaag ttggaacttt cactgtcctg ggaggagaga gggaaatgcc atgggcctac   1080

gagcgagttt tcaagtatga catcacagag gttgcagata gacttaaaat taagttatgg   1140

ggacaccctt taacttccgg aactggagat cacatcctta cgaatggaat cggtggtaaa   1200

caagagccta cccaaatcct ttcatcatct acagacctgc caatcatgac tacgatgttc   1260

ttgttatccc agtanggaag aaaccttcac atccctccca aagttgtcgt caagaaaggc   1320
```

-continued

```
acccgcatcg agttccaccc agtcgatgat tcagttacga gaccagttgt tgatcttgga   1380

agctacactg cactcttcaa ctgtgtggta ccaccgttca cataccacgg attcgaactg   1440

aaccacgtct attctgtcaa gcctggtgac tactatgtta ctggacccac gagagacctt   1500

tgccagaatg cagatgtcag gattcatatc catgttgagg atgagtaa                 1548
```

```
<210> SEQ ID NO 96
<211> LENGTH: 966
<212> TYPE: DNA
<213> ORGANISM: Megathura crenulata

<400> SEQUENCE: 96

ggcctaccgt actgggactg gactgaaccc atgacacaca ttccgggtct ggcaggaaac     60

aaaacttatg tggattctca tggtgcatcc cacacaaatc cttttcatag ttcagtgatt    120

gcatttgaag aaaatgctcc ccacaccaaa agacaaatag atcaaagact ctttaaaccc    180

gctacctttg gacaccacac agacctgttc aaccagattt tgtatgcctt tgaacaagaa    240

gattactgtg actttgaagt ccaatttgag attacccata acacgattca cgcttggaca    300

ggaggaagcg aacatttctc aatgtcgtcc ctacattaca cagctttcga tcctttgttt    360

tactttcacc attctaacgt tgatcgtctt tgggccgttt ggcaagcctt acagatgaga    420

cggcataaac cctacagggc ccactgcgcc atatctctgg aacatatgca tctgaaacca    480

ttcgcctttt catctcccct taacaataac gaaaagactc atgccaatgc catgccaaac    540

aagatctacg actatgaaaa tgtcctccat tacacatacg aagatttaac atttggaggc    600

atctctctgg aaaacataga aaagatgatc cacgaaaacc agcaagaaga cagaatatat    660

gccggttttc tcctggctgg catacgtact tcagcaaatg ttgatatctt cattaaaact    720

accgattccg tgcaacataa ggctggaaca tttgcagtgc tcggtggaag caaggaaatg    780

aagtggggat ttgatcgcgt tttcaagttt gacatcacgc acgttttgaa agatctcgat    840

ctcactgctg atggcgattt cgaagttact gttgacatca ctgaagtcga tggaactaaa    900

cttgcatcca gtcttattcc acatgcttct gtcattcgtg agcatgcacg tggtaagctg    960

aataga                                                               966
```

```
<210> SEQ ID NO 97
<211> LENGTH: 1242
<212> TYPE: DNA
<213> ORGANISM: Megathura crenulata

<400> SEQUENCE: 97

gttaaatttg acaaagtgcc aaggagtcgt cttattcgaa aaaatgtaga ccgtttgagc     60

cccgaggaga tgaatgaact tcgtaaagcc ctagccttac tgaaagagga caaaagtgcc    120

ggtggatttc agcagcttgg tgcattccat ggggagccaa aatggtgtcc tagtcccgaa    180

gcatctaaaa aatttgcctg ctgtgttcac ggcatgtctg tgttccctca ctggcatcga    240

ctgttgacgg ttcagagtga aaatgctttg agacgacatg gctacgatgg agctttgccg    300

tactgggatt ggacctctcc tcttaatcac cttcccgaac tggcagatca tgagaagtac    360

gtcgaccctg aagatggggt agagaagcat aacccttggt tcgatggtca tatagataca    420

gtcgacaaaa caacaacaag aagtgttcag aataaactct tcgaacagcc tgagtttggt    480

cattatacaa gcattgccaa acaagtactg ctagcgttgg aacaggacaa tttctgtgac    540

tttgaaatcc aatatgagat tgcccataac tacatccatg cacttgtagg aggcgctcag    600

ccttatggta tggcatcgct tcgctacact gcttttgatc cactattcta cttgcatcac    660
```

-continued tctaatacag atcgtatatg ggcaatatgg caggctttac agaagtacag aggaaaaccg 720
tacaacgttg ctaactgtgc tgttacatcg atgagagaac ctttgcaacc atttggcctc 780
tctgccaata tcaacacaga ccatgtaacc aaggagcatt cagtgccatt caacgttttt 840
gattacaaga ccaatttcaa ttatgaatat gacactttgg aatttaacgg tctctcaatc 900
tctcagttga ataaaaagct cgaagcgata aagagccaag acaggttctt tgcaggcttc 960
ctgttatctg gtttcaagaa atcatctctt gttaaattca atatttgcac cgatagcagc 1020
aactgtcacc ccgctggaga gttttacctt ctgggtgatg aaaacgagat gccatgggca 1080
tacgatagag tcttcaaata tgacataacc gaaaaactcc acgatctaaa gctgcatgca 1140
gaagaccact tctacattga ctatgaagta tttgacctta aaccagcaag cctgggaaaa 1200
gatttgttca agcagccttc agtcattcat gaaccaagaa ta 1242

<210> SEQ ID NO 98
<211> LENGTH: 1236
<212> TYPE: DNA
<213> ORGANISM: Megathura crenulata

<400> SEQUENCE: 98
ggtcaccatg aaggcgaagt atatcaagct gaagtaactt ctgccaaccg tattcgaaaa 60
aacattgaaa atctgagcct tggtgaactc gaaagtctga gagctgcctt cctggaaatt 120
gaaaacgatg gaacttacga atcaatagct aaattccatg gtagccctgg tttgtgccag 180
ttaaatggta accccatctc ttgttgtgtc catggcatgc caactttccc tcactggcac 240
agactgtacg tggttgtcgt tgagaatgcc ctcctgaaaa aaggatcatc tgtagctgtt 300
ccctattggg actggacaaa acgaatcgaa catttacctc acctgatttc agacgccact 360
tactacaatt ccaggcaaca tcactatgag acaaacccat tccatcatgg caaaatcaca 420
cacgagaatg aaatcactac tagggatccc aaggacagcc tcttccattc agactacttt 480
tacgagcagg tcctttacgc cttggagcag gataacttct gtgatttcga gattcagttg 540
gagatattac acaatgcatt gcattcttta cttggtggca aaggtaaata ttccatgtca 600
aaccttgatt acgctgcttt tgatcctgtg ttcttccttc atcacgcaac gactgacaga 660
atctgggcaa tctggcaaga ccttcagagg ttccgaaaac ggccataccg agaagcgaat 720
tgcgctatcc aattgatgca cacgccactc cagccgtttg ataagagcga caacaatgac 780
gaggcaacga aaacgcatgc cactccacat gatggttttg aatatcaaaa cagctttggt 840
tatgcttacg ataatctgga actgaatcac tactcgattc ctcagcttga tcacatgctg 900
caagaaagaa aaaggcatga cagagtattc gctggcttcc tccttcacaa tattggaaca 960
tctgccgatg gccatgtatt tgtatgtctc ccaactgggg aacacacgaa ggactgcagt 1020
catgaggctg gtatgttctc catcttaggc ggtcaaacgg agatgtcctt tgtatttgac 1080
agactttaca aacttgacat aactaaagcc ttgaaaaaga acggtgtgca cctgcaaggg 1140
gatttcgatc tggaaattga gattacggct gtgaatggat ctcatctaga cagtcatgtc 1200
atccactctc ccactatact gtttgaggcc ggaaca 1236

<210> SEQ ID NO 99
<211> LENGTH: 1257
<212> TYPE: DNA
<213> ORGANISM: Megathura crenulata -continued

<400> SEQUENCE: 99
gattctgccc acacagatga tggacacact gaaccagtga tgattcgcaa agatatcaca 60
caattggaca agcgtcaaca actgtcactg gtgaaagccc tcgagtccat gaaagccgac 120
cattcatctg atgggttcca ggcaatcgct tccttccatg ctcttcctcc tctttgtcca 180
tcaccagctg cttcaaagag gtttgcgtgc tgcgtccatg gcatggcaac gttcccacaa 240
tggcaccgtc tgtacacagt ccaattccaa gattctctca gaaaacatgg tgcagtcgtt 300
ggacttccgt actgggactg gaccctacct cgttctgaat taccagagct cctgaccgtc 360
tcaactattc atgacccgga gacaggcaga gatataccaa atccatttat tggttctaaa 420
atagagtttg aaggagaaaa cgtacatact aaaagagata tcaataggga tcgtctcttc 480
cagggatcaa caaaaacaca tcataactgg tttattgagc aagcactgct tgctcttgaa 540
caaaccaact actgcgactt cgaggttcag tttgaaatta tgcataatgg tgttcatacc 600
tgggttggag gcaaggagcc ctatggaatt ggccatctgc attatgcttc ctatgatcca 660
cttttctaca tccatcactc ccaaactgat cgtatttggg ctatatggca atcgttgcag 720
cgtttcagag gactttctgg atctgaggct aactgtgctg taaatctcat gaaaactcct 780
ctgaagcctt tcagctttgg agcaccatat aatcttaatg atcacacgca tgatttctca 840
aagcctgaag atacattcga ctaccaaaag tttggataca tatatgacac tctggaattt 900
gcagggtggt caattcgtgg cattgaccat attgtccgta acaggcagga acattcaagg 960
gtctttgccg gattcttgct tgaaggattt ggcacctctg ccactgtcga tttccaggtc 1020
tgtcgcacag cgggagactg tgaagatgca gggtacttca ccgtgttggg aggtgaaaaa 1080
gaaatgcctt gggcctttga tcggctttac aagtacgaca taacagaaac cttagacaag 1140
atgaaccttc gacatgacga aatcttccag attgaagtaa ccattacatc ctacgatgga 1200
actgtactcg atagtggcct tattcccaca ccgtcaatca tctatgatcc tgctcat 1257

<210> SEQ ID NO 100
<211> LENGTH: 1254
<212> TYPE: DNA
<213> ORGANISM: Megathura crenulata

<400> SEQUENCE: 100
catgatatta gttcgcacca cctgtcgctc aacaaggttc gtcatgatct gagtacactg 60
agtgagcgag atattggaag ccttaaatat gctttgagca gcttgcaggc agatacctca 120
gcagatggtt ttgctgccat tgcatccttc catggtctgc ctgccaaatg taatgacagc 180
cacaataacg aggtggcatg ctgtatccat ggaatgccta cattccccca ctggcacaga 240
ctctacaccc tccaatttga gcaagctcta agaagacatg gctctagtgt agcagtaccc 300
tactgggact ggacaaagcc aatacataat attccacatc tgttcacaga caaagaatac 360
tacgatgtct ggagaaataa agtaatgcca aatccatttg cccgagggta tgtcccctca 420
cacgatacat acacggtaag agacgtccaa gaaggcctgt tccacctgac atcaacgggt 480
gaacactcag cgcttctgaa tcaagctctt ttggcgctgg aacagcacga ctactgcgat 540
tttgcagtcc agtttgaagt catgcacaac acaatccatt acctagtggg aggacctcaa 600
gtctattctt tgtcatccct tcattatgct tcatatgatc cgatcttctt catacaccac 660
tcctttgtag acaaggtttg ggctgtctgg caggctcttc aagaaaagag aggccttcca 720
tcagaccgtg ctgactgcgc tgttagtctg atgactcaga acatgaggcc tttccattac 780
gaaattaacc ataaccagtt caccaagaaa catgcagttc caaatgatgt tttcaagtac 840

-continued

```
gaactcctgg gttacagata cgacaatctg gaaatcggtg gcatgaattt gcatgaaatt    900
gaaaaggaaa tcaaagacaa acagcaccat gtgagagtgt ttgcagggtt cctccttcac    960
ggaattagaa cctcagctga tgtccaattc cagatttgta aaacatcaga agattgtcac   1020
catggaggcc aaatcttcgt tcttgggggg actaaagaga tggcctgggc ttataaccgt   1080
ttattcaagt acgatattac ccatgctctt catgacgcac acatcactcc agaagacgta   1140
ttccatccct ctgaaccatt cttcatcaag gtgtcagtga cagccgtcaa cggaacagtt   1200
cttccggctt caatcctgca tgcaccaacc attatctatg aacctggtct cggt         1254
```

<210> SEQ ID NO 101
<211> LENGTH: 510
<212> TYPE: DNA
<213> ORGANISM: Megathura crenulata

<400> SEQUENCE: 101

```
gaccatcacg aagatcatca ttcttcttct atggctggac atggtgtcag aaaggaaatc     60
aacacactta ccactgcaga ggtggacaat ctcaaagatg ccatgagagc cgtcatggca    120
gaccacggtc caaatggata ccaggctata gcagcgttcc atggaaaccc accaatgtgc    180
cctatgccag atggaaagaa ttactcgtgt tgtacacatg gcatggctac tttcccccac    240
tggcacagac tgtacacaaa acagatggaa gatgccttga ccgcccatgg tgccagagtc    300
ggccttcctt actgggacgg gacaactgcc tttacagctt tgccaacttt tgtcacagat    360
gaagaggaca atcctttcca tcatggtcac atagactatt tgggagtgga tacaactcgg    420
tcgccccgag acaagttgtt caatgatcca gagcgaggat cagaatcgtt cttctacagg    480
caggttctct tggctttgga gcagacagat                                     510
```

<210> SEQ ID NO 102
<211> LENGTH: 942
<212> TYPE: DNA
<213> ORGANISM: Megathura crenulata

<400> SEQUENCE: 102

```
ggcctgccct actgggattg gaccatgcca atgagtcatt tgccagaact ggctacaagt     60
gagacctacc tcgatccagt tactggggaa actaaaaaca accctttcca tcacgcccaa    120
gtggcgtttg aaaatggtgt aacaagcagg aatcctgatg ccaaactttt tatgaaacca    180
acttacggag accacactta cctcttcgac agcatgatct acgcatttga gcaggaagac    240
ttctgcgact ttgaagtcca atatgagctc acgcataatg caatacatgc atgggttgga    300
ggcagtgaaa agtattcaat gtcttctctt cactacactg cttttgatcc tatattttac    360
ctccatcact caaatgttga tcgtctctgg gccatttggc aagctcttca aatcaggaga    420
ggcaagtctt acaaggccca ctgcgcctcg tctcaagaaa gagaaccatt aaagcctttt    480
gcattcagtt ccccactgaa caacaacgag aaaacgtacc acaactctgt ccccactaac    540
gtttatgact atgtgggagt tttgcactat cgatatgatg accttcagtt tggcggtatg    600
accatgtcag aacttgagga atatattcac aagcagacac aacatgatag aacctttgca    660
ggattcttcc tttcatatat tggaacatca gcaagcgtag atatcttcat caatcgagaa    720
ggtcatgata aatacaaagt gggaagtttt gtagtacttg gtggatccaa agaaatgaaa    780
tggggctttg atagaatgta caagtatgag atcactgagg ctctgaagac gctgaatgtt    840
gcagtggatg atgggttcag cattactgtt gagatcaccg atgttgatgg atctccccca    900
tctgcagatc tcattccacc tcctgctata atctttgaac gt                       942
```

-continued

<210> SEQ ID NO 103
<211> LENGTH: 1248
<212> TYPE: DNA
<213> ORGANISM: Megathura crenulata

<400> SEQUENCE: 103
gctgatgcca aagactttgg ccatagcaga aaaatcagga aagccgttga ttctctgaca 60
gtcgaagaac aaacttcgtt gaggcgagct atggcagatc tacaggacga caaaacatca 120
gggggtttcc agcagattgc agcattccac ggagaaccaa aatggtgtcc aagccccgaa 180
gcggagaaaa aatttgcatg ctgtgttcat ggaatggctg ttttccctca ctggcacaga 240
ttgctgacag ttcaaggaga aaatgctctg aggaaacatg gctttactgg tggactgccc 300
tactgggact ggactcgatc aatgagcgcc cttccacatt ttgttgctga tcctacttac 360
aatgatgcta tttccagcca ggaagaagat aacccatggc atcatggtca catagactct 420
gttgggcatg atactacaag agatgtgcgt gatgatcttt atcaatctcc tggtttcggt 480
cactacacag atattgcaaa acaagtcctt ctggcctttg agcaggacga tttctgtgat 540
tttgaggtac aatttgaaat tgcccataat ttcatacatg ctctggttgg tggtaacgaa 600
ccatacagta tgtcatcttt gaggtatact acatacgatc caatcttctt cttgcaccgc 660
tccaatacag accgactttg ggccatttgg caagctttgc aaaaataccg gggggaaacca 720 tacaacactg caaactgtgc cattgcatcc atgagaaaac cacttcagcc atttggtctt 780
gatagtgtca taaatccaga tgacgaaact cgtgaacatt cggttccttt ccgagtcttc 840
gactacaaga acaacttcga ctatgagtat gagagcctgg catttaatgg tctgtctatt 900
gcccaactgg accgagagtt gcagagaaga aagtcacatg acagagtctt tgcaggattc 960
cttcttcatg aaattggaca gtctgcactc gtgaaattct acgtttgcaa acacaatgta 1020
tctgactgtg accattatgc tggagaattc tacattttgg gagatgaagc tgagatgcct 1080
tggaggtatg accgtgtgta caagtacgag ataacacagc agctgcacga tttagatcta 1140
catgttggag ataatttctt ccttaaatat gaagcctttg atctgaatgg cggaagtctt 1200
ggtggaagta tcttttctca gccttcggtg attttcgagc cagctgca 1248

<210> SEQ ID NO 104
<211> LENGTH: 1257
<212> TYPE: DNA
<213> ORGANISM: Megathura crenulata

<400> SEQUENCE: 104
ggttcacacc aggctgatga atatcgtgag gcagtaacaa gcgctagcca cataagaaaa 60
aatatccggg acctctcaga gggagaaatt gagagcatca gatctgcttt cctccaaatt 120
caaaaagagg gtatatatga aaacattgca aagttccatg gaaaaccagg actttgtgaa 180
catgatggac atcctgttgc ttgttgtgtc catggcatgc ccacctttcc ccactggcac 240
agactgtacg ttcttcaggt ggagaatgcg ctcttagaac gagggtctgc agttgctgtt 300
ccttactggg actggaccga gaaagctgac tctctgccat cattaatcaa tgatgcaact 360
tatttcaatt cacgatccca gacctttgat cctaatcctt tcttcagggg acatattgcc 420
ttcgagaatg ctgtgacgtc cagagatcct cagccagaac tatgggacaa taaggacttc 480
tacgagaatg tcatgctggc tcttgagcaa gacaacttct gtgactttga gattcagctt 540
gagctgatac acaacgccct tcattctaga cttggaggaa gggctaaata ctccctttcg 600
tctcttgatt ataccgcatt tgatcctgta tttttccttc accatgcaaa cgttgacaga 660

-continued

```
atctgggcca tctggcagga cttgcagaga tatagaaaga aaccatacaa tgaggctgac    720

tgcgcagtca acgagatgcg taaacctctt caaccattta ataacccaga acttaacagt    780

gattccatga cgcttaaaca caacctccca caagacagtt ttgattatca aaaccgcttc    840

aggtaccaat atgataacct tcaatttaac cacttcagca tacaaaagct agaccaaact    900

attcaggcta gaaaacaaca cgacagagtt tttgctggct ttattcttca caacattggg    960

acatctgctg ttgtagatat ttatatttgc gttgaacaag gaggagaaca aaactgcaag   1020

acaaaggcgg gttccttcac gattctgggg ggagaaacag aaatgccatt ccactttgac   1080

cgcttgtaca aatttgacat aacgtctgct ctgcataaac ttggtgttcc cttggacgga   1140

catggattcg acatcaaagt tgacgtcaga gctgtcaatg gatcgcatct tgatcaacac   1200

atcctcaacg aaccgagtct gctttttgtt cctggtgaac gtaagaatat atattat      1257
```

<210> SEQ ID NO 105
<211> LENGTH: 1239
<212> TYPE: DNA
<213> ORGANISM: Megathura crenulata

<400> SEQUENCE: 105

```
gatgggcttt cacaacataa tcttgtgcga aaagaagtaa gctctcttac aacactggag     60

aaacattttt tgaggaaagc tctcaagaac atgcaagcag atgattctcc agacggatat    120

caagctattg cttctttcca cgctttgcct cctctttgtc caagtccatc tgctgcacat    180

agacacgctt gttgcctcca tggtatggct accttccctc agtggcacag actctacaca    240

gttcagttcg aagattcttt gaaacgacat ggttctattg tcggacttcc atattgggat    300

tggctgaaac cgcagtctgc actccctgat ttggtgacac aggagacata cgagcacctg    360

ttttcacaca aaaccttccc aaatccgttc ctcaaggcaa atatagaatt tgagggagag    420

ggagtaacaa cagagaggga tgttgatgct gaacacctct ttgcaaaagg aaatctggtt    480

tacaacaact ggttttgcaa tcaggcacta tatgcactag aacaagaaaa ttactgtgac    540

tttgaaatac agttcgaaat tttgcataat ggaattcatt catgggttgg aggatcaaag    600

acccattcaa taggtcatct tcattacgca tcatacgatc cactgttcta tatccaccat    660

tcgcagacag atcgcatttg ggctatctgg caagctctcc aggagcacag aggtctttca    720

gggaaggaag cacactgcgc cctggagcaa atgaaagacc ctctcaaacc tttcagcttt    780

ggaagtccct ataatttgaa caaacgcact caagagttct ccaagcctga agacacattt    840

gattatcacc gattcgggta tgagtatgat tccctcgaat ttgttggcat gtctgtttca    900

agtttacata actatataaa acaacaacag gaagctgata gagtcttcgc aggattcctt    960

cttaaaggat ttggacaatc agcatccgta tcgtttgata tctgcagacc agaccagagt   1020

tgccaagaag ctggatactt ctcagttctc ggtggaagtt cagaaatgcc gtggcagttt   1080

gacaggcttt acaagtacga cattacaaaa acgttgaaag acatgaaact gcgatacgat   1140

gacacattta ccatcaaggt tcacataaag gatatagctg gagctgagtt ggacagcgat   1200

ctgattccaa ctccttctgt tctccttgaa gaaggaaag                          1239
```

<210> SEQ ID NO 106
<211> LENGTH: 1251
<212> TYPE: DNA
<213> ORGANISM: Megathura crenulata -continued

<400> SEQUENCE: 106

```
catgggatca atgtacgtca cgttggtcgt aatcggattc gtatggaact atctgaactc     60
accgagagag atctcgccag cctgaaatct gcaatgaggt ctctacaagc tgacgatggg    120
gtgaacggtt atcaagccat tgcatcattc cacggtctcc cggcttcttg tcatgatgat    180
gagggacatg agattgcctg ttgtatccac ggaatgccag tattcccaca ctggcacagg    240
ctttacaccc tgcaaatgga catggctctg ttatctcacg gatctgctgt tgctattcca    300
tactgggact ggaccaaacc tatcagcaaa ctgcctgatc tcttcaccag ccctgaatat    360
tacgatcctt ggagggatgc agttgtcaat aatccatttg ctaaaggcta cattaaatcc    420
gaggacgctt acacggttag ggatcctcag gacattttgt accacttgca ggacgaaacg    480
ggaacatctg ttttgttaga tcaaactctt ttagccttag agcagacaga tttctgtgat    540
tttgaggttc aatttgaggt cgtccataat gctattcact acttggtggg tggtcgacaa    600
gtttatgctc tttcttctca acactatgct tcatatgacc cagccttctt tattcatcac    660
tcctttgttg acaaaatatg ggcagtctgg caagctctgc aaaagaagag aaagcgtccc    720
tatcataaag cggattgtgc tcttaacatg atgaccaaac caatgcgacc atttgcacac    780
gatttcaatc acaatggatt cacaaaaatg cacgcagtcc ccaacactct atttgacttt    840
caggaccttt tctacacgta tgacaactta gaaattgctg gcatgaatgt taatcagttg    900
gaagcggaaa tcaaccggcg aaaaagccaa acaagagtct ttgccgggtt ccttctacat    960
ggcattggaa gatcagctga tgtacgattt tggatttgca agacagctga cgactgccac   1020
gcatctggca tgatctttat cttaggaggt tctaaagaga tgcactgggc ctatgacagg   1080
aactttaaat acgacatcac ccaagctttg aaggctcagt ccatacaccc tgaagatgtg   1140
tttgacactg atgctccttt cttcattaaa gtggaggtcc atggtgtaaa caagactgct   1200
ctcccatctt cagctatccc agcacctact ataatctact cagctggtga a            1251
```

<210> SEQ ID NO 107
<211> LENGTH: 1185
<212> TYPE: DNA
<213> ORGANISM: Megathura crenulata
<220> FEATURE:
<221> NAME/KEY: misc_feature
<222> LOCATION: (164)..(164)
<223> OTHER INFORMATION: "n" is a, g, c, or t

<400> SEQUENCE: 107

```
gatcatattg ctggcagtgg agtcaggaaa gacgtgacgt ctcttaccgc atctgagata     60
gagaacctga ggcatgctct gcaaagcgtg atggatgatg atggacccaa tggattccag    120
gcaattgctg cttatcacgg aagtcctccc atgtgtcaca tgcntgatgg tagagacgtt    180
gcatgttgta ctcatggaat ggcatctttc cctcactggc acagactgtt tgtgaaacag    240
atggaggatg cactggctgc gcatggagct cacattggca taccatactg ggattggaca    300
agtgcgttta gtcatctgcc tgccctagtg actgaccacg agcacaatcc cttccaccac    360
ggacatattg ctcatcggaa tgtggataca tctcgatctc cgagagacat gctgttcaat    420
gaccccgaac acgggtcaga atcattcttc tatagacagg ttctcttggc tctagaacag    480
acagacttct gccaatttga agttcagttt gaaataacac acaatgcaat ccactcttgg    540
actggaggac atactccata tggaatgtca tcactggaat atacagcata tgatccactc    600
ttttatctcc accattccaa cactgatcgt atctgggcca tctggcaggc actccagaaa    660
tacagaggtt ttcaatacaa cgcagctcat tgcgatatcc aggttctgaa acaacctctt    720
```

-continued

```
aaaccattca gcgagtccag gaatccaaac ccagtcacca gagccaattc tagggcagtc    780

gattcatttg attatgagag actcaattat caatatgaca cacttacctt ccacggacat    840

tctatctcag aacttgatgc catgcttcaa gagagaaaga aggaagagag aacatttgca    900

gccttcctgt tgcacggatt tggcgccagt gctgatgttt cgtttgatgt ctgcacacct    960

gatggtcatt gtgcctttgc tggaaccttc gcggtacttg gtggggagct tgagatgccc   1020

tggtcctttg aaagattgtt ccgttacgat atcacaaagg ttctcaagca gatgaatctt   1080

cactatgatt ctgagttcca ctttgagttg aagattgttg gcacagatgg aacagaactg   1140

ccatcggatc gtatcaagag ccctaccatt gaacaccatg gagga                   1185
```

```
<210> SEQ ID NO 108
<211> LENGTH: 309
<212> TYPE: DNA
<213> ORGANISM: Megathura crenulata

<400> SEQUENCE: 108

ggtcacgatc acagtgaacg tcacgatgga tttttcagga aggaagtcgg ttccctgtcc     60

ctggatgaag ccaatgacct taaaaatgca ctgtacaagc tgcagaatga tcagggtccc    120

aatggatatg aatcaatagc cggttaccat ggctatccat tcctctgccc tgaacatggt    180

gaagaccagt acgcatgctg tgtccacgga atgcctgtat ttccacattg gcacagactt    240

catacaatcc agtttgagag agctctcaaa gaacatggtt ctcatttggg tctgccatac    300

tgggactgg                                                            309
```

```
<210> SEQ ID NO 109
<211> LENGTH: 2561
<212> TYPE: DNA
<213> ORGANISM: Haliotis tuberculata

<400> SEQUENCE: 109

gtaagtcaac gtctttgttt taagtttgat gcatatctat cattgcgttt taaaatacca     60

ttacaaccaa cgtgtctcta ttggtcttca cctgtttaac gtatatattg tttttaatgt    120

gaaaatctga gattattttc atttccgtca atattcgtaa aatactatac aaataaaatt    180

gcttcagcct attgcattgg cagttttcgc agaataacga gggaaggcgt acataaaata    240

taaaccagtg tatattcaag catgtttata atttctttat agattataac atcatatcaa    300

aacaccaatc tggatttaaa cccgtgaatc caaagtatac caattaacgg aactttatca    360

tgttttatca aaggttttag atgagggtaa agaagtccga gctatatttt gcgatatcag    420

caaagccttc tatcacgtct tgcacacagg gctggtatct aaactcgaat ccacaggaat    480

aaatatttca gccgatagag aacagtcggt ggctatcatt ggtcacaaaa caagtccaaa    540

atctgcatta gccggtgttc cccaaggctc tgtcttgggg ccactattat ttctcaccta    600

tataaacgat tcaactaatg gaatataaag caacgtaaac ctcaccgcag atgaaacact    660

aagttataga caatccgttt aaaacccagc cactgcttaa taatgactta ggccgtcttt    720

cagactgggc tagtaagcgg caggttaaat ttcaccttga aaagacagaa accatggtat    780

atttcaaaaa cacgaatgca agtcctaaac ttcaactact acttgatgat actgggattt    840

ctaaagtgtg tgaacaaaaa cacattggcc tgatcctaca agataaccag acagaaacca    900

tgttttttttt caataacacg aatgcaagtc ctaaacttca actactactt gatgatactg    960

ggatttctaa agtgtgtggt gaacacaaac accttggcct gattctgcaa gataatggaa   1020

aatgtcagaa acataagcaa gttgatgtgg ggttttctgg gggttgtgac aacaccgaaa   1080
```

-continued

```
gaccctgcaa ctaatgttag ctcaaagggt tttacacccg gtcacaagtg gggatcgacc   1140

caggcacctt ttgcctttga cagctcgcct ttcaaaaaat ctcaattcga aaacgaaatc   1200

taataatttc atgagcgata caaccgtttt tcataatgct gtggtaccgc atactgtgga   1260

aacatctgtc tacccatttg gtagtccccc ataaaatgta tttatgttta taaacacaat   1320

gtttataggg ttacagttag aagaagcatt tctattggct aatgtacatt gcttgttttt   1380

actattgtgc aaaggcatat tacaggtctt ttaggaaatt aaatactgtt taaatcacat   1440

acactaccgg taatcctatt atgcttatcc tgccaacatt ctgcccaagc aaacgcatga   1500

aagttaaagc tgagtgtaaa atactgattg ctgtgttact tcacaaccag tggactgaat   1560

acaaccatgt tttttcttga aagtcacaaa catccagtcg gtttctaatg tgttaagttt   1620

ctagtttcat aaagagcatg acgtaatggt gaataggagt tatcaatgtt tctatctaat   1680

gactcctagt tcgttacttt tttaataaaa catccatgtg tttaatgttt ggccacagat   1740

ataacaagaa agaaatcgga taaaatctac attttgacca atcggaaggc tgccccctcc   1800

ctaatcctaa tcatttttgt gcctcaaaac atactcaacc agacatttga actatgtata   1860

tatcagaatg aaatggtaac aataaacttg tatgttgacc agacagaatt agggtgaatc   1920

tgaataccaa ctattgtcac atatgaatat ggataagctc tgcgcgtgcg tgcgggcggt   1980

gtagtgcgtg tgtgtctgtg tgtgtgtgtg tgtgcgtttg tgtgtgtgtc tgcgtgcgtg   2040

tgtgtgcgcg tgtgtgcgtg tgtgtgtgtg tgcagtgtgc cgagtgtgtg tgtgtgtgtg   2100

tgcacagaca tgtggttgag acacacttga ttcagtgcag gattatgtcc ttcaaccgag   2160

tgtagtcttt aagtgtgcct ggaaacaaaa aactgcgttg ggttgcatcg cctctgtagc   2220

aagcttggac gcgtcacgca gctctgatac cacgtattgg caccatgttt catcggtctc   2280

acgcgaatat tatgctatgt gtggcgtatc ataccatagg ttgggaacgt ttcaatactg   2340

taccgagctt gggcgtgtca caaagctatg ataagatgac aacacgtctt ggcatcttgt   2400

ttcctcggta tcacgcgctg ttatgctatg tgtggctatc acaccttagg ttgggaaagt   2460

ttccacattt tccagcctcg tacatgtttc cttttgtttt ttccttagtt atcagcatac   2520

cgtatattct atatttaatg agcatttgta tttttctaca g                        2561
```

<210> SEQ ID NO 110
<211> LENGTH: 5043
<212> TYPE: DNA
<213> ORGANISM: Haliotis tuberculata
<220> FEATURE:
<221> NAME/KEY: misc_feature
<222> LOCATION: (2928)..(2928)
<223> OTHER INFORMATION: “n” is a, g, c or t

<400> SEQUENCE: 110

```
gtgagtttct taacattgtc atggtacatg gatatacgct cagtgggaaa gcaggatatc     60

cccttggttc aagtattcac ttgtcacgcc aagtgttcga ttcccaacat ggaatactgt    120

catatagtaa attgatacac tacttacatt taattctcca ctaaacgtca acgtccttta    180

cttcatggcc cacatggtcc gtattagtga gtgagtgagt cagggcataa gtatttaacg    240

tcaaatcagc aatatttcag ccatattgtg acaagaattg aatataaata attatactta    300

taatgcttat aaatataaat tatataaata cctataacta taaattagtt atactagtat    360

ttatcaaaac atatttgcca cgacactgca cgccgatact tcaagtgtct tcacctcaag    420

cgtgtaactc ctcatactct gtaataagta tgtacactaa gtgagtgcta tcatctccat    480

gcttcattag tttcgtcaga tgcgtgtatc catacgagta cattcagatt atgggatcca    540
```

-continued

```
gagctttctt atctcaagta tttccgattg taaagccata ctacttcccc aatgactgac    600
gagacagatg gcaaccgttc tttcctcctg actaggtgag tgccactgat aaatcattat    660
gcctttaaca ttaggaatgt tagcagtgca catgtttcag aattgcgacc ttatggttgt    720
aaagattaca aactttacaa cttacttgag acaggttcca tatgtcgtat ctgaaatagt    780
gtgaaggtat ctgattcgat gcaatacaca gacatataaa catattgtcg ccctgctatt    840
ccggaaaggt cattttgtat gtaacgttcc ttaatggaca caaacggaat tattagttaa    900
acatactcaa caaaactatg ttattttgca atgggtagca ccgaaatcta ccgacagtgg    960
ttcgtaaaag tagaacattc tgacataaag aaaaatcatt ggctttaaat atatgcaagt   1020
tacttgtctc taacaaccag ttttatacac atttcagaga acggggaatc cgcgatgaca   1080
atatcaacga gtatatacag aatatataat taaaaacgat gagtgcctgg caagggaaag   1140
agcgagattt gccaaacagg ggggtggtgt tgagcttgaa tcgtggagaa acgtagattg   1200
aaagacaaga tgacatctaa tgatccgaaa atcaaacaca ggattaactg ggatgcagaa   1260
gaatgaatat ctcaagcata catgcaacac ttcatgaatg catctcaaac attttcgtca   1320
gatcggatgc atgaagattt gtaaagcaat ggtttaaatt gtccctaaac gtttagttgg   1380
agatgtatga ggctaggctg tatgttgaac gaaaccattt aacattgttg ttcatgatta   1440
tttaatattt tttcatttta tagatgtaca ataaaattgg aaactaaaca tttcccttta   1500
ttgttttgta tttacctgtt catgggtatg ttttgaaaga tcgtgatatt tagttggcat   1560
tcacaagttg gaaaaaggtc actcagtttg atttcaagtt tatgtaacct ctttatctga   1620
cgctccaaaa tatgtatagc cttgttcatc tgtcggtatg tggatattcc tacttcaggg   1680
tagggtagca ttaatactta caaaacataa cgtgtaccag atttcagtca cctcagagat   1740
gataatgcat gtcgatatga taggtcaaaa ctttcgatat caatcacaat gaacctatgg   1800
accctgaatc ggaatgatac gttacacttt agaaacaatt cacaaatatg actgtcaccc   1860
tttcaggtaa taatgtttga cggactacga tagtgctgaa cagcaggaga ggcaacatgg   1920
ttcgattgtg agacaggttt agtgtatttg tttgcgaatt taaggttctg aatcacaata   1980
gacacggttc agttaatgga taaaccaatc attagataga tagagattag tcgcgatatt   2040
gctgggataa agcttagtgg gacgttaagt cccatctcaa tctctctcat tttttccaaa   2100
acagttttaa ttcaggctca tgacaaggtc gtactgttgc aaaggattct acttcaagca   2160
gagatgtctc atgaatacag tacagggttt ttgaagttta tccagtgcag cgctggcacc   2220
atctctgcat gcgaattata ccatccatgc cgctctaggc tatttgtatt aagtctgtag   2280
aattaaattc gcgagttgca aatactgctc accattatct gcctcaaccc agtttgggta   2340
catgcgattt acacaatatt atgtataatg ttcgcttttc gaaaacaaaa cacctaaatt   2400
catccaaagt tttgggagat tttattcgag aaatcaacct gagatgttga atcgggagct   2460
gcgcttattc aatggtggac tcggaaggga agtaaccgct gatgaggcaa aacaataacg   2520
caaacatatg gaagtggaac tctttgaacc agtattatgt ttgtgtggac atgtatgtgt   2580
taatttgacc attcgaacaa ctttactatt ctattcataa tgtgtttaga tttacatttg   2640
aattaaaaga gatgagttta agatattaat attttccttt tatagtctgt cgtgattgta   2700
gggcaatatt tatgtatgtt cgttcatttt tcatttatca tttggaaagg tatatcataa   2760
gattattatt atcattcttg aagtaatgta tacatatata tatgtcttga gtagcttatt   2820
ttcaatttat tatcatccgt catccaattt tatttcacga aagtataaga aataacgaga   2880
gagagagaga gagagagaga aaagacagaa atgaagttag gagatatnag ttatcaagaa   2940
```

-continued

```
aacaacagtt tgaatttttt gtttagacaa gatatcatat caataacctc gcactattac   3000
gggaataggc gggcgttcca tatgcacaat gaatcgtcag ttaaaatcaa cattaaactt   3060
aaaatactcc tcatatttaa agttgatcta cctcttgtat tattgtagac tattagacag   3120
aagtcgacag tgacaccagc aaccagatat catacccaga cttaaaaagc tgtttccttg   3180
atgtttcaat ttatttccat ttccattatt tccctttatt ggtttccatt tatcaaactt   3240
accatctgca ccagtgggag attgatatgt tgtatttatt tatatttctt gtactacaat   3300
atcaagaatg tataggagct attccttgtt cctaaaaccg gatagatcca taatttccat   3360
tttgggataa atggaaacta aacacaactt ttacagtaaa cacgagtgag caagttgagt   3420
tttacgccgt ttttagtagt attccagcaa tatcgcggcg ggggacacca gaaatgggct   3480
tcacacagtg aatgcatgtg gggattcgaa cccgggtctt cggcgtgacg agtgaacgct   3540
ttagccacta ggctacccca ccgcctattt atagttaaga cgaatacttt tctcaagcct   3600
caaatatgtc cattctagag agactgaatc tgatcctgaa tctgcggacc ggtcttgaat   3660
atcatcccac taactcattg tacaaagtac ctgtagattg tcagttcaaa gacagatttc   3720
acaaccctat tatattttgt cctgctcatt aagatattca gactcactca aactgctaaa   3780
tgattttaat cctactttga gatgttttaa cttttattcg atgcattttt gcgttctgcg   3840
tcctgtataa aggtaaagca ggtaaactaa cctaacctgt tgatttattt catagttttg   3900
cgatcagatt gaaaccggaa tgcacagtga agtgtggcat acatctttcc acagagatac   3960
tggatactag gtggtacaac cgcattggct ttgtgaaagg atattagtgt tttatgagac   4020
tgactcatgt ttcaatgctt agagcggaat gatctcggtc ttcatgaaaa atattgtgtt   4080
gaagtaaccc cccagtccct aacagaacgt ggggaaagca gatggatatg ccaagacatc   4140
ttcgcatggt gtgaagatga tcgttacaac atctgcagaa aaagttattt ctgtgaagaa   4200
tatgccaaag catcactgtg agtgttttga agatgtgata tggcaacacg cagcgtgtaa   4260
ttatgctttg tgtgtatttc tgaagatccg tatgagcatg gcgccaaact atcagttaaa   4320
tggctatgcg aagatcttcc cgagatggta aacacatatt ttggccattt tctttgtaag   4380
tgggcgacac agaagatccc cctgattgtg tggatgagga cacaaaaacg ggtccccctt   4440
cctttgctga tgctaatgac gccctggaaa cattgaaaga cttcttctcc agcaagcaag   4500
ccaccaacca caagttgtat aaatcgcttg cggacttgaa tacggcagtt ggacagatac   4560
atacagccag agagggccga actaaaacat ctaaacatgg aaaaactgta aagacaggct   4620
ttgttgtacg acgtacgtaa attcattgaa tgtttgaaaa ggtagaaaat tattaaatct   4680
ttgaaacctc gctctgtttg tttgttattg tcccccacat ttgcaaatgg tatccaaaaa   4740
gggcagacac atttgtttta atcttagcca ggttcaattt agccttgcgc ccagactcat   4800
tgtatctggt gaaggctata ggtggccacg tcttctaaga tgctatgcta ttcttaccag   4860
aatccaatgt aaagagttca aacgcatggt tcgctttgat tgtgattctt tcttagcacc   4920
tctctcctac ccagagttca cctgcactgc tcctgactca caataagctg acgtgctgtc   4980
atatatgtgc aacattgtat acgttggcgt taagcccaac tcacttccgc tgtcttttgg   5040
cag                                                                 5043
```

<210> SEQ ID NO 111
<211> LENGTH: 659
<212> TYPE: DNA
<213> ORGANISM: Haliotis tuberculata -continued

<400> SEQUENCE: 111

```
gtaactacaa acgtcgtccc attcatacag gagaaatata caattgtgtt gtaagagcgg     60
tatactgttt gccaactgtg taattgaaac gttgatgatg gtgtctttgt atttcaattt    120
gtatgcactt agacatgatc aatgtttctg atgtgtcaag gatgttcggt gtgtcacttt    180
caaaagatca aattcatatg acgtacacag agcaagaacc aacagtaaga agtctgtatg    240
acttcgctct taaaagcaat ggaaaaatat tttcacttaa cacctagccc ataatcacgc    300
atattagatt attcaagcga tgtcaacatg tttttaatat caatctcatg gttctgatat    360
taccggagac atgcaacagg ctgccattat agccaggaaa tcttatgaat atgtgcatat    420
tttttctttg attctgtatg acgagaaata ttcggaggca aagattgtgt tttcagaaca    480
gaatcagggt atcagtgaca tcgtcactgc atggctacaa tattgctgat gtgactgttt    540
ctccaaggat tttcatctca ctgtctgtac tttgaatcta caaattcgta ttaaagttat    600
gacaatttta cccctgccta tttgtaaacg aaatataaca tgagtgttta tgctgacag     659
```

<210> SEQ ID NO 112
<211> LENGTH: 904
<212> TYPE: DNA
<213> ORGANISM: Haliotis tuberculata

<400> SEQUENCE: 112

```
gtaagtttgg tttacagttt cattataaaa acatagcagt tttaagttta ggggcagatt     60
ctaatctcta atattccttt caactcactt tattggtgcc ttcttggagt gacatttaga    120
aactaagaca agaggaagat gaacaatgtt tgtagggata gacagcttgg atgcaatttc    180
ggaccagatt ctaacagcgt catgaagcaa gtgatacaca acgttatcaa taacgagaat    240
atacacatag atggtttgag tttataaatg aactattaac ggcattgtgg ttatagacag    300
tgaggaagac gccagataga caaagggtag gggccttggt tagataatga gaagttgaag    360
aggtgtaata acttaaatct ctcttgacta ttgattgtgt ctaagagttt tcttatctta    420
cagtcggcca gttgggtcaa agatggtgtg attcggatgt gctttgtgtg ttctgcgatg    480
gctgatttag agtcagttta cttcagatga atgaagttcc ccgattctta tgtttaagtt    540
tgtttcacct acgcatgaag acatcaccag cagggtcgtc tttatttcta gtagcttatt    600
tacagcaagc ttgtaacgta tgctgaattg ctgtgcctct gtagaacaca gcatctatgt    660
ttgcttgctt ctttagtaga ctgcggatgt gatggttggt tacctggtat gctgacgaaa    720
gaattgttga cgtggtggtt tgccttgatg ggttcgttga cttggtttgt tggatactga    780
ttaaggtgac tctgctggga ggcttggatt ctggggccgg tgttctttgc tctcctgtct    840
agggtggcga ttatttccca acccacttgt tccattacac tcaaaacctg ctatcaattt    900
acag                                                                 904
```

<210> SEQ ID NO 113
<211> LENGTH: 543
<212> TYPE: DNA
<213> ORGANISM: Haliotis tuberculata

<400> SEQUENCE: 113

```
gtgagacatt attacacttc tatttagtag tgggggcggg atagctcagg tggtagagcg     60
tcggccttca gcttctagtc tcgcccacaa gagcgcgctg gctaaagggc cggagttaga    120
ttcccgcggg cggcaggcaa tatctccgaa ggggagaaca gttctccagt cggtgaaatt    180
ggggtgcaat gttgtaccac tgaaatgcgt gcagcaccaa ccatccaaat accagccttg    240
```

-continued

```
ccgcgctggt ctgactacat agtaccaccc ggattcaacc gggctatata ggttctcctc    300

cagcagtaaa tctgacagtc gccatatagc tgggatattg ctgagtgcga cgttaagccc    360

caactcactc actttatatt tagtattcta tttagtatcg acgcatgacc atgtgtggtg    420

gtctactcat ctcaacacga ccgattaacg ttaagagctg ccaacatgat tctctttctc    480

tctttagcct ctttatgcca aaagctatat attaatgtag gaccctacat atattatttc    540

cag                                                                   543
```

<210> SEQ ID NO 114
<211> LENGTH: 2689
<212> TYPE: DNA
<213> ORGANISM: Haliotis tuberculata

<400> SEQUENCE: 114

```
gtaagttgat tgtcttaata ttgttttaat ttttgcagaa atttgatttt aaattgtgta     60

ataacagtac acatttttac gcaacagcag tcattattgt gtgtgaagat gtcaaaccag    120

aaaggtttca atcgtgaaaa caaaaacaat tctctatctg tataccccctc aataccagta    180

tgatcacaaa tctaggaaat attacaatac tgcttcatag agtaactgct gtttgtggca    240

gagctggata cgaagtttct gatagttcac agctacatga tagtaaatga acctgtacac    300

atcaacggtt gatcatgaaa attttgtatg tgtgaaagtg ctacctgtat tagtgaacgt    360

gctacctgta taactgaaag tgctacctgt atgactgaaa gtgctacctg tatgctgaaa    420

gtgctacctg tattagtgaa cgtgctacct gtataactga aagtgctacc tgtatgactg    480

aaagtgctac ctgtattagt gaaagtgcta cctgtatgag tgaacgtgct acctgtataa    540

ctgaaagtgc tacctgtatg actgaaagtg ctacctgtat tagtgaaagt gctgcctgta    600

ttagtgaaag tgctacctgt atgactgagc gtgttacctg tatgactgaa cgtgctacct    660

gtattagtga aagtgtaatc tgtatgagtg aaagtgctac ctgtattagt gaaagtgcta    720

cttgtattag tgaaagtgct acatgtatga ctgaaagtgc tacatgtatg aatgagagtg    780

ctacctgtgt gactgaaagt gctacctgta ttagtgaaag tgctacctgt atgactgaac    840

gtgctacctg tattagtgat agtgtcactg gtaccaactg gatgttctca cttctttggc    900

gaatatctgg gctcaaaaca gtttttcagt atcatagtcg tatcagtttg atttgtatgt    960

gcagtggaat cattttcgtc aaataatcaa aactggtgtt gaactggcgt tcacgtttta   1020

tggttgtaaa acaaattctg taagtaaaga tattttaggg atatctgtat gacatgaact   1080

gaattgctta aggttagcat gccatgacaa attgctgaat gtctgaggat tggtggagca   1140

ataaatcatt attaagacaa aaatcagaaa cgtccatttt cacttttaac agtgtatctg   1200

tctgaatgcc ccctactttt tggaagagta tatatgaatt atcggcaata taaaacgtta   1260

aatggcaaat gtcgggcata tgtcaggaca ttattaccgc agtttatagt catatttacc   1320

gggtctagga caattgtcac cccgacaatt gccacccgga caattgccac ccaaaaataa   1380

aatatacgta aacagaaaac aaatattgct ttcagccttt attgagttag ataatgacat   1440

ttatgttgat aaatatgtcg tttgataata ataataacaa taatataata ttacaatact   1500

gcaatagtac tatcagtact tatcatttta tcacagatta tatatagatt ctagagtccg   1560

atgttgtagg caacacttcg tcggtaggcc gttaggtagt tatcattagg gctgagtatt   1620

gcgccaaatt tcgtattgct atatactgcg atacacggtt acctgttttg caatacgtaa   1680

acttaggcaa atatgacagt ttttccatga ttattttcac gtttcaatgc ttaaaatggt   1740

cttatctgtt atctccttga aggtttaata aaataacaat aaacataaat cattattgaa   1800
```

-continued aattaatgaa caaaagtaaa gcgcttctca gttaccttaa cctaacttat ttatgaatgg 1860
gattactatc caagaatgtg aaattcacaa acaccttggg ataacactgc aaaacgactg 1920
ttcatgggac ggacatgaaa aaggtgagtc ccatgttaaa ctgttgagaa agtttcctat 1980
actgtttgtc ccgaaaaagg ctaaagacca tgtactaatc aattattcta tctattttcg 2040
attactgttc tcatatttgg gacaactgtg cagatcggta gcatccaagc tcgtctaaat 2100
cggtttgata aaccttgtca aataacatgt tgtctcaaca tccaagctca cctaaacctt 2160
gtcaatacct gcatctgaac aaatgtatat ttaagacgat agcatccaag ctcatcttta 2220
aaatgaatat tttctctttt tctaccaaaa cattatttgg ttgacagttg tcctccctat 2280
tatagtaaaa agaactgggt ggcaattgtc ctaggtggca attgtccgga tggcaattgt 2340
ccgggtggca attgtccggg tggcagttgt ccaggtggct attgtcctgt tcccatattt 2400
acgtatccca ttttctgctc tgtaatttta aataaactca cctgcctaag gtaagacgac 2460
atgtgtcacg tgaacatcgt ttgggggcaa gggcggaatc ccttcgttga aagtaaatga 2520
atactgtaca tagagatgcg tatcttgaac tctttattag ctttgatatt gtgcttaata 2580
ttacatgaat gtatttcaat atgtaattat gtgttcaaat gaatggttga cttgaatggt 2640
tttattgctt tatatgctac atcaacatgt gtgtttcttt tcatttcag 2689

<210> SEQ ID NO 115
<211> LENGTH: 561
<212> TYPE: DNA
<213> ORGANISM: Haliotis tuberculata

<400> SEQUENCE: 115
gtaagtaaat ttacaaaatt tggtgttctc taactatcct aagtattcaa tcgttagcgt 60
gtacctatct gcataatgca ataccctgac tccatataag tatagtatat ttactctggt 120
cgaaaacaaa caaattgaaa acaagagtgg acgtgctgtt atgatttctt tttcattctt 180
ggttcgttgt gtaatgccac agccagcaat tccagatata tagcgacggt ctatgaatac 240
tccagtctgg accagacaat cgtgtggaat ggtttaggca cattatatca aattcattgt 300
tgaagatatg agttatgagg tcacaatgtt gtcttgttac cccgtgtcag tagtgacgtc 360
atttcatgac tgaaatctct tcaacgccgt ttagcaataa taggctcagt agtattcaac 420
caattacaat cagtagaaaa ttctctatac tattcttatg ttgcatcctg atatccctat 480
gcaaaaatta gtcatctaat ataatcattt tcgataaata ctttgggcaa acaaatcaat 540
gtaacatcta ttttctttca g 561

<210> SEQ ID NO 116
<211> LENGTH: 334
<212> TYPE: DNA
<213> ORGANISM: Haliotis tuberculata

<400> SEQUENCE: 116
gtacgtggat ttgattacat agcaatgcta tatgatttca gtaattacaa cctcaagtca 60
tgtagccgtt ttagattgca ttacatcaaa cagcattgga ttaaattggg ggattgtcca 120
ggccgcatta tgttgcattc cgaaaatagt ttgtgtccag tgtccacgtt taaaattaaa 180
ccattttaat catattaggg ataattttaa tagatgttat agtgctttat ttcatattgt 240
tacagtggac agtcaccaag gacatatttt actctataga tacacaaaca ccaattaaaa 300
ccctgctttg gaaagtctaa ctttttcccc acag 334

<210> SEQ ID NO 117
<211> LENGTH: 283
<212> TYPE: DNA
<213> ORGANISM: Haliotis tuberculata

<400> SEQUENCE: 117
gtaatgccat cttaatacag ttcgttcgtt aaattatata tgttcgttta caacaccata 60
ccttgaattg aggtaataca tcacttgata ttgataatgt aatggtaatt gttcttgttt 120
gtaaaaccgt ttctggggtg tttattcact atccacctgg tggatagtga gtaaacacat 180
tcggtttaat atgggtatct aatggacagt gaagtgtgct ggctaggcag ataccttggt 240
ttctgtgaat ggaggtagta gaaaggggtt ttgatgattg cag 283

<210> SEQ ID NO 118
<211> LENGTH: 174
<212> TYPE: DNA
<213> ORGANISM: Haliotis tuberculata

<400> SEQUENCE: 118
gtgagtacct gtttgcacta agacttctgt aggctaaaag tgtaagaaat atcaattaat 60
ttcaattcac ccaaacttga aaacggtacc tatataggtt aacttttttgt ctacagtaaa 120 ctgaacatac ctacacattt catgaaatga tctctcaata ttttccacca acag 174

<210> SEQ ID NO 119
<211> LENGTH: 703
<212> TYPE: DNA
<213> ORGANISM: Haliotis tuberculata
<220> FEATURE:
<221> NAME/KEY: misc_feature
<222> LOCATION: (478)..(478)
<223> OTHER INFORMATION: "n" is a, g, c, or t

<400> SEQUENCE: 119
gtaaatttac agagctttat gaagtgtgtt cagagtgaag agaccaagat atacttatac 60
ccaaaactag ctagcaacag acgatttcac ttgtttcgga cactttgtat tatacgttgg 120
atcccaaggt aaacggaaac gtaaccgaga atcagtccgt aaagtgagtg agtgagtttg 180
gggcttaacg tcgcactcag caatacccca gctatgtggc gactctcaga tttactgctg 240
gaggagaacc tacatagccc ggtttaaccc gtgtggtatg tagtaagacc agcgcggcat 300
ggctggtatc tgacggacga agggtggcgc tgcacgtatt ccagtggtac aacactgcac 360
cccaatttca ccgaccggag aactgatctc cccttcggag atatcgcctg ccttccacgg 420
gattcgaact cggtgacctt caagccagcg cgcttctagc gggggcgatt agaggttnaa 480
ggccgacggc tctaccacct taactatccc ccggccccac tcctgacgga aatgtttata 540
attcagcctt tgttttctta ttaaacactc ttggcagatt ttctatagat aatggattca 600
catgtagaca gtctcccatt gttgtaactg gtagtcaaga gttagaatct gaatacattc 660
tccaagatgg atcaaggaaa acaataatta cttgatgttg cag 703

<210> SEQ ID NO 120
<211> LENGTH: 298
<212> TYPE: DNA
<213> ORGANISM: Haliotis tuberculata

<400> SEQUENCE: 120
gtgagatata tgcaaattga atgttgtcca gatgcgttgt ttacatttat atgcttggaa 60
ttgtcctgaa cgaatacagt ggaataacca aaagctgaaa aataaaaaga tatatacttc 120

-continued

```
attctgaatt tgtcagtatt gctgacccaa aaacacgtta tccatgtcga cactatattt    180

gcctttctga atctgagact gcgttatgtt tctaataatc acgaaatatg gtatacaggt    240

tgtgtatctg tagaataccc aaggcagaat ttaaagggtc acaccctgtt taatacag      298


<210> SEQ ID NO 121
<211> LENGTH: 963
<212> TYPE: DNA
<213> ORGANISM: Haliotis tuberculata

<400> SEQUENCE: 121

gtaagtttgt gttggttagt gttggttgca tgttttgcca tatcgatagt atcagtgtgg     60

taacatctgg tttctagttc attcagttca ccttatcaga agctgtttgc tctcgtctac    120

aatagtgacg tctttcagtt ttagaaccgt gtacatccgg gttatattgg tctccagcaa    180

cccgtgcttg tcgtgggagg ccactgatgg gaacgggtgg tcagactcgc tcacttagtt    240

gacacatgtc aattgcgaag atcgatgctg aggttgttaa acattggatt gtctggtcca    300

gactcgatta tttacagaca gccgccatgt acctggaata ttgctgagtg cggcgttaaa    360

caacaaacta gtcagactaa tctttcactg tttataatga tggctcgaac ctagcactca    420

tgtcccaagt tggcgaacat ctggaaggga atttcaaatg aaaagaacaa tctttcacgt    480

ctattggtat cacgctcctg gagaagaaca tgatgttcac ggcgttactt cctcttacct    540

gttttacttg ttcccacgtt tcttcatatt taaagagtat ttgggtatta gagctttggt    600

gctgttacaa tgctactcaa ctgttcagtg cgggcgaccg cgcttgttta cacattaagt    660

tttgtttgtt ggttggtttg tgtgtgtgtg tgtatgtgtg tgtgtgtgtg tgtgtgtgta    720

tgtgtgtgtg tgtgtatcta tgtctatgtg tctgtgtctg tgtgtctgtc tatgtgtgtg    780

tgtgtctgtg tctatgtgtg tgtctgcgtg tgtgtctgtg tccgtatgtg gctgtgtcta    840

tgtgtgtgtg tgtctgtgtt tatgtgtgta tatgcgtgtg tgtctgtgtc cgtatgtggc    900

tgtgtctatg tgtgtgacat gcaatacatg ctgtgatact cactagctgc gtctatcgac    960

cag                                                                  963


<210> SEQ ID NO 122
<211> LENGTH: 650
<212> TYPE: DNA
<213> ORGANISM: Haliotis tuberculata

<400> SEQUENCE: 122

gtaagagcgg ggtagggatg gggtggtagg gggtgggttg ttctattact tcccgcttca     60

cttgtatgaa atggataacc ttggctgcat cccaattgcg tgatcgattc tctttcgatt    120

cactcgtgcg attagactgc cttatttact atagtagtta gaatgttgct cagtgcgccg    180

ttaaacaact aatacacaaa accgcatttg ttttatatgg tcactctact gtttatcacg    240

tatatgtatg ttccgactca ctggttggtg cgtaccattc tactgtcaca ctgagagcca    300

atgttctcag atgtgtgaaa tgtttgaaag ccgtttctac ataatattgc aggaatacca    360

ttgtagaatg tagtcaaaca ggtaacaatc tgttagtgag cccagttcga ggttgcgttg    420

tagggtgtag tccaacaggt aggcagtcca taagcatagt ttttaagcat tttagatcat    480

ctataattaa ccacatggtt agccgctatg tttagtttaa tccagtataa gttagaactg    540

ttatatttcg aagggaagtg agtaaatcct tattccttga ctaccattta atagatttcc    600

caatgactcc attcaactcc taactttcac atcactgctc tcttcaacag                650
```

-continued

<210> SEQ ID NO 123
<211> LENGTH: 583
<212> TYPE: DNA
<213> ORGANISM: Haliotis tuberculata

<400> SEQUENCE: 123
gtgagtacga caggcatttc tagtaaaaac ctacttttgg taaaaggttc gagaaatcac 60
ttgaagcaac aacatgattt tgtaacgcct attacacgtg aacatgtcac acccggtgat 120
gccgtttaat ggacatgcct ctgttaatga aaggggtaag tacatgtgta tggggatggg 180
atgggagcca cctgtcccaa tttcataggt ccctaggatc ccagttgcgt aggaatcccc 240
tgattaatgc cttgtgaatt cctcctggaa ttgtcctggc ccaaattttt acaaacccgc 300
cccgatatac cttggaaata attgggccta agggtggggc ttttaaggac caagaaccca 360
acctaaaccc caacccattt tttcccaccc attccaggtt ttgttttacc aaataaaaag 420
gtttccactt tgaggaaacc ctttaagggt tcttttcagg gctttttttc ttttctggga 480
attccaattc cgggggaaca aaatacatat atttcacaga cctttggtca aatttatata 540
atttccgact tcatgtcata ggtttgtctt tcttcctaca cag 583

<210> SEQ ID NO 124
<211> LENGTH: 475
<212> TYPE: DNA
<213> ORGANISM: Haliotis tuberculata

<400> SEQUENCE: 124
gtgaggagaa ggccccaggc tagcagggca atggatgaag gaaatagggg caaagggaat 60
agcagttaca ccatcgacat ttccaacctc ctcagaaact aatatatagc cttaatacaa 120
ccagccaaga ctcaacgggc agccggggtg gggggatttg gtggtcgctg tttcagacca 180
gggtgcaaaa tatcagtgcg caaatcaaca tgttgcgtgt cagacactga cacagcagtc 240
attgaacctg cagacccata acaggaaaat ggggcagata cgatcaaaga cagtgtaaaa 300
tagggataag taggcatatg caaccacctg atggaaatga aaaggggtaa gtttaaaccc 360
cggctaccaa aggtccaatg gttccttaac ccagcttacg ctatccctct aatttcagta 420
ttgagctgat ttctgtcgag ttcatgtaaa ctgtatactt tctgtattat tacag 475

<210> SEQ ID NO 125
<211> LENGTH: 1002
<212> TYPE: DNA
<213> ORGANISM: Haliotis tuberculata

<400> SEQUENCE: 125
gtaagggatc tcagatccgt cagagtgagt gagtgagtga gtgagtgccc agcaactgaa 60
gctaggccgc cctactgggg atcacaggga atgtatgtca atggttgaag aaaggagcag 120
tgggttacaa cgccgcgttc aaagtcatgg cagtttcata gcgcattgtg cgcgcgtgtg 180
tatctgtgtg cgcgcgtgtg tgcttgcgtg cgtgtgagtg agtccgcttg tgcatttgta 240
ctagcacaga ctaatgctgg ttctagagag cctactgata aatgtttaca ttaagatctt 300
tacagtatac tgagattcga gcccagacca gcggaacacc aggcagggta acaacaaata 360
acgcctttcc acacaaccga cgcagcctaa agtggctctg ataggctgat accggtgtat 420
tcttagaact tgtaatttgt gctttgccat aatacatgta cttcagttaa ctgtaataca 480
gcataagact ggaccggtgt ttacgacgca atgagcaata attactctac gaaaagattt 540
ggttagacat attcaataat tgtaacattc attaacaatg aacaccacgt gcactctcgt 600

-continued

```
ttgtgtcaac gtattcataa tcattctcat gcatctgtta gctcagatat tttgatgttt    660

caagagattt gtacgaacgt atgggctggt gccccatgaa attacataca atgaattcag    720

gtgaaatacc tggcgagaca ataagatctt actagtgctg ccacttcagt atggtgtccc    780

cgatggtgtc tggtgtatgg gtgtgtttgg cgtcagttgt tactggaaaa gtcagctcta    840

attatgtctt tatgtggtta aagaccccat aacctagatg tctgggttta acttaacatg    900

atagtaacag tcggctgtat agcctgacgc ttaaacgtta gatgaataag gactatattg    960

tgttgtataa catttctata acctcctttc tatatcattt ag                      1002
```

<210> SEQ ID NO 126
<211> LENGTH: 597
<212> TYPE: DNA
<213> ORGANISM: Haliotis tuberculata

<400> SEQUENCE: 126

```
gtgagtcacg ttctctgatg gtcacgagtc acgttctctg atggtcacga gtcacgttct     60

ctgatggtca cgagtcacgt tctctgatgg tcacgagtca cattctctga tggtcacgag    120

tcacattctc tgttgagtga agtctcagta ccatttattt ctcttacctt cttctaacca    180

ggggtttcag cgtggatcgt ctgagaagtt agcgcaaatc tatattgaag tcatttttct    240

atcatataac catcgttata tccacgtgcg aaagtgttca ttaattattt ttattttcat    300

ttatgaaggt ctaaaagaaa atatgtattg ttggaaacta tattcgaagg tgaaggcaac    360

acgagtgtat taatattctc aatatcaatg tacgctctgt cagcacctgt ttcaccagga    420

actacacctt tagcgtacca aaatatcagc tgatgatttc gaagcggact ataccctcac    480

cacttgtttt gtgtgtgtat ttatgtgtgc atgtgtgtgc gtgcgtgcgt gtgtgtgtgt    540

gtcctacgta tgttgatatt ttgttctgac tgtatatgtt cgtgcttacc attgaag      597
```

<210> SEQ ID NO 127
<211> LENGTH: 689
<212> TYPE: DNA
<213> ORGANISM: Haliotis tuberculata

<400> SEQUENCE: 127

```
gtatgtatga ttctaataat gaatgttttt acctccggtt taaacaatat tttagtatta     60

cgaaaggaga agtacctcga gaggtctagg tctcagatgt ttagaaaccc atgaagacag    120

gtatgcttct gaaaaacaaa gtaacatcat gaggctaaag ttcagattca aaccatcgta    180

gttcgaatcc agcatgcaaa gggccctaac cctgtagatg gcgctgcttg aaacagagta    240

gtctgttcag ggtcagtact gtccccacaa acatcatagt cagggtcagt actgtcccca    300

caaacatcat agtcagggtc agtactgtcc ccacaaacat cacagtcagg gttaattttg    360

gattcggttt cgaatgcgaa gaagacagtc acgccctgac actggaccga ggttgccgag    420

aaagctcgtg atattgctgg aatactgccc agtaaaacca tcatttattt taggctattt    480

attacgaaaa ataataatat gtatagaaat gcatatgatc gctgtttgaa tgtaaaattt    540

agaatgggtt tgggagtgtt cactattttt tcatcaaaat ttcatgtatt ttaaccgatc    600

gacgctgaag acaaactacc gttaatcagg cagttcattc atatctgata gggaatattg    660

gttgttaacc aacgctacat tgtgtccag                                      689
```

<210> SEQ ID NO 128
<211> LENGTH: 846
<212> TYPE: DNA
<213> ORGANISM: Haliotis tuberculata -continued

<400> SEQUENCE: 128
gtaaatggcc attgtataca tgcattcatt tggactttga gtgagtgagt ggatgcgtat 60
tcagtaagtg agagtgtgag tgggtattag gtctgtgagt gggttggtga gtggatgggt 120
gagtaagagt gggttggtga gaaagtgagt gagtcacttg gtgggtgcgt tagtggaagc 180
gtgattgagt ggatgggagg taggtgagtg agtgaattgg tgggggggtg agtgaggtta 240
acgctgttct gctgttcaat cacaccacat gttgccagct tactgtgcag gacgaatcca 300
gggttgtgtt aaattttata tgtttatata taacgatgga cgtgtctgga tgtggcgaat 360
gtgtcaagag aattatgcgg ctttgtgctg ctccgcgtat ttattgcacg cgcgttggta 420
cgcggttgat aaagtagttc aaaacatttc ccagccatct ttgtctgttg tgaaaaccta 480
ctccaggacc atccatttca atatgtgtct gcgttcatgg agttatacat gttaaactgt 540
agagcgcaga tgagcacact tgagcatttc ttcagtaaat cagaatgtgt atatttcaaa 600
atttaccaaa tgcaatatca tcaagcaaat tatgcagctc tatagtaaca tcggagtcaa 660
tggtccagtg tgccctcggc tgccattccg acctccctgg ccagaataca ccccggtcag 720
gatcagttat ccgtcagaag gcacggtgcg gaatgaaaac ataaacacat agtcgcttag 780
tagtatgctg atttaggcac gcaaaatccg aatgtgaatt actgtgaatt gcattacctg 840
ttacag 846

<210> SEQ ID NO 129
<211> LENGTH: 474
<212> TYPE: DNA
<213> ORGANISM: Haliotis tuberculata

<400> SEQUENCE: 129
gtaagtagct acctgtttat tcaatttttt cgctttgcca atcaattcat tcagcttgaa 60
attcaataat tgtgttttgc atggctgaaa accaatttga actcttttct tttctcaggt 120
cgaactcaaa taaataatca ctaattgtta tgcacgcggg tagggcatac atactatatc 180
cacatcggtc atctcaaaat gcaaacaaat tgtcttattt ccgttgggac aagcaaaccc 240
cctttcctgt aatcttgcct ttggcatcca ctggaattaa tgttgactgg taattgatac 300
tggctctctt cttgcataga gttaatatct atagtttgta aatctttatg attttgctat 360
ttatatttcg acagcatgct atagacaccc tagactattg tatagccact tgtattgttt 420
ttccatttat tatttataac agaacatggc ttgtaatttt tatttacctt ccag 474

<210> SEQ ID NO 130
<211> LENGTH: 290
<212> TYPE: DNA
<213> ORGANISM: Haliotis tuberculata

<400> SEQUENCE: 130
gtgagaacat tgataatagt tcaaatgaag tatatccgat tcaagctgtc gatacaagat 60
gagatacata atcacaatgt ttgtattaga tatctctctt aatttaatgc cgcttttatc 120
aatattcgag caatccttca gcaacataca ccagcaaatg tttcatcaac agactatatt 180
atttaatatt ttaaaaatcc ttctctgttg ttataaatac ttaaagtatc gaattccttg 240
aatgcgtctt ctctgcagca tatagttaag ttgttgtgtt tctctgtcag 290

<210> SEQ ID NO 131
<211> LENGTH: 298
<212> TYPE: DNA
<213> ORGANISM: Haliotis tuberculata -continued

<400> SEQUENCE: 131
gtaagaaagt ttcactgtct aaatcttttt ttatgataga gggtagagaa gtggagacaa 60
tgtgacaata tattgaataa agttgtttaa aatttataac tctcataagt tcatattatg 120
ctgaagctgt agccatctat aactgtgtaa catgaaatgt taagacatta acctaaatac 180
ttcagctgat aacaaaacaa tgttaataca tacgtcaatg taacattttc ttatctttag 240
gttatagcat aaacacttca gagatacagt gacgaaaacc tctatttaaa tatttcag 298

<210> SEQ ID NO 132
<211> LENGTH: 189
<212> TYPE: DNA
<213> ORGANISM: Haliotis tuberculata

<400> SEQUENCE: 132
gtaagtagta aactgctcag attgttttca taattactcc actattaagt aaaaagtact 60
agtaattcaa tagtactgtt cacagagaaa tgtaacacaa tagaccacag agtccatttg 120
ttaaacgcct ttggcttggt aagtctgaga ttttggtgac tgatggaaag ctaaaatata 180
ttttgacag 189

<210> SEQ ID NO 133
<211> LENGTH: 821
<212> TYPE: DNA
<213> ORGANISM: Haliotis tuberculata

<400> SEQUENCE: 133
gtatatttaa gtattttatc ttacgcatga ccctgaccct atttattttt ttttaatcct 60
cggatttgtt taatcctgtt accagcgaag gtccgggtta gaattgatct tcagtcaact 120
attcttgtcg taggactaac gagttgtctg gcttgcttac tcggttgaca cgtgtcaacg 180
gatcccaatt gcaattagat cgatgctcat gctgttgatc cctggattgc ctggtccgga 240
ctccacatac cgccgccata ttgctggtat attgtcgaat gcgacgctaa acagcaagcc 300
aaccaacaat actgagacct ggtggtacat gtcagttctc tattgctggg gttccaaaca 360
tagccatcag ttgaaatatt tcatacatag aagaatacct ctgaatatga tgatgaaaca 420
tttacttaga cttgcctgtg agccccaggc aaaatgcact gtaaaaatac actgacagag 480
gattaggcat tcttgggagt actgtatagt tagttgcata catattagcg ttccctcact 540
aaaacgaatc tctgaatgct atcaattaaa gatcatgatg ctttgattgt gtctactgta 600
tttaaaatgg tgttaagatt tgcaattaca atatacacaa acacgtttcc tgcatctcgg 660
agaatgcaat ctttcgttgt acgcgtctgt tttcatattt ttatgcatgt agtttgcact 720
acttagcgtc caataaatcc attcacaaaa tcacacaaac aaacgatttt aggaatgtga 780
ctgtagctgc aacgaatata cctgatcctt tcttgttcca g 821

<210> SEQ ID NO 134
<211> LENGTH: 866
<212> TYPE: DNA
<213> ORGANISM: Haliotis tuberculata

<400> SEQUENCE: 134
gtgagagaac cagtaatagc tactgtctac aaagaatgtg ttcatttaaa gacctgactg 60
taggccgatg gctgctgtca tctcctccgc ctcctcctcc tgttcctcct ccgaaggggt 120
cagcttcagg ttctcttgcc aatatgccaa gcagacctcc tgagcaggca gtatatatac 180
gtaagggaag caagtatgga ccatcgcgcg gcatgtagag atacaatgat cagctgtctg 240

-continued

```
ctgttccact cctgtcagac aatgagataa acatgaatac agtattactc agcagcgttc    300
caattttcaa ccctcgtatt tattaaaaaa aggaattttt aatatatttt tctccttgtt    360
gaaatatttt agtaactgtt aatcgatata gagtggagta gtgacgcttt atttcggttc    420
attctcgaaa caaaaatata atagtccact gaactctctt aaattgtttt tacaaccttc    480
aactgccaca gacgtaatcc ctcacgttat tttgagctga caacgtgttg aattgagtgt    540
gttccgaatt ctaaataagc atgtatatat ttacgtctca tgcaagtaat atatgtttaa    600
ctgatgacgt cacttggtga ccactgattt agttcctttg tcataattgc agtttctgtt    660
gtcacgggga cggtggggaa gccaggttcc tcctgtcacg ctgaatatcc cgttcgaatc    720
ccccacatgg gtacaaagtg tgatgcctat ttctggtgtc ccccaccgtg atattgctgg    780
aataagtggc ttaataccat atacactcac tctattgtca cactactgcc accggctcac    840
acctctgatg cttctgttct atccag                                         866
```

<210> SEQ ID NO 135
<211> LENGTH: 785
<212> TYPE: DNA
<213> ORGANISM: Haliotis tuberculata

<400> SEQUENCE: 135

```
gtaattaatg gatgtgaagt caatgtccga gggtataata aggatttaaa tacttcagtc     60
gtgtaatact gtatgacatg tgtattggat ggtgtaggta ttacaggtta taaggccagt    120
gtgtgttggg acggttactt tcctgcacta gtaataagca ttgtatttag ctagctttta    180
tcatataact ttagtttcat ggtttgtggc aattgaaatc gaaattttct ttcatttcaa    240
ggttatcgca ctcgtgtgtt agaatagtta ctatgctgca ttgagaataa cactatagta    300
ataaagcata tcatacagta agaataacac tatagtaata aagtatatca tacagtaaga    360
atgtcattgt atgataaata ggttatcaca ctcgtgtgtt ttagaatggt tactatccca    420
ggaataacca ctatgtatta catgtatatt gggcagtgta agtagtagca ttgtatatta    480
aatcagtata tcgtgcttca aaacaccagg atatatgggg tatacagtgg gcagtgtaag    540
tagcaacatt gtatattaaa tcagtatatc gtacttcaaa acaccaggat tatggggtat    600
acagtgggca gtgtaagtag tagcattgta tattaaatca gtatatcgta cttcaaaaca    660
ccaggatata attcagtata tcgtgcttca aaacaccagg atataattca gtatatcgtg    720
cttcaaaaca ccaggatata tgggatatac agtgcgggtt tgcatacaac ctccaccctt    780
tacag                                                                785
```

<210> SEQ ID NO 136
<211> LENGTH: 378
<212> TYPE: DNA
<213> ORGANISM: Haliotis tuberculata

<400> SEQUENCE: 136

```
gtcagtttag tctcctgtct gagctaacga taccaatttc ctattttcga gaaccacgat     60
gacgagaaaa caagcaatat agatatagat gcagtataga tcaagttaat gaattcattg    120
ctatatgttt gcttgtaata aactttaaga aaacgagagc atgcacacaa atgaaacaaa    180
caattatgtg tttgatagga atatgatata tgtatttggg ggctgacgtg agcagggttg    240
aagggacagt ttacattgtc agtaacactg ggagtattct ttgatccaca atatatagtt    300
tcattgtgtt cagcagttac aactaacatt atatcataca ttacgtcgta acatgcttct    360
tttgtcctct tctgccag                                                  378
```

-continued

<210> SEQ ID NO 137
<211> LENGTH: 398
<212> TYPE: DNA
<213> ORGANISM: Haliotis tuberculata

<400> SEQUENCE: 137
gtatgttatc ttattatcaa atgtgtaatc agatactgga gacgttttca tattaacttg 60
gtcagcatta gttgatgatt ttggtgcgat attgacgaca aggagttaag cattaacacg 120
ttcaacacat ctttaatctg atatgagaag ggaataaatt gatccagtat tgatgattga 180
agttagatta acagtgaaag atataccagt tttgataatc gtataaaaca gtagcagaat 240
tgtatcgtga aaactaaatg tgggaaggcg aacgccaagc agattttaga ttacgatcgt 300
gtgctagaat aattcacaat aacccagacg tcggaaatgt ggttgtctat ggcaatagtt 360
acgattaatt gctaacatgc acgatttacc tatttcag 398

<210> SEQ ID NO 138
<211> LENGTH: 522
<212> TYPE: DNA
<213> ORGANISM: Haliotis tuberculata

<400> SEQUENCE: 138
gtgagataag aaacccttct aacagtaata cgacaccaca ttacagctta aacatgattg 60
ccatcgatgt tttcatgtgt agtatacgct tttcagttct acataatttt gtttttcaaa 120
tcaagtttag caaatgaatc tatcactgga aaatagggta gggtagccaa gtggttaaag 180
cggtcactga tcacgccaaa gacgagtgtc ctaacctgca tgggtacaaa agtgaagacc 240
attgctggtg tctaccgccg taatattgtt tttagtattg ctaaaactta tactcaccca 300
tgcgctgtaa aagtggaata ataatcatat ttcaacaaaa gcacaaaacc atttcatttt 360
catgaaagcc tcttgttcac ctgaaagacg caagagaaca atagttccta acattatttt 420
cagacattgg aaatgtcctg cacgtgtaaa ccatatatcc tttgaaattt ttacgactgc 480
atcgtataca atttatgata taaatttaaa actttatttc ag 522

<210> SEQ ID NO 139
<211> LENGTH: 673
<212> TYPE: DNA
<213> ORGANISM: Megathura crenulata

<400> SEQUENCE: 139
gttttgtaat aattatgtag aattctttac ctcagaataa gatgaggtca catgggtttt 60
gcaaaactat tacgttcgaa ttaatattaa taataccgga ccctccactg gtacatattt 120
atctttataa cgataatagc gatgatgatg atgatgatga tgatgatgat gatgatgata 180
atgatgatgc cggtattgca cgtaatccag ccgacttaga tgacacccta agggtgcaga 240
aagtataaca attagattgc gtttgcatct gtgtatgcgt gtgctttaac caaaagtcaa 300
aataaaagtg caaaccctta gtttattcat ttgatagagc cttttacgat aagaacaatg 360
taataaatta gaacataact gaaacctccg aaagaaggcc tgtttgtcaa gagaggtatc 420
gacatgattg acttataaac ctgtgcttct atattttgga actgtccact ttcttgttgt 480
gtgtactgta atcacatcgc actatggctg caagacgtgt acgagtacac tatatactta 540
cctaatgacc aaccacaagg ctggctttgt taatattgtt atttcacaga aataaacaca 600
gaattccagc atttggctgg tgtatttagc aaaacaccga tatgacactc atgttttatt 660
acattttttt cag 673

-continued

<210> SEQ ID NO 140
<211> LENGTH: 273
<212> TYPE: DNA
<213> ORGANISM: Megathura crenulata

<400> SEQUENCE: 140
gtacttgtta tatgtttcga atattgccga taccttcaat atatatactt tatcaaagta 60
attgattaat ctgaagtaat tttcctttcc agtagagatt cagttgatac aacaagaatt 120
cgccctgttg tatgtcactt tattttcatc aaacgattcg aagtgagctg tccatgccac 180
aatggggtct ctgtaacttt ctcgtatggg gtatagatta tatagacgtg gcagacctta 240
cgtataacta atatttgtgt aatgtcgttt cag 273

<210> SEQ ID NO 141
<211> LENGTH: 241
<212> TYPE: DNA
<213> ORGANISM: Megathura crenulata

<400> SEQUENCE: 141
gtaactattt tgtcactgta accaacaact gcagtctatt ttgcaattac gataataaca 60
atttttgaaa tatatcttta ttaaagcaaa ggtttctaga gacaaacagc cggctctaat 120
tattttttcg aacttacgct tgagtaaaga tctgcaaatg gcaaccctac ctatactatt 180
aaaaatataa tgttacattc gtatctgaat gtttaataaa tcacttcata ttctgttgca 240
g 241

<210> SEQ ID NO 142
<211> LENGTH: 327
<212> TYPE: DNA
<213> ORGANISM: Megathura crenulata

<400> SEQUENCE: 142
gtaagtatac acacattatt tctcttctgc tatatcagat gaagagaacg ttgtatcact 60
aacctagtct tgtttgattt gtggtttcgt ttgcttcctg aacagtaggg ttgatttaac 120
ttctctgttt cgtctgtacc aatgaaagac tatgatgctt gtgtgaagat gctttgttca 180
tgagtcagtc tgttcttgta atgctttgat ctttgccatc aacattcttg aaattaatta 240
tggtttccct taaatactta catattacat ttaaacgtcg ctgcttgtct gattgcatat 300
tctttcaaaa ataactatat attccag 327

<210> SEQ ID NO 143
<211> LENGTH: 958
<212> TYPE: DNA
<213> ORGANISM: Megathura crenulata
<220> FEATURE:
<221> NAME/KEY: misc_feature
<222> LOCATION: (584)..(584)
<223> OTHER INFORMATION: “n” is a, g, c, t
<220> FEATURE:
<221> NAME/KEY: misc_feature
<222> LOCATION: (596)..(596)
<223> OTHER INFORMATION: “n” is a, g, c, t

<400> SEQUENCE: 143
gtaaatatac agtgaaatcc ggataagtaa aatccagata agaaaaaaaa cattttctgt 60
ggtcccggca tgtttcttct tcatctatca ttattttgat acggataagt aaaaatcggc 120
tgagtaaaac atccgggtaa gtaaaatgat tttcgaggtc tcttcatcgg ataagtaaga 180
tacacaagtg atcattccaa taaacactaa ctgatgcaac acaataccag cgcacagtgt 240

-continued

```
tttcactacg tttgtttgta ttgtaattaa caattaacac ttaagtgttt cccaatgtgt    300

ccgtgtgcaa actgattggg acaaagcttg caacaagccc ggcaattcca tgtcgtttat    360

gtctacgttt gttattctga ctgcttggag gggttcggaa aaaaataaaa aacgggtaaa    420

tattataaaa aattcacggt gccttgaaat tttaggtgtc cggatttcac tgtagatgat    480

taatttctca cttgtaaaca aaaggacccc agtaccctca ttcgtgacgt acgttataaa    540

atgtaattat aaaaagccca ttatcatgtt atacgtgatc ttgncttgca attatnctac    600

cgctttcttg atttttaaa gcaatttctc cctctatgaa cttattaaca tagcactcct    660

gcaaaagaaa acagtcactg catggatcca tattgaatgt tgctgcttat ttctcatttt    720

attactcaca gatatttcaa gaacatcgta ctctctaacc aggctaaagc aaagagggtt    780

acattttagc cgacaagttc actagctgag tggaacacgt atatattaat ggagatgact    840

ctggtcatga tgattaggac aattatcatg acgttatcat tgatcatgac catgtcagta    900

taatagatag ctaacaaata atgtaattac taattatgaa gcaatggtgc atttgcag      958
```

<210> SEQ ID NO 144
<211> LENGTH: 868
<212> TYPE: DNA
<213> ORGANISM: Megathura crenulata

<400> SEQUENCE: 144

```
gtctcggtga gttattaaaa gaaacaaaat atttaccatt accattgtta actacaaaaa     60

tgagtgagat atcttatatc actggtacac tactgatatt ttatgcaatg aaattactat    120

ttttccaggt acgcttcaac ccctcccccc cccccccccc cccccccccc cccccccccc    180

cccatcatgc ttttctgtaa aacataaaac accaattaac aatgttctta gtgtgtttgt    240

tgactccctt ccactgcaac gcctacataa tcaaagtgtt cgttttttc caaactttcc    300

agttagtgtt gaagactaaa aagttaaata agcattcaca taacttctaa gagcaactgg    360

gaccatgcag ttacgtattg atatttctgt gagagtgaag caaaacactg tttttcaagc    420

ttaggtttat caatcaaaat gtccaatagt tcatgttatc gaaaaggcag cgaaggataa    480

gaggctccga gacatcttgt ctattctcgt gttcatatga tatcaactga ggagcttcca    540

ttacattttt gaccttatca tttaaagaca tacatggaac attttcattt tacagttaaa    600

gtgaaccact tcaggttcaa cttcaacttc gaattcaact tctgttgtgt gttttatgag    660

ccgactgaaa tagagtgcct tactttcact tctagtttcg ttctgtctcg tcatcgttgt    720

ttctttcagt gtgcatagta cacgcctagt atagaacaca cgaacttgtc cttacttaat    780

agattctgaa actattatgt ggaaagttgg caggctatag taacatcctg gcaaaattat    840

catgtatcct cttgtttgtc ataattag                                       868
```

<210> SEQ ID NO 145
<211> LENGTH: 1766
<212> TYPE: DNA
<213> ORGANISM: Megathura crenulata

<400> SEQUENCE: 145

```
gtatgtattt cccactggtg gtcgctgact gccaacacat acttgtaatt tattcatgaa     60

agtataatag tttgtttgaa agtatattta taaccatctt gcacaagcgt cacgaatttt    120

caccacaaag cttcaaaacg cccaaaacat tctaatagcg atatatttgt taaaagacca    180

aaatatagcc ttacaacaat agattatttt aataagacca gtcagtgcat gcaaatcgat    240

tggaaacttt gaaataaaat attctatgta ctaactgcca atctcataat acttgccttg    300
```

-continued

```
gatgtgcttc tttttcacat tcgcgtcgag cttcaactcc aatgcataag cttaaaaata    360
atcataaaca caaacaaata gccacagagg cgacgatccc tccaggccag gctttatttg    420
tctcttatag aatatatcgc tattagaatg tttttgacgt tttgaagctt tgtgggtgaa    480
aattcgtgat gtttatgcgt ggtatttatg taagatgaaa ataaatatat cttttcaaac    540
aagattttag tattttgaag acttctatga ataaattaca cttatgtgtt aggttattgg    600
tcactgagcg cttgtggtat tttcccttct tcaatttgtt tgttctttgt tcaatttcga    660
atagttatcc tactgtggat agtctatatg agaatcgttg aaagaataat acaattctaa    720
tggattgcaa cttctttaac ttttatttgc aactgccacg tttcggtata cgttcttatg    780
ccgtcatcaa gcatacgagt gtacatgtat gccaaaacgc tgcaaataaa aattaaagaa    840
gttgcaatcc ataagaattt caatgttctt tcatcatcac atcaacttct aaaaatgcct    900
ataaaacaat caacaaacgt acaatagtac attaccggat ctcgcagcat gaccacgtcg    960
atatctaaac aatatcacta tccattaata ggatcaagag taggtacaga catgttcagt   1020
tataaatact cttcaaaaaa gtaggggaac ttggaatttc aaggtcaata acaaactaat   1080
gataataaca attggtccca aataataaca attggtccca aactaattgt atctttacaa   1140
agaagaaatt gagtgaacaa ttcacccggt attttattac ctaaaccgtt tctcttgctg   1200
ttatggtgcg tgaaagaaga aatgggtaag aaacggaaat tgacattttt gcgtcagtgg   1260
tgcgtaatgc ccccattgtt ggccaaacac tgattgattc gctgaggcat cgtgcatacg   1320
cgtctaccta tggtaatttg atgcagtctg tcccattctt ccaccaacgc ctggacaagt   1380
tcatctagcg tggctggtgg cctttcacgt tgacgcacac gtcggcccaa gatgtcccag   1440
acattttcaa tggccagggc tcattgctgg tcagggcatc ctatggatat tgtgccgttg   1500
aaggtggtta tgttgttcac attgaaattc caagttctcc tactcttttt aagaggaggt   1560
tcacaaagta cgttctttca tgttggtgaa gagaatatca aggtcttcta agggattgtg   1620
tcttataata tttgatttta agaagtttga tattatctgc atccttccca agaaattgca   1680
aatgttcaca cactattgcg tttgataatg tttttgggga aataaactgt ccaggactgc   1740
taaatagtaa ttattgctac ttttag                                        1766
```

<210> SEQ ID NO 146
<211> LENGTH: 1049
<212> TYPE: DNA
<213> ORGANISM: Megathura crenulata
<220> FEATURE:
<221> NAME/KEY: misc_feature
<222> LOCATION: (290)..(318)
<223> OTHER INFORMATION: “n” is a, g, c, t

<400> SEQUENCE: 146

```
gtgagttcac gtaagcctac gagatcaaca ttactcctta acagccacgg catcatgtac     60
cgatatatca caaacaaaag tattcaaagc tttaaacacg atatgtatgg ttcaagaatg    120
acatcattaa acaaggacat gagtctgaaa taaacatgac ttgacaccgt tgtggtcaca    180
gttttgtttc tcattggtga acctgtgaaa caacctttca aaccaaaaga tgcctattaa    240
tattgttaat tcccatgaat taggagatac acacattcta ctgtcatttn nnnnnnnnnn    300
nnnnnnnnnn nnnnnnnnaa taaccgcttc cagcatgaaa acacaatatg attatctcaa    360
ttctaccatt actaattata attttgactg gcattatttg acgacgcgta aaacatcgct    420
gctttacaga ctgcactgcg gtaactgtga cgttttcatg acgtcactac attctattca    480
aaacatttcc acagaagagc gagaccacgg ccgtgatggg ttctgggcag atgattaccc    540
```

-continued

```
aagtatatat ttataataac ttgactgctt gcctgaataa tgttgacaca tgacaacgaa    600
tttgtgatag cgtaagaagc gtgaatactg tgaatagtgt gaggggtgtt tgctgagagt    660
taaccaccgt taattgcaaa attcccgaat acttgcattt gcagtcgaag aagaattgca    720
ttcttactcc tgtgaatgga ctcattgtta tttagcagcg gttattgagg ttttgatcac    780
ctctaaatag acaatcagga tgcggcaaac cggaaaatta tagcagaatc tgtaattcaa    840
gatgggcttg cctgtgaaaa tatgctgcga gttcagtaac acttttccct ttcgatcatg    900
gcctgttttg ctctgaatct ggtctttcag aggatccctg cttttttaaa actaaagtcc    960
tcccaactca cttatattta tgttttttaa ttatttatag ttttaatatg aacaacaaat   1020
catatttatt tacacattat atttttcag                                    1049
```

<210> SEQ ID NO 147
<211> LENGTH: 1846
<212> TYPE: DNA
<213> ORGANISM: Megathura crenulata

<400> SEQUENCE: 147

```
gtatttaaaa aagtaataaa accatatttt cgaatgcgct ttatgaaata tcgtgtgact     60
ggttctttag tttacatgga gtgtaacaac atgctccatc agttgacata tactgctcac    120
acaaagtaag ggatatttga taatgataac aaatataatc aaagcggtta tactatcaag    180
acttattcac ataattacag gtgaagggag gtgtgatcgt gttcactgat caggttgagg    240
ccagagaagt cccagtttga gtcttgcaga agatgatgtt taggcatggg gtcgaatcac    300
caaaatcaca tgacttcaat aacgggttgg accacctcga gcgacgatgc aagcagtaga    360
gcgtctacgc atgctcctga taaggcgacc aatctgttcc tggggaatca gtcgccactc    420
ctcttgtagt gccacgctca tttctgctac ggtcctgggt acctgctatc gggtcttgat    480
ccgtatccca aggatgtccc acacatgttc aaggtgagag gtcgggggaac atcgctggcc    540
acggtaaggt ctgaatttga tgccgttgaa agtgagctct gacaacctga gcatggtgag    600
ctctgacgtt gtcgtcctga aagatgaatc cagctccatg acagcgagca aagggcagga    660
cgtgttggtc aatgcagttg tctctgcagt acacacctgt cactcgccac tcacaagcgt    720
gtagatctgt acgaccagtc atggagatcc cagcccacat cataacggac ccctatccat    780
accgatcatg agccaccata gcagcgtctt gatgacgttc tccctgtcgc ctcgacatcc    840
tcacacggcc aaaaggaacg tggactcgtc actgaacatg acattagcca acctggcact    900
tgtccaccgc tgatgttggc gagaccattc cagtcgagct cttcggtgtc tggctttcat    960
cgataacacg acgtaaggtc tgcgggcgtg caagacggct ctatgcaggc gatttcggat   1020
tgtctgggtg ctaactctga tcccaggtgc ctgctgaagt tgatgctgga tctgtgtggc   1080
attgagatgg cgattcctta ggactgtgga gatgatgaat cgatcttgac ttatggtggt   1140
gacattagga cgtcgggttc gtgtcctatc ctgcactctt ccagttgttc ggtgacgctc   1200
tggtacccgg ctgattactg actgagaata tccatctgcc gtgcgacatg agcctgtgtt   1260
ggcccagcct gaagcattgc aatcgccaga gacgctcttc aaaagtcatt cgacgcatgg   1320
ttttctgttc acaaatgaca gcgtaaaaca gtttttggtg cttttatgct tcccaagagc   1380
atgaaaaaca cgttctatgg gtcgtgcaca ccttacatga caagtgtgaa aagtgacttg   1440
cacccccttg tgtgttcgga tgcacactct gtttacgtac tgatgcgatt tggcgtctaa   1500
acatgttttg gcgtctaaac atgttttcct gcatgattca tatactattt tgtcatattc   1560
ctggcatcaa accaaactac agtgaaatat atttcaatat cccctacttt gtgtgagtag   1620
```

-continued tatagatcac tgcagacaac atatagacaa tgcagttaca ccgtcaacaa tcccagtcat 1680
taattatgat gacacttcca cacatagtgt cagtgattgt aattcaactg tacacacttt 1740
tcccgtgaac attcaggatc tatatgacta aatatataac attagtatac gtgcagtttt 1800
gtatcgctac gacattgttg taactctttg tttaatcatt taacag 1846

<210> SEQ ID NO 148
<211> LENGTH: 166
<212> TYPE: DNA
<213> ORGANISM: Megathura crenulata

<400> SEQUENCE: 148
gtatgtttta aatgtcactt atccgtgatc tgtaatgaag ttagcaattc actttatcaa 60
ctgtttggct gtactgtttc agtgcgagtt ttacttaggt tggattaatt aaaatattca 120
agctcataaa tgttttgatt caacttttgt tatttatttc aaacag 166

<210> SEQ ID NO 149
<211> LENGTH: 726
<212> TYPE: DNA
<213> ORGANISM: Megathura crenulata
<220> FEATURE:
<221> NAME/KEY: misc_feature
<222> LOCATION: (388)..(388)
<223> OTHER INFORMATION: “n” is a, g, c, t

<400> SEQUENCE: 149
gttataaagc agtatattct cttcaaaaaa gtaggggaac ttggaatttc aaggtaaata 60
acataactac cttcaacggc acaatatcca tatgatgccc tggccagcaa tgaggcctga 120
tcttttcccc attaaaaatg tctggaacat cttgggcaaa cgtgtgcgtc aacgtaaaac 180
gccaccagtc acgctagatg aacttgtcca ggcgttggtg gaagaatggg acagactgca 240
tcaattacca taagtagact catttgcagc gaatcagtca gtgtttgacc aataacgggg 300
gcattacgca ctactgacgc aaaacaatgt caatttccgt ttcttaccca ttccttcttt 360
cacggaccat aacagcaaga gaaactgntt aggtaatgaa ataccggtga attattgtta 420
actggattcc ttctttgtaa agatacaatt agtttgggac caattattat tatcattagt 480
ttgttattga ccttgaaatt cgaagttcct ctacattttt taaggagttt atttgattga 540
caatgaaatg taagaaaaga gcaaatcgta aaatacgtta aaaattattc cttaaacatc 600
agtctctaac ttcagtttaa attgccagta acacgtgtta tatgatgttt ccgtttctct 660
ttgtttttta gcattcaact tatttgatat aacgttttac tgttttagat tcacatcaaa 720
ctgcag 726

<210> SEQ ID NO 150
<211> LENGTH: 383
<212> TYPE: DNA
<213> ORGANISM: Megathura crenulata

<400> SEQUENCE: 150
gtatgtatct catgtttctc aaataatttg attttcaatg cccttactat aaagcacagt 60
tattgttcag tgccagtaac cgtttattta cgtaaatgtt acaggctatt ataatcaaaa 120
atacattacc gatattgttt accacacaat tatatcattg tcaaaatcta cccccattac 180
ctgcgttttg aatttgtaac cttctgacaa aaatgaatta gcaagagctc tgatgaagaa 240
cataatgaac aacacctatc tttcttcttt caatgacggt ttaacaatac aatgcacaat 300

-continued gtaaaaaaat atatatatat atataatttt atatctacag ttaatgcaaa tgactccact 360
aattcaggga aacacatttt cag 383

<210> SEQ ID NO 151
<211> LENGTH: 306
<212> TYPE: DNA
<213> ORGANISM: Megathura crenulata

<400> SEQUENCE: 151
gtaaaataaa acgtccagtc atcggaaacc cgcccagata tatgggtttt tttctattta 60
aacaaaaaag cagagacaaa aagattatta aaagtcacat ttaacttgat atcagatcaa 120
tagtttggct agttagtgct ctatatccct caaatccttc gaatctttaa gcctcgtgat 180
attttgacaa acagagaaga cttagtagcc cagactttcc cttatttttt cctgaaaatc 240
ttaatacgga tattaaatgg attcattctg caacctacaa ccatagccca tatgttatta 300
tttcag 306

<210> SEQ ID NO 152
<211> LENGTH: 627
<212> TYPE: DNA
<213> ORGANISM: Megathura crenulata

<400> SEQUENCE: 152
gtgagagaaa ctataatagt gtatgtcggc aaaaaatgtg ctcatatcat gactctgttg 60
gccggtggtt gctctcctct cctcctccac caccaccggt acctccacct gtcagggcat 120
caatgtacca tgaaaatgtc tacaatacta ggcctcctgt agaagcacgt aagatttaca 180
tggccggttt gtaactagtt taaagtgctt cacagtaacc aaaaccagtc tctaaagatt 240
aatgtctgtt taaaatttaa tgccacattt tcaactgaca tattcttgca attaagtaca 300
aatgaagtag tataaattat ccacaaatag cgtgatgcac cacaaatata aaccgagtgc 360
ttttttggca ttccccactt gttctggcat gatcacatca tagatctcgt tcatgaagat 420
actgttggat gctttttccc aatatgcccc aatctgttaa attatttaca cgaccgcagt 480
gtgtactttc atcactcaga tctttacaat gtgtttgtaa cgtttacaat tagcgttatg 540
attgaaatat taccccctgc tacgttaaat cacattcact cactcatctg atgtacttta 600
caggtcatac cgatgatcac ggctcag 627

<210> SEQ ID NO 153
<211> LENGTH: 266
<212> TYPE: DNA
<213> ORGANISM: Megathura crenulata

<400> SEQUENCE: 153
gtcagtattc tccaatatgt ttgactagtg tcttgctcat gtatcaacta ttttaggcaa 60
cgtttttgat tgttatggta ttttcatgat atgattttat tgctacctct atacccaaac 120
aaaaatgttt tatcaacaat tgtttgagtt ttaatgcaag aaaattatca ggagtagcgt 180
gcaaaaatga ctggaaggca tggtgtactt ctgtgtgtac atacaagtgg gtaatgcctt 240
attgaactcg taatcactcg tttcag 266

<210> SEQ ID NO 154
<211> LENGTH: 266
<212> TYPE: DNA
<213> ORGANISM: Megathura crenulata -continued

<400> SEQUENCE: 154

```
gtcagtattc tccaatatgt ttgactagtg tcttgctcat gtatcaacta ttttaggcaa     60

cgtttttgat tgttatggta ttttcatgat atgattttat tgctacctct atacccaaac    120

aaaaatgttt tatcaacaat tgtttgagtt ttaatgcaag aaaattatca ggagtagcgt    180

gcaaaaatga ctggaaggca tggtgtactt ctgtgtgtac atacaagtgg gtaatgcctt    240

attgaactcg taatcactcg tttcag                                          266
```

<210> SEQ ID NO 155
<211> LENGTH: 190
<212> TYPE: DNA
<213> ORGANISM: Megathura crenulata

<400> SEQUENCE: 155

```
gtatgttttg agatccacat aatcttctac cctgtctcat ttctaatgct cttcaataca     60

caatttatat agcctttgag cttcagatgt attacggaca ggcattacag tatacatgta    120

atatggtttt ctgctatttg caaaaattgt gtcctatctc tgttcagatc atcatggcgg    180

tgacacctag                                                            190
```

<210> SEQ ID NO 156
<211> LENGTH: 403
<212> TYPE: PRT
<213> ORGANISM: Haliotis tuberculata

<400> SEQUENCE: 156

```
Gly Leu Pro Tyr Trp Asp Trp Thr Gln His Leu Thr Gln Leu Pro Asp
  1               5                  10                  15

Leu Val Ser Asp Pro Leu Phe Val Asp Pro Glu Gly Gly Lys Ala His
             20                  25                  30

Asp Asn Ala Trp Tyr Arg Gly Asn Ile Lys Phe Glu Asn Lys Lys Thr
         35                  40                  45

Ala Arg Ala Val Asp Asp Arg Leu Phe Glu Lys Val Gly Pro Gly Glu
     50                  55                  60

Asn Thr Arg Leu Phe Glu Gly Ile Leu Asp Ala Leu Glu Gln Asp Glu
 65                  70                  75                  80

Phe Cys Asn Phe Glu Ile Gln Phe Glu Leu Ala His Asn Ala Ile His
                 85                  90                  95

Tyr Leu Val Gly Gly Arg His Thr Tyr Ser Met Ser His Leu Glu Tyr
            100                 105                 110

Thr Ser Tyr Asp Pro Leu Phe Phe Leu His His Ser Asn Thr Asp Arg
        115                 120                 125

Ile Phe Ala Ile Trp Gln Arg Leu Gln Val Leu Arg Gly Lys Asp Pro
    130                 135                 140

Asn Thr Ala Asp Cys Ala His Asn Leu Ile His Glu Pro Met Glu Pro
145                 150                 155                 160

Phe Arg Arg Asp Ser Asn Pro Leu Asp Leu Thr Arg Glu Asn Ser Lys
                165                 170                 175

Pro Ile Asp Ser Phe Asp Tyr Ala His Leu Gly Tyr Gln Tyr Asp Asp
            180                 185                 190

Leu Thr Leu Asn Gly Met Thr Pro Glu Glu Leu Asn Ser Tyr Leu His
        195                 200                 205

Glu Arg Ser Gly Lys Glu Gly Val Phe Ala Ser Phe Arg Leu Ser Gly
    210                 215                 220
```

-continued

```
Phe Gly Gly Ser Ala Asn Val Val Val Tyr Ala Cys Arg Pro Ala His
225                 230                 235                 240

Asp Glu Met Ala Val Asp Gln Cys Asp Lys Ala Gly Asp Phe Phe Val
            245                 250                 255

Leu Gly Gly Pro Thr Glu Met Pro Trp Arg Phe Tyr Arg Ala Phe His
            260                 265                 270

Phe Asp Val Thr Asp Ser Ile Asp Asn Ile Asp Lys Asp Arg His Gly
        275                 280                 285

His Tyr Tyr Val Lys Ala Glu Leu Phe Ser Val Asn Gly Ser Ala Leu
    290                 295                 300

Pro Asn Asp Leu Leu Pro Gln Pro Thr Ile Ser His Arg Pro Ala Arg
305                 310                 315                 320

Gly His Val Asp Glu Ala Pro Ala Pro Ser Ser Asp Ala His Leu Ala
                325                 330                 335

Val Arg Lys Asp Ile Asn His Leu Thr Arg Glu Glu Val Tyr Glu Leu
            340                 345                 350

Arg Arg Ala Met Glu Arg Phe Gln Ala Asp Thr Ser Val Asp Gly Tyr
        355                 360                 365

Gln Ala Thr Val Glu Tyr His Gly Leu Pro Ala Arg Cys Pro Phe Pro
    370                 375                 380

Glu Ala Thr Asn Arg Phe Ala Cys Cys Ile His Gly Met Ala Thr Phe
385                 390                 395                 400

Pro His Trp
```

<210> SEQ ID NO 157
<211> LENGTH: 973
<212> TYPE: DNA
<213> ORGANISM: Haliotis tuberculata
<220> FEATURE:
<223> OTHER INFORMATION: Domain a, parts 1-4

<400> SEQUENCE: 157

```
ggtcttccgt actgggactg gacgcagcat ctgactcaac tcccagatct ggtgtcagac     60

cccttgtttg tcgacccgga aggaggaaag gcccatgaca acgcatggta tcgtggaaac    120

atcaagtttg agaataagaa gactgcaaga gctgttgacg atcgcctttt cgagaaggtt    180

ggaccaggag agaataccog actctttgaa ggaattctcg atgctcttga acaggatgaa    240

ttctgcaact tcgagatcca gtttgagttg gctcacaacg ctatccacta cctggttggc    300

ggccgtcaca cgtactccat gtctcatctc gagtacacct cctacgaccc cctcttcttc    360

ctccatcact ccaacaccga ccgcatcttc gccatctggc aacgtcttca ggtactcaga    420

ggaaaggacc ccaacaccgc cgactgcgca cacaacctca tccatgagcc catggaaccg    480

ttccgtcggg actcgaaccc tcttgacctc accagggaaa actccaaacc aattgacagc    540

tttgattatg cccaccttgg ctaccagtat gatgacttga ccctgaacgg tatgacccca    600

gaggaattga actcatatct gcatgaacgg tcaggcaagg agggggtgtt cgcaagcttc    660

cgactctcag gttttggcgg ctctgctaac gttgttgtct acgcatgccg tcctgcccac    720

gatgaaatgg ctgtcgatca gtgcgacaaa gccggcgact tctttgtgtt gggcggaccc    780

accgagatgc cctggaggtt ttacagagca ttccacttcg acgtcaccga cagcatcgac    840

aacatcgaca aggaccgcca cggccactat tatgtaaagg cggaattatt cagtgtaaat    900

ggaagtgcgc taccgaatga tctcctgcct caacccacca tctcacacag gccagcccgc    960

ggacacgttg atg                                                       973
```

-continued

<210> SEQ ID NO 158
<211> LENGTH: 103
<212> TYPE: PRT
<213> ORGANISM: Megathura crenulata

<400> SEQUENCE: 158

```
Gly His Asp His Ser Glu Arg His Asp Gly Phe Phe Arg Lys Glu Val
  1               5                  10                  15

Gly Ser Leu Ser Leu Asp Glu Ala Asn Asp Leu Lys Asn Ala Leu Tyr
             20                  25                  30

Lys Leu Gln Asn Asp Gln Gly Pro Asn Gly Tyr Glu Ser Ile Ala Gly
         35                  40                  45

Tyr His Gly Tyr Pro Phe Leu Cys Pro Glu His Gly Glu Asp Gln Tyr
     50                  55                  60

Ala Cys Cys Val His Gly Met Pro Val Phe Pro His Trp His Arg Leu
 65                  70                  75                  80

His Thr Ile Gln Phe Glu Arg Ala Leu Lys Glu His Gly Ser His Leu
                 85                  90                  95

Gly Leu Pro Tyr Trp Asp Trp
            100
```

<210> SEQ ID NO 159
<211> LENGTH: 310
<212> TYPE: DNA
<213> ORGANISM: Megathura crenulata

<400> SEQUENCE: 159

```
gtcacgatca cagtgaacgt cacgatggat ttttcaggaa ggaagtcggt tccctgtccc     60

tggatgaagc caatgacctt aaaaatgcac tgtacaagct gcagaatgat cagggtccca    120

atggatatga atcaatagcc ggttaccatg gctatccatt cctctgccct gaacatggtg    180

aagaccagta cgcatgctgt gtccacggaa tgcctgtatt tccacattgg cacagacttc    240

atacaatcca gtttgagaga gctctcaaag aacatggttc tcatttgggt ctgccatact    300

gggactggac                                                           310
```

<210> SEQ ID NO 160
<211> LENGTH: 32
<212> TYPE: DNA
<213> ORGANISM: Haliotis tuberculata

<400> SEQUENCE: 160

```
ggcttgttca gtttctactc gtcgcccttg tg                                   32
```

<210> SEQ ID NO 161
<211> LENGTH: 16
<212> TYPE: DNA
<213> ORGANISM: Haliotis tuberculata

<400> SEQUENCE: 161

```
gtgggggctg gagcag                                                     16
```

<210> SEQ ID NO 162
<211> LENGTH: 350
<212> TYPE: DNA
<213> ORGANISM: Haliotis tuberculata

<400> SEQUENCE: 162

```
acaacgtcgt cagaaaggac gtgagtcacc tcacagttga cgaggtgcaa gctcttcacg     60

gcgccctcca tgacgtcact gcatctacag ggcctctgag tttcgaagac ataacatctt    120
```

-continued

```
accatgccgc accagcgtcg tgtgactaca agggacggaa gatcgcctgc tgtgtccacg    180

gtatgcccag tttccccttc tggcacaggg catatgtcgt ccaagccgag cgggcactgt    240

tgtccaaacg gaagactgtc ggaatgcctt actgggactg gacgcaaacg ctgactcact    300

taccatctct tgtgactgaa cccatctaca ttgacagtaa aggtggaaag               350
```

<210> SEQ ID NO 163
<211> LENGTH: 221
<212> TYPE: DNA
<213> ORGANISM: Haliotis tuberculata

<400> SEQUENCE: 163

```
gctcaaacca actactggta ccgcggcgag atagcgttca tcaataagaa gactgcgcga     60

gctgtagatg atcgcctatt cgagaaggtg gagcctggtc actacacaca tcttatggag    120

actgtcctcg acgctctcga acaggacgaa ttctgtaaat ttgaaatcca gttcgagttg    180

gctcataatg ctatccatta cttggttggc ggtaaatttg a                        221
```

<210> SEQ ID NO 164
<211> LENGTH: 255
<212> TYPE: DNA
<213> ORGANISM: Haliotis tuberculata

<400> SEQUENCE: 164

```
atattcaatg tcaaacttgg aatacacctc ctacgacccc atcttcttcc tccaccactc     60

caacgttgac cgcctcttcg ccatctggca gcgtcttcag gaactgcgag gaaagaatcc    120

caatgcaatg gactgtgcac atgaactcgc tcaccagcaa ctccaaccct tcaacaggga    180

cagcaatcca gtccagctca caaaggacca ctcgacacct gctgacctct ttgattacaa    240

acaacttgga tacag                                                     255
```

<210> SEQ ID NO 165
<211> LENGTH: 407
<212> TYPE: DNA
<213> ORGANISM: Haliotis tuberculata

<400> SEQUENCE: 165

```
ctacgacagc ttaaacctga atggaatgac gccagaacag ctgaaaacag aactagacga     60

acgccactcc aaagaacgtg cgtttgcaag cttccgactc agtggctttg ggggttctgc    120

caacgttgtt gtctatgcat gtgtccctga tgatgatcca cgcagtgatg actactgcga    180

gaaagcaggc gacttcttca ttcttggggg tcaaagcgaa atgccgtgga gattctacag    240

acccttcttc tatgatgtaa ctgaagcggt acatcacctt ggagtcccgc taagtggcca    300

ctactatgtg aaaacagaac tcttcagcgt gaatggcaca gcactttcac ctgatcttct    360

tcctcaacca actgttgcct accgacctgg gaaaggtcac cttgacc                  407
```

<210> SEQ ID NO 166
<211> LENGTH: 1245
<212> TYPE: DNA
<213> ORGANISM: Haliotis tuberculata

<400> SEQUENCE: 166

```
cacctgtgca tcatcgccac gatgacgatc ttattgttcg aaaaaatata gatcatttga     60

ctcgtgaaga ggaatacgag ctaaggatgg ctctggagag attccaggcc gacacatccg    120

ttgatgggta ccaggctaca gtagagtacc atggccttcc tgctcgttgt ccacgaccag    180

atgcaaaagt caggttcgcc tgttgtatgc atggcatggc atccttccct cactggcacc    240
```

-continued

```
ggctgttcgt tacccaggtg gaagatgctc ttgtacggcg tggatcgcct atcggtgttc    300
cttattggga ctggacaaaa cctatgactc accttccaga cttggcatca aatgagacgt    360
acgtagaccc gtatggacat acacatcata atccattctt caatgcaaat atatcttttg    420
aggagggaca ccatcacacg agcaggatga tagattcgaa actgtttgcc ccagtcgctt    480
ttggggagca ttcccatctg tttgatggaa tcctgtacgc atttgagcag gaagatttct    540
gcgactttga gattcagttt gagttagtcc ataattctat tcatgcgtgg ataggcggtt    600
ccgaagatta ctccatggcc accctgcatt acacagcctt tgaccccatt ttctaccttc    660
atcattccaa tgtcgatcgt ctatgggcaa tctggcaagc tcttcaaatc aggagacaca    720
agccatatca agcccactgt gcacagtctg tggaacagtt gccaatgaag ccatttgctt    780
tcccatcacc tcttaacaac aacgagaaga cacatagtca ttcagtcccg actgacattt    840
atgactacga ggaagtgctg cactacagct acgatgatct aacgtttggt gggatgaacc    900
ttgaagaaat agaagaagct atacatctca gacaacagca tgaacgagtc ttcgcgggat    960
ttctccttgc tggaatagga acatctgcac ttgttgacat tttcataaat aaaccgggga   1020
accaaccact caaagctgga gatattgcca ttcttggtgg tgccaaggaa atgccttggg   1080
cgtttgaccg cttgtataag gtcgaaataa ctgactcatt gaagacactt tctctcgatg   1140
tcgatggaga ttatgaagtc acttttaaaa ttcatgatat gcacggaaac gctcttgata   1200
cggacctgat tccacacgca gcagttgttt ctgagccagc tcacc                   1245
```

<210> SEQ ID NO 167
<211> LENGTH: 1242
<212> TYPE: DNA
<213> ORGANISM: Haliotis tuberculata

<400> SEQUENCE: 167

```
ctacctttga ggatgaaaag cacagcttac gaatcagaaa aaatgtcgac agcttgactc     60
ctgaagaaac aaatgaactg cgtaaagccc tggagcttct tgaaaatgat catactgcag    120
gtggattcaa tcagcttggc gccttccatg gagagcctaa atggtgccct aatcctgaag    180
cggagcacaa ggttgcatgc tgtgttcatg gcatggctgt tttccctcat tggcacaggc    240
ttcttgctct ccaggcggag aatgctctta gaaagcatgg gtacagtggt gctctaccat    300
actgggattg gactcgcccc ctttcccaac ttcctgatct ggttagtcat gagcagtata    360
cagatccttc cgaccatcac gtgaagcata acccgtggtt caatggccac atcgatacag    420
taaatcagga taccaccaga agcgtacggg aggatcttta tcaacaacct gaatttggac    480
atttcacgga tattgctcaa caagtcctct tagcattaga acaagatgac ttctgttcgt    540
ttgaagtgca gtatgagatt tcccataatt ttatccatgc acttgtagga ggaaccgacg    600
cttatggcat ggcatcgctg agatatacag catacgatcc aatctttttc ttgcatcatt    660
caaacaccga caggatctgg gctatttggc aatccctgca aaaatacaga ggcaaaccgt    720
acaacactgc caactgcgcc atagaatcta tgagaaggcc cctgcaacca tttggactaa    780
gcagtgccat taaccctgac agaatcacca gagagcatgc tatcccgttt gatgtcttca    840
actatagaga taaccttcat tacgtatatg ataccctgga atttaatggt ttgtcgattt    900
cacaacttga tagagagctg gaaaaaatca agagtcacga aagagtattt gctggattct    960
tgctgtcggg gattaaaaaa tctgctcttg tgaaattcga agtttgtact ccacctgata   1020
attgtcataa agcaggggag ttttatctac tcggggacga aaacgagatg gcttgggcct   1080
atgaccgact tttcaagtat gatattactc aggttctgga agcaaaccat ctacacttct   1140
```

-continued

```
atgatcatct cttcattcgc tacgaagtct ttgatcttaa aggagtgagt ttgggaactg   1200

acctgttcca cactgcaaat gtggtacatg attccggcac ag                      1242


<210> SEQ ID NO 168
<211> LENGTH: 1239
<212> TYPE: DNA
<213> ORGANISM: Haliotis tuberculata

<400> SEQUENCE: 168

gcacccgtga tcgtgataac tacgttgaag aagttactgg ggccagtcat atcaggaaga     60

atttgaacga cctcaatacc ggagaaatgg aaagccttag agctgctttc ctgcatattc    120

aggacgacgg aacatatgaa tctattgccc agtaccatgg caaaccaggc aaatgtcaat    180

tgaatgatca taatattgcg tgttgtgtcc atggtatgcc taccttcccc cagtggcaca    240

gactgtatgt ggttcaggtg gagaatgctc tcctaaacag gggatctggt gtggctgttc    300

cttactggga gtggactgct cccatagacc atctacctca tttcattgat gatgcaacat    360

acttcaattc ccgacaacag cggtacgacc ctaacccttt cttcagggga aaggttactt    420

ttgaaaacgc agtcacaaca agggacccac aagccgggct cttcaactca gattatatgt    480

atgagaatgt tttacttgca ctggagcagg aaaattattg tgactttgaa attcagtttg    540

agcttgttca taacgcactt cattccatgc tgggaggtaa agggcagtac tccatgtcct    600

ccctggacta ttctgcgttt gatcccgtct tcttcctaca tcatgccaac acggacagac    660

tgtgggcaat ctggcaggaa ctacaaagat tccgagaact gccttatgaa gaagcgaact    720

gtgcaatcaa cctcatgcat caaccactga agccgttcag tgatccacat gagaatcacg    780

acaatgtcac tttgaaatac tcaaaaccac aggacggatt cgactaccag aaccacttcg    840

gatacaagta tgacaacctt gagttccatc acttatctat cccaagtctt gatgctaccc    900

tgaagcaaag gagaaatcac gacagagtgt ttgcgggctt ccttcttcat aacataggaa    960

cttctgctga cataactatc tacatatgtc tgcctgacgg acggcgtggc aatgactgca   1020

gtcatgaggc gggaacattc tatatcctcg gaggcgaaac agagatgcct tttatctttg   1080

accgtttgta taaatttgaa atcaccaaac cactgcaaca gttaggagtc aagctgcatg   1140

gtggagtttt cgaactggag cttgagatca aggcatacaa cggttcctat ctggatcccc   1200

ataccttga tccaactatc atctttgaac ctggaacag                           1239


<210> SEQ ID NO 169
<211> LENGTH: 1260
<212> TYPE: DNA
<213> ORGANISM: Haliotis tuberculata

<400> SEQUENCE: 169

atacccatat cttggaccac gaccatgagg aagagatact tgtcaggaag aatataattg     60

atttgagccc aagggagagg gtttctctag tcaaagcttt gcaaagaatg aagaatgatc    120

gctccgctga tgggtaccaa gccattgcct ctttccatgc cctgccacca ctctgtccca    180

atccatctgc agctcaccgt tatgcttgct gtgtccatgg catggctaca tttccccagt    240

ggcacagact gtacactgtt caggttcagg atgccctgag gagacatggt tcacttgttg    300

gtattcctta ctgggactgg acaaaaccag tcaacgagtt acccgagctt ctttcttcag    360

caacatttta tcatccaatc cggaatatta atatttcaaa tccattcctc ggggctgaca    420

tagaatttga aggaccgggc gttcatacag agaggcacat aaatactgag cgcctgtttc    480

acagtgggga tcatgacgga taccacaact ggttcttcga aactgttctc tttgctttgg    540
```

-continued

```
aacaggaaga ttactgcgat tttgaaatac aatttgagat agcccataat ggcatccaca    600

catggattgg tggaagcgca gtatatggca tgggacacct tcactatgca tcatatgatc    660

caattttcta catccaccat tcacagacgg acagaatatg ggctatttgg caagagctgc    720

agaagtacag gggtctatct ggttcggaag caaactgtgc cattgaacat atgagaacac    780

ccttgaagcc tttcagcttt gggccaccct acaatttgaa tagtcatacg caagaatatt    840

caaagcctga ggacacgttt gactataaga agtttggata cagatatgat agtctggaat    900

tggaggggcg atcaatttct cgcattgatg aacttatcca gcagagacag gagaaagaca    960

gaacttttgc agggttcctc cttaaaggtt ttggtacatc cgcatctgtg tcattgcaag   1020

tttgcagagt tgatcacacc tgtaaagatg cgggctattt cactattctg ggaggatcag   1080

ccgaaatgcc atgggcattc gacaggcttt ataagtatga cattactaaa actcttcacg   1140

acatgaacct gaggcacgag gacactttct ctatagacgt aactatcacg tcttacaatg   1200

gaacagtact ctcgggagac ctcattcaga cgccctccat tatatttgta cctggacgcc   1260
```

<210> SEQ ID NO 170
<211> LENGTH: 191
<212> TYPE: DNA
<213> ORGANISM: Haliotis tuberculata

<400> SEQUENCE: 170

```
ataaactcaa ctcacggaaa catacaccta acagagtccg ccatgagcta agtagcctta     60

gttcccgtga catagcaagc ttgaaggcag ctttgacaag ccttcaacat gataatggga    120

ctgatggtta tcaagctatt gctgccttcc atggcgttcc tgcgcagtgc cacgagccat    180

ctggacgtga g                                                         191
```

<210> SEQ ID NO 171
<211> LENGTH: 1060
<212> TYPE: DNA
<213> ORGANISM: Haliotis tuberculata

<400> SEQUENCE: 171

```
atcgcctgtt gcatccacgg catggcgacg tttcctcact ggcaccggtt gtacactctg     60

cagttggagc aagcgctgcg cagacacggg tccagtgttg ctgttccata ctgggactgg    120

accaagccaa tcaccgaact gccacacatt ctgacagacg gagaatatta tgacgtttgg    180

caaaatgccg tcttggccaa tccgtttgca agaggttatg tgaaaattaa agatgcattt    240

acggtgagaa atgtccagga aagtctgttc aaaatgtcaa gttttggaaa gcactcgctt    300

ctgtttgacc aggctttgtt ggctcttgaa caaactgact actgtgactt cgaagttcag    360

tttgaagtga tgcataacac gatccattat ctcgtaggag ggcgtcaaac gtacgccttc    420

tcctctctcg agtattcctc atacgatcca atcttcttta ttcaccactc gtttgttgac    480

aaaatatggg ctgtatggca agaactgcaa agcaggagac atctacagtt tagaacagct    540

gattgtgctg tgggcctcat gggtcaggca atgaggcctt tcaacaagga tttcaaccac    600

aactcgttca ccaagaagca cgcagtccct aatacagtat ttgattatga agatcttggc    660

tataactatg acaaccttga aatcagtggt ttaaacttaa atgagatcga ggcgttaata    720

gcaaaacgca agtcacatgc tagagtcttt gctgggttcc tgttgtttgg attaggaact    780

tcggctgata tacatctgga aatttgcaag acatcggaaa actgccatga tgctggtgtg    840

attttcatcc ttggaggttc tgcagagatg cattgggcat acaaccgcct ctacaagtat    900

gacattacag aagcattgca ggaatttgac atcaaccctg aagatgtttt ccatgctgat    960
```

-continued gaaccatttt tcctgaggct gtcggttgtt gctgtgaatg gaactgtcat tccatcgtct 1020
catcttcacc agccaacgat aatctatgaa ccaggcgaag 1060

<210> SEQ ID NO 172
<211> LENGTH: 219
<212> TYPE: DNA
<213> ORGANISM: Haliotis tuberculata

<400> SEQUENCE: 172
atcaccatga cgaccatcag tcgggaagca tagcaggatc cggggtccgc aaggacgtga 60
acaccttgac taaggctgag accgacaacc tgagggaggc gctgtggggt gtcatggcag 120
accacggtcc caatggcttt caagctattg ctgctttcca tggaaaacca gctttgtgtc 180
ccatgcctga tggccacaac tactcatgtt gtactcacg 219

<210> SEQ ID NO 173
<211> LENGTH: 164
<212> TYPE: DNA
<213> ORGANISM: Haliotis tuberculata

<400> SEQUENCE: 173
gcatggctac cttcccacac tggcatcgcc tctacaccaa gcagatggag gatgcaatga 60
gggcgcatgg gtctcatgtc ggcctgccct actgggactg gactgctgcc ttcacccacc 120
tgccaacact ggtcaccgac acggacaaca accccttcca acat 164

<210> SEQ ID NO 174
<211> LENGTH: 826
<212> TYPE: DNA
<213> ORGANISM: Haliotis tuberculata

<400> SEQUENCE: 174
ggacacattg attatctcaa tgtcagcaca actcgatctc cccgagacat gctgttcaac 60
gaccccgagc atggatcaga gtcgttcttc tacagacaag tcctcttagc tctggaacaa 120
actgatttct gcaaattcga agttcagttt gagataaccc acaatgccat ccattcctgg 180
acaggtggcc acagccccta cggaatgtcc actctcgact tcactgccta cgatcctctc 240
ttctggcttc accactccaa caccgacaga atctgggctg tctggcaagc tttgcaagaa 300
tacagaggac ttccatacaa ccatgccaat tgtgagatcc aggcaatgaa aacgcccctg 360
aggcctttca gtgacgatat caaccacaac ccagtcacaa aggctaacgc gaagccatta 420
gatgtgttcg agtataatcg gttgagcttc cagtacgaca acctcatctt ccatggatac 480
agtattccgg aacttgatcg cgtgcttgaa gaaagaaagg aggaggacag aatatttgct 540
gccttccttc tcagtggaat caagcgtagt gctgatgtag tgttcgacat atgccagcca 600
gaacacgaat gtgtgttcgc agggactttt gcgattttgg gaggggagct agaaatgccc 660
tggtccttcg acagactgtt ccgctatgat atcaccaagg tgatgaagca gctacacctg 720
aggcatgact ctgactttac cttcagggtg aagattgtcg gcaccgacga ccacgagctt 780
ccttcagaca gtgtcaaagc accaactatt gaatttgaac cgggcg 826

<210> SEQ ID NO 175
<211> LENGTH: 1535
<212> TYPE: DNA
<213> ORGANISM: Haliotis tuberculata -continued

<400> SEQUENCE: 175

```
tgcacagagg cggaaaccac gaagatgaac accatgatga cagactcgca gatgtcctga     60
tcaggaaaga agttgacttc ctctccctgc aagaggccaa cgcaattaag gatgcactgt    120
acaagctcca gaatgacgac agtaaagggg gctttgaggc catagctggc tatcacgggt    180
atcctaatat gtgtccagaa agaggtaccg acaagtatcc ctgctgtgtc cacggaatgc    240
ccgtgttccc ccactggcac cgcctgcata ccattcagat ggagagagct ctgaaaaacc    300
atggctctcc aatgggcatt ccttactggg attggacaaa gaagatgtcg agtcttccat    360
ctttctttgg agattccagc aacaacaacc ctttctacaa atattacatc cggggcgtgc    420
agcacgaaac aaccagggac attaatcaga gactctttaa tcaaaccaag tttggtgaat    480
ttgattacct atattaccta actctgcaag tcctggagga aaactcgtac tgtgactttg    540
aagttcagta tgagatcctc cataacgccg tccactcctg gcttggagga actggaaagt    600
attccatgtc taccctggag cattcggcct ttgaccctgt cttcatgatt caccactcga    660
gtttggatag aatctggatc ctttggcaga agttgcaaaa gataagaatg aagccttact    720
acgcattgga ttgtgctggc gacagactta tgaaagaccc cctgcatccc ttcaactacg    780
aaaccgttaa tgaagatgaa ttcacccgca tcaactcttt cccaagcata ctgtttgacc    840
actacaggtt caactatgaa tacgataaca tgagaatcag ggtcaggac atacatgaac     900
ttgaagaggt aattcaggaa ttaagaaaca aagatcgcat atttgctggt tttgttttgt    960
cgggcttacg gatatcagct acagtgaaag tattcattca ttcgaaaaac gatacaagtc   1020
acgaagaata tgcaggagaa tttgcagttt tgggaggtga gaaggagatg ccgtgggcat   1080
atgaaagaat gctgaaattg gacatctccg atgctgtaca caagcttcac gtgaaagatg   1140
aagacatccg ttttagagtg gttgttactg cctacaacgg tgacgttgtt accaccaggc   1200
tgtctcagcc attcatcgtc caccgtccag cccatgtggc tcacgacatc ttggtaatcc   1260
cagtaggtgc gggccatgac cttccgccta aagtcgtagt aaagagcggc accaaagtcg   1320
agtttacacc aatagattcg tcggtgaaca aagcaatggt ggagctgggc agctatactg   1380
ctatggctaa atgcatcgtt ccccctttct cttaccacgg ctttgaactg gacaaagtct   1440
acagcgtcga tcacggagac tactacattg ctgcaggtac ccacgcgttg tgtgagcaga   1500
acctcaggct ccacatccac gtggaacacg agtag                              1535
```

<210> SEQ ID NO 176
<211> LENGTH: 7
<212> TYPE: DNA
<213> ORGANISM: Haliotis tuberculata

<400> SEQUENCE: 176

```
ttcacag                                                                7
```

<210> SEQ ID NO 177
<211> LENGTH: 471
<212> TYPE: DNA
<213> ORGANISM: Haliotis tuberculata

<400> SEQUENCE: 177

```
gttgctatgc cgactgcgct atattggtga acgagacgat gaggacatct ctgaaagagt     60
tcgccaagtg atgtgtaggt cacggaagta ttgttgagct aacaatatga tgatttcaaa    120
atgacttggc gctctaggac aaagacataa ttcatcagca ccctgtgcac caactctttg    180
tttgctgcaa acgtctgaca agcgacacgt caatcaacaa gctgttcaaa ctcaagtgga    240
```

-continued

```
tgtaactaga atcgttgggc catcgttcac aaagtattga cagatgtcac acatgatggc    300

gagaaacact ttagaacttt taatgaccta gagtgacttg taaatatgta aatatattct    360

tcaaagactc agctgaacta ttgttggata acacatcaat tccctcaaca aaatgcttta    420

tcttcacatg gatgtatgta atgtggccgg caataaagta tatatatgta t             471


<210> SEQ ID NO 178
<211> LENGTH: 15
<212> TYPE: PRT
<213> ORGANISM: Haliotis tuberculata

<400> SEQUENCE: 178

Leu Val Gln Phe Leu Leu Val Ala Leu Val Val Gly Ala Gly Ala
  1               5                  10                  15


<210> SEQ ID NO 179
<211> LENGTH: 407
<212> TYPE: PRT
<213> ORGANISM: Haliotis tuberculata

<400> SEQUENCE: 179

Asp Asn Val Val Arg Lys Asp Val Ser His Leu Thr Val Asp Glu Val
  1               5                  10                  15

Gln Ala Leu His Gly Ala Leu His Asp Val Thr Ala Ser Thr Gly Pro
             20                  25                  30

Leu Ser Phe Glu Asp Ile Thr Ser Tyr His Ala Ala Pro Ala Ser Cys
         35                  40                  45

Asp Tyr Lys Gly Arg Lys Ile Ala Cys Cys Val His Gly Met Pro Ser
     50                  55                  60

Phe Pro Phe Trp His Arg Ala Tyr Val Val Gln Ala Glu Arg Ala Leu
 65                  70                  75                  80

Leu Ser Lys Arg Lys Thr Val Gly Met Pro Tyr Trp Asp Trp Thr Gln
                 85                  90                  95

Thr Leu Thr His Leu Pro Ser Leu Val Thr Glu Pro Ile Tyr Ile Asp
            100                 105                 110

Ser Lys Gly Gly Lys Ala Gln Thr Asn Tyr Trp Tyr Arg Gly Glu Ile
        115                 120                 125

Ala Phe Ile Asn Lys Lys Thr Ala Arg Ala Val Asp Asp Arg Leu Phe
    130                 135                 140

Glu Lys Val Glu Pro Gly His Tyr Thr His Leu Met Glu Thr Val Leu
145                 150                 155                 160

Asp Ala Leu Glu Gln Asp Glu Phe Cys Lys Phe Glu Ile Gln Phe Glu
                165                 170                 175

Leu Ala His Asn Ala Ile His Tyr Leu Val Gly Gly Lys Phe Glu Tyr
            180                 185                 190

Ser Met Ser Asn Leu Glu Tyr Thr Ser Tyr Asp Pro Ile Phe Phe Leu
        195                 200                 205

His His Ser Asn Val Asp Arg Leu Phe Ala Ile Trp Gln Arg Leu Gln
    210                 215                 220

Glu Leu Arg Gly Lys Asn Pro Asn Ala Met Asp Cys Ala His Glu Leu
225                 230                 235                 240

Ala His Gln Gln Leu Gln Pro Phe Asn Arg Asp Ser Asn Pro Val Gln
                245                 250                 255

Leu Thr Lys Asp His Ser Thr Pro Ala Asp Leu Phe Asp Tyr Lys Gln
            260                 265                 270
```

-continued

```
Leu Gly Tyr Ser Tyr Asp Ser Leu Asn Leu Asn Gly Met Thr Pro Glu
        275                 280                 285

Gln Leu Lys Thr Glu Leu Asp Glu Arg His Ser Lys Glu Arg Ala Phe
    290                 295                 300

Ala Ser Phe Arg Leu Ser Gly Phe Gly Gly Ser Ala Asn Val Val Val
305                 310                 315                 320

Tyr Ala Cys Val Pro Asp Asp Asp Pro Arg Ser Asp Asp Tyr Cys Glu
                325                 330                 335

Lys Ala Gly Asp Phe Phe Ile Leu Gly Gly Gln Ser Glu Met Pro Trp
            340                 345                 350

Arg Phe Tyr Arg Pro Phe Phe Tyr Asp Val Thr Glu Ala Val His His
        355                 360                 365

Leu Gly Val Pro Leu Ser Gly His Tyr Tyr Val Lys Thr Glu Leu Phe
    370                 375                 380

Ser Val Asn Gly Thr Ala Leu Ser Pro Asp Leu Leu Pro Gln Pro Thr
385                 390                 395                 400

Val Ala Tyr Arg Pro Gly Lys
                405


<210> SEQ ID NO 180
<211> LENGTH: 419
<212> TYPE: PRT
<213> ORGANISM: Haliotis tuberculata

<400> SEQUENCE: 180

Gly His Leu Asp Pro Pro Val His His Arg His Asp Asp Asp Leu Ile
  1               5                  10                  15

Val Arg Lys Asn Ile Asp His Leu Thr Arg Glu Glu Glu Tyr Glu Leu
            20                  25                  30

Arg Met Ala Leu Glu Arg Phe Gln Ala Asp Thr Ser Val Asp Gly Tyr
        35                  40                  45

Gln Ala Thr Val Glu Tyr His Gly Leu Pro Ala Arg Cys Pro Arg Pro
     50                  55                  60

Asp Ala Lys Val Arg Phe Ala Cys Cys Met His Gly Met Ala Ser Phe
 65                  70                  75                  80

Pro His Trp His Arg Leu Phe Val Thr Gln Val Glu Asp Ala Leu Val
                85                  90                  95

Arg Arg Gly Ser Pro Ile Gly Val Pro Tyr Trp Asp Trp Thr Lys Pro
            100                 105                 110

Met Thr His Leu Pro Asp Leu Ala Ser Asn Glu Thr Tyr Val Asp Pro
        115                 120                 125

Tyr Gly His Thr His His Asn Pro Phe Phe Asn Ala Asn Ile Ser Phe
    130                 135                 140

Glu Glu Gly His His His Thr Ser Arg Met Ile Asp Ser Lys Leu Phe
145                 150                 155                 160

Ala Pro Val Ala Phe Gly Glu His Ser His Leu Phe Asp Gly Ile Leu
                165                 170                 175

Tyr Ala Phe Glu Gln Glu Asp Phe Cys Asp Phe Glu Ile Gln Phe Glu
            180                 185                 190

Leu Val His Asn Ser Ile His Ala Trp Ile Gly Gly Ser Glu Asp Tyr
        195                 200                 205

Ser Met Ala Thr Leu His Tyr Thr Ala Phe Asp Pro Ile Phe Tyr Leu
    210                 215                 220

His His Ser Asn Val Asp Arg Leu Trp Ala Ile Trp Gln Ala Leu Gln
225                 230                 235                 240
```

-continued

```
Ile Arg Arg His Lys Pro Tyr Gln Ala His Cys Ala Gln Ser Val Glu
                245                 250                 255

Gln Leu Pro Met Lys Pro Phe Ala Phe Pro Ser Pro Leu Asn Asn Asn
            260                 265                 270

Glu Lys Thr His Ser His Ser Val Pro Thr Asp Ile Tyr Asp Tyr Glu
        275                 280                 285

Glu Val Leu His Tyr Ser Tyr Asp Asp Leu Thr Phe Gly Gly Met Asn
    290                 295                 300

Leu Glu Glu Ile Glu Glu Ala Ile His Leu Arg Gln Gln His Glu Arg
305                 310                 315                 320

Val Phe Ala Gly Phe Leu Leu Ala Gly Ile Gly Thr Ser Ala Leu Val
                325                 330                 335

Asp Ile Phe Ile Asn Lys Pro Gly Asn Gln Pro Leu Lys Ala Gly Asp
            340                 345                 350

Ile Ala Ile Leu Gly Gly Ala Lys Glu Met Pro Trp Ala Phe Asp Arg
        355                 360                 365

Leu Tyr Lys Val Glu Ile Thr Asp Ser Leu Lys Thr Leu Ser Leu Asp
    370                 375                 380

Val Asp Gly Asp Tyr Glu Val Thr Phe Lys Ile His Asp Met His Gly
385                 390                 395                 400

Asn Ala Leu Asp Thr Asp Leu Ile Pro His Ala Ala Val Val Ser Glu
                405                 410                 415

Pro Ala His


<210> SEQ ID NO 181
<211> LENGTH: 414
<212> TYPE: PRT
<213> ORGANISM: Haliotis tuberculata

<400> SEQUENCE: 181

Pro Thr Phe Glu Asp Glu Lys His Ser Leu Arg Ile Arg Lys Asn Val
  1               5                  10                  15

Asp Ser Leu Thr Pro Glu Glu Thr Asn Glu Leu Arg Lys Ala Leu Glu
            20                  25                  30

Leu Leu Glu Asn Asp His Thr Ala Gly Gly Phe Asn Gln Leu Gly Ala
        35                  40                  45

Phe His Gly Glu Pro Lys Trp Cys Pro Asn Pro Glu Ala Glu His Lys
     50                  55                  60

Val Ala Cys Cys Val His Gly Met Ala Val Phe Pro His Trp His Arg
 65                  70                  75                  80

Leu Leu Ala Leu Gln Ala Glu Asn Ala Leu Arg Lys His Gly Tyr Ser
                 85                  90                  95

Gly Ala Leu Pro Tyr Trp Asp Trp Thr Arg Pro Leu Ser Gln Leu Pro
            100                 105                 110

Asp Leu Val Ser His Glu Gln Tyr Thr Asp Pro Ser Asp His His Val
        115                 120                 125

Lys His Asn Pro Trp Phe Asn Gly His Ile Asp Thr Val Asn Gln Asp
    130                 135                 140

Thr Thr Arg Ser Val Arg Glu Asp Leu Tyr Gln Gln Pro Glu Phe Gly
145                 150                 155                 160

His Phe Thr Asp Ile Ala Gln Gln Val Leu Leu Ala Leu Glu Gln Asp
                165                 170                 175

Asp Phe Cys Ser Phe Glu Val Gln Tyr Glu Ile Ser His Asn Phe Ile
            180                 185                 190
```

-continued

```
His Ala Leu Val Gly Gly Thr Asp Ala Tyr Gly Met Ala Ser Leu Arg
            195                 200                 205

Tyr Thr Ala Tyr Asp Pro Ile Phe Phe Leu His His Ser Asn Thr Asp
    210                 215                 220

Arg Ile Trp Ala Ile Trp Gln Ser Leu Gln Lys Tyr Arg Gly Lys Pro
225                 230                 235                 240

Tyr Asn Thr Ala Asn Cys Ala Ile Glu Ser Met Arg Arg Pro Leu Gln
                245                 250                 255

Pro Phe Gly Leu Ser Ser Ala Ile Asn Pro Asp Arg Ile Thr Arg Glu
            260                 265                 270

His Ala Ile Pro Phe Asp Val Phe Asn Tyr Arg Asp Asn Leu His Tyr
        275                 280                 285

Val Tyr Asp Thr Leu Glu Phe Asn Gly Leu Ser Ile Ser Gln Leu Asp
    290                 295                 300

Arg Glu Leu Glu Lys Ile Lys Ser His Glu Arg Val Phe Ala Gly Phe
305                 310                 315                 320

Leu Leu Ser Gly Ile Lys Lys Ser Ala Leu Val Lys Phe Glu Val Cys
                325                 330                 335

Thr Pro Pro Asp Asn Cys His Lys Ala Gly Glu Phe Tyr Leu Leu Gly
            340                 345                 350

Asp Glu Asn Glu Met Ala Trp Ala Tyr Asp Arg Leu Phe Lys Tyr Asp
        355                 360                 365

Ile Thr Gln Val Leu Glu Ala Asn His Leu His Phe Tyr Asp His Leu
    370                 375                 380

Phe Ile Arg Tyr Glu Val Phe Asp Leu Lys Gly Val Ser Leu Gly Thr
385                 390                 395                 400

Asp Leu Phe His Thr Ala Asn Val Val His Asp Ser Gly Thr
                405                 410
```

<210> SEQ ID NO 182
<211> LENGTH: 413
<212> TYPE: PRT
<213> ORGANISM: Haliotis tuberculata

<400> SEQUENCE: 182

```
Gly Thr Arg Asp Arg Asp Asn Tyr Val Glu Glu Val Thr Gly Ala Ser
  1               5                  10                  15

His Ile Arg Lys Asn Leu Asn Asp Leu Asn Thr Gly Glu Met Glu Ser
             20                  25                  30

Leu Arg Ala Ala Phe Leu His Ile Gln Asp Asp Gly Thr Tyr Glu Ser
         35                  40                  45

Ile Ala Gln Tyr His Gly Lys Pro Gly Lys Cys Gln Leu Asn Asp His
     50                  55                  60

Asn Ile Ala Cys Cys Val His Gly Met Pro Thr Phe Pro Gln Trp His
 65                  70                  75                  80

Arg Leu Tyr Val Val Gln Val Glu Asn Ala Leu Leu Asn Arg Gly Ser
                 85                  90                  95

Gly Val Ala Val Pro Tyr Trp Glu Trp Thr Ala Pro Ile Asp His Leu
            100                 105                 110

Pro His Phe Ile Asp Asp Ala Thr Tyr Phe Asn Ser Arg Gln Gln Arg
        115                 120                 125

Tyr Asp Pro Asn Pro Phe Phe Arg Gly Lys Val Thr Phe Glu Asn Ala
    130                 135                 140

Val Thr Thr Arg Asp Pro Gln Ala Gly Leu Phe Asn Ser Asp Tyr Met
145                 150                 155                 160
```

-continued

```
Tyr Glu Asn Val Leu Leu Ala Leu Glu Gln Glu Asn Tyr Cys Asp Phe
                165                 170                 175

Glu Ile Gln Phe Glu Leu Val His Asn Ala Leu His Ser Met Leu Gly
            180                 185                 190

Gly Lys Gly Gln Tyr Ser Met Ser Ser Leu Asp Tyr Ser Ala Phe Asp
        195                 200                 205

Pro Val Phe Phe Leu His His Ala Asn Thr Asp Arg Leu Trp Ala Ile
    210                 215                 220

Trp Gln Glu Leu Gln Arg Phe Arg Glu Leu Pro Tyr Glu Glu Ala Asn
225                 230                 235                 240

Cys Ala Ile Asn Leu Met His Gln Pro Leu Lys Pro Phe Ser Asp Pro
                245                 250                 255

His Glu Asn His Asp Asn Val Thr Leu Lys Tyr Ser Lys Pro Gln Asp
            260                 265                 270

Gly Phe Asp Tyr Gln Asn His Phe Gly Tyr Lys Tyr Asp Asn Leu Glu
        275                 280                 285

Phe His His Leu Ser Ile Pro Ser Leu Asp Ala Thr Leu Lys Gln Arg
    290                 295                 300

Arg Asn His Asp Arg Val Phe Ala Gly Phe Leu Leu His Asn Ile Gly
305                 310                 315                 320

Thr Ser Ala Asp Ile Thr Ile Tyr Ile Cys Leu Pro Asp Gly Arg Arg
                325                 330                 335

Gly Asn Asp Cys Ser His Glu Ala Gly Thr Phe Tyr Ile Leu Gly Gly
            340                 345                 350

Glu Thr Glu Met Pro Phe Ile Phe Asp Arg Leu Tyr Lys Phe Glu Ile
        355                 360                 365

Thr Lys Pro Leu Gln Gln Leu Gly Val Lys Leu His Gly Gly Val Phe
    370                 375                 380

Glu Leu Glu Leu Glu Ile Lys Ala Tyr Asn Gly Ser Tyr Leu Asp Pro
385                 390                 395                 400

His Thr Phe Asp Pro Thr Ile Ile Phe Glu Pro Gly Thr
                405                 410


<210> SEQ ID NO 183
<211> LENGTH: 420
<212> TYPE: PRT
<213> ORGANISM: Haliotis tuberculata

<400> SEQUENCE: 183

Asp Thr His Ile Leu Asp His Asp His Glu Glu Glu Ile Leu Val Arg
  1               5                  10                  15

Lys Asn Ile Ile Asp Leu Ser Pro Arg Glu Arg Val Ser Leu Val Lys
            20                  25                  30

Ala Leu Gln Arg Met Lys Asn Asp Arg Ser Ala Asp Gly Tyr Gln Ala
        35                  40                  45

Ile Ala Ser Phe His Ala Leu Pro Pro Leu Cys Pro Asn Pro Ser Ala
    50                  55                  60

Ala His Arg Tyr Ala Cys Cys Val His Gly Met Ala Thr Phe Pro Gln
 65                  70                  75                  80

Trp His Arg Leu Tyr Thr Val Gln Val Gln Asp Ala Leu Arg Arg His
                 85                  90                  95

Gly Ser Leu Val Gly Ile Pro Tyr Trp Asp Trp Thr Lys Pro Val Asn
            100                 105                 110

Glu Leu Pro Glu Leu Leu Ser Ser Ala Thr Phe Tyr His Pro Ile Arg
        115                 120                 125
```

-continued

```
Asn Ile Asn Ile Ser Asn Pro Phe Leu Gly Ala Asp Ile Glu Phe Glu
    130                 135                 140

Gly Pro Gly Val His Thr Glu Arg His Ile Asn Thr Glu Arg Leu Phe
145                 150                 155                 160

His Ser Gly Asp His Asp Gly Tyr His Asn Trp Phe Phe Glu Thr Val
                165                 170                 175

Leu Phe Ala Leu Glu Gln Glu Asp Tyr Cys Asp Phe Glu Ile Gln Phe
            180                 185                 190

Glu Ile Ala His Asn Gly Ile His Thr Trp Ile Gly Gly Ser Ala Val
        195                 200                 205

Tyr Gly Met Gly His Leu His Tyr Ala Ser Tyr Asp Pro Ile Phe Tyr
    210                 215                 220

Ile His His Ser Gln Thr Asp Arg Ile Trp Ala Ile Trp Gln Glu Leu
225                 230                 235                 240

Gln Lys Tyr Arg Gly Leu Ser Gly Ser Glu Ala Asn Cys Ala Ile Glu
                245                 250                 255

His Met Arg Thr Pro Leu Lys Pro Phe Ser Phe Gly Pro Pro Tyr Asn
            260                 265                 270

Leu Asn Ser His Thr Gln Glu Tyr Ser Lys Pro Glu Asp Thr Phe Asp
        275                 280                 285

Tyr Lys Lys Phe Gly Tyr Arg Tyr Asp Ser Leu Glu Leu Glu Gly Arg
    290                 295                 300

Ser Ile Ser Arg Ile Asp Glu Leu Ile Gln Gln Arg Gln Glu Lys Asp
305                 310                 315                 320

Arg Thr Phe Ala Gly Phe Leu Leu Lys Gly Phe Gly Thr Ser Ala Ser
                325                 330                 335

Val Ser Leu Gln Val Cys Arg Val Asp His Thr Cys Lys Asp Ala Gly
            340                 345                 350

Tyr Phe Thr Ile Leu Gly Gly Ser Ala Glu Met Pro Trp Ala Phe Asp
        355                 360                 365

Arg Leu Tyr Lys Tyr Asp Ile Thr Lys Thr Leu His Asp Met Asn Leu
    370                 375                 380

Arg His Glu Asp Thr Phe Ser Ile Asp Val Thr Ile Thr Ser Tyr Asn
385                 390                 395                 400

Gly Thr Val Leu Ser Gly Asp Leu Ile Gln Thr Pro Ser Ile Ile Phe
                405                 410                 415

Val Pro Gly Arg
            420


<210> SEQ ID NO 184
<211> LENGTH: 417
<212> TYPE: PRT
<213> ORGANISM: Haliotis tuberculata

<400> SEQUENCE: 184

His Lys Leu Asn Ser Arg Lys His Thr Pro Asn Arg Val Arg His Glu
  1               5                  10                  15

Leu Ser Ser Leu Ser Ser Arg Asp Ile Ala Ser Leu Lys Ala Ala Leu
            20                  25                  30

Thr Ser Leu Gln His Asp Asn Gly Thr Asp Gly Tyr Gln Ala Ile Ala
        35                  40                  45

Ala Phe His Gly Val Pro Ala Gln Cys His Glu Pro Ser Gly Arg Glu
     50                  55                  60

Ile Ala Cys Cys Ile His Gly Met Ala Thr Phe Pro His Trp His Arg
 65                  70                  75                  80
```

-continued

```
Leu Tyr Thr Leu Gln Leu Glu Gln Ala Leu Arg Arg His Gly Ser Ser
                85                  90                  95

Val Ala Val Pro Tyr Trp Asp Trp Thr Lys Pro Ile Thr Glu Leu Pro
            100                 105                 110

His Ile Leu Thr Asp Gly Glu Tyr Tyr Asp Val Trp Gln Asn Ala Val
        115                 120                 125

Leu Ala Asn Pro Phe Ala Arg Gly Tyr Val Lys Ile Lys Asp Ala Phe
    130                 135                 140

Thr Val Arg Asn Val Gln Glu Ser Leu Phe Lys Met Ser Ser Phe Gly
145                 150                 155                 160

Lys His Ser Leu Leu Phe Asp Gln Ala Leu Leu Ala Leu Glu Gln Thr
                165                 170                 175

Asp Tyr Cys Asp Phe Glu Val Gln Phe Glu Val Met His Asn Thr Ile
            180                 185                 190

His Tyr Leu Val Gly Gly Arg Gln Thr Tyr Ala Phe Ser Ser Leu Glu
        195                 200                 205

Tyr Ser Ser Tyr Asp Pro Ile Phe Phe Ile His His Ser Phe Val Asp
    210                 215                 220

Lys Ile Trp Ala Val Trp Gln Glu Leu Gln Ser Arg Arg His Leu Gln
225                 230                 235                 240

Phe Arg Thr Ala Asp Cys Ala Val Gly Leu Met Gly Gln Ala Met Arg
                245                 250                 255

Pro Phe Asn Lys Asp Phe Asn His Asn Ser Phe Thr Lys Lys His Ala
            260                 265                 270

Val Pro Asn Thr Val Phe Asp Tyr Glu Asp Leu Gly Tyr Asn Tyr Asp
        275                 280                 285

Asn Leu Glu Ile Ser Gly Leu Asn Leu Asn Glu Ile Glu Ala Leu Ile
    290                 295                 300

Ala Lys Arg Lys Ser His Ala Arg Val Phe Ala Gly Phe Leu Leu Phe
305                 310                 315                 320

Gly Leu Gly Thr Ser Ala Asp Ile His Leu Glu Ile Cys Lys Thr Ser
                325                 330                 335

Glu Asn Cys His Asp Ala Gly Val Ile Phe Ile Leu Gly Gly Ser Ala
            340                 345                 350

Glu Met His Trp Ala Tyr Asn Arg Leu Tyr Lys Tyr Asp Ile Thr Glu
        355                 360                 365

Ala Leu Gln Glu Phe Asp Ile Asn Pro Glu Asp Val Phe His Ala Asp
    370                 375                 380

Glu Pro Phe Phe Leu Arg Leu Ser Val Val Ala Val Asn Gly Thr Val
385                 390                 395                 400

Ile Pro Ser Ser His Leu His Gln Pro Thr Ile Ile Tyr Glu Pro Gly
                405                 410                 415

Glu


<210> SEQ ID NO 185
<211> LENGTH: 403
<212> TYPE: PRT
<213> ORGANISM: Haliotis tuberculata

<400> SEQUENCE: 185

Asp His His Asp Asp His Gln Ser Gly Ser Ile Ala Gly Ser Gly Val
  1               5                  10                  15

Arg Lys Asp Val Asn Thr Leu Thr Lys Ala Glu Thr Asp Asn Leu Arg
             20                  25                  30
```

-continued

```
Glu Ala Leu Trp Gly Val Met Ala Asp His Gly Pro Asn Gly Phe Gln
        35                  40                  45

Ala Ile Ala Ala Phe His Gly Lys Pro Ala Leu Cys Pro Met Pro Asp
    50                  55                  60

Gly His Asn Tyr Ser Cys Cys Thr His Gly Met Ala Thr Phe Pro His
65                  70                  75                  80

Trp His Arg Leu Tyr Thr Lys Gln Met Glu Asp Ala Met Arg Ala His
                85                  90                  95

Gly Ser His Val Gly Leu Pro Tyr Trp Asp Trp Thr Ala Ala Phe Thr
            100                 105                 110

His Leu Pro Thr Leu Val Thr Asp Thr Asp Asn Asn Pro Phe Gln His
        115                 120                 125

Gly His Ile Asp Tyr Leu Asn Val Ser Thr Thr Arg Ser Pro Arg Asp
    130                 135                 140

Met Leu Phe Asn Asp Pro Glu His Gly Ser Glu Ser Phe Phe Tyr Arg
145                 150                 155                 160

Gln Val Leu Leu Ala Leu Glu Gln Thr Asp Phe Cys Lys Phe Glu Val
                165                 170                 175

Gln Phe Glu Ile Thr His Asn Ala Ile His Ser Trp Thr Gly Gly His
            180                 185                 190

Ser Pro Tyr Gly Met Ser Thr Leu Asp Phe Thr Ala Tyr Asp Pro Leu
        195                 200                 205

Phe Trp Leu His His Ser Asn Thr Asp Arg Ile Trp Ala Val Trp Gln
    210                 215                 220

Ala Leu Gln Glu Tyr Arg Gly Leu Pro Tyr Asn His Ala Asn Cys Glu
225                 230                 235                 240

Ile Gln Ala Met Lys Thr Pro Leu Arg Pro Phe Ser Asp Asp Ile Asn
                245                 250                 255

His Asn Pro Val Thr Lys Ala Asn Ala Lys Pro Leu Asp Val Phe Glu
            260                 265                 270

Tyr Asn Arg Leu Ser Phe Gln Tyr Asp Asn Leu Ile Phe His Gly Tyr
        275                 280                 285

Ser Ile Pro Glu Leu Asp Arg Val Leu Glu Glu Arg Lys Glu Glu Asp
    290                 295                 300

Arg Ile Phe Ala Ala Phe Leu Leu Ser Gly Ile Lys Arg Ser Ala Asp
305                 310                 315                 320

Val Val Phe Asp Ile Cys Gln Pro Glu His Glu Cys Val Phe Ala Gly
                325                 330                 335

Thr Phe Ala Ile Leu Gly Gly Glu Leu Glu Met Pro Trp Ser Phe Asp
            340                 345                 350

Arg Leu Phe Arg Tyr Asp Ile Thr Lys Val Met Lys Gln Leu His Leu
        355                 360                 365

Arg His Asp Ser Asp Phe Thr Phe Arg Val Lys Ile Val Gly Thr Asp
    370                 375                 380

Asp His Glu Leu Pro Ser Asp Ser Val Lys Ala Pro Thr Ile Glu Phe
385                 390                 395                 400

Glu Pro Gly
```

<210> SEQ ID NO 186
<211> LENGTH: 511
<212> TYPE: PRT
<213> ORGANISM: Haliotis tuberculata -continued

<400> SEQUENCE: 186

```
Val His Arg Gly Gly Asn His Glu Asp Glu His His Asp Asp Arg Leu
  1               5                  10                  15

Ala Asp Val Leu Ile Arg Lys Glu Val Asp Phe Leu Ser Leu Gln Glu
             20                  25                  30

Ala Asn Ala Ile Lys Asp Ala Leu Tyr Lys Leu Gln Asn Asp Asp Ser
         35                  40                  45

Lys Gly Gly Phe Glu Ala Ile Ala Gly Tyr His Gly Tyr Pro Asn Met
     50                  55                  60

Cys Pro Glu Arg Gly Thr Asp Lys Tyr Pro Cys Cys Val His Gly Met
 65                  70                  75                  80

Pro Val Phe Pro His Trp His Arg Leu His Thr Ile Gln Met Glu Arg
                 85                  90                  95

Ala Leu Lys Asn His Gly Ser Pro Met Gly Ile Pro Tyr Trp Asp Trp
            100                 105                 110

Thr Lys Lys Met Ser Ser Leu Pro Ser Phe Phe Gly Asp Ser Ser Asn
        115                 120                 125

Asn Asn Pro Phe Tyr Lys Tyr Tyr Ile Arg Gly Val Gln His Glu Thr
    130                 135                 140

Thr Arg Asp Ile Asn Gln Arg Leu Phe Asn Gln Thr Lys Phe Gly Glu
145                 150                 155                 160

Phe Asp Tyr Leu Tyr Tyr Leu Thr Leu Gln Val Leu Glu Glu Asn Ser
                165                 170                 175

Tyr Cys Asp Phe Glu Val Gln Tyr Glu Ile Leu His Asn Ala Val His
            180                 185                 190

Ser Trp Leu Gly Gly Thr Gly Lys Tyr Ser Met Ser Thr Leu Glu His
        195                 200                 205

Ser Ala Phe Asp Pro Val Phe Met Ile His His Ser Ser Leu Asp Arg
    210                 215                 220

Ile Trp Ile Leu Trp Gln Lys Leu Gln Lys Ile Arg Met Lys Pro Tyr
225                 230                 235                 240

Tyr Ala Leu Asp Cys Ala Gly Asp Arg Leu Met Lys Asp Pro Leu His
                245                 250                 255

Pro Phe Asn Tyr Glu Thr Val Asn Glu Asp Glu Phe Thr Arg Ile Asn
            260                 265                 270

Ser Phe Pro Ser Ile Leu Phe Asp His Tyr Arg Phe Asn Tyr Glu Tyr
        275                 280                 285

Asp Asn Met Arg Ile Arg Gly Gln Asp Ile His Glu Leu Glu Glu Val
    290                 295                 300

Ile Gln Glu Leu Arg Asn Lys Asp Arg Ile Phe Ala Gly Phe Val Leu
305                 310                 315                 320

Ser Gly Leu Arg Ile Ser Ala Thr Val Lys Val Phe Ile His Ser Lys
                325                 330                 335

Asn Asp Thr Ser His Glu Glu Tyr Ala Gly Glu Phe Ala Val Leu Gly
            340                 345                 350

Gly Glu Lys Glu Met Pro Trp Ala Tyr Glu Arg Met Leu Lys Leu Asp
        355                 360                 365

Ile Ser Asp Ala Val His Lys Leu His Val Lys Asp Glu Asp Ile Arg
    370                 375                 380

Phe Arg Val Val Val Thr Ala Tyr Asn Gly Asp Val Val Thr Thr Arg
385                 390                 395                 400

Leu Ser Gln Pro Phe Ile Val His Arg Pro Ala His Val Ala His Asp
                405                 410                 415
```

-continued

```
Ile Leu Val Ile Pro Val Gly Ala Gly His Asp Leu Pro Pro Lys Val
            420                 425                 430

Val Val Lys Ser Gly Thr Lys Val Glu Phe Thr Pro Ile Asp Ser Ser
        435                 440                 445

Val Asn Lys Ala Met Val Glu Leu Gly Ser Tyr Thr Ala Met Ala Lys
    450                 455                 460

Cys Ile Val Pro Pro Phe Ser Tyr His Gly Phe Glu Leu Asp Lys Val
465                 470                 475                 480

Tyr Ser Val Asp His Gly Asp Tyr Tyr Ile Ala Ala Gly Thr His Ala
                485                 490                 495

Leu Cys Glu Gln Asn Leu Arg Leu His Ile His Val Glu His Glu
            500                 505                 510


<210> SEQ ID NO 187
<211> LENGTH: 90
<212> TYPE: DNA
<213> ORGANISM: Haliotis tuberculata

<400> SEQUENCE: 187

ggtcttccgt actgggactg gacgcagcat ctgactcaac tcccagatct ggtgtcagac      60

cccttgtttg tcgacccgga aggaggaaag                                        90


<210> SEQ ID NO 188
<211> LENGTH: 221
<212> TYPE: DNA
<213> ORGANISM: Haliotis tuberculata

<400> SEQUENCE: 188

gcccatgaca acgcatggta tcgtggaaac atcaagtttg agaataagaa gactgcaaga      60

gctgttgacg atcgcctttt cgagaaggtt ggaccaggag agaatacccg actctttgaa     120

ggaattctcg atgctcttga acaggatgaa ttctgcaact tcgagatcca gtttgagttg     180

gctcacaacg ctatccacta cctggttggc ggccgtcaca c                         221


<210> SEQ ID NO 189
<211> LENGTH: 255
<212> TYPE: DNA
<213> ORGANISM: Haliotis tuberculata

<400> SEQUENCE: 189

gtactccatg tctcatctcg agtacacctc ctacgacccc ctcttcttcc tccatcactc      60

caacaccgac cgcatcttcg ccatctggca acgtcttcag gtactcagag gaaaggaccc     120

caacaccgcc gactgcgcac acaacctcat ccatgagccc atggaaccgt tccgtcggga     180

ctcgaaccct cttgacctca ccagggaaaa ctccaaacca attgacagct ttgattatgc     240

ccaccttggc tacca                                                      255


<210> SEQ ID NO 190
<211> LENGTH: 407
<212> TYPE: DNA
<213> ORGANISM: Haliotis tuberculata

<400> SEQUENCE: 190

gtatgatgac ttgaccctga acggtatgac cccagaggaa ttgaactcat atctgcatga      60

acggtcaggc aaggaggggg tgttcgcaag cttccgactc tcaggttttg gcggctctgc     120

taacgttgtt gtctacgcat gccgtcctgc ccacgatgaa atggctgtcg atcagtgcga     180

caaagccggc gacttctttg tgttgggcgg acccaccgag atgccctgga ggttttacag     240
```

-continued

```
agcattccac ttcgacgtca ccgacagcat cgacaacatc gacaaggacc gccacggcca    300

ctattatgta aaggcggaat tattcagtgt aaatggaagt gcgctaccga atgatctcct    360

gcctcaaccc accatctcac acaggccagc ccgcggacac gttgatg                   407
```

<210> SEQ ID NO 191
<211> LENGTH: 1239
<212> TYPE: DNA
<213> ORGANISM: Haliotis tuberculata

<400> SEQUENCE: 191

```
aggccccagc tccctcctcg gatgctcacc tcgccgtcag gaaggatatc aaccatctga     60

cacgcgagga ggtgtacgag ctgcgcagag ctatggagag attccaggcc gacacatccg    120

ttgatgggta ccaggctacg gttgagtatc acggcttacc tgctcgatgt ccattccccg    180

aggccacaaa taggttcgcc tgttgcatcc acggcatggc gacattccct cattggcaca    240

gactgttcgt tacccaggtg gaagatgcac tgatcaggcg aggatcccct ataggggtcc    300

cctactggga ctggactcag cctatggcac atctcccagg acttgcagac aacgccacct    360

atagagatcc catcagcgga gacagcagac acaacccgtt ccacgatgtt gaagttgcct    420

ttgaaaatgg gcgtacagaa cgtcacccag atagtagatt gtttgaacaa cctctatttg    480

gcaaacatac gcgtctcttc gacagtatag tctatgcttt tgagcaggag gacttctgcg    540

attttgaagt tcaatttgag atgacccata ataatattca cgcctggatt ggtggcggcg    600

ggaagtattc catgtcttct ctacactaca cagccttcga ccctatctcc taccttcatc    660

actccaacac tgaccgtctc tgggcaattt ggcaagcgtt gcagatacga agaaacaaac    720

cgtataaggc tcattgtgct tggtctgagg aacgccagcc tctcaaacct ttcgccttca    780

gttccccact gaacaacaac gaaaaaacct acgaaaactc ggtgcccacc aacgtttacg    840

actacgaagg agtccttggc tatacttatg atgacctcaa cttcgggggc atggacctgg    900

gtcagcttga ggaatacatc cagaggcaga gacagagaga caggaccttt gctggcttct    960

ttctgtcaca tattggtaca tcagcgaatg ttgaaatcat tatagaccat gggactcttc   1020

atacctccgt gggcacgttt gctgttcttg gcggagagaa ggagatgaaa tggggatttg   1080

accgtttgta caaatatgag attacagatg aactgaggca acttaatctc cgtgctgatg   1140

atggtttcag catctctgtt aaagtaactg atgttgatgg cagtgagctg tcctctgaac   1200

tcatcccatc tgctgctatc atcttcgaac gaagccata                          1239
```

<210> SEQ ID NO 192
<211> LENGTH: 1245
<212> TYPE: DNA
<213> ORGANISM: Haliotis tuberculata

<400> SEQUENCE: 192

```
ttgaccatca ggaccctcat caggacacaa tcatcaggaa aaatgttgat aatcttacac     60

ccgaggaaat taattctctg aggagggcaa tggcagacct tcaatcagac aaaaccgccg    120

gtggattcca gcaaattgct gcttttcacg gggaacccaa atggtgccca agtcccgatg    180

ctgagaagaa gttctcctgc tgtgtccatg gaatggctgt cttccctcac tggcacagac    240

tcctgaccgt gcaaggcgag aatgccctga gaaagcatgg atgtctcgga gctctcccct    300

actgggactg gactcggccc ctgtctcacc tacctgattt ggtaagtcag cagaactaca    360

ccgatgccat atccaccgtg gaagcccgaa acccctggta cagcggccat attgatacag    420

ttggtgttga cacaacaaga agcgtccgtc aagaactgta tgaagctccc ggatttggtc    480
```

-continued

```
attatactgg ggtcgctaag caagtgcttc tggctttgga gcaggatgac ttctgtgatt    540
ttgaagtcca gtttgagata gctcacaatt tcatccacgc tcttgtcggc ggaagcgagc    600
catatggtat ggcgtcactc cgttacacta cttatgatcc aattttctac ctccatcatt    660
ctaacactga cagactctgg gctatatggc aggctctaca aaagtacagg ggcaaacctt    720
acaattccgc caactgtgcc attgcttcta tgagaaaacc cctacagccc tttggtctga    780
ctgatgagat caacccggat gatgagacaa gacagcatgc tgttcctttc agtgtctttg    840
attacaagaa caacttcaat tatgaatatg acacccttga cttcaacgga ctatcaatct    900
cccagctgga ccgtgaactg tcacggagaa agtctcatga cagagtattt gccggatttt    960
tgctgcatgg tattcagcag tctgcactag ttaaattctt tgtctgcaaa tcagatgatg   1020
actgtgacca ctatgctggt gaattctaca tccttggtga tgaagctgaa atgccatggg   1080
gctatgatcg tctttacaaa tatgagatca ctgagcagct caatgccctg gatctacaca   1140
tcggagatag attcttcatc agatacgaag cgtttgatct tcatggtaca agtcttggaa   1200
gcaacatctt ccccaaacct tctgtcatac atgacgaagg ggcag                   1245
```

<210> SEQ ID NO 193
<211> LENGTH: 1242
<212> TYPE: DNA
<213> ORGANISM: Haliotis tuberculata

<400> SEQUENCE: 193

```
gtcaccatca ggctgacgag tacgacgaag ttgtaactgc tgcaagccac atcagaaaga     60
atttaaaaga tctgtcaaag ggagaagtag agagcctaag gtctgccttc ctgcaacttc    120
agaacgacgg agtctatgag aatattgcca aattccacgg caagcctggg ttgtgtgatg    180
ataacggtcg caaggttgcc tgttgtgtcc atggaatgcc caccttcccc cagtggcaca    240
gactctatgt cctccaggtg gagaatgctt tgctggagag aggatctgcc gtctctgtgc    300
catactggga ctggactgaa acatttacag agctgccatc tttgattgct gaggctacct    360
atttcaattc ccgtcaacaa acgtttgacc ctaatccttt cttcagaggt aaaatcagtt    420
ttgagaatgc tgttacaaca cgtgatcccc agcctgagct gtacgttaac aggtactact    480
accaaaacgt catgttggct tttgaacagg acaactactg cgacttcgag atacagtttg    540
agatggttca caatgttctc catgcttggc ttggtggaag agctacttat tctatttctt    600
ctcttgatta ttctgcattc gaccctgtgt ttttccttca ccatgcgaac acagatagat    660
tgtgggccat ctggcaggag ctgcagaggt acaggaagaa gccatacaat gaagcggatt    720
gtgccattaa cctaatgcgc aaacctctac atcccttcga caacagtgat ctcaatcatg    780
atcctgtaac ctttaaatac tcaaaaccca ctgatggctt tgactaccag aacaactttg    840
gatacaagta tgacaacctt gagttcaatc atttcagtat tcccaggctt gaagaaatca    900
ttcgtattag acaacgtcaa gatcgtgtgt ttgcaggatt cctccttcac aacattggga    960
catccgcaac tgttgagata ttcgtctgtg tccctaccac cagcggtgag caaaactgtg   1020
aaaacaaagc cggaacattt gccgtactcg gaggagaaac agagatggcg tttcattttg   1080
acagactcta caggtttgac atcagtgaaa cactgaggga cctcggcata cagctggaca   1140
gccatgactt tgacctcagc atcaagattc aaggagtaaa tggatcctac cttgatccac   1200
acatcctgcc agagccatcc ttgatttttg tgcctggttc aa                      1242
```

-continued

<210> SEQ ID NO 194
<211> LENGTH: 1257
<212> TYPE: DNA
<213> ORGANISM: Haliotis tuberculata

<400> SEQUENCE: 194
gttctttcct gcgtcctgat gggcattcag atgacatcct tgtgagaaaa gaagtgaaca 60
gcctgacaac cagggagact gcatctctga tccatgctct gaaaagtatg caggaagacc 120
attcacctga tgggttccaa gccattgcct ctttccatgc cctgccacca ctctgccctt 180
caccatctgc aactcaccgt tatgcttgct gtgtccacgg catggctaca tttccccagt 240
ggcacagact gtacactgta cagttccagg atgcactgag gagacatgga gctgcagtag 300
gtgtaccgta ttgggattgg ctgcgaccgc agtctcacct accagagctt gtcaccatgg 360
agacatacca tgatatttgg agtaacagag atttccccaa tcctttctac caagccaata 420
ttgagtttga aggagaaaac attacaacag agagagaagt cattgcagac aaactttttg 480
tcaaaggtgg acacgttttt gataactggt tcttcaaaca agccatccta gcgcttgagc 540
aggaaaacta ctgtgacttt gagattcagt ttgaaattct tcacaacggc gttcacacgt 600
gggtcggagg cagtcgtacc cactctatcg gacatctcca ttacgcatcc tacgaccctc 660
ttttctacct ccaccattcc cagacagacc gtatttgggc aatctggcaa gaactccagg 720
aacagagagg gctctcaggt gatgaggctc actgtgctct cgagcaaatg agagaaccat 780
tgaagccttt cagcttcggc gctccttata acttgaatca gctaacacag gatttctccc 840
gacccgagga caccttcgac tacaggaagt ttggttatga atatgacaat ttagaattcc 900
taggaatgtc agttgctgaa ctggatcaat acattattga acatcaagaa aatgatagag 960
tattcgctgg gttcctgttg agtggattcg gaggttccgc atcagttaat ttccaggttt 1020
gtagagctga ttccacatgt caggatgctg ggtacttcac cgttcttggt ggcagtgctg 1080
agatggcgtg ggcatttgac aggctataca aatatgacat tactgaaact ctggagaaaa 1140
tgcaccttcg atatgatgat gacttcacaa tctctgtcag tctgaccgcc aacaacggaa 1200
ctgtcctgag cagcagtcta atcccaacac cgagtgtcat attccagcgg ggacatc 1257

<210> SEQ ID NO 195
<211> LENGTH: 191
<212> TYPE: DNA
<213> ORGANISM: Haliotis tuberculata

<400> SEQUENCE: 195
gtgacataaa taccaagagc atgtcagcga accgtgttcg ccgtgagctg agcgatctgt 60
ctgcgaggga cccgtctagt ctcaagtctg ctctgcgaga cctacaggag gatgatggcc 120
ccaacggata ccaggctctt gcagccttcc atgggctacc agcaggctgc catgatagcc 180
agggaaatga g 191

<210> SEQ ID NO 196
<211> LENGTH: 1057
<212> TYPE: DNA
<213> ORGANISM: Haliotis tuberculata

<400> SEQUENCE: 196
atcgcatgtt gcattcacgg tatgccgacc ttcccccagt ggcacagact gtacaccctg 60
cagttggaga tggctctgag gagacatgga tcatctgtcg ccatccccta ctgggactgg 120
acaaagccta tctccgaact cccctcgctc ttcaccagcc ctgagtatta tgacccatgg 180

-continued

```
catgatgctg tggtaaacaa cccattctcc aaaggttttg tcaaatttgc aaatacctac    240

acagtaagag acccacagga gatgctgttc cagctttgtg aacatggaga gtcaatcctc    300

tatgagcaaa ctcttcttgc tctagagcaa accgactact gtgattttga ggtacagttt    360

gaggtcctcc ataacgtgat ccactacctt gttggcggac gtcagaccta cgcattgtct    420

tctctgcatt atgcatccta cgacccattc ttctttatac accattcctt tgtggataag    480

atgtgggtag tatggcaagc tcttcaaaag aggaggaaac ttccatacaa gcgagctgac    540

tgtgctgtca acctaatgac taaaccaatg aggccatttg actccgatat gaatcagaac    600

ccattcacaa agatgcacgc agttcccaac acactctatg actacgagac actgtactac    660

agctacgata atctcgaaat aggtggcagg aatctcgacc agcttcaggc tgaaattgac    720

agaagcagaa gccacgatcg cgtttttgct ggattcttgc ttcgtggaat cggaacttct    780

gctgatgtca ggttttggat ttgtagaaat gaaaatgact gccacagggg tggaataatt    840

ttcatcttag gtggagccaa ggaaatgcca tggtcatttg acagaaactt caagtttgat    900

atcacccatg tactcgagaa agctggcatt agcccagagg acgtgtttga tgctgaggag    960

ccattttata tcaaggttga gatccatgct gttaacaaga ccatgatacc atcgtctgtg   1020

atcccagccc caactatcat ctattctcct ggggaag                            1057
```

<210> SEQ ID NO 197
<211> LENGTH: 219
<212> TYPE: DNA
<213> ORGANISM: Haliotis tuberculata

<400> SEQUENCE: 197

```
gtcgcgctgc tgacagtgca cactcagcca acattgctgg ctctggggtg aggaaggacg     60

tcacgaccct cactgtgtct gagaccgaga acctaagaca ggctcttcaa ggtgtcatcg    120

atgatactgg tcccaatggt taccaagcaa tagcatcctt ccacggaagt cctccaatgt    180

gcgagatgaa cggccgcaag gttgcctgtt gtgctcacg                          219
```

<210> SEQ ID NO 198
<211> LENGTH: 164
<212> TYPE: DNA
<213> ORGANISM: Haliotis tuberculata

<400> SEQUENCE: 198

```
gtatggcctc cttcccacac tggcacagac tgtatgtgaa gcagatggaa gacgccctgg     60

ctgaccacgg atcacatatc ggcatccctt actgggactg gacaactgcc ttcacagagt    120

tacccgccct tgtcacagac tccgagaaca atcccttcca tgag                     164
```

<210> SEQ ID NO 199
<211> LENGTH: 826
<212> TYPE: DNA
<213> ORGANISM: Haliotis tuberculata

<400> SEQUENCE: 199

```
ggtcgcattg atcatctcgg tgtaaccacg tcacgttccc ccagagacat gctgtttaac     60

gacccagagc aaggatcaga gtcgttcttc tatagacaag tcctcctggc tttggagcag    120

actgactact gccagttcga agtccagttt gagctgaccc acaacgccat tcactcctgg    180

acaggtggac gtagccctta cggaatgtcg accctcgagt tcacagccta cgatcctctc    240

ttctggcttc accactccaa caccgacaga atctgggctg tctggcaagc actgcagaaa    300

taccgaggac tcccatacaa cgaagcacac tgtgaaatcc aggttctgaa acagcccttg    360
```

-continued

```
aggccattca acgatgacat caaccacaat ccaatcacca agactaatgc caggcctatc    420

gattcatttg attatgagag gtttaactat cagtatgaca cccttagctt ccatggtaag    480

agcatccctg aactgaatga cctgctcgag gaaagaaaaa gagaagagag aacatttgct    540

gccttccttc ttcgtggaat cggttgcagt gctgatgtcg tctttgacat ctgccgcccc    600

aatggtgact gtgtctttgc aggaaccttt gctgtgctgg gaggggagct agaaatgcct    660

tggtccttcg acagactgtt ccgctatgac atcaccagag tcatgaatca gctccatctc    720

cagtatgatt cagatttcag tttcagggtg aagcttgttg caaccaatgg cactgagctt    780

tcatcagacc tcctcaagtc accaacaatt gaacatgaac ttggag                   826
```

<210> SEQ ID NO 200
<211> LENGTH: 1535
<212> TYPE: DNA
<213> ORGANISM: Haliotis tuberculata

<400> SEQUENCE: 200

```
cccacagagg accagttgaa gaaacagaag tcactcacca aaatactgac ggcaatgcac     60

acttccatcg taaggaagtt gattcgctgt ccctggatga agcaaacaac ttgaagaatg    120

ccctttacaa gctacagaac gaccacagtc taacaggata cgaagcaatc tctggttacc    180

atggataccc gaatctgtgt ccggaagaag gcgatgacaa ataccccctgc tgcgtccacg    240

gaatggccat cttcccccac tggcacagac tcttgaccat ccaactggaa agagctctcg    300

agcacaatgg tgcactgctt ggtgttcctt actgggactg gaccaaggac ctgtcgtcac    360

tgccggcgtt cttctccgac tccagcaaca acaatcccta cttcaagtac cacatcgcag    420

gtgttggtca cgacaccgtc agagagccaa ctagtcttat atataaccag ccccaaatcc    480

atggttatga ttatctctat tacctagcat tgaccacgct tgaagaaaac aattactgtg    540

actttgaggt tcagtatgag atcctccaca acgccgtcca ctcctggctt ggaggatccc    600

agaagtattc catgtctacc ctggagtatt cggcctttga ccctgtcttt atgatccttc    660

actcgggtct agacagactt tggatcatct ggcaagaact tcagaagatc aggagaaagc    720

cctacaactt cgctaaatgt gcttatcata tgatggaaga gccactggcg cccttcagct    780

atccatctat caaccaggac gagttcaccc gtgccaactc caagccttct acagtttttg    840

acagccataa gttcggctac cattacgata acctgaatgt tagaggtcac agcatccaag    900

aactcaacac aatcatcaat gacttgagaa acacagacag aatctacgca ggatttgttt    960

tgtcaggcat cggtacgtct gctagtgtca agatctatct ccgaacagat gacaatgacg   1020

aagaagttgg aactttcact gtcctgggag gagagaggga aatgccatgg gcctacgagc   1080

gagttttcaa gtatgacatc acagaggttg cagatagact taaactaagt tatggggaca   1140

cctttaactt ccgactagag atcacatcct acgatggatc ggtggtaaac aagagcctac   1200

ccaatccttt catcatctac agacctgcca atcatgacta cgatgttctt gttatcccag   1260

taggaagaaa ccttcacatc cctcccaaag ttgtcgtcaa gagaggcacc cgcatcgagt   1320

tccacccagt cgatgattca gttacgagac cagttgttga tcttggaagc tacactgcac   1380

tcttcaactg tgtggtacca ccgttcacat accgcggatt cgaactgaac cacgtctatt   1440

ctgtcaagcc tggtgactac tatgttaccg gaccaacgag agacctttgc cagaatgcag   1500

atgtcaggat tcatatccat gttgaggatg agtaa                              1535
```

-continued

<210> SEQ ID NO 201
<211> LENGTH: 8
<212> TYPE: DNA
<213> ORGANISM: Haliotis tuberculata

<400> SEQUENCE: 201 cgcaacag 8

<210> SEQ ID NO 202
<211> LENGTH: 211
<212> TYPE: DNA
<213> ORGANISM: Haliotis tuberculata

<400> SEQUENCE: 202
gtttcttggt ctccacatat tcacacatca gcaccaaacg gtttcgaagg acattggcgt 60
tcttctctgg caatgcattt caatacaaca ttgaaaatga cttcagcata tcagtgtgct 120
tcgaacgtgt tccggaagta ctcaaatgtg ctatgactga attattgtac atacataact 180
tattgatgtt caataaataa atgttgaaac g 211

<210> SEQ ID NO 203
<211> LENGTH: 334
<212> TYPE: PRT
<213> ORGANISM: Haliotis tuberculata

<400> SEQUENCE: 203

His Arg Leu Phe Val Thr Gln Val Glu Asp Ala Leu Ile Arg Arg Gly
1 5 10 15

Ser Pro Ile Gly Val Pro Tyr Trp Asp Trp Thr Gln Pro Met Ala His
20 25 30

Leu Pro Gly Leu Ala Asp Asn Ala Thr Tyr Arg Asp Pro Ile Ser Gly
35 40 45

Asp Ser Arg His Asn Pro Phe His Asp Val Glu Val Ala Phe Glu Asn
50 55 60

Gly Arg Thr Glu Arg His Pro Asp Ser Arg Leu Phe Glu Gln Pro Leu
65 70 75 80

Phe Gly Lys His Thr Arg Leu Phe Asp Ser Ile Val Tyr Ala Phe Glu
85 90 95

Gln Glu Asp Phe Cys Asp Phe Glu Val Gln Phe Glu Met Thr His Asn
100 105 110

Asn Ile His Ala Trp Ile Gly Gly Gly Gly Lys Tyr Ser Met Ser Ser
115 120 125

Leu His Tyr Thr Ala Phe Asp Pro Ile Ser Tyr Leu His His Ser Asn
130 135 140

Thr Asp Arg Leu Trp Ala Ile Trp Gln Ala Leu Gln Ile Arg Arg Asn
145 150 155 160

Lys Pro Tyr Lys Ala His Cys Ala Trp Ser Glu Glu Arg Gln Pro Leu
165 170 175

Lys Pro Phe Ala Phe Ser Ser Pro Leu Asn Asn Asn Glu Lys Thr Tyr
180 185 190

Glu Asn Ser Val Pro Thr Asn Val Tyr Asp Tyr Glu Gly Val Leu Gly
195 200 205

Tyr Thr Tyr Asp Asp Leu Asn Phe Gly Gly Met Asp Leu Gly Gln Leu
210 215 220

Glu Glu Tyr Ile Gln Arg Gln Arg Gln Arg Asp Arg Thr Phe Ala Gly
225 230 235 240

-continued

```
Phe Phe Leu Ser His Ile Gly Thr Ser Ala Asn Val Glu Ile Ile Ile
                245                 250                 255

Asp His Gly Thr Leu His Thr Ser Val Gly Thr Phe Ala Val Leu Gly
            260                 265                 270

Gly Glu Lys Glu Met Lys Trp Gly Phe Asp Arg Leu Tyr Lys Tyr Glu
        275                 280                 285

Ile Thr Asp Glu Leu Arg Gln Leu Asn Leu Arg Ala Asp Asp Gly Phe
    290                 295                 300

Ser Ile Ser Val Lys Val Thr Asp Val Asp Gly Ser Glu Leu Ser Ser
305                 310                 315                 320

Glu Leu Ile Pro Ser Ala Ala Ile Ile Phe Glu Arg Ser His
                325                 330


<210> SEQ ID NO 204
<211> LENGTH: 415
<212> TYPE: PRT
<213> ORGANISM: Haliotis tuberculata

<400> SEQUENCE: 204

Ile Asp His Gln Asp Pro His Gln Asp Thr Ile Ile Arg Lys Asn Val
  1               5                  10                  15

Asp Asn Leu Thr Pro Glu Glu Ile Asn Ser Leu Arg Arg Ala Met Ala
             20                  25                  30

Asp Leu Gln Ser Asp Lys Thr Ala Gly Gly Phe Gln Gln Ile Ala Ala
         35                  40                  45

Phe His Gly Glu Pro Lys Trp Cys Pro Ser Pro Asp Ala Glu Lys Lys
     50                  55                  60

Phe Ser Cys Cys Val His Gly Met Ala Val Phe Pro His Trp His Arg
 65                  70                  75                  80

Leu Leu Thr Val Gln Gly Glu Asn Ala Leu Arg Lys His Gly Cys Leu
                 85                  90                  95

Gly Ala Leu Pro Tyr Trp Asp Trp Thr Arg Pro Leu Ser His Leu Pro
            100                 105                 110

Asp Leu Val Ser Gln Gln Asn Tyr Thr Asp Ala Ile Ser Thr Val Glu
        115                 120                 125

Ala Arg Asn Pro Trp Tyr Ser Gly His Ile Asp Thr Val Gly Val Asp
    130                 135                 140

Thr Thr Arg Ser Val Arg Gln Glu Leu Tyr Glu Ala Pro Gly Phe Gly
145                 150                 155                 160

His Tyr Thr Gly Val Ala Lys Gln Val Leu Leu Ala Leu Glu Gln Asp
                165                 170                 175

Asp Phe Cys Asp Phe Glu Val Gln Phe Glu Ile Ala His Asn Phe Ile
            180                 185                 190

His Ala Leu Val Gly Gly Ser Glu Pro Tyr Gly Met Ala Ser Leu Arg
        195                 200                 205

Tyr Thr Thr Tyr Asp Pro Ile Phe Tyr Leu His His Ser Asn Thr Asp
    210                 215                 220

Arg Leu Trp Ala Ile Trp Gln Ala Leu Gln Lys Tyr Arg Gly Lys Pro
225                 230                 235                 240

Tyr Asn Ser Ala Asn Cys Ala Ile Ala Ser Met Arg Lys Pro Leu Gln
                245                 250                 255

Pro Phe Gly Leu Thr Asp Glu Ile Asn Pro Asp Asp Glu Thr Arg Gln
            260                 265                 270

His Ala Val Pro Phe Ser Val Phe Asp Tyr Lys Asn Asn Phe Asn Tyr
        275                 280                 285
```

-continued

```
Glu Tyr Asp Thr Leu Asp Phe Asn Gly Leu Ser Ile Ser Gln Leu Asp
    290                 295                 300

Arg Glu Leu Ser Arg Arg Lys Ser His Asp Arg Val Phe Ala Gly Phe
305                 310                 315                 320

Leu Leu His Gly Ile Gln Gln Ser Ala Leu Val Lys Phe Phe Val Cys
                325                 330                 335

Lys Ser Asp Asp Asp Cys Asp His Tyr Ala Gly Glu Phe Tyr Ile Leu
            340                 345                 350

Gly Asp Glu Ala Glu Met Pro Trp Gly Tyr Asp Arg Leu Tyr Lys Tyr
        355                 360                 365

Glu Ile Thr Glu Gln Leu Asn Ala Leu Asp Leu His Ile Gly Asp Arg
    370                 375                 380

Phe Phe Ile Arg Tyr Glu Ala Phe Asp Leu His Gly Thr Ser Leu Gly
385                 390                 395                 400

Ser Asn Ile Phe Pro Lys Pro Ser Val Ile His Asp Glu Gly Ala
                405                 410                 415


<210> SEQ ID NO 205
<211> LENGTH: 415
<212> TYPE: PRT
<213> ORGANISM: Haliotis tuberculata

<400> SEQUENCE: 205

Gly His His Gln Ala Asp Glu Tyr Asp Glu Val Val Thr Ala Ala Ser
  1               5                  10                  15

His Ile Arg Lys Asn Leu Lys Asp Leu Ser Lys Gly Glu Val Glu Ser
            20                  25                  30

Leu Arg Ser Ala Phe Leu Gln Leu Gln Asn Asp Gly Val Tyr Glu Asn
        35                  40                  45

Ile Ala Lys Phe His Gly Lys Pro Gly Leu Cys Asp Asp Asn Gly Arg
    50                  55                  60

Lys Val Ala Cys Cys Val His Gly Met Pro Thr Phe Pro Gln Trp His
65                  70                  75                  80

Arg Leu Tyr Val Leu Gln Val Glu Asn Ala Leu Leu Glu Arg Gly Ser
                85                  90                  95

Ala Val Ser Val Pro Tyr Trp Asp Trp Thr Glu Thr Phe Thr Glu Leu
            100                 105                 110

Pro Ser Leu Ile Ala Glu Ala Thr Tyr Phe Asn Ser Arg Gln Gln Thr
        115                 120                 125

Phe Asp Pro Asn Pro Phe Phe Arg Gly Lys Ile Ser Phe Glu Asn Ala
    130                 135                 140

Val Thr Thr Arg Asp Pro Gln Pro Glu Leu Tyr Val Asn Arg Tyr Tyr
145                 150                 155                 160

Tyr Gln Asn Val Met Leu Ala Phe Glu Gln Asp Asn Tyr Cys Asp Phe
                165                 170                 175

Glu Ile Gln Phe Glu Met Val His Asn Val Leu His Ala Trp Leu Gly
            180                 185                 190

Gly Arg Ala Thr Tyr Ser Ile Ser Ser Leu Asp Tyr Ser Ala Phe Asp
        195                 200                 205

Pro Val Phe Phe Leu His His Ala Asn Thr Asp Arg Leu Trp Ala Ile
    210                 215                 220

Trp Gln Glu Leu Gln Arg Tyr Arg Lys Lys Pro Tyr Asn Glu Ala Asp
225                 230                 235                 240

Cys Ala Ile Asn Leu Met Arg Lys Pro Leu His Pro Phe Asp Asn Ser
                245                 250                 255
```

-continued

```
Asp Leu Asn His Asp Pro Val Thr Phe Lys Tyr Ser Lys Pro Thr Asp
            260                 265                 270

Gly Phe Asp Tyr Gln Asn Asn Phe Gly Tyr Lys Tyr Asp Asn Leu Glu
        275                 280                 285

Phe Asn His Phe Ser Ile Pro Arg Leu Glu Glu Ile Ile Arg Ile Arg
    290                 295                 300

Gln Arg Gln Asp Arg Val Phe Ala Gly Phe Leu Leu His Asn Ile Gly
305                 310                 315                 320

Thr Ser Ala Thr Val Glu Ile Phe Val Cys Val Pro Thr Thr Ser Gly
                325                 330                 335

Glu Gln Asn Cys Glu Asn Lys Ala Gly Thr Phe Ala Val Leu Gly Gly
            340                 345                 350

Glu Thr Glu Met Ala Phe His Phe Asp Arg Leu Tyr Arg Phe Asp Ile
        355                 360                 365

Ser Glu Thr Leu Arg Asp Leu Gly Ile Gln Leu Asp Ser His Asp Phe
    370                 375                 380

Asp Leu Ser Ile Lys Ile Gln Gly Val Asn Gly Ser Tyr Leu Asp Pro
385                 390                 395                 400

His Ile Leu Pro Glu Pro Ser Leu Ile Phe Val Pro Gly Ser Ser
                405                 410                 415


<210> SEQ ID NO 206
<211> LENGTH: 418
<212> TYPE: PRT
<213> ORGANISM: Haliotis tuberculata

<400> SEQUENCE: 206

Ser Phe Leu Arg Pro Asp Gly His Ser Asp Asp Ile Leu Val Arg Lys
  1               5                  10                  15

Glu Val Asn Ser Leu Thr Thr Arg Glu Thr Ala Ser Leu Ile His Ala
            20                  25                  30

Leu Lys Ser Met Gln Glu Asp His Ser Pro Asp Gly Phe Gln Ala Ile
        35                  40                  45

Ala Ser Phe His Ala Leu Pro Pro Leu Cys Pro Ser Pro Ser Ala Thr
     50                  55                  60

His Arg Tyr Ala Cys Cys Val His Gly Met Ala Thr Phe Pro Gln Trp
 65                  70                  75                  80

His Arg Leu Tyr Thr Val Gln Phe Gln Asp Ala Leu Arg Arg His Gly
                85                  90                  95

Ala Ala Val Gly Val Pro Tyr Trp Asp Trp Leu Arg Pro Gln Ser His
            100                 105                 110

Leu Pro Glu Leu Val Thr Met Glu Thr Tyr His Asp Ile Trp Ser Asn
        115                 120                 125

Arg Asp Phe Pro Asn Pro Phe Tyr Gln Ala Asn Ile Glu Phe Glu Gly
    130                 135                 140

Glu Asn Ile Thr Thr Glu Arg Glu Val Ile Ala Asp Lys Leu Phe Val
145                 150                 155                 160

Lys Gly Gly His Val Phe Asp Asn Trp Phe Phe Lys Gln Ala Ile Leu
                165                 170                 175

Ala Leu Glu Gln Glu Asn Tyr Cys Asp Phe Glu Ile Gln Phe Glu Ile
            180                 185                 190

Leu His Asn Gly Val His Thr Trp Val Gly Gly Ser Arg Thr His Ser
        195                 200                 205

Ile Gly His Leu His Tyr Ala Ser Tyr Asp Pro Leu Phe Tyr Leu His
    210                 215                 220
```

-continued

```
His Ser Gln Thr Asp Arg Ile Trp Ala Ile Trp Gln Glu Leu Gln Glu
225                 230                 235                 240

Gln Arg Gly Leu Ser Gly Asp Glu Ala His Cys Ala Leu Glu Gln Met
                245                 250                 255

Arg Glu Pro Leu Lys Pro Phe Ser Phe Gly Ala Pro Tyr Asn Leu Asn
            260                 265                 270

Gln Leu Thr Gln Asp Phe Ser Arg Pro Glu Asp Thr Phe Asp Tyr Arg
        275                 280                 285

Lys Phe Gly Tyr Glu Tyr Asp Asn Leu Glu Phe Leu Gly Met Ser Val
    290                 295                 300

Ala Glu Leu Asp Gln Tyr Ile Ile Glu His Gln Glu Asn Asp Arg Val
305                 310                 315                 320

Phe Ala Gly Phe Leu Leu Ser Gly Phe Gly Gly Ser Ala Ser Val Asn
                325                 330                 335

Phe Gln Val Cys Arg Ala Asp Ser Thr Cys Gln Asp Ala Gly Tyr Phe
            340                 345                 350

Thr Val Leu Gly Gly Ser Ala Glu Met Ala Trp Ala Phe Asp Arg Leu
        355                 360                 365

Tyr Lys Tyr Asp Ile Thr Glu Thr Leu Glu Lys Met His Leu Arg Tyr
    370                 375                 380

Asp Asp Asp Phe Thr Ile Ser Val Ser Leu Thr Ala Asn Asn Gly Thr
385                 390                 395                 400

Val Leu Ser Ser Ser Leu Ile Pro Thr Pro Ser Val Ile Phe Gln Arg
                405                 410                 415

Gly His
```

<210> SEQ ID NO 207
<211> LENGTH: 416
<212> TYPE: PRT
<213> ORGANISM: Haliotis tuberculata

<400> SEQUENCE: 207

```
Arg Asp Ile Asn Thr Lys Ser Met Ser Ala Asn Arg Val Arg Arg Glu
  1               5                  10                  15

Leu Ser Asp Leu Ser Ala Arg Asp Pro Ser Ser Leu Lys Ser Ala Leu
            20                  25                  30

Arg Asp Leu Gln Glu Asp Asp Gly Pro Asn Gly Tyr Gln Ala Leu Ala
        35                  40                  45

Ala Phe His Gly Leu Pro Ala Gly Cys His Asp Ser Gln Gly Asn Glu
     50                  55                  60

Ile Ala Cys Cys Ile His Gly Met Pro Thr Phe Pro Gln Trp His Arg
 65                  70                  75                  80

Leu Tyr Thr Leu Gln Leu Glu Met Ala Leu Arg Arg His Gly Ser Ser
                 85                  90                  95

Val Ala Ile Pro Tyr Trp Asp Trp Thr Lys Pro Ile Ser Glu Leu Pro
            100                 105                 110

Ser Leu Phe Thr Ser Pro Glu Tyr Tyr Asp Pro Trp His Asp Ala Val
        115                 120                 125

Val Asn Asn Pro Phe Ser Lys Gly Phe Val Lys Phe Ala Asn Thr Tyr
    130                 135                 140

Thr Val Arg Asp Pro Gln Glu Met Leu Phe Gln Leu Cys Glu His Gly
145                 150                 155                 160

Glu Ser Ile Leu Tyr Glu Gln Thr Leu Leu Ala Leu Glu Gln Thr Asp
                165                 170                 175
```

-continued

```
Tyr Cys Asp Phe Glu Val Gln Phe Glu Val Leu His Asn Val Ile His
            180                 185                 190

Tyr Leu Val Gly Gly Arg Gln Thr Tyr Ala Leu Ser Ser Leu His Tyr
        195                 200                 205

Ala Ser Tyr Asp Pro Phe Phe Phe Ile His His Ser Phe Val Asp Lys
    210                 215                 220

Met Trp Val Val Trp Gln Ala Leu Gln Lys Arg Arg Lys Leu Pro Tyr
225                 230                 235                 240

Lys Arg Ala Asp Cys Ala Val Asn Leu Met Thr Lys Pro Met Arg Pro
                245                 250                 255

Phe Asp Ser Asp Met Asn Gln Asn Pro Phe Thr Lys Met His Ala Val
            260                 265                 270

Pro Asn Thr Leu Tyr Asp Tyr Glu Thr Leu Tyr Tyr Ser Tyr Asp Asn
        275                 280                 285

Leu Glu Ile Gly Gly Arg Asn Leu Asp Gln Leu Gln Ala Glu Ile Asp
    290                 295                 300

Arg Ser Arg Ser His Asp Arg Val Phe Ala Gly Phe Leu Leu Arg Gly
305                 310                 315                 320

Ile Gly Thr Ser Ala Asp Val Arg Phe Trp Ile Cys Arg Asn Glu Asn
                325                 330                 335

Asp Cys His Arg Gly Gly Ile Ile Phe Ile Leu Gly Gly Ala Lys Glu
            340                 345                 350

Met Pro Trp Ser Phe Asp Arg Asn Phe Lys Phe Asp Ile Thr His Val
        355                 360                 365

Leu Glu Lys Ala Gly Ile Ser Pro Glu Asp Val Phe Asp Ala Glu Glu
    370                 375                 380

Pro Phe Tyr Ile Lys Val Glu Ile His Ala Val Asn Lys Thr Met Ile
385                 390                 395                 400

Pro Ser Ser Val Ile Pro Ala Pro Thr Ile Ile Tyr Ser Pro Gly Glu
                405                 410                 415


<210> SEQ ID NO 208
<211> LENGTH: 402
<212> TYPE: PRT
<213> ORGANISM: Haliotis tuberculata

<400> SEQUENCE: 208

Gly Arg Ala Ala Asp Ser Ala His Ser Ala Asn Ile Ala Gly Ser Gly
  1               5                  10                  15

Val Arg Lys Asp Val Thr Thr Leu Thr Val Ser Glu Thr Glu Asn Leu
             20                  25                  30

Arg Gln Ala Leu Gln Gly Val Ile Asp Asp Thr Gly Pro Asn Gly Tyr
         35                  40                  45

Gln Ala Ile Ala Ser Phe His Gly Ser Pro Pro Met Cys Glu Met Asn
     50                  55                  60

Gly Arg Lys Val Ala Cys Cys Ala His Gly Met Ala Ser Phe Pro His
 65                  70                  75                  80

Trp His Arg Leu Tyr Val Lys Gln Met Glu Asp Ala Leu Ala Asp His
                 85                  90                  95

Gly Ser His Ile Gly Ile Pro Tyr Trp Asp Trp Thr Thr Ala Phe Thr
            100                 105                 110

Glu Leu Pro Ala Leu Val Thr Asp Ser Glu Asn Asn Pro Phe His Glu
        115                 120                 125

Gly Arg Ile Asp His Leu Gly Val Thr Thr Ser Arg Ser Pro Arg Asp
    130                 135                 140
```

-continued

```
Met Leu Phe Asn Asp Pro Glu Gln Gly Ser Glu Ser Phe Phe Tyr Arg
145                 150                 155                 160

Gln Val Leu Leu Ala Leu Glu Gln Thr Asp Tyr Cys Gln Phe Glu Val
                165                 170                 175

Gln Phe Glu Leu Thr His Asn Ala Ile His Ser Trp Thr Gly Gly Arg
            180                 185                 190

Ser Pro Tyr Gly Met Ser Thr Leu Glu Phe Thr Ala Tyr Asp Pro Leu
        195                 200                 205

Phe Trp Leu His His Ser Asn Thr Asp Arg Ile Trp Ala Val Trp Gln
    210                 215                 220

Ala Leu Gln Lys Tyr Arg Gly Leu Pro Tyr Asn Glu Ala His Cys Glu
225                 230                 235                 240

Ile Gln Val Leu Lys Gln Pro Leu Arg Pro Phe Asn Asp Asp Ile Asn
                245                 250                 255

His Asn Pro Ile Thr Lys Thr Asn Ala Arg Pro Ile Asp Ser Phe Asp
            260                 265                 270

Tyr Glu Arg Phe Asn Tyr Gln Tyr Asp Thr Leu Ser Phe His Gly Lys
        275                 280                 285

Ser Ile Pro Glu Leu Asn Asp Leu Leu Glu Glu Arg Lys Arg Glu Glu
    290                 295                 300

Arg Thr Phe Ala Ala Phe Leu Leu Arg Gly Ile Gly Cys Ser Ala Asp
305                 310                 315                 320

Val Val Phe Asp Ile Cys Arg Pro Asn Gly Asp Cys Val Phe Ala Gly
                325                 330                 335

Thr Phe Ala Val Leu Gly Gly Glu Leu Glu Met Pro Trp Ser Phe Asp
            340                 345                 350

Arg Leu Phe Arg Tyr Asp Ile Thr Arg Val Met Asn Gln Leu His Leu
        355                 360                 365

Gln Tyr Asp Ser Asp Phe Ser Phe Arg Val Lys Leu Val Ala Thr Asn
    370                 375                 380

Gly Thr Glu Leu Ser Ser Asp Leu Leu Lys Ser Pro Thr Ile Glu His
385                 390                 395                 400

Glu Leu


<210> SEQ ID NO 209
<211> LENGTH: 512
<212> TYPE: PRT
<213> ORGANISM: Haliotis tuberculata

<400> SEQUENCE: 209

Gly Ala His Arg Gly Pro Val Glu Glu Thr Glu Val Thr His Gln Asn
  1               5                  10                  15

Thr Asp Gly Asn Ala His Phe His Arg Lys Glu Val Asp Ser Leu Ser
            20                  25                  30

Leu Asp Glu Ala Asn Asn Leu Lys Asn Ala Leu Tyr Lys Leu Gln Asn
        35                  40                  45

Asp His Ser Leu Thr Gly Tyr Glu Ala Ile Ser Gly Tyr His Gly Tyr
     50                  55                  60

Pro Asn Leu Cys Pro Glu Glu Gly Asp Asp Lys Tyr Pro Cys Cys Val
 65                  70                  75                  80

His Gly Met Ala Ile Phe Pro His Trp His Arg Leu Leu Thr Ile Gln
                 85                  90                  95
```

-continued

```
Leu Glu Arg Ala Leu Glu His Asn Gly Ala Leu Leu Gly Val Pro Tyr
            100                 105                 110

Trp Asp Trp Thr Lys Asp Leu Ser Ser Leu Pro Ala Phe Phe Ser Asp
        115                 120                 125

Ser Ser Asn Asn Asn Pro Tyr Phe Lys Tyr His Ile Ala Gly Val Gly
    130                 135                 140

His Asp Thr Val Arg Glu Pro Thr Ser Leu Ile Tyr Asn Gln Pro Gln
145                 150                 155                 160

Ile His Gly Tyr Asp Tyr Leu Tyr Tyr Leu Ala Leu Thr Thr Leu Glu
                165                 170                 175

Glu Asn Asn Tyr Cys Asp Phe Glu Val Gln Tyr Glu Ile Leu His Asn
            180                 185                 190

Ala Val His Ser Trp Leu Gly Gly Ser Gln Lys Tyr Ser Met Ser Thr
        195                 200                 205

Leu Glu Tyr Ser Ala Phe Asp Pro Val Phe Met Ile Leu His Ser Gly
    210                 215                 220

Leu Asp Arg Leu Trp Ile Ile Trp Gln Glu Leu Gln Lys Ile Arg Arg
225                 230                 235                 240

Lys Pro Tyr Asn Phe Ala Lys Cys Ala Tyr His Met Met Glu Glu Pro
                245                 250                 255

Leu Ala Pro Phe Ser Tyr Pro Ser Ile Asn Gln Asp Glu Phe Thr Arg
            260                 265                 270

Ala Asn Ser Lys Pro Ser Thr Val Phe Asp Ser His Lys Phe Gly Tyr
        275                 280                 285

His Tyr Asp Asn Leu Asn Val Arg Gly His Ser Ile Gln Glu Leu Asn
    290                 295                 300

Thr Ile Ile Asn Asp Leu Arg Asn Thr Asp Arg Ile Tyr Ala Gly Phe
305                 310                 315                 320

Val Leu Ser Gly Ile Gly Thr Ser Ala Ser Val Lys Ile Tyr Leu Arg
                325                 330                 335

Thr Asp Asp Asn Asp Glu Glu Val Gly Thr Phe Thr Val Leu Gly Gly
            340                 345                 350

Glu Arg Glu Met Pro Trp Ala Tyr Glu Arg Val Phe Lys Tyr Asp Ile
        355                 360                 365

Thr Glu Val Ala Asp Arg Leu Lys Leu Ser Tyr Gly Asp Thr Phe Asn
    370                 375                 380

Phe Arg Leu Glu Ile Thr Ser Tyr Asp Gly Ser Val Val Asn Lys Ser
385                 390                 395                 400

Leu Pro Asn Pro Phe Ile Ile Tyr Arg Pro Ala Asn His Asp Tyr Asp
                405                 410                 415

Val Leu Val Ile Pro Val Gly Arg Asn Leu His Ile Pro Pro Lys Val
            420                 425                 430

Val Val Lys Arg Gly Thr Arg Ile Glu Phe His Pro Val Asp Asp Ser
        435                 440                 445

Val Thr Arg Pro Val Val Asp Leu Gly Ser Tyr Thr Ala Leu Phe Asn
    450                 455                 460

Cys Val Val Pro Pro Phe Thr Tyr Arg Gly Phe Glu Leu Asn His Val
465                 470                 475                 480

Tyr Ser Val Lys Pro Gly Asp Tyr Tyr Val Thr Gly Pro Thr Arg Asp
                485                 490                 495

Leu Cys Gln Asn Ala Asp Val Arg Ile His Ile His Val Glu Asp Glu
            500                 505                 510
```

-continued

<210> SEQ ID NO 210
<211> LENGTH: 967
<212> TYPE: DNA
<213> ORGANISM: Megathura crenulata

<400> SEQUENCE: 210
ggcctaccgt actgggactg gactgaaccc atgacacaca ttccgggtct ggcaggaaac 60
aaaacttatg tggattctca tggtgcatcc cacacaaatc cttttcatag ttcagtgatt 120
gcatttgaag aaaatgctcc ccacaccaaa agacaaatag atcaaagact ctttaaaccc 180
gctacctttg gacaccacac agacctgttc aaccagattt tgtatgcctt tgaacaagaa 240
gattactgtg actttgaagt ccaatttgag attacccata acacgattca cgcttggaca 300
ggaggaagcg aacatttctc aatgtcgtcc ctacattaca cagctttcga tcctttgttt 360
tactttcacc attctaacgt tgatcgtctt tgggccgttt ggcaagcctt acagatgaga 420
cggcataaac cctacagggc ccactgcgcc atatctctgg aacatatgca tctgaaacca 480
ttcgcctttt catctcccct taacaataac gaaaagactc atgccaatgc catgccaaac 540
aagatctacg actatgaaaa tgtcctccat tacacatacg aagatttaac atttggaggc 600
atctctctgg aaaacataga aaagatgatc cacgaaaacc agcaagaaga cagaatatat 660
gccggttttc tcctggctgg catacgtact tcagcaaatg ttgatatctt cattaaaact 720
accgattccg tgcaacataa ggctggaaca tttgcagtgc tcggtggaag caaggaaatg 780
aagtggggat ttgatcgcgt tttcaagttt gacatcacgc acgttttgaa agatctcgat 840
ctcactgctg atggcgattt cgaagttact gttgacatca ctgaagtcga tggaactaaa 900
cttgcatcca gtcttattcc acatgcttct gtcattcgtg agcatgcacg tggtaagctg 960
aatagag 967

<210> SEQ ID NO 211
<211> LENGTH: 1242
<212> TYPE: DNA
<213> ORGANISM: Megathura crenulata

<400> SEQUENCE: 211
ttaaatttga caaagtgcca aggagtcgtc ttattcgaaa aaatgtagac cgtttgagcc 60
ccgaggagat gaatgaactt cgtaaagccc tagccttact gaaagaggac aaaagtgccg 120
gtggatttca gcagcttggt gcattccatg gggagccaaa atggtgtcct agtcccgaag 180
catctaaaaa atttgcctgc tgtgttcacg gcatgtctgt gttccctcac tggcatcgac 240
tgttgacggt tcagagtgaa aatgctttga gacgacatgg ctacgatgga gctttgccgt 300
actgggattg gacctctcct cttaatcacc ttcccgaact ggcagatcat gagaagtacg 360
tcgaccctga agatggggta gagaagcata acccttggtt cgatggtcat atagatacag 420
tcgacaaaac aacaacaaga agtgttcaga ataaactctt cgaacagcct gagtttggtc 480
attatacaag cattgccaaa caagtactgc tagcgttgga acaggacaat ttctgtgact 540
ttgaaatcca atatgagatt gcccataact acatccatgc acttgtagga ggcgctcagc 600
cttatggtat ggcatcgctt cgctacactg cttttgatcc actattctac ttgcatcact 660
ctaatacaga tcgtatatgg gcaatatggc aggctttaca gaagtacaga ggaaaaccgt 720
acaacgttgc taactgtgct gttacatcga tgagagaacc tttgcaacca tttggcctct 780
ctgccaatat caacacagac catgtaacca aggagcattc agtgccattc aacgtttttg 840
attacaagac caatttcaat tatgaatatg acactttgga atttaacggt ctctcaatct 900

-continued

```
ctcagttgaa taaaaagctc gaagcgataa agagccaaga caggttcttt gcaggcttcc    960

tgttatctgg tttcaagaaa tcatctcttg ttaaattcaa tatttgcacc gatagcagca   1020

actgtcaccc cgctggagag ttttaccttc tgggtgatga aaacgagatg ccatgggcat   1080

acgatagagt cttcaaatat gacataaccg aaaaactcca cgatctaaag ctgcatgcag   1140

aagaccactt ctacattgac tatgaagtat ttgaccttaa accagcaagc ctgggaaaag   1200

atttgttcaa gcagccttca gtcattcatg aaccaagaat ag                      1242
```

```
<210> SEQ ID NO 212
<211> LENGTH: 1236
<212> TYPE: DNA
<213> ORGANISM: Megathura crenulata

<400> SEQUENCE: 212

gtcaccatga aggcgaagta tatcaagctg aagtaacttc tgccaaccgt attcgaaaaa     60

acattgaaaa tctgagcctt ggtgaactcg aaagtctgag agctgccttc ctggaaattg    120

aaaacgatgg aacttacgaa tcaatagcta aattccatgg tagccctggt ttgtgccagt    180

taaatggtaa ccccatctct tgttgtgtcc atggcatgcc aactttccct cactggcaca    240

gactgtacgt ggttgtcgtt gagaatgccc tcctgaaaaa aggatcatct gtagctgttc    300

cctattggga ctggacaaaa cgaatcgaac atttacctca cctgatttca gacgccactt    360

actacaattc caggcaacat cactatgaga caaacccatt ccatcatggc aaaatcacac    420

acgagaatga aatcactact agggatccca aggacagcct cttccattca gactactttt    480

acgagcaggt cctttacgcc ttggagcagg ataacttctg tgatttcgag attcagttgg    540

agatattaca caatgcattg cattctttac ttggtggcaa aggtaaatat tccatgtcaa    600

accttgatta cgctgctttt gatcctgtgt tcttccttca tcacgcaacg actgacagaa    660

tctgggcaat ctggcaagac cttcagaggt tccgaaaacg gccataccga gaagcgaatt    720

gcgctatcca attgatgcac acgccactcc agccgtttga taagagcgac aacaatgacg    780

aggcaacgaa aacgcatgcc actccacatg atggttttga atatcaaaac agctttggtt    840

atgcttacga taatctggaa ctgaatcact actcgattcc tcagcttgat cacatgctgc    900

aagaaagaaa aaggcatgac agagtattcg ctggcttcct ccttcacaat attggaacat    960

ctgccgatgg ccatgtattt gtatgtctcc caactgggga acacacgaag gactgcagtc   1020

atgaggctgg tatgttctcc atcttaggcg gtcaaacgga gatgtccttt gtatttgaca   1080

gactttacaa acttgacata actaaagcct tgaaaaagaa cggtgtgcac ctgcaagggg   1140

atttcgatct ggaaattgag attacggctg tgaatggatc tcatctagac agtcatgtca   1200

tccactctcc cactatactg tttgaggccg gaacag                             1236
```

```
<210> SEQ ID NO 213
<211> LENGTH: 1257
<212> TYPE: DNA
<213> ORGANISM: Megathura crenulata

<400> SEQUENCE: 213

attctgccca cacagatgat ggacacactg aaccagtgat gattcgcaaa gatatcacac     60

aattggacaa gcgtcaacaa ctgtcactgg tgaaagccct cgagtccatg aaagccgacc    120

attcatctga tgggttccag gcaatcgctt ccttccatgc tcttcctcct ctttgtccat    180

caccagctgc ttcaaagagg tttgcgtgct gcgtccatgg catggcaacg ttcccacaat    240

ggcaccgtct gtacacagtc caattccaag attctctcag aaaacatggt gcagtcgttg    300
```

-continued

```
gacttccgta ctgggactgg accctacctc gttctgaatt accagagctc ctgaccgtct    360

caactattca tgacccggag acaggcagag atataccaaa tccatttatt ggttctaaaa    420

tagagtttga aggagaaaac gtacatacta aaagagatat caatagggat cgtctcttcc    480

agggatcaac aaaaacacat cataactggt ttattgagca agcactgctt gctcttgaac    540

aaaccaacta ctgcgacttc gaggttcagt ttgaaattat gcataatggt gttcatacct    600

gggttggagg caaggagccc tatggaattg gccatctgca ttatgcttcc tatgatccac    660

ttttctacat ccatcactcc caaactgatc gtatttgggc tatatggcaa tcgttgcagc    720

gtttcagagg actttctgga tctgaggcta actgtgctgt aaatctcatg aaaactcctc    780

tgaagccttt cagctttgga gcaccatata atcttaatga tcacacgcat gatttctcaa    840

agcctgaaga tacattcgac taccaaaagt ttggatacat atatgacact ctggaatttg    900

cagggtggtc aattcgtggc attgaccata ttgtccgtaa caggcaggaa cattcaaggg    960

tctttgccgg attcttgctt gaaggatttg gcacctctgc cactgtcgat ttccaggtct   1020

gtcgcacagc gggagactgt gaagatgcag ggtacttcac cgtgttggga ggtgaaaaag   1080

aaatgccttg ggcctttgat cggctttaca agtacgacat aacagaaacc ttagacaaga   1140

tgaaccttcg acatgacgaa atcttccaga ttgaagtaac cattacatcc tacgatggaa   1200

ctgtactcga tagtggcctt attcccacac cgtcaatcat ctatgatcct gctcatc      1257
```

<210> SEQ ID NO 214
<211> LENGTH: 191
<212> TYPE: DNA
<213> ORGANISM: Megathura crenulata

<400> SEQUENCE: 214

```
atgatattag ttcgcaccac ctgtcgctca acaaggttcg tcatgatctg agtacactga     60

gtgagcgaga tattggaagc cttaaatatg ctttgagcag cttgcaggca gatacctcag    120

cagatggttt tgctgccatt gcatccttcc atggtctgcc tgccaaatgt aatgacagcc    180

acaataacga g                                                         191
```

<210> SEQ ID NO 215
<211> LENGTH: 1063
<212> TYPE: DNA
<213> ORGANISM: Megathura crenulata

<400> SEQUENCE: 215

```
gtggcatgct gtatccatgg aatgcctaca ttccccccact ggcacagact ctacaccctc     60

caatttgagc aagctctaag aagacatggc tctagtgtag cagtacccta ctgggactgg    120

acaaagccaa tacataatat tccacatctg ttcacagaca aagaatacta cgatgtctgg    180

agaaataaag taatgccaaa tccatttgcc cgagggtatg tcccctcaca cgatacatac    240

acggtaagag acgtccaaga aggcctgttc cacctgacat caacgggtga acactcagcg    300

cttctgaatc aagctctttt ggcgctggaa cagcacgact actgcgattt tgcagtccag    360

tttgaagtca tgcacaacac aatccattac ctagtgggag gacctcaagt ctattctttg    420

tcatcccttc attatgcttc atatgatccg atcttcttca tacaccactc ctttgtagac    480

aaggtttggg ctgtctggca ggctcttcaa gaaaagagag gccttccatc agaccgtgct    540

gactgcgctg ttagtctgat gactcagaac atgaggcctt tccattacga aattaaccat    600

aaccagttca ccaagaaaca tgcagttcca aatgatgttt tcaagtacga actcctgggt    660

tacagatacg acaatctgga aatcggtggc atgaatttgc atgaaattga aaaggaaatc    720
```

-continued

```
aaagacaaac agcaccatgt gagagtgttt gcagggttcc tccttcacgg aattagaacc    780

tcagctgatg tccaattcca gatttgtaaa acatcagaag attgtcacca tggaggccaa    840

atcttcgttc ttggggggac taaagagatg gcctgggctt ataaccgttt attcaagtac    900

gatattaccc atgctcttca tgacgcacac atcactccag aagacgtatt ccatccctct    960

gaaccattct tcatcaaggt gtcagtgaca gccgtcaacg gaacagttct tccggcttca   1020

atcctgcatg caccaaccat tatctatgaa cctggtctcg gtg                     1063


<210> SEQ ID NO 216
<211> LENGTH: 219
<212> TYPE: DNA
<213> ORGANISM: Megathura crenulata

<400> SEQUENCE: 216

accatcacga agatcatcat tcttcttcta tggctggaca tggtgtcaga aaggaaatca     60

acacacttac cactgcagag gtggacaatc tcaaagatgc catgagagcc gtcatggcag    120

accacggtcc aaatggatac caggctatag cagcgttcca tggaaaccca ccaatgtgcc    180

ctatgccaga tggaaagaat tactcgtgtt gtacacatg                           219


<210> SEQ ID NO 217
<211> LENGTH: 164
<212> TYPE: DNA
<213> ORGANISM: Megathura crenulata

<400> SEQUENCE: 217

gcatggctac tttcccccac tggcacagac tgtacacaaa acagatggaa gatgccttga     60

ccgcccatgg tgccagagtc ggccttcctt actgggacgg gacaactgcc tttacagctt    120

tgccaacttt tgtcacagat gaagaggaca atcctttcca tcat                     164


<210> SEQ ID NO 218
<211> LENGTH: 126
<212> TYPE: DNA
<213> ORGANISM: Megathura crenulata

<400> SEQUENCE: 218

ggtcacatag actatttggg agtggataca actcggtcgc cccgagacaa gttgttcaat     60

gatccagagc gaggatcaga atcgttcttc tacaggcagg ttctcttggc tttggagcag    120

acagat                                                               126


<210> SEQ ID NO 219
<211> LENGTH: 322
<212> TYPE: PRT
<213> ORGANISM: Megathura crenulata

<400> SEQUENCE: 219

Gly Leu Pro Tyr Trp Asp Trp Thr Glu Pro Met Thr His Ile Pro Gly
  1               5                  10                  15

Leu Ala Gly Asn Lys Thr Tyr Val Asp Ser His Gly Ala Ser His Thr
             20                  25                  30

Asn Pro Phe His Ser Ser Val Ile Ala Phe Glu Glu Asn Ala Pro His
         35                  40                  45

Thr Lys Arg Gln Ile Asp Gln Arg Leu Phe Lys Pro Ala Thr Phe Gly
     50                  55                  60

His His Thr Asp Leu Phe Asn Gln Ile Leu Tyr Ala Phe Glu Gln Glu
 65                  70                  75                  80
```

-continued

```
Asp Tyr Cys Asp Phe Glu Val Gln Phe Glu Ile Thr His Asn Thr Ile
                85                  90                  95

His Ala Trp Thr Gly Gly Ser Glu His Phe Ser Met Ser Ser Leu His
            100                 105                 110

Tyr Thr Ala Phe Asp Pro Leu Phe Tyr Phe His His Ser Asn Val Asp
        115                 120                 125

Arg Leu Trp Ala Val Trp Gln Ala Leu Gln Met Arg Arg His Lys Pro
    130                 135                 140

Tyr Arg Ala His Cys Ala Ile Ser Leu Glu His Met His Leu Lys Pro
145                 150                 155                 160

Phe Ala Phe Ser Ser Pro Leu Asn Asn Asn Glu Lys Thr His Ala Asn
                165                 170                 175

Ala Met Pro Asn Lys Ile Tyr Asp Tyr Glu Asn Val Leu His Tyr Thr
            180                 185                 190

Tyr Glu Asp Leu Thr Phe Gly Gly Ile Ser Leu Glu Asn Ile Glu Lys
        195                 200                 205

Met Ile His Glu Asn Gln Gln Glu Asp Arg Ile Tyr Ala Gly Phe Leu
    210                 215                 220

Leu Ala Gly Ile Arg Thr Ser Ala Asn Val Asp Ile Phe Ile Lys Thr
225                 230                 235                 240

Thr Asp Ser Val Gln His Lys Ala Gly Thr Phe Ala Val Leu Gly Gly
                245                 250                 255

Ser Lys Glu Met Lys Trp Gly Phe Asp Arg Val Phe Lys Phe Asp Ile
            260                 265                 270

Thr His Val Leu Lys Asp Leu Asp Leu Thr Ala Asp Gly Asp Phe Glu
        275                 280                 285

Val Thr Val Asp Ile Thr Glu Val Asp Gly Thr Lys Leu Ala Ser Ser
    290                 295                 300

Leu Ile Pro His Ala Ser Val Ile Arg Glu His Ala Arg Gly Lys Leu
305                 310                 315                 320

Asn Arg


<210> SEQ ID NO 220
<211> LENGTH: 414
<212> TYPE: PRT
<213> ORGANISM: Megathura crenulata

<400> SEQUENCE: 220

Val Lys Phe Asp Lys Val Pro Arg Ser Arg Leu Ile Arg Lys Asn Val
  1               5                  10                  15

Asp Arg Leu Ser Pro Glu Glu Met Asn Glu Leu Arg Lys Ala Leu Ala
             20                  25                  30

Leu Leu Lys Glu Asp Lys Ser Ala Gly Gly Phe Gln Gln Leu Gly Ala
         35                  40                  45

Phe His Gly Glu Pro Lys Trp Cys Pro Ser Pro Glu Ala Ser Lys Lys
     50                  55                  60

Phe Ala Cys Cys Val His Gly Met Ser Val Phe Pro His Trp His Arg
 65                  70                  75                  80

Leu Leu Thr Val Gln Ser Glu Asn Ala Leu Arg Arg His Gly Tyr Asp
                 85                  90                  95

Gly Ala Leu Pro Tyr Trp Asp Trp Thr Ser Pro Leu Asn His Leu Pro
            100                 105                 110

Glu Leu Ala Asp His Glu Lys Tyr Val Asp Pro Glu Asp Gly Val Glu
        115                 120                 125
```

-continued

```
Lys His Asn Pro Trp Phe Asp Gly His Ile Asp Thr Val Asp Lys Thr
    130                 135                 140

Thr Thr Arg Ser Val Gln Asn Lys Leu Phe Glu Gln Pro Glu Phe Gly
145                 150                 155                 160

His Tyr Thr Ser Ile Ala Lys Gln Val Leu Leu Ala Leu Glu Gln Asp
                165                 170                 175

Asn Phe Cys Asp Phe Glu Ile Gln Tyr Glu Ile Ala His Asn Tyr Ile
            180                 185                 190

His Ala Leu Val Gly Gly Ala Gln Pro Tyr Gly Met Ala Ser Leu Arg
        195                 200                 205

Tyr Thr Ala Phe Asp Pro Leu Phe Tyr Leu His His Ser Asn Thr Asp
    210                 215                 220

Arg Ile Trp Ala Ile Trp Gln Ala Leu Gln Lys Tyr Arg Gly Lys Pro
225                 230                 235                 240

Tyr Asn Val Ala Asn Cys Ala Val Thr Ser Met Arg Glu Pro Leu Gln
                245                 250                 255

Pro Phe Gly Leu Ser Ala Asn Ile Asn Thr Asp His Val Thr Lys Glu
            260                 265                 270

His Ser Val Pro Phe Asn Val Phe Asp Tyr Lys Thr Asn Phe Asn Tyr
        275                 280                 285

Glu Tyr Asp Thr Leu Glu Phe Asn Gly Leu Ser Ile Ser Gln Leu Asn
    290                 295                 300

Lys Lys Leu Glu Ala Ile Lys Ser Gln Asp Arg Phe Phe Ala Gly Phe
305                 310                 315                 320

Leu Leu Ser Gly Phe Lys Lys Ser Ser Leu Val Lys Phe Asn Ile Cys
                325                 330                 335

Thr Asp Ser Ser Asn Cys His Pro Ala Gly Glu Phe Tyr Leu Leu Gly
            340                 345                 350

Asp Glu Asn Glu Met Pro Trp Ala Tyr Asp Arg Val Phe Lys Tyr Asp
        355                 360                 365

Ile Thr Glu Lys Leu His Asp Leu Lys Leu His Ala Glu Asp His Phe
    370                 375                 380

Tyr Ile Asp Tyr Glu Val Phe Asp Leu Lys Pro Ala Ser Leu Gly Lys
385                 390                 395                 400

Asp Leu Phe Lys Gln Pro Ser Val Ile His Glu Pro Arg Ile
                405                 410
```

```
<210> SEQ ID NO 221
<211> LENGTH: 411
<212> TYPE: PRT
<213> ORGANISM: Megathura crenulata

<400> SEQUENCE: 221

Gly His His Glu Gly Glu Val Tyr Gln Ala Glu Val Thr Ser Ala Asn
  1               5                  10                  15

Arg Ile Arg Lys Asn Ile Glu Asn Leu Ser Leu Gly Glu Leu Glu Ser
            20                  25                  30

Leu Arg Ala Ala Phe Leu Glu Ile Glu Asn Asp Gly Thr Tyr Glu Ser
        35                  40                  45

Ile Ala Lys Phe His Gly Ser Pro Gly Leu Cys Gln Leu Asn Gly Asn
     50                  55                  60

Pro Ile Ser Cys Cys Val His Gly Met Pro Thr Phe Pro His Trp His
 65                  70                  75                  80

Arg Leu Tyr Val Val Val Val Glu Asn Ala Leu Leu Lys Lys Gly Ser
                 85                  90                  95
```

-continued

```
Ser Val Ala Val Pro Tyr Trp Asp Trp Thr Lys Arg Ile Glu His Leu
            100                 105                 110

Pro His Leu Ile Ser Asp Ala Thr Tyr Tyr Asn Ser Arg Gln His His
        115                 120                 125

Tyr Glu Thr Asn Pro Phe His His Gly Lys Ile Thr His Glu Asn Glu
    130                 135                 140

Ile Thr Thr Arg Asp Pro Lys Asp Ser Leu Phe His Ser Asp Tyr Phe
145                 150                 155                 160

Tyr Glu Gln Val Leu Tyr Ala Leu Glu Gln Asp Asn Phe Cys Asp Phe
                165                 170                 175

Glu Ile Gln Leu Glu Ile Leu His Asn Ala Leu His Ser Leu Leu Gly
            180                 185                 190

Gly Lys Gly Lys Tyr Ser Met Ser Asn Leu Asp Tyr Ala Ala Phe Asp
        195                 200                 205

Pro Val Phe Phe Leu His His Ala Thr Thr Asp Arg Ile Trp Ala Ile
    210                 215                 220

Trp Gln Asp Leu Gln Arg Phe Arg Lys Arg Pro Tyr Arg Glu Ala Asn
225                 230                 235                 240

Cys Ala Ile Gln Leu Met His Thr Pro Leu Gln Pro Phe Asp Lys Ser
                245                 250                 255

Asp Asn Asn Asp Glu Ala Thr Lys Thr His Ala Thr Pro His Asp Gly
            260                 265                 270

Phe Glu Tyr Gln Asn Ser Phe Gly Tyr Ala Tyr Asp Asn Leu Glu Leu
        275                 280                 285

Asn His Tyr Ser Ile Pro Gln Leu Asp His Met Leu Gln Glu Arg Lys
    290                 295                 300

Arg His Asp Arg Val Phe Ala Gly Phe Leu Leu His Asn Ile Gly Thr
305                 310                 315                 320

Ser Ala Asp Gly His Val Phe Val Cys Leu Pro Thr Gly Glu His Thr
                325                 330                 335

Lys Asp Cys Ser His Glu Ala Gly Met Phe Ser Ile Leu Gly Gly Gln
            340                 345                 350

Thr Glu Met Ser Phe Val Phe Asp Arg Leu Tyr Lys Leu Asp Ile Thr
        355                 360                 365

Lys Ala Leu Lys Lys Asn Gly Val His Leu Gln Gly Asp Phe Asp Leu
    370                 375                 380

Glu Ile Glu Ile Thr Ala Val Asn Gly Ser His Leu Asp Ser His Val
385                 390                 395                 400

Ile His Ser Pro Thr Ile Leu Phe Glu Ala Gly
                405                 410


<210> SEQ ID NO 222
<211> LENGTH: 420
<212> TYPE: PRT
<213> ORGANISM: Megathura crenulata

<400> SEQUENCE: 222

Thr Asp Ser Ala His Thr Asp Asp Gly His Thr Glu Pro Val Met Ile
  1               5                  10                  15

Arg Lys Asp Ile Thr Gln Leu Asp Lys Arg Gln Gln Leu Ser Leu Val
             20                  25                  30

Lys Ala Leu Glu Ser Met Lys Ala Asp His Ser Ser Asp Gly Phe Gln
         35                  40                  45

Ala Ile Ala Ser Phe His Ala Leu Pro Pro Leu Cys Pro Ser Pro Ala
     50                  55                  60
```

-continued

Ala Ser Lys Arg Phe Ala Cys Cys Val His Gly Met Ala Thr Phe Pro
65 70 75 80

Gln Trp His Arg Leu Tyr Thr Val Gln Phe Gln Asp Ser Leu Arg Lys
85 90 95

His Gly Ala Val Val Gly Leu Pro Tyr Trp Asp Trp Thr Leu Pro Arg
100 105 110

Ser Glu Leu Pro Glu Leu Leu Thr Val Ser Thr Ile His Asp Pro Glu
115 120 125

Thr Gly Arg Asp Ile Pro Asn Pro Phe Ile Gly Ser Lys Ile Glu Phe
130 135 140

Glu Gly Glu Asn Val His Thr Lys Arg Asp Ile Asn Arg Asp Arg Leu
145 150 155 160

Phe Gln Gly Ser Thr Lys Thr His His Asn Trp Phe Ile Glu Gln Ala
165 170 175

Leu Leu Ala Leu Glu Gln Thr Asn Tyr Cys Asp Phe Glu Val Gln Phe
180 185 190

Glu Ile Met His Asn Gly Val His Thr Trp Val Gly Gly Lys Glu Pro
195 200 205

Tyr Gly Ile Gly His Leu His Tyr Ala Ser Tyr Asp Pro Leu Phe Tyr
210 215 220

Ile His His Ser Gln Thr Asp Arg Ile Trp Ala Ile Trp Gln Ser Leu
225 230 235 240

Gln Arg Phe Arg Gly Leu Ser Gly Ser Glu Ala Asn Cys Ala Val Asn
245 250 255

Leu Met Lys Thr Pro Leu Lys Pro Phe Ser Phe Gly Ala Pro Tyr Asn
260 265 270

Leu Asn Asp His Thr His Asp Phe Ser Lys Pro Glu Asp Thr Phe Asp
275 280 285

Tyr Gln Lys Phe Gly Tyr Ile Tyr Asp Thr Leu Glu Phe Ala Gly Trp
290 295 300

Ser Ile Arg Gly Ile Asp His Ile Val Arg Asn Arg Gln Glu His Ser
305 310 315 320

Arg Val Phe Ala Gly Phe Leu Leu Glu Gly Phe Gly Thr Ser Ala Thr
325 330 335

Val Asp Phe Gln Val Cys Arg Thr Ala Gly Asp Cys Glu Asp Ala Gly
340 345 350

Tyr Phe Thr Val Leu Gly Gly Glu Lys Glu Met Pro Trp Ala Phe Asp
355 360 365

Arg Leu Tyr Lys Tyr Asp Ile Thr Glu Thr Leu Asp Lys Met Asn Leu
370 375 380

Arg His Asp Glu Ile Phe Gln Ile Glu Val Thr Ile Thr Ser Tyr Asp
385 390 395 400

Gly Thr Val Leu Asp Ser Gly Leu Ile Pro Thr Pro Ser Ile Ile Tyr
405 410 415

Asp Pro Ala His
420

<210> SEQ ID NO 223
<211> LENGTH: 418
<212> TYPE: PRT
<213> ORGANISM: Megathura crenulata

<400> SEQUENCE: 223

His Asp Ile Ser Ser His His Leu Ser Leu Asn Lys Val Arg His Asp
1 5 10 15

Leu Ser Thr Leu Ser Glu Arg Asp Ile Gly Ser Leu Lys Tyr Ala Leu
20 25 30

Ser Ser Leu Gln Ala Asp Thr Ser Ala Asp Gly Phe Ala Ala Ile Ala
35 40 45

Ser Phe His Gly Leu Pro Ala Lys Cys Asn Asp Ser His Asn Asn Glu
50 55 60

Val Ala Cys Cys Ile His Gly Met Pro Thr Phe Pro His Trp His Arg
65 70 75 80

Leu Tyr Thr Leu Gln Phe Glu Gln Ala Leu Arg Arg His Gly Ser Ser
85 90 95

Val Ala Val Pro Tyr Trp Asp Trp Thr Lys Pro Ile His Asn Ile Pro
100 105 110

His Leu Phe Thr Asp Lys Glu Tyr Tyr Asp Val Trp Arg Asn Lys Val
115 120 125

Met Pro Asn Pro Phe Ala Arg Gly Tyr Val Pro Ser His Asp Thr Tyr
130 135 140

Thr Val Arg Asp Val Gln Glu Gly Leu Phe His Leu Thr Ser Thr Gly
145 150 155 160

Glu His Ser Ala Leu Leu Asn Gln Ala Leu Leu Ala Leu Glu Gln His
165 170 175

Asp Tyr Cys Asp Phe Ala Val Gln Phe Glu Val Met His Asn Thr Ile
180 185 190

His Tyr Leu Val Gly Gly Pro Gln Val Tyr Ser Leu Ser Ser Leu His
195 200 205

Tyr Ala Ser Tyr Asp Pro Ile Phe Phe Ile His His Ser Phe Val Asp
210 215 220

Lys Val Trp Ala Val Trp Gln Ala Leu Gln Glu Lys Arg Gly Leu Pro
225 230 235 240

Ser Asp Arg Ala Asp Cys Ala Val Ser Leu Met Thr Gln Asn Met Arg
245 250 255

Pro Phe His Tyr Glu Ile Asn His Asn Gln Phe Thr Lys Lys His Ala
260 265 270

Val Pro Asn Asp Val Phe Lys Tyr Glu Leu Leu Gly Tyr Arg Tyr Asp
275 280 285

Asn Leu Glu Ile Gly Gly Met Asn Leu His Glu Ile Glu Lys Glu Ile
290 295 300

Lys Asp Lys Gln His His Val Arg Val Phe Ala Gly Phe Leu Leu His
305 310 315 320

Gly Ile Arg Thr Ser Ala Asp Val Gln Phe Gln Ile Cys Lys Thr Ser
325 330 335

Glu Asp Cys His His Gly Gly Gln Ile Phe Val Leu Gly Gly Thr Lys
340 345 350

Glu Met Ala Trp Ala Tyr Asn Arg Leu Phe Lys Tyr Asp Ile Thr His
355 360 365

Ala Leu His Asp Ala His Ile Thr Pro Glu Asp Val Phe His Pro Ser
370 375 380

Glu Pro Phe Phe Ile Lys Val Ser Val Thr Ala Val Asn Gly Thr Val
385 390 395 400

-continued

```
Leu Pro Ala Ser Ile Leu His Ala Pro Thr Ile Ile Tyr Glu Pro Gly
                405                 410                 415

Leu Gly


<210> SEQ ID NO 224
<211> LENGTH: 170
<212> TYPE: PRT
<213> ORGANISM: Megathura crenulata

<400> SEQUENCE: 224

Asp His His Glu Asp His His Ser Ser Ser Met Ala Gly His Gly Val
  1               5                  10                  15

Arg Lys Glu Ile Asn Thr Leu Thr Thr Ala Glu Val Asp Asn Leu Lys
             20                  25                  30

Asp Ala Met Arg Ala Val Met Ala Asp His Gly Pro Asn Gly Tyr Gln
         35                  40                  45

Ala Ile Ala Ala Phe His Gly Asn Pro Pro Met Cys Pro Met Pro Asp
     50                  55                  60

Gly Lys Asn Tyr Ser Cys Cys Thr His Gly Met Ala Thr Phe Pro His
 65                  70                  75                  80

Trp His Arg Leu Tyr Thr Lys Gln Met Glu Asp Ala Leu Thr Ala His
                 85                  90                  95

Gly Ala Arg Val Gly Leu Pro Tyr Trp Asp Gly Thr Thr Ala Phe Thr
            100                 105                 110

Ala Leu Pro Thr Phe Val Thr Asp Glu Glu Asp Asn Pro Phe His His
        115                 120                 125

Gly His Ile Asp Tyr Leu Gly Val Asp Thr Thr Arg Ser Pro Arg Asp
    130                 135                 140

Lys Leu Phe Asn Asp Pro Glu Arg Gly Ser Glu Ser Phe Phe Tyr Arg
145                 150                 155                 160

Gln Val Leu Leu Ala Leu Glu Gln Thr Asp
                165                 170


<210> SEQ ID NO 225
<211> LENGTH: 949
<212> TYPE: DNA
<213> ORGANISM: Megathura crenulata

<400> SEQUENCE: 225

ggcctgccct actgggattg gaccatgcca atgagtcatt tgccagaact ggctacaagt      60

gagacctacc tcgatccagt tactggggaa actaaaaaca acccttttcca tcacgcccaa    120

gtggcgtttg aaaatggtgt aacaagcagg aatcctgatg ccaaactttt tatgaaacca    180

acttacggag accacactta cctcttcgac agcatgatct acgcatttga gcaggaagac    240

ttctgcgact ttgaagtcca atatgagctc acgcataatg caatacatgc atgggttgga    300

ggcagtgaaa agtattcaat gtcttctctt cactacactg cttttgatcc tatattttac    360

ctccatcact caaatgttga tcgtctctgg gccatttggc aagctcttca aatcaggaga    420

ggcaagtctt acaaggccca ctgcgcctcg tctcaagaaa gagaaccatt aaagcctttt    480

gcattcagtt ccccactgaa caacaacgag aaaacgtacc acaactctgt ccccactaac    540

gtttatgact atgtgggagt tttgcactat cgatatgatg accttcagtt tggcggtatg    600

accatgtcag aacttgagga atatattcac aagcagacac aacatgatag aacctttgca    660

ggattcttcc tttcatatat tggaacatca gcaagcgtag atatcttcat caatcgagaa    720

ggtcatgata aatacaaagt gggaagtttt gtagtacttg gtggatccaa agaaatgaaa    780
```

-continued

```
tggggctttg atagaatgta caagtatgag atcactgagg ctctgaagac gctgaatgtt    840

gcagtggatg atgggttcag cattactgtt gagatcaccg atgttgatgg atctccccca    900

tctgcagatc tcattccacc tcctgctata atctttgacg tggtcagag              949
```

<210> SEQ ID NO 226
<211> LENGTH: 1248
<212> TYPE: DNA
<213> ORGANISM: Megathura crenulata

<400> SEQUENCE: 226

```
ctgatgccaa agactttggc catagcagaa aaatcaggaa agccgttgat tctctgacag     60

tcgaagaaca aacttcgttg aggcgagcta tggcagatct acaggacgac aaaacatcag    120

ggggtttcca gcagattgca gcattccacg gagaaccaaa atggtgtcca agccccgaag    180

cggagaaaaa atttgcatgc tgtgttcatg gaatggctgt tttccctcac tggcacagat    240

tgctgacagt tcaaggagaa aatgctctga ggaaacatgg atttactggt ggattgccct    300

attgggactg gactcggcca atgagcgccc ttccacattt tgttgctgat cctacttaca    360

atgattctgt ttccagcctc gaagaagata acccatggta tcatggtcac atagattctg    420

ttgggcatga tactacaaga gctgtgcgtg atgatcttta tcaatctcct ggtttcggtc    480

actacacaga tattgcaaaa caagtccttc tggcctttga gcaggacgat ttctgtgatt    540

ttgaggtaca atttgaaatt gcccataatt tcatacatgc tctggttggt ggtaacgaac    600

catacagtat gtcatctttg aggtatacta catacgatcc aatcttcttc ttgcaccgct    660

ccaatacaga ccgactttgg gccatttggc aagctttgca aaaataccgg gggaaaccat    720

acaacactgc aaactgtgcc attgcatcca tgagaaaacc acttcagcca tttggtcttg    780

atagtgtcat aaatccagat gacgaaactc gtgaacattc ggttcctttc cgagtcttcg    840

actacaagaa caacttcgac tatgagtatg agagcctggc atttaatggt ctgtctattg    900

cccaactgga ccgagagttg cagagaagaa agtcacatga cagagtcttt gcaggattcc    960

ttcttcatga aattggacag tctgcactcg tgaaattcta cgtttgcaaa cacaatgtat   1020

ctgactgtga ccattatgct ggagaattct acattttggg agatgaagct gagatgcctt   1080

ggaggtatga ccgtgtgtac aagtacgaga taacacagca gctgcacgat ttagatctac   1140

atgttggaga taatttcttc cttaaatatg aagcctttga tctgaatggc ggaagtcttg   1200

gtggaagtat cttttctcag ccttcggtga ttttcgagcc agctgcag                1248
```

<210> SEQ ID NO 227
<211> LENGTH: 1257
<212> TYPE: DNA
<213> ORGANISM: Megathura crenulata

<400> SEQUENCE: 227

```
gttcacacca ggctgatgaa tatcgtgagg cagtaacaag cgctagccac ataagaaaaa     60

atatccggga cctctcagag ggagaaattg agagcatcag atctgctttc ctccaaattc    120

aaaaagaggg tatatatgaa aacattgcaa agttccatgg aaaaccagga ctttgtgaac    180

atgatggaca tcctgttgct tgttgtgtcc atggcatgcc cacctttccc cactggcaca    240

gactgtacgt tcttcaggtg gagaatgcgc tcttagaacg agggtctgca gttgctgttc    300

cttactggga ctggaccgag aaagctgact ctctgccatc attaatcaat gatgcaactt    360

atttcaattc acgatcccag acctttgatc ctaatccttt cttcagggga catattgcct    420

tcgagaatgc tgtgacgtcc agagatcctc agccagaact atgggacaat aaggacttct    480
```

-continued

```
acgagaatgt catgctggct cttgagcaag acaacttctg tgactttgag attcagcttg    540
agctgataca caacgccctt cattctagac ttggaggaag ggctaaatac tccctttcgt    600
ctcttgatta taccgcattt gatcctgtat tttccttca ccatgcaaac gttgacagaa    660
tctgggccat ctggcaggac ttgcagagat atagaaagaa accatacaat gaggctgact    720
gcgcagtcaa cgagatgcgt aaacctcttc aaccatttaa taacccagaa cttaacagtg    780
attccatgac gcttaaacac aacctcccac aagacagttt tgattatcaa aaccgcttca    840
ggtaccaata tgataacctt caatttaacc acttcagcat acaaaagcta gaccaaacta    900
ttcaggctag aaaacaacac gacagagttt ttgctggctt tattcttcac aacattggga    960
catctgctgt tgtagatatt tatatttgcg ttgaacaagg aggagaacaa aactgcaaga   1020
caaaggcggg ttccttcacg attctggggg gagaaacaga aatgccattc cactttgacc   1080
gcttgtacaa atttgacata acgtctgctc tgcataaact tggtgttccc ttggacggac   1140
atggattcga catcaaagtt gacgtcagag ctgtcaatgg atcgcatctt gatcaacaca   1200
tcctcaacga accgagtctg ctttttgttc ctggtgaacg taagaatata tattatg      1257
```

<210> SEQ ID NO 228
<211> LENGTH: 1239
<212> TYPE: DNA
<213> ORGANISM: Megathura crenulata

<400> SEQUENCE: 228

```
atgggctttc acaacataat cttgtgcgaa aagaagtaag ctctcttaca acactggaga     60
aacatttttt gaggaaagct ctcaagaaca tgcaagcaga tgattctcca gacggatatc    120
aagctattgc ttctttccac gctttgcctc ctctttgtcc aagtccatct gctgcacata    180
gacacgcttg ttgcctccat ggtatggcta ccttccctca gtggcacaga ctctacacag    240
ttcagttcga agattctttg aaacgacatg gttctattgt cggacttcca tattgggatt    300
ggctgaaacc gcagtctgca ctccctgatt tggtgacaca ggagacatac gagcacctgt    360
tttcacacaa aaccttccca aatccgttcc tcaaggcaaa tatagaattt gagggagagg    420
gagtaacaac agagagggat gttgatgctg aacacctctt tgcaaaagga aatctggttt    480
acaacaactg gttttgcaat caggcactat atgcactaga acaagaaaat tactgtgact    540
ttgaaataca gttcgaaatt ttgcataatg gaattcattc atgggttgga ggatcaaaga    600
cccattcaat aggtcatctt cattacgcat catacgatcc actgttctat atccaccatt    660
cgcagacaga tcgcatttgg gctatctggc aagctctcca ggagcacaga ggtctttcag    720
ggaaggaagc acactgcgcc ctggagcaaa tgaaagaccc tctcaaacct ttcagctttg    780
gaagtcccta taatttgaac aaacgcactc aagagttctc caagcctgaa gacacatttg    840
attatcaccg attcgggtat gagtatgatt ccctcgaatt tgttggcatg tctgtttcaa    900
gtttacataa ctatataaaa caacaacagg aagctgatag agtcttcgca ggattccttc    960
ttaaaggatt tggacaatca gcatccgtat cgtttgatat ctgcagacca gaccagagtt   1020
gccaagaagc tggatacttc tcagttctcg gtggaagttc agaaatgccg tggcagtttg   1080
acaggcttta caagtacgac attacaaaaa cgttgaaaga catgaaactg cgatacgatg   1140
acacatttac catcaaggtt cacataaagg atatagctgg agctgagttg gacagcgatc   1200
tgattccaac tccttctgtt ctccttgaag aaggaaagc                          1239
```

-continued

<210> SEQ ID NO 229
<211> LENGTH: 191
<212> TYPE: DNA
<213> ORGANISM: Megathura crenulata

<400> SEQUENCE: 229
atgggatcaa tgtacgtcac gttggtcgta atcggattcg tatggaacta tctgaactca 60
ccgagagaga tctcgccagc ctgaaatctg caatgaggtc tctacaagct gacgatgggg 120
tgaacggtta tcaagccatt gcatcattcc acggtctccc ggcttcttgt catgatgatg 180
agggacatga g 191

<210> SEQ ID NO 230
<211> LENGTH: 1060
<212> TYPE: DNA
<213> ORGANISM: Megathura crenulata

<400> SEQUENCE: 230
attgcctgtt gtatccacgg aatgccagta ttcccacact ggcacaggct ttacaccctg 60
caaatggaca tggctctgtt atctcacgga tctgctgttg ctattccata ctgggactgg 120
accaaaccta tcagcaaact gcctgatctc ttcaccagcc ctgaatatta cgatccttgg 180
agggatgcag ttgtcaataa tccatttgct aaaggctaca ttaaatccga ggacgcttac 240
acggttaggg atcctcagga cattttgtac cacttgcagg acgaaacggg aacatctgtt 300
ttgttagatc aaactctttt agccttagag cagacagatt tctgtgattt tgaggttcaa 360
tttgaggtcg tccataatgc tattcactac ttggtgggtg gtcgacaagt ttatgctctt 420
tcttctcaac actatgcttc atatgaccca gccttcttta ttcatcactc ctttgttgac 480
aaaatatggg cagtctggca agctctgcaa aagaagagaa agcgtcccta tcataaagcg 540
gattgtgctc ttaacatgat gaccaaacca atgcgaccat ttgcacacga tttcaatcac 600
aatggattca caaaaaatgca cgcagtcccc aacactctat ttgactttca ggaccttttc 660
tacacgtatg acaacttaga aattgctggc atgaatgtta atcagttgga agcggaaatc 720
aaccggcgaa aaagccaaac aagagtcttt gccgggttcc ttctacatgg cattggaaga 780
tcagctgatg tacgattttg gatttgcaag acagctgacg actgccacgc atctggcatg 840
atctttatct taggaggttc taaagagatg cactgggcct atgacaggaa ctttaaatac 900
gacatcaccc aagctttgaa ggctcagtcc atacaccctg aagatgtgtt tgacactgat 960
gctcctttct tcattaaagt ggaggtccat ggtgtaaaca agactgctct cccatcttca 1020
gctatcccag cacctactat aatctactca gctggtgaag 1060

<210> SEQ ID NO 231
<211> LENGTH: 195
<212> TYPE: DNA
<213> ORGANISM: Megathura crenulata

<400> SEQUENCE: 231
atcatattgc tggcagtgga gtcaggaaag acgtgacgtc tcttaccgca tctgagatag 60
agaacctgag gcatgctctg caaagcgtga tggatgatga tggacccaat ggattccagg 120
caattgctgc ttatcacgga agtcctccca tgtgtcacat gcctgatggt agagacgttg 180
catgttgtac tcatg 195

-continued

<210> SEQ ID NO 232
<211> LENGTH: 164
<212> TYPE: DNA
<213> ORGANISM: Megathura crenulata

<400> SEQUENCE: 232
gaatggcatc tttccctcac tggcacagac tgtttgtgaa acagatggag gatgcactgg 60
ctgcgcatgg agctcacatt ggcataccat actgggattg gacaagtgcg tttagtcatc 120
tgcctgccct agtgactgac cacgagcaca atcccttcca ccac 164

<210> SEQ ID NO 233
<211> LENGTH: 826
<212> TYPE: DNA
<213> ORGANISM: Megathura crenulata

<400> SEQUENCE: 233
ggacatattg ctcatcggaa tgtggataca tctcgatctc cgagagacat gctgttcaat 60
gaccccgaac acgggtcaga atcattcttc tatagacagg ttctcttggc tctagaacag 120
acagacttct gccaatttga agttcagttt gaaataacac acaatgcaat ccactcttgg 180
actggaggac atactccata tggaatgtca tcactggaat atacagcata tgatccactc 240
ttttatctcc accattccaa cactgatcgt atctgggcca tctggcaggc actccagaaa 300
tacagaggtt ttcaatacaa cgcagctcat tgcgatatcc aggttctgaa acaacctctt 360
aaaccattca gcgagtccag gaatccaaac ccagtcacca gagccaattc tagggcagtc 420
gattcatttg attatgagag actcaattat caatatgaca cacttacctt ccacggacat 480
tctatctcag aacttgatgc catgcttcaa gagagaaaga aggaagagag aacatttgca 540
gccttcctgt tgcacggatt tggcgccagt gctgatgttt cgtttgatgt ctgcacacct 600
gatggtcatt gtgcctttgc tggaaccttc gcggtacttg gtggggagct tgagatgccc 660
tggtcctttg aaagattgtt ccgttacgat atcacaaagg ttctcaagca gatgaatctt 720
cactatgatt ctgagttcca ctttgagttg aagattgttg gcacagatgg aacagaactg 780
ccatcggatc gtatcaagag ccctaccatt gaacaccatg gaggag 826

<210> SEQ ID NO 234
<211> LENGTH: 316
<212> TYPE: PRT
<213> ORGANISM: Megathura crenulata

<400> SEQUENCE: 234

Gly Leu Pro Tyr Trp Asp Trp Thr Met Pro Met Ser His Leu Pro Glu
1 5 10 15

Leu Ala Thr Ser Glu Thr Tyr Leu Asp Pro Val Thr Gly Glu Thr Lys
20 25 30

Asn Asn Pro Phe His His Ala Gln Val Ala Phe Glu Asn Gly Val Thr
35 40 45

Ser Arg Asn Pro Asp Ala Lys Leu Phe Met Lys Pro Thr Tyr Gly Asp
50 55 60

His Thr Tyr Leu Phe Asp Ser Met Ile Tyr Ala Phe Glu Gln Glu Asp
65 70 75 80

Phe Cys Asp Phe Glu Val Gln Tyr Glu Leu Thr His Asn Ala Ile His
85 90 95

Ala Trp Val Gly Gly Ser Glu Lys Tyr Ser Met Ser Ser Leu His Tyr
100 105 110

-continued

```
Thr Ala Phe Asp Pro Ile Phe Tyr Leu His His Ser Asn Val Asp Arg
        115                 120                 125

Leu Trp Ala Ile Trp Gln Ala Leu Gln Ile Arg Arg Gly Lys Ser Tyr
    130                 135                 140

Lys Ala His Cys Ala Ser Ser Gln Glu Arg Glu Pro Leu Lys Pro Phe
145                 150                 155                 160

Ala Phe Ser Ser Pro Leu Asn Asn Asn Glu Lys Thr Tyr His Asn Ser
                165                 170                 175

Val Pro Thr Asn Val Tyr Asp Tyr Val Gly Val Leu His Tyr Arg Tyr
            180                 185                 190

Asp Asp Leu Gln Phe Gly Gly Met Thr Met Ser Glu Leu Glu Glu Tyr
        195                 200                 205

Ile His Lys Gln Thr Gln His Asp Arg Thr Phe Ala Gly Phe Phe Leu
    210                 215                 220

Ser Tyr Ile Gly Thr Ser Ala Ser Val Asp Ile Phe Ile Asn Arg Glu
225                 230                 235                 240

Gly His Asp Lys Tyr Lys Val Gly Ser Phe Val Val Leu Gly Gly Ser
                245                 250                 255

Lys Glu Met Lys Trp Gly Phe Asp Arg Met Tyr Lys Tyr Glu Ile Thr
            260                 265                 270

Glu Ala Leu Lys Thr Leu Asn Val Ala Val Asp Asp Gly Phe Ser Ile
        275                 280                 285

Thr Val Glu Ile Thr Asp Val Asp Gly Ser Pro Pro Ser Ala Asp Leu
    290                 295                 300

Ile Pro Pro Pro Ala Ile Ile Phe Asp Val Val Arg
305                 310                 315


<210> SEQ ID NO 235
<211> LENGTH: 416
<212> TYPE: PRT
<213> ORGANISM: Megathura crenulata

<400> SEQUENCE: 235

Ala Asp Ala Lys Asp Phe Gly His Ser Arg Lys Ile Arg Lys Ala Val
  1               5                  10                  15

Asp Ser Leu Thr Val Glu Glu Gln Thr Ser Leu Arg Arg Ala Met Ala
            20                  25                  30

Asp Leu Gln Asp Asp Lys Thr Ser Gly Gly Phe Gln Gln Ile Ala Ala
        35                  40                  45

Phe His Gly Glu Pro Lys Trp Cys Pro Ser Pro Glu Ala Glu Lys Lys
    50                  55                  60

Phe Ala Cys Cys Val His Gly Met Ala Val Phe Pro His Trp His Arg
 65                  70                  75                  80

Leu Leu Thr Val Gln Gly Glu Asn Ala Leu Arg Lys His Gly Phe Thr
                85                  90                  95

Gly Gly Leu Pro Tyr Trp Asp Trp Thr Arg Pro Met Ser Ala Leu Pro
            100                 105                 110

His Phe Val Ala Asp Pro Thr Tyr Asn Asp Ser Val Ser Ser Leu Glu
        115                 120                 125

Glu Asp Asn Pro Trp Tyr His Gly His Ile Asp Ser Val Gly His Asp
    130                 135                 140

Thr Thr Arg Ala Val Arg Asp Asp Leu Tyr Gln Ser Pro Gly Phe Gly
145                 150                 155                 160

His Tyr Thr Asp Ile Ala Lys Gln Val Leu Leu Ala Phe Glu Gln Asp
                165                 170                 175
```

-continued

```
Asp Phe Cys Asp Phe Glu Val Gln Phe Glu Ile Ala His Asn Phe Ile
            180                 185                 190

His Ala Leu Val Gly Gly Asn Glu Pro Tyr Ser Met Ser Ser Leu Arg
        195                 200                 205

Tyr Thr Thr Tyr Asp Pro Ile Phe Phe Leu His Arg Ser Asn Thr Asp
    210                 215                 220

Arg Leu Trp Ala Ile Trp Gln Ala Leu Gln Lys Tyr Arg Gly Lys Pro
225                 230                 235                 240

Tyr Asn Thr Ala Asn Cys Ala Ile Ala Ser Met Arg Lys Pro Leu Gln
                245                 250                 255

Pro Phe Gly Leu Asp Ser Val Ile Asn Pro Asp Asp Glu Thr Arg Glu
            260                 265                 270

His Ser Val Pro Phe Arg Val Phe Asp Tyr Lys Asn Asn Phe Asp Tyr
        275                 280                 285

Glu Tyr Glu Ser Leu Ala Phe Asn Gly Leu Ser Ile Ala Gln Leu Asp
    290                 295                 300

Arg Glu Leu Gln Arg Arg Lys Ser His Asp Arg Val Phe Ala Gly Phe
305                 310                 315                 320

Leu Leu His Glu Ile Gly Gln Ser Ala Leu Val Lys Phe Tyr Val Cys
                325                 330                 335

Lys His Asn Val Ser Asp Cys Asp His Tyr Ala Gly Glu Phe Tyr Ile
            340                 345                 350

Leu Gly Asp Glu Ala Glu Met Pro Trp Arg Tyr Asp Arg Val Tyr Lys
        355                 360                 365

Tyr Glu Ile Thr Gln Gln Leu His Asp Leu Asp Leu His Val Gly Asp
    370                 375                 380

Asn Phe Phe Leu Lys Tyr Glu Ala Phe Asp Leu Asn Gly Gly Ser Leu
385                 390                 395                 400

Gly Gly Ser Ile Phe Ser Gln Pro Ser Val Ile Phe Glu Pro Ala Ala
                405                 410                 415
```

<210> SEQ ID NO 236
<211> LENGTH: 419
<212> TYPE: PRT
<213> ORGANISM: Megathura crenulata

<400> SEQUENCE: 236

```
Gly Ser His Gln Ala Asp Glu Tyr Arg Glu Ala Val Thr Ser Ala Ser
  1               5                  10                  15

His Ile Arg Lys Asn Ile Arg Asp Leu Ser Glu Gly Glu Ile Glu Ser
             20                  25                  30

Ile Arg Ser Ala Phe Leu Gln Ile Gln Lys Glu Gly Ile Tyr Glu Asn
         35                  40                  45

Ile Ala Lys Phe His Gly Lys Pro Gly Leu Cys Glu His Asp Gly His
     50                  55                  60

Pro Val Ala Cys Cys Val His Gly Met Pro Thr Phe Pro His Trp His
 65                  70                  75                  80

Arg Leu Tyr Val Leu Gln Val Glu Asn Ala Leu Leu Glu Arg Gly Ser
                 85                  90                  95

Ala Val Ala Val Pro Tyr Trp Asp Trp Thr Glu Lys Ala Asp Ser Leu
            100                 105                 110

Pro Ser Leu Ile Asn Asp Ala Thr Tyr Phe Asn Ser Arg Ser Gln Thr
        115                 120                 125

Phe Asp Pro Asn Pro Phe Phe Arg Gly His Ile Ala Phe Glu Asn Ala
    130                 135                 140
```

-continued

```
Val Thr Ser Arg Asp Pro Gln Pro Glu Leu Trp Asp Asn Lys Asp Phe
145                 150                 155                 160

Tyr Glu Asn Val Met Leu Ala Leu Glu Gln Asp Asn Phe Cys Asp Phe
                165                 170                 175

Glu Ile Gln Leu Glu Leu Ile His Asn Ala Leu His Ser Arg Leu Gly
            180                 185                 190

Gly Arg Ala Lys Tyr Ser Leu Ser Ser Leu Asp Tyr Thr Ala Phe Asp
        195                 200                 205

Pro Val Phe Phe Leu His His Ala Asn Val Asp Arg Ile Trp Ala Ile
    210                 215                 220

Trp Gln Asp Leu Gln Arg Tyr Arg Lys Lys Pro Tyr Asn Glu Ala Asp
225                 230                 235                 240

Cys Ala Val Asn Glu Met Arg Lys Pro Leu Gln Pro Phe Asn Asn Pro
                245                 250                 255

Glu Leu Asn Ser Asp Ser Met Thr Leu Lys His Asn Leu Pro Gln Asp
            260                 265                 270

Ser Phe Asp Tyr Gln Asn Arg Phe Arg Tyr Gln Tyr Asp Asn Leu Gln
        275                 280                 285

Phe Asn His Phe Ser Ile Gln Lys Leu Asp Gln Thr Ile Gln Ala Arg
    290                 295                 300

Lys Gln His Asp Arg Val Phe Ala Gly Phe Ile Leu His Asn Ile Gly
305                 310                 315                 320

Thr Ser Ala Val Val Asp Ile Tyr Ile Cys Val Glu Gln Gly Gly Glu
                325                 330                 335

Gln Asn Cys Lys Thr Lys Ala Gly Ser Phe Thr Ile Leu Gly Gly Glu
            340                 345                 350

Thr Glu Met Pro Phe His Phe Asp Arg Leu Tyr Lys Phe Asp Ile Thr
        355                 360                 365

Ser Ala Leu His Lys Leu Gly Val Pro Leu Asp Gly His Gly Phe Asp
    370                 375                 380

Ile Lys Val Asp Val Arg Ala Val Asn Gly Ser His Leu Asp Gln His
385                 390                 395                 400

Ile Leu Asn Glu Pro Ser Leu Leu Phe Val Pro Gly Glu Arg Lys Asn
                405                 410                 415

Ile Tyr Tyr


<210> SEQ ID NO 237
<211> LENGTH: 413
<212> TYPE: PRT
<213> ORGANISM: Megathura crenulata

<400> SEQUENCE: 237

Asp Gly Leu Ser Gln His Asn Leu Val Arg Lys Glu Val Ser Ser Leu
  1               5                  10                  15

Thr Thr Leu Glu Lys His Phe Leu Arg Lys Ala Leu Lys Asn Met Gln
            20                  25                  30

Ala Asp Asp Ser Pro Asp Gly Tyr Gln Ala Ile Ala Ser Phe His Ala
        35                  40                  45

Leu Pro Pro Leu Cys Pro Ser Pro Ser Ala Ala His Arg His Ala Cys
     50                  55                  60

Cys Leu His Gly Met Ala Thr Phe Pro Gln Trp His Arg Leu Tyr Thr
 65                  70                  75                  80

Val Gln Phe Glu Asp Ser Leu Lys Arg His Gly Ser Ile Val Gly Leu
                 85                  90                  95
```

-continued

```
Pro Tyr Trp Asp Trp Leu Lys Pro Gln Ser Ala Leu Pro Asp Leu Val
            100                 105                 110

Thr Gln Glu Thr Tyr Glu His Leu Phe Ser His Lys Thr Phe Pro Asn
        115                 120                 125

Pro Phe Leu Lys Ala Asn Ile Glu Phe Glu Gly Glu Gly Val Thr Thr
    130                 135                 140

Glu Arg Asp Val Asp Ala Glu His Leu Phe Ala Lys Gly Asn Leu Val
145                 150                 155                 160

Tyr Asn Asn Trp Phe Cys Asn Gln Ala Leu Tyr Ala Leu Glu Gln Glu
                165                 170                 175

Asn Tyr Cys Asp Phe Glu Ile Gln Phe Glu Ile Leu His Asn Gly Ile
            180                 185                 190

His Ser Trp Val Gly Gly Ser Lys Thr His Ser Ile Gly His Leu His
        195                 200                 205

Tyr Ala Ser Tyr Asp Pro Leu Phe Tyr Ile His His Ser Gln Thr Asp
    210                 215                 220

Arg Ile Trp Ala Ile Trp Gln Ala Leu Gln Glu His Arg Gly Leu Ser
225                 230                 235                 240

Gly Lys Glu Ala His Cys Ala Leu Glu Gln Met Lys Asp Pro Leu Lys
                245                 250                 255

Pro Phe Ser Phe Gly Ser Pro Tyr Asn Leu Asn Lys Arg Thr Gln Glu
            260                 265                 270

Phe Ser Lys Pro Glu Asp Thr Phe Asp Tyr His Arg Phe Gly Tyr Glu
        275                 280                 285

Tyr Asp Ser Leu Glu Phe Val Gly Met Ser Val Ser Ser Leu His Asn
    290                 295                 300

Tyr Ile Lys Gln Gln Gln Glu Ala Asp Arg Val Phe Ala Gly Phe Leu
305                 310                 315                 320

Leu Lys Gly Phe Gly Gln Ser Ala Ser Val Ser Phe Asp Ile Cys Arg
                325                 330                 335

Pro Asp Gln Ser Cys Gln Glu Ala Gly Tyr Phe Ser Val Leu Gly Gly
            340                 345                 350

Ser Ser Glu Met Pro Trp Gln Phe Asp Arg Leu Tyr Lys Tyr Asp Ile
        355                 360                 365

Thr Lys Thr Leu Lys Asp Met Lys Leu Arg Tyr Asp Asp Thr Phe Thr
    370                 375                 380

Ile Lys Val His Ile Lys Asp Ile Ala Gly Ala Glu Leu Asp Ser Asp
385                 390                 395                 400

Leu Ile Pro Thr Pro Ser Val Leu Leu Glu Glu Gly Lys
                405                 410
```

<210> SEQ ID NO 238
<211> LENGTH: 417
<212> TYPE: PRT
<213> ORGANISM: Megathura crenulata

<400> SEQUENCE: 238

```
His Gly Ile Asn Val Arg His Val Gly Arg Asn Arg Ile Arg Met Glu
  1               5                  10                  15

Leu Ser Glu Leu Thr Glu Arg Asp Leu Ala Ser Leu Lys Ser Ala Met
             20                  25                  30

Arg Ser Leu Gln Ala Asp Asp Gly Val Asn Gly Tyr Gln Ala Ile Ala
         35                  40                  45

Ser Phe His Gly Leu Pro Ala Ser Cys His Asp Asp Glu Gly His Glu
     50                  55                  60
```

-continued

```
Ile Ala Cys Cys Ile His Gly Met Pro Val Phe Pro His Trp His Arg
 65                  70                  75                  80

Leu Tyr Thr Leu Gln Met Asp Met Ala Leu Leu Ser His Gly Ser Ala
                85                  90                  95

Val Ala Ile Pro Tyr Trp Asp Trp Thr Lys Pro Ile Ser Lys Leu Pro
            100                 105                 110

Asp Leu Phe Thr Ser Pro Glu Tyr Tyr Asp Pro Trp Arg Asp Ala Val
        115                 120                 125

Val Asn Asn Pro Phe Ala Lys Gly Tyr Ile Lys Ser Glu Asp Ala Tyr
    130                 135                 140

Thr Val Arg Asp Pro Gln Asp Ile Leu Tyr His Leu Gln Asp Glu Thr
145                 150                 155                 160

Gly Thr Ser Val Leu Leu Asp Gln Thr Leu Leu Ala Leu Glu Gln Thr
                165                 170                 175

Asp Phe Cys Asp Phe Glu Val Gln Phe Glu Val Val His Asn Ala Ile
            180                 185                 190

His Tyr Leu Val Gly Gly Arg Gln Val Tyr Ala Leu Ser Ser Gln His
        195                 200                 205

Tyr Ala Ser Tyr Asp Pro Ala Phe Phe Ile His His Ser Phe Val Asp
    210                 215                 220

Lys Ile Trp Ala Val Trp Gln Ala Leu Gln Lys Lys Arg Lys Arg Pro
225                 230                 235                 240

Tyr His Lys Ala Asp Cys Ala Leu Asn Met Met Thr Lys Pro Met Arg
                245                 250                 255

Pro Phe Ala His Asp Phe Asn His Asn Gly Phe Thr Lys Met His Ala
            260                 265                 270

Val Pro Asn Thr Leu Phe Asp Phe Gln Asp Leu Phe Tyr Thr Tyr Asp
        275                 280                 285

Asn Leu Glu Ile Ala Gly Met Asn Val Asn Gln Leu Glu Ala Glu Ile
    290                 295                 300

Asn Arg Arg Lys Ser Gln Thr Arg Val Phe Ala Gly Phe Leu Leu His
305                 310                 315                 320

Gly Ile Gly Arg Ser Ala Asp Val Arg Phe Trp Ile Cys Lys Thr Ala
                325                 330                 335

Asp Asp Cys His Ala Ser Gly Met Ile Phe Ile Leu Gly Gly Ser Lys
            340                 345                 350

Glu Met His Trp Ala Tyr Asp Arg Asn Phe Lys Tyr Asp Ile Thr Gln
        355                 360                 365

Ala Leu Lys Ala Gln Ser Ile His Pro Glu Asp Val Phe Asp Thr Asp
    370                 375                 380

Ala Pro Phe Phe Ile Lys Val Glu Val His Gly Val Asn Lys Thr Ala
385                 390                 395                 400

Leu Pro Ser Ser Ala Ile Pro Ala Pro Thr Ile Ile Tyr Ser Ala Gly
                405                 410                 415

Glu
```

<210> SEQ ID NO 239
<211> LENGTH: 395
<212> TYPE: PRT
<213> ORGANISM: Megathura crenulata -continued

<400> SEQUENCE: 239

```
Asp His Ile Ala Gly Ser Gly Val Arg Lys Asp Val Thr Ser Leu Thr
  1               5                  10                  15

Ala Ser Glu Ile Glu Asn Leu Arg His Ala Leu Gln Ser Val Met Asp
             20                  25                  30

Asp Asp Gly Pro Asn Gly Phe Gln Ala Ile Ala Ala Tyr His Gly Ser
         35                  40                  45

Pro Pro Met Cys His Met Pro Asp Gly Arg Asp Val Ala Cys Cys Thr
     50                  55                  60

His Gly Met Ala Ser Phe Pro His Trp His Arg Leu Phe Val Lys Gln
 65                  70                  75                  80

Met Glu Asp Ala Leu Ala Ala His Gly Ala His Ile Gly Ile Pro Tyr
                 85                  90                  95

Trp Asp Trp Thr Ser Ala Phe Ser His Leu Pro Ala Leu Val Thr Asp
            100                 105                 110

His Glu His Asn Pro Phe His His Gly His Ile Ala His Arg Asn Val
        115                 120                 125

Asp Thr Ser Arg Ser Pro Arg Asp Met Leu Phe Asn Asp Pro Glu His
    130                 135                 140

Gly Ser Glu Ser Phe Phe Tyr Arg Gln Val Leu Leu Ala Leu Glu Gln
145                 150                 155                 160

Thr Asp Phe Cys Gln Phe Glu Val Gln Phe Glu Ile Thr His Asn Ala
                165                 170                 175

Ile His Ser Trp Thr Gly Gly His Thr Pro Tyr Gly Met Ser Ser Leu
            180                 185                 190

Glu Tyr Thr Ala Tyr Asp Pro Leu Phe Tyr Leu His His Ser Asn Thr
        195                 200                 205

Asp Arg Ile Trp Ala Ile Trp Gln Ala Leu Gln Lys Tyr Arg Gly Phe
    210                 215                 220

Gln Tyr Asn Ala Ala His Cys Asp Ile Gln Val Leu Lys Gln Pro Leu
225                 230                 235                 240

Lys Pro Phe Ser Glu Ser Arg Asn Pro Asn Pro Val Thr Arg Ala Asn
                245                 250                 255

Ser Arg Ala Val Asp Ser Phe Asp Tyr Glu Arg Leu Asn Tyr Gln Tyr
            260                 265                 270

Asp Thr Leu Thr Phe His Gly His Ser Ile Ser Glu Leu Asp Ala Met
        275                 280                 285

Leu Gln Glu Arg Lys Lys Glu Glu Arg Thr Phe Ala Ala Phe Leu Leu
    290                 295                 300

His Gly Phe Gly Ala Ser Ala Asp Val Ser Phe Asp Val Cys Thr Pro
305                 310                 315                 320

Asp Gly His Cys Ala Phe Ala Gly Thr Phe Ala Val Leu Gly Gly Glu
                325                 330                 335

Leu Glu Met Pro Trp Ser Phe Glu Arg Leu Phe Arg Tyr Asp Ile Thr
            340                 345                 350

Lys Val Leu Lys Gln Met Asn Leu His Tyr Asp Ser Glu Phe His Phe
        355                 360                 365

Glu Leu Lys Ile Val Gly Thr Asp Gly Thr Glu Leu Pro Ser Asp Arg
    370                 375                 380

Ile Lys Ser Pro Thr Ile Glu His His Gly Gly
385                 390                 395
```